United States Patent
Boss et al.

(10) Patent No.: US 9,732,075 B2
(45) Date of Patent: Aug. 15, 2017

(54) BENZIMIDAZOLE-PROLINE DERIVATIVES

(71) Applicant: IDORSIA PHARMACEUTICALS LTD, Allschwil (CH)

(72) Inventors: Christoph Boss, Allschwil (CH); Christine Brotschi, Allschwil (CH); Markus Gude, Allschwil (CH); Bibia Heidmann, Allschwil (CH); Thierry Sifferlen, Allschwil (CH); Jodi Williams, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 9 days.

(21) Appl. No.: 14/405,649

(22) PCT Filed: Jun. 3, 2013

(86) PCT No.: PCT/IB2013/054567
§ 371 (c)(1),
(2) Date: Dec. 4, 2014

(87) PCT Pub. No.: WO2013/182972
PCT Pub. Date: Dec. 12, 2013

(65) Prior Publication Data
US 2015/0166527 A1 Jun. 18, 2015

(30) Foreign Application Priority Data

Jun. 4, 2012 (EP) .................................... 12170748
Mar. 11, 2013 (EP) .................................... 13158520

(51) Int. Cl.
C07D 403/14 (2006.01)
C07D 417/14 (2006.01)
C07D 401/14 (2006.01)
C07D 403/04 (2006.01)

(52) U.S. Cl.
CPC ......... C07D 417/14 (2013.01); C07D 401/14 (2013.01); C07D 403/04 (2013.01); C07D 403/14 (2013.01)

(58) Field of Classification Search
CPC ................................................... C07D 403/14
See application file for complete search history.

(56) References Cited

U.S. PATENT DOCUMENTS

| | | | |
|---|---|---|---|
| 3,282,927 A | 11/1966 | Montzka | |
| 7,763,638 B2 | 7/2010 | Aissaoui et al. | |
| 7,994,336 B2 | 8/2011 | Aissaoui et al. | |
| 8,063,099 B2 | 11/2011 | Aissaoui et al. | |
| 8,106,215 B2 | 1/2012 | Aissaoui et al. | |
| 8,236,801 B2 | 8/2012 | Aissaoui et al. | |
| 8,236,964 B2 | 8/2012 | Aissaoui et al. | |
| 8,288,411 B2 | 10/2012 | Aissaoui et al. | |
| 8,288,429 B2 | 10/2012 | Aissaoui et al. | |
| 8,288,435 B2 | 10/2012 | Aissaoui et al. | |
| 8,895,606 B2 | 11/2014 | Boss et al. | |
| 9,000,029 B2 | 4/2015 | Boss et al. | |
| 2003/0055037 A1 | 3/2003 | DeLombaert et al. | |
| 2009/0082394 A1 | 3/2009 | Jenck et al. | |
| 2010/0016401 A1 | 1/2010 | Aissaoui et al. | |
| 2010/0222328 A1 | 9/2010 | Aissaoui et al. | |
| 2010/0234420 A1 | 9/2010 | Jenck | |
| 2011/0105491 A1 | 5/2011 | Aissaoui et al. | |
| 2013/0150424 A1 | 6/2013 | Boss et al. | |
| 2013/0237525 A1 | 9/2013 | Aissaoui et al. | |
| 2013/0324579 A1 | 12/2013 | Bolli et al. | |
| 2015/0252032 A1 | 9/2015 | Bolli et al. | |
| 2016/0024064 A1 | 1/2016 | Bolli et al. | |

FOREIGN PATENT DOCUMENTS

| | | |
|---|---|---|
| WO | WO 01/96302 A1 | 12/2001 |
| WO | WO 02/44172 A1 | 6/2002 |
| WO | WO 02/089800 A2 | 11/2002 |
| WO | WO 02/090355 A1 | 11/2002 |
| WO | WO 03/002559 A2 | 1/2003 |
| WO | WO 03/002561 A1 | 1/2003 |
| WO | WO 03/032991 A1 | 4/2003 |
| WO | WO 03/041711 A1 | 5/2003 |
| WO | WO 03/051368 A1 | 6/2003 |
| WO | WO 03/051873 A1 | 6/2003 |

(Continued)

OTHER PUBLICATIONS

Chemical Abstracts Registry No. 950165-87-4, indexed in the Registry file on STN CAS Online Oct. 11, 2007.*
Adam, T.C. et al., "Stress, Eating, and the Reward System", Physiology & Behavior (2007), vol. 91, pp. 449-458.
Aston-Jones, G., et al., "Lateral Hypothalamic Orexin/Hypocretin Neurons: A Role in Reward-Seeking and Addiction", Brain Research, (2009), doi:10.1016/j.brainres.2009.09.106 (Uncorrected Proof).
Berridge, C.W., et al., "Hypocretin/Orexin in Arousal and Stress", Brain Research, (2009), doi:10.1016/j.brainres.2009.09.019 (Accepted Manuscript).

(Continued)

Primary Examiner — Laura L. Stockton
(74) Attorney, Agent, or Firm — Hoxie & Associates LLC

(57) ABSTRACT

The present invention relates to compounds of the formula (I)

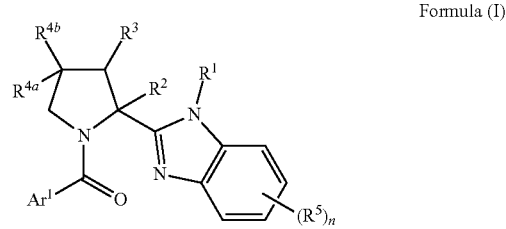

Formula (I)

wherein $Ar^1$, $R^1$, $R^2$, $R^3$, $R^{4a}$, $R^{4b}$ and $(R^5)_n$ are as described in the description, to their preparation, to pharmaceutically acceptable salts thereof, and to their use as pharmaceuticals, to pharmaceutical compositions containing one or more compounds of formula (I), and especially to their use as orexin receptor antagonists.

12 Claims, No Drawings

(56) References Cited

FOREIGN PATENT DOCUMENTS

| | | |
|---|---|---|
| WO | WO 2004/026866 A1 | 4/2004 |
| WO | WO 2004/041791 A1 | 5/2004 |
| WO | WO 2004/041807 A1 | 5/2004 |
| WO | WO 2004/041816 A1 | 5/2004 |
| WO | WO 2005/118548 | 12/2005 |
| WO | WO 2007/105177 A1 | 9/2007 |
| WO | WO 2008/020405 A2 | 2/2008 |
| WO | WO 2008/038251 A2 | 4/2008 |
| WO | WO 2008/069997 A1 | 6/2008 |
| WO | WO 2008/081399 A2 | 7/2008 |
| WO | WO 2008/087611 A2 | 7/2008 |
| WO | WO 2008/117241 A2 | 10/2008 |
| WO | WO 2008/139416 A1 | 11/2008 |
| WO | WO 2008/150364 A1 | 12/2008 |
| WO | WO 2009/003993 A1 | 1/2009 |
| WO | WO 2009/003997 A1 | 1/2009 |
| WO | WO 2009/004584 A1 | 1/2009 |
| WO | WO 2009/016560 A2 | 2/2009 |
| WO | WO 2009/016564 A2 | 2/2009 |
| WO | WO 2009/040730 A2 | 4/2009 |
| WO | WO 2009/047723 | 4/2009 |
| WO | WO 2009/104155 A1 | 8/2009 |
| WO | WO 2009/124956 A1 | 10/2009 |
| WO | WO 2010/004507 A1 | 1/2010 |
| WO | WO 2010/038200 A1 | 4/2010 |
| WO | WO 2010/060470 A1 | 6/2010 |
| WO | WO 2010/060471 A1 | 6/2010 |
| WO | WO 2010/060472 A1 | 6/2010 |
| WO | WO 2010/063662 A1 | 6/2010 |
| WO | WO 2010/063663 A1 | 6/2010 |
| WO | WO 2010/072722 A1 | 7/2010 |
| WO | WO 2010/122151 A1 | 10/2010 |
| WO | WO 2012/025877 | 3/2012 |
| WO | WO 2012/063207 | 5/2012 |
| WO | WO 2012/110986 | 8/2012 |
| WO | WO 2013/068935 A1 | 5/2013 |
| WO | WO 2015/083070 | 6/2015 |
| WO | WO 2015/083071 | 6/2015 |
| WO | WO 2015/083094 | 6/2015 |

OTHER PUBLICATIONS

Borgland, S.L., et al., "Orexin A in the VTA is Critical for the Induction of Synaptic Plasticity and Behavioral Sensitization to Cocaine", Neuron. (Feb. 16, 2006), vol. 49, pp. 589-601.

Boss, C, et al., "Biomedical Application of Orexin/Hypocretin Receptor Ligands in Neuroscience", Journal of Medicinal Chemistry, (2009), vol. 52, No. 4, pp. 891-903, (Published on Web).

Boutrel, B., et al., "Role for Hypocretin in Mediating Stress-Induced Reinstatement of Cocaine-Seeking Behavior", Proc. Natl. Acad. Sci. (2005), vol. 102, No. 52, pp. 19168-19173.

Carter, M.E., et al., "The Brain Hypocretins and their Receptors: Mediators of Allostatic Arousal", Curr. Op. Pharmacol. (2009), vol. 9, pp. 1-7 (doi:10.1016/j.coph.2008.12.018.

Chemelli, R.M. et al., "Narcolepsy in Orexin Knockout Mice: Molecular Genetics of Sleep Regulation", Cell, (Aug. 20, 1999), vol. 98, pp. 437-451.

Chrousos, G.P., et al., "The Concepts of Stress and Stress System Disorders", JAMA (1992), vol. 267, No. 9, 1244-1252.

Dietrich, H., et al., "Intact Learning and Memory in Rats Following Treatment with the Dual Orexin Receptor Antagonist Almorexant", Psychopharmacology (2010), vol. 212, pp. 145-154.

Fendt, M. et al., "The Neuroanatomical and Neurochemical Basis of Conditioned Fear", Neuroscience Biobehavioral Reviews, (1999), vol. 23, pp. 743-760.

Feng, P. et al., "Changes in Brian Orexin Levels in a Rat Model of Depression Induced by Neonatal Administration of Clomipramine", J. Psychopharmacol., (Feb. 28, 2008), doi:10.1177/ 0269881107082899.

Foulds Mathes, W., et al., "The Biology of Binge Eating", Appetite (2009), vol. 52, 545-553.

Furlong, T. M. et al., "Hypocretin/Orexin Contributes to the Expression of Some but not All Forms of Stress and Arousal", European Journal of Neuroscience, (2009), pp. 1-12, doi:10.1111/j.1460-9568. 2009.06952.x.

Gould, P.L., "Salt Selection for Basic Drugs", Int. J. Pharm. (1986), vol. 33, pp. 201-217.

Gozzi, A. et al., "Functional Magnetic Resonance Imaging Reveals Different Neural Substrates for the Effects of Orexin-1 and Orexin-2 Receptor Antagonists", PLoS One (2011), vol. 6, Issue 1, e16406.

Hamamoto, H., et al., "Chemoenzymatic Synthesis of the C-13 side chain of Paclitaxel (Taxol) and Docetaxel (Taxotere)", Tetrahedron: Asymmetry (2000), vol. 11, pp. 4485-4497.

Hollander, J.A. et al., "Insular Hypocretin Transmission Regulates Nicotine Reward", Proc. Natl. Acad. Sci. (2008), vol. 105, No. 49, pp. 19479-19484.

Hutcheson, D.M. et al., "Orexin-1 Receptor Antagonist SB-334867 Reduces the Acquisition and Expression of Cocaine-Conditioned Reinforcement and the Expression of Ampehetamine-Conditioned Reward", Behav. Pharmacol. (2011), (Original Article), vol. 22(2), 173-181.

Jenck, F., et al., "Promotion of Sleep by Targeting the Orexin System in Rats, Dogs and Humans" Nature Medicine, (2007), (Advance Online Publication), pp. 1-6, doi:10.1038/nm1544.

Kang, J., et al, "Amyloid-β Dynamics are Regulated by Orexin and the Sleep-Wake Cycle", Sciencexpress (2009), doi:10.1126/science. 1180962.

Kayaba, Y., et al., "Attenuated Defense Response and Low Basal Blood Pressure in Orexin Knockout Mice", Am. J. Physiol. Regul. Integr. Comp. Physiol., vol. 285, (2003), pp. R581-R593.

Koob, G.F. et al., "Neurobiological Mechanisms of Addiction: Focus on Corticotropin-Releasing Factor", Curr. Opin. Investig. Drugs (2010), vol. 11, No. 1, pp. 63-71.

Lesage, M.G. et al., "Nicotine Self-Administration in the Rat: Effects of Hypocretin Antagonists and Changes in Hypocretin mRNA", Psychopharmacology (2010), vol. 209, pp. 203-212.

Langmead, C.J., et al., "Characterisation of the Binding of [$^3$H]-SB-674042, a Novel Nonpeptide Antagonist, to the Human Orexin-1 Receptor", Brit. J. Pharmacol.(2004), vol. 141, pp. 340-346.

Lawrence, A.J. et al., "The Orexin System Regulates Alcohol-Seeking in Rats", Brit. J. Pharmacol. (2006), vol. 148(6), 752-759.

Liu, X., et al., "Insomnia and Hypersomnia Associated with Depressive Phenomenology and Comorbidity in Childhood Depression", Sleep (2007), vol. 30, No. 1, pp. 83-90.

Majzoub, J.A. et al., "Corticotropin-Releasing Hormone Physiology", European Journal of Endocrinology, (2006), vol. 155, S71-S76.

Nollet, M., et al., "Activation of Orexin Neurons in Dorsomedial/ Perifornical Hypothalamus and Antidepressant Reversal in a Rodent Model of Depression ", Neuropharmacology, (2011), doi :10.1016/ j.neuropharm.2011.04.022, pp. 1-11.

Prud'Homme, M.J. et al., "Nutritional Status Modulates Behavioural and Olfactory Bulb Fos Responses to Isoamyl Acetate or Food Odour in Rats : Roles of Orexins and Leptin", Neuroscience, (2009), vol. 162, pp. 1287-1298.

Quarta, D. et al., "The Orexin-1 Receptor Antagonist SB-334867 Reduces Amphetamine-Evoked Dopamine Outflow in the Shell of the Nucleus Accumbens and Decreases the Expression of Amphetamine Sensitization", Neurochemistry International, (2010), doi :10.1016/j.neuint.2009.08.012.

Remington, The Science and Practice of Pharmacy, 21st Edition (2005), Part 5, Pharmaceutical Manufacturing, (book cover and table of contents).

Sakurai, T. et al., Orexins and Orexin Receptors : A Family of Hypothalamic Neuropeptides and G Protein-Coupled Receptors that Regulate Feeding Behavior, Cell, (Feb. 20, 1998), vol. 92, pp. 573-585.

Salomon, R.M. et al., "Diurnal Variation of Cerebospinal Fluid Hypocretin-1 (Orexin A) Levels in Control and Depressed Subjects", Biol. Psychiatry, (2003), vol. 54, pp. 96-104.

Sharf, R. et al., "Role of Orexin/Hypocretin in Dependence and Addiction", Brain Res. (2010), vol. 1314, pp. 130-138.

(56) References Cited

OTHER PUBLICATIONS

Shippenberg, T.S. and Koob, G.F., Neuropsychopharmacology: The Fifth Generation of Progress, (2002); Chapter 97, pp. 1381-1397.
Smith, R.J. et al., "Orexin/Hypocretin Signaling at the $OX_1$ Receptor Regulates Cue-elicited Cocaine-Seeking", Eur. J. Neurosci. (2009), vol. 30, No. 3, pp. 493-503, (author manuscript).
Smith, R.J. et al., "Orexin/Hypocretin is Necessary for Context-driven Cocaine-seeking", Neuropharmacology, (2010), (Uncorrected Proof), pp. 1-6, doi:10.1016/j.neuropharm.2009.06.042.
Spealman, R.D., et al, "Pharmacological and Environmental Determinants of Relapse to Cocaine-Seeking Behavior", Pharmacol. Biochem. Behav., (1999), vol. 64, 327-336.
Stahl, P.H., et al. Handbook of Pharmaceutical Salts. Properties, Selection and Use., (title page, appendix, and pp. 330-350, (2008), ISBN-10 3-906390-58-6, ISBN-13 978-3-906390-58-1, Verlag Helvetica Chimica Acta, Zurich, Switzerland.
Stickgold, R., et al., "Sleep-dependent Memory Consolidation", Nature, (2005), vol. 437, pp. 1272-1278.
Sutcliffe, J.G. et al., "The Hypocretins : Setting the Arousal Threshold", Nat. Rev. Neurosci., (May 2002), vol. 3, pp. 339-349.
Tsujino, N. and Sakurai T., "Orexin/Hypocretin : A Neuropeptide at the Interface of Sleep, Energy Homeostasis, and Reward System", Pharmacol. Rev. (2009), vol. 61, No. 2, pp. 162-176.
Vanderschuren L.J.M.J. et al., "Sensitization Process in Drug Addiction", Current Topics in Behavioral Neurosciences, vol. 3 (2009), pp. 179-195.
Vinkers, C.H., et al., "Translational Aspects of Pharmacological Research into Anxiety Disorders : The Stress-Induced Hyperthermia (SIH) Paradigm", European J. Pharmacol., (2008), vol. 585, pp. 407-425.
Winrow, C.J., et al., "Orexin Receptor Antagonism Prevents Transcriptional and Behavioural Plasticity Resulting from Stimulant Exposure", Neuropharmacology, (2009), doi :10.1016/4. neuropharm.2009.07.008, (Uncorrected Proof).
Wouters, J. and Quéré, L, "Pharmaceutical Salts and Co-crystals", (2012), (title page and table of contents).
Zhang, W et al., "Multiple Components of the Defense Response Depend on Orexin : Evidence from Orexin Knockout Mice and Orexin Neuron-Ablated Mice", Autonomic Neuroscience : Basic and Clinical, (2006), pp. 126-127, 139-145.
U.S. Appl. No. 14/357,159, filed May 8, 2014, Bolli et al.
U.S. Appl. No. 14/434,997, filed Apr. 10, 2015, Bolli et al.
U.S. Appl. No. 14/639,934, filed Mar. 5, 2015, Boss et al.
Adam, T.C. et al., "Stress, Eating, and the Reward System", Physiology & Behavior (2007). vol. 91, pp. 449-458.
Aston-Jones, G., et al., "Lateral Hypothalamic Orexin/Hypocretin Neurons : A Role in Reward-Seeking and Addiction", Brain Research, (2009), doi : 10.1016/j.brainres.2009.09.106 (Uncorrected Proof).
Berridge, C.W., et al., "Hypocretin/Orexin in Arousal and Stress", Brain Research, (2009), doi : 10.1016/j.brainres.2009.09.019 (Accepted Manuscript).
Boss, C, et al., "Biomedical Application of Orexin/Hypocretin Receptor Ligands in Neuroscience", Journal of Medicinal Chemistry, (2009), vol. 52, No. 4, pp. 891-903 (Article indicates "published on Web Jan. 20, 2009"—contents not verified by undersigned).
Boutrel, B., et al., "Role for Hyprocretin in Mediating Stress-Induced Reinstatement of Cocaine-Seeking Behavior", Proc. Natl. Acad. Sci. (2005), vol. 102, No. 52, pp. 19168-19173.
Carter, M.E., et al., "The Brain Hypocretins and their Receptors: Mediators of Allostatic Arousal", Curr. Op. Pharmacol. (2009), doi: 10.1016/j.coph.2008.12.018.
Dietrich, H., et al., "Intact Learning and Memory in Rats Following Treatment with the Dual Orexin Receptor Antagonist Almorexant", Psychopharmacology (2010), vol. 212, pp. 145-154 (Article indicates "published online Jul. 15, 2010"—contents not verified by undersigned).
Fendt, M. et al., "The Neuroanatomical and Neurochemical Basis of Conditioned Fear", Neurosciences Biobehavioral Reviews, (1999), vol. 23, pp. 743-760.

Feng, P. et al., "Changes in Brain Orexin Levels in a Rat Model of Depression Induced by Neonatal Administration of Clomipramine", J. Psychopharmacol., (Feb. 28, 2008), doi: 10.1177/ 0269881107082899.
Foulds Mathes, W., et al, "The Biology of Binge Eating", Appetite (2009), vol. 52, 545-553.
Furlong, T.M. et al., "Hypocretin/Orexin Contributes to the Expression of Some but not All Forms of Stress and Arousal", European Journal of Neuroscience, (2009), pp. 1-12, doi: 10.111/j.1460-9568. 2009.06952.x.
Jenck, F., et al., "Promotion of Sleep by Targeting the Orexin System in Rats, Dogs and Humans" Nature Medicine, (2007), (Advance Online Publication), pp. 1-6, doi: 10,1038/nm1544.
Kang, J., et al, "Amyloid-B Dynamics are Regulated by Orexin and the Sleep-Wake Cycle", Sciencexpress (2009), doi: 10.1126/science.1180962.
Langmead, C.J., et al., "Characterisation of the Binding of [$^3$H]-SB-674042, a Novel Nonpeptide Antagonist, to the Human Orexin-1 Receptor", Brit. J. Pharmacol. (2004), vol. 141, pp. 340-346 (Article indicates published on Web Dec. 22, 2003—contents not verified by undersigned).
Nollet, M., et al., "Activation of Orexin Neurons in Dorsomedial/ Perifornical Hypothalamus and Antidepressant Reversal in a Rodent Model of Depression", Neuropharmacology, (2011), doi:10.1016/j. neuropharm.2011.04.022, pp. 1-11.
Prud'Homme, M.J. et al., "Nutritional Status Modulates Behavioural and Olfactory Bulb Fos Responses to Isoamyl Acetate or Food Odour in Rats: Roles of Orexins and Leptin", Neuroscience, (2009), vol. 162, pp. 1287-1298.
Quarta, D. et al., "The Orexin-1 Receptor Antagonist SB0334867 Reduces Amphetamine-Evoked Dopamine Outflow in the Shell of the Nucleus Accumbens and Decreases the Expression of Amphetamine Sensitization", Neurochemistry International (2009), doi: 10.1016/j.neuint.2009.08.012.
Remington, The Science and Practice of Pharmacy, 21$^{st}$ Edition (2005), Part 5, "Pharmaceutical Manufacturing", (book cover and table of contents).
Sakurai, T. et al., Orexins and Orexin Receptors: A Family of Hypothalamic Neuropeptides and G Protein-Coupled Receptors that Regulate Feeding Behavior, Cell, (Feb. 20, 1998), vol. 92, pp. 573-585.
Salomon, R.M. et al., "Dirunal Variation of Cerebospinal Fluid Hypocretin-1 (Orexin A) Levels in Control and Depressed Subjects", Biol. Phychiatry, (2003), vol. 54, pp. 96-104.
Sharf, R. et al., "Role of Orexin/Hypocretin in Dependence and Addiction", Brain Res. (2010), vol. 1314, pp. 130-138 (Article indicates "Available online Aug. 20, 2009"—contents not verified by undersigned).
Shippenberg, T.S. and Koob, G.F., Neuropsychopharmacology: The Fifth Generation of Progress, (2002); Chapter 97, pp. 1381-1397.
Smith, R.J. et al., "Orexin/Hypocretin Signaling at the OX1 Receptor Regulates Cue-elicited Cocaine-Seeking", Eur. J. Neurosci. (2009), vol. 30, No. 3, pp. 493-503, (author manuscript).
Smith, R.J. et al., "Orexin/Hypocretin is Necessary for Context-driven Cocaine-seeking", Neuropharmacology, (2009), (Uncorrected Proof), pp. 1-6, doi: 10.1016/j.neuropharm.2009.06.042.
Stahl, P.H., et al. Handbook of Pharmaceutical Salts, Properties, Selection and Use, (title page, appendix and pp. 330-350, (2008), ISBN-10 3-906390-58-6, ISBN-13 978-3-906390-58-1, Verlag Helvetica Chimica Acta, Zurich, Switzerland.
Stickgold, R., et al., "Sleep-dependent Memory Consolidation". Nature, (2005), vol. 437, pp. 1272-1278.
Sutcliffe, J.G. et al., "The Hypocretins: Setting the Arousal Threshold". Nat. Rev. Neurosci. (May 2002), vol. 3, pp. 339-349.
Tsujino, N. and Sakurai T., "Orexin/Hypocretin: A Neuropeptide at the Interface of Sleep, Energy Homeostasis, and Reward System", Pharmacol. Rev. (2009), vol. 61, No. 2, pp. 162-176.
Vanderschuren L.J.M.J. et al., "Sensitization Process in Drug Addiction", Current Topics in Behavioral Neurosciences, vol. 3 (2009), pp. 179-195 (Article indicates "published online Sep. 3, 2009"—contents not verified by undersigned).

(56) References Cited

OTHER PUBLICATIONS

Vinkers, C.H., et al., "Translational Aspects of Pharmacological Research into Anxiety Disorders: The Stress-Induced Hyperthermia (SIH) Paradigm", European J. Pharmacol., (2008), vol. 585, pp. 407-425 (Article indicates "Available online Mar. 18, 2008"—contents not verified by undersigned).

Winrow, C.J., et al., "Orexin Receptor Antagonism Prevents Transcriptional and Behavioural Plasticity Resulting from Stimulant Exposure", Neuropharmacology, (2009), doi: 10.1016/4.neuropharm.2009.07.008, (Uncorrected Proof).

Wouters, J. and Quere, L. "Pharmaceutical Salts and Co-Crystals", (2012), (title page and table of contents).

Zhang, W et al., "Multiple Components of the Defense Response Depend on Orexin: Evidence from Orexin Knockout Mice and Orexin Neuron-Ablated Mice", Autonomic Neuroscience: Basic and Clinical, (2006), pp. 126-127, 139-145.

International Search Report of International Application No. PCT/IB2013/054567 mailed Sep. 26, 2013, 4 pages.

\* cited by examiner

BENZIMIDAZOLE-PROLINE DERIVATIVES

CROSS REFERENCE TO RELATED APPLICATIONS

This application is a United States Application under 35 U.S.C. 371 claiming benefit of PCT Application Ser. No. PCT/IB2013/054567, filed on Jun. 3, 2013, which claims the benefit of European Patent Application 13158520.0, filed on Mar. 11, 2013, and European Patent Application 12170748.3, filed on Jun. 4, 2012.

The present invention relates to novel benzimidazole-proline derivatives of formula (I) and their use as pharmaceuticals. The invention also concerns related aspects including processes for the preparation of the compounds, pharmaceutical compositions containing one or more compounds of formula (I), and their use as orexin receptor antagonists, especially as orexin-1 receptor antagonists.

Orexins (orexin A or OX-A and orexin B or OX-B) are neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexin receptor antagonists are a novel type of nervous system or psychotropic drugs. Their mode of action in animals and humans involves either blockade of both orexin-1 and orexin-2 receptor (dual antagonists), or individual and selective blockade of either the orexin-1 or the orexin-2 receptor (selective antagonists) in the brain. Orexins were initially found to stimulate food consumption in rats suggesting a physiological role for these peptides as mediators in the central feedback mechanism that regulates feeding behaviour (Sakurai T. et al., Cell, 1998, 92, 573-585).

On the other hand, orexin neuropeptides and orexin receptors play an essential and central role in regulating circadian vigilance states. In the brain, orexin neurons collect sensory input about internal and external states and send short intrahypothalamic axonal projections as well as long projections to many other brain regions. The particular distribution of orexin fibers and receptors in basal forebrain, limbic structures and brainstem regions—areas related to the regulation of waking, sleep and emotional reactivity—suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter M E et al., "The brain hypocretins and their receptors: mediators of allostatic arousal.", Curr Op Pharmacol. 2009, 9: 39-45] that are described in the following sections. It was also observed that orexins regulate states of sleep and wakefulness opening potentially novel therapeutic approaches to insomnia and other sleep disorders (Chemelli R. M. et al., Cell, 1999, 98, 437-451).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declarative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

In addition, both anatomical and functional evidence from in vitro and in vivo studies suggest an important positive interaction of the endogenous orexin system with reward pathways of the brain [Aston-Jones G et al., Brain Res 2010, 1314, 74-90; Sharf R et al., Brain Res 2010, 1314, 130-138]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. Orexin-1 receptor antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397].

Several converging lines of evidence furthermore demonstrate a direct role of the orexin system as modulator of the acute stress response. For instance, stress (i.e. psychological stress or physical stress) is associated with increased arousal and vigilance which in turn is controlled by orexins [Sutcliffe, J G et al., Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., JAMA 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

As outlined above the orexin system regulates homeostatic functions such as sleep-wake cycle, energy balance, emotions and reward. Orexins are also involved in mediating the acute behavioral and autonomous nervous system response to stress [Zhang W et al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., NeuroPharm 2011, 61(1-2):336-46].

The orexin system is also involved in stress-related appetitive/reward seeking behaviour (Berridge C W et al., Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Orexins have been found to increase food intake and appetite [Tsujino, N, Sakurai, T, Pharmacol Rev 2009, 61(2) 162-176]. As an additional environmental factor, stress can contribute to binge eating behaviour, and lead to obesity [Adam, T C et al. Physiol Behav 2007, 91(4) 449-458]. Animal models that are clinically relevant models of binge eating in humans are described for example in W. Foulds Mathes et al.; Appetite 2009, 52, 545-553.

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L., Curr Op Pharmacol. 2009, 9: 39-45; C Boss, C Brisbare-Roch, F Jenck, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155]. The compound further attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/047723) which relates to emotional states of fear and anxiety diseases such as anxieties including phobias and post traumatic stress disorders (PTSDs). In addition, intact declarative and non-declarative learning and memory has been demonstrated in rats treated with this compound [WO2007/105177, H Dietrich, F Jenck, Psychopharmacology 2010, 212, 145-154]. Said compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound has also been shown to induce antidepressant-like activity in a mouse model of depression, when administered chronically [Nollet et al., NeuroPharm 2011, 61(1-2):336-46]. Moreover, the compound has been shown to attenuate the natural activation induced by orexin A in fasted hungry rats exposed to food odors [M J Prud'homme et al., Neuroscience 2009, 162(4), 1287-1298]. The compound also displayed pharmacological activity in a rat model of nicotine self-administration [LeSage M G et al., Psychopharmacology 2010, 209(2), 203-212]. Another dual orexin receptor antagonist, N-biphenyl-2-yl-1-{[(1-methyl-1H-benzimidazol-2-yl)sulfanyl]acetyl}-L-prolinamide inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

Orexin receptor antagonists comprising a 2-substituted saturated cyclic amide derivatives (such as 2-substituted pyrrolidine-1-carboxamides) are known for example from WO2008/020405, WO2008/038251, WO2008/081399, WO2008/087611, WO2008/117241, WO2008/139416, WO2009/004584, WO2009/016560, WO2009/016564, WO2009/040730, WO2009/104155, WO2010/004507, WO2010/038200, WO2001/096302, WO2002/044172, WO2002/089800, WO2002/090355, WO2003/002559, WO2003/032991, WO2003/041711, WO2003/051368, WO2003/051873, WO2004/026866, WO2004/041791, WO2004/041807, WO2004/041816, WO2009/003993, WO2009/003997, WO2009/124956, WO2010/060470, WO2010/060471, WO2010/060472, WO2010/063662, WO2010/063663, WO2010/072722, WO2010/122151, and WO2008/150364. A particular pyrrolidine derived compound is disclosed in Langmead et. al, Brit. J. Pharmacol. 2004, 141, 340-346 as being highly orexin-1 selective. WO2003/002561 discloses certain N-aroyl cyclic amine derivatives, encompassing benzimidazol-2-yl-methyl substituted pyrrolidine derivatives, as orexin receptor antagonists. Despite the great number of prior art compounds and their high structural variability, all compounds share a common structural feature, i.e. in position 2 of the saturated cyclic amide a linker group such as at least a methylene group (or longer groups such as —CH$_2$—NH—CO—, —CH$_2$—NH—, —CH$_2$—O—, —CH$_2$—S—, etc.) link the cyclic amide to the respective aromatic ring system substituent. It has now surprisingly been found that, despite the substantial conformational changes that may be expected from the removal of a linker between two rigid structural elements, the present compounds, that have a benzimidazole ring directly attached to a pyrrolidine amide in position 2, are potent orexin receptor antagonists.

The present invention, thus, provides novel benzimidazole-proline derivatives, which are non-peptide antagonists of human orexin receptors. These compounds are in particular of potential use in the treatment of disorders relating to orexinergic dysfunctions, comprising especially sleep disorders, anxiety disorders, addiction disorders, cognitive dysfunctions, mood disorders, or appetite disorders.

1) A first aspect of the invention relates to compounds of the formula (I)

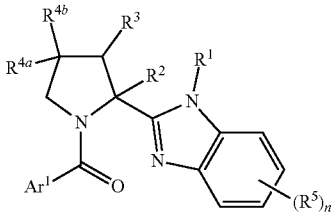

Formula (I)

wherein
Ar$^1$ represents
phenyl or 5- or 6-membered heteroaryl, wherein said phenyl or 5- or 6-membered heteroaryl independently is mono-, di-, or tri-substituted; wherein one of said substituents is attached in ortho-position to the point of attachment of Ar$^1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from (C$_{1-4}$)alkyl, (C$_{1-4}$)alkoxy, halogen, cyano, (C$_{1-3}$)fluoroalkyl, and (C$_{1-3}$)fluoroalkoxy; or said ortho substituent is benzo[1,3]dioxolyl, or 2-(3-methoxy-phenyl)-ethynyl;
and the other of said substituents, if present, is/are independently selected from (C$_{1-4}$)alkyl; (C$_{1-4}$)alkoxy; (C$_{3-6}$)cycloalkyl; halogen; cyano; (C$_{1-3}$)fluoroalkyl; (C$_{1-3}$)fluoroalkoxy; —NR$^{10}$R$^{11}$, wherein R$^{10}$ and R$^{11}$ independently represent hydrogen or (C$_{1-4}$)alkyl, or R$^{10}$ and R$^{11}$ together with the nitrogen to which they are attached to form a pyrrolidine ring; unsubstituted pyridinyl; and phenyl which is unsubstituted, or mono- or di-substituted, wherein the substituents are independently selected from (C$_{1-4}$)alkyl, (C$_{1-4}$)alkoxy, cyano, and halogen;
one of R$^2$ and R$^3$ represents hydrogen, and the other represents hydrogen or (C$_{1-4}$)alkyl (notably one of R$^2$ and R$^3$ represents hydrogen, and the other represents hydrogen or methyl); and
one of R$^{4a}$ and R$^{4b}$ represents hydrogen, and the other represents hydrogen, (C$_{1-4}$)alkoxy (especially methoxy), or halogen (especially fluorine); or R$^{4a}$ and R$^{4b}$ together represent a group H$_2$C=; or both R$^{4a}$ and R$^{4b}$ represent fluorine; wherein, in case R$^3$ is different from hydrogen, both R$^{4a}$ and R$^{4b}$ represent hydrogen;
R$^1$ represents hydrogen, (C$_{1-4}$)alkyl (especially methyl or ethyl), (C$_{3-6}$)cycloalkyl-(CH$_2$)— (especially cyclopropyl-methyl), (C$_{2-3}$)fluoroalkyl (especially 2-fluoro-ethyl), or (C$_{1-4}$)alkoxy-(C$_{2-4}$)alkyl (especially 2-methoxy-ethyl); and
(R$^5$)$_n$ represents one to three optional substituents (i.e. n represents the integer 0, 1, 2, or 3) independently selected from (C$_{1-4}$)alkyl, (C$_{1-4}$)alkoxy (especially methoxy), halogen, (C$_{1-4}$)alkyl-thio- (especially H$_3$C—S—), (C$_{1-3}$)fluoroalkyl (especially trifluoromethyl), (C$_{1-3}$)fluoroalkoxy (especially trifluoromethoxy), (C$_{1-3}$)fluoroalkyl-thio- (especially F$_3$C—S—), hydroxy-(C$_{1-4}$)alkyl- (especially HO—CH$_2$—), (C$_{1-4}$)alkoxy-carbonyl- (especially H$_3$CO—CO—), nitro, hydroxy, and cyano; or (R$^5$)$_n$ represents a group —O—CH$_2$—CH$_2$—O—; or (R$^5$)$_n$ represents a fused phenyl group which, together with the benzimidazole moiety to which it is fused to, forms a 1H-naphtho[2,3-d]imidazol-2-yl group;
with the exception of
[2-(1H-benzimidazol-2-yl)-1-pyrrolidinyl][2-(1H-pyrazol-1-yl)phenyl]-methanone (CAS Reg. No. 1293846-63-5);
[2-(1H-benzimidazol-2-yl)-1-pyrrolidinyl][5-(2,5-dimethyl-1H-pyrrol-1-yl)-1-methyl-1H-pyrazol-4-yl]-methanone (CAS Reg. No. 1288543-08-7);
[2-(1H-benzimidazol-2-yl)-1-pyrrolidinyl][1,1'-biphenyl]-2-yl-methanone (CAS Reg. No. 1277849-61-2);
[2-(6-methyl-1H-benzimidazol-2-yl)-pyrrolidin-1-yl][3-phenyl-isoxazol-4-yl]-methanone (CAS Reg. No. 1413410-98-6);
[2-(1H-imidazol-2-yl)phenyl][2-(6-methyl-1H-benzimidazol-2-yl)-pyrrolidin-1-yl]-methanone (CAS Reg. No. 1378205-71-0);
[2-(6-methyl-1H-benzimidazol-2-yl)-pyrrolidin-1-yl][3-(thien-2-yl)-1H-pyrazol-4-yl]-methanone (CAS Reg. No. 1377970-45-0);

[2-(6-methyl-1H-benzimidazol-2-yl)-pyrrolidin-1-yl][3-phenyl-1H-pyrazol-4-yl]-methanone (CAS Reg. No. 1377872-25-7);

[2-(1H-benzimidazol-2-yl)-pyrrolidin-1-yl][3-cyclopropyl-1-phenyl-1H-pyrazol-5-yl]-methanone (CAS Reg. No. 1331048-98-5); and

[2-(1H-benzimidazol-2-yl)-pyrrolidin-1-yl][1-(2-fluorophenyl)-5-(1H-pyrrol-1-yl)-1H-pyrazol-4-yl]-methanone (CAS Reg. No. 1290361-06-6).

2) A second aspect of the invention relates to compounds of the formula (I) according to embodiment 1), which are also compounds of the formula (II); wherein the absolute configuration is as depicted in formula (II):

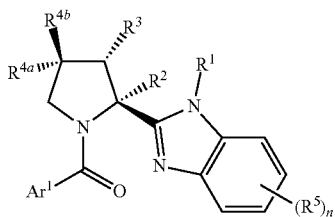

Formula (II)

wherein

Ar$^1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of Ar$^1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from $(C_{1-4})$alkyl, $(C_{1-4})$alkoxy, halogen, cyano, $(C_{1-3})$ fluoroalkyl, and $(C_{1-3})$fluoroalkoxy; or said ortho substituent is benzo[1,3]dioxolyl, or 2-(3-methoxyphenyl)-ethynyl;

and the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$fluoroalkoxy; —NR$^{10}$R$^{11}$, wherein R$^{10}$ and R$^{11}$ independently represent hydrogen or $(C_{1-4})$alkyl, or R$^{10}$ and R$^{11}$ together with the nitrogen to which they are attached to form a pyrrolidine ring; unsubstituted pyridinyl; and phenyl which is unsubstituted, or mono- or di-substituted, wherein the substituents are independently selected from $(C_{1-4})$alkyl, $(C_{1-4})$alkoxy, cyano, and halogen;

one of R$^2$ and R$^3$ represents hydrogen, and the other represents hydrogen or $(C_{1-4})$alkyl (notably one of R$^2$ and R$^3$ represents hydrogen, and the other represents hydrogen or methyl); and one of R$^{4a}$ and R$^{4b}$ represents hydrogen, and the other represents hydrogen, $(C_{1-4})$alkoxy (especially methoxy), or halogen (especially fluorine); or R$^{4a}$ and R$^{4b}$ together represent a group H$_2$C=; or both R$^{4a}$ and R$^{4b}$ represent fluorine; wherein, in case R$^3$ is different from hydrogen, both R$^{4a}$ and R$^{4b}$ represent hydrogen;

R$^1$ represents hydrogen, $(C_{1-4})$alkyl (especially methyl or ethyl), $(C_{3-6})$cycloalkyl-(CH$_2$)— (especially cyclopropylmethyl), $(C_{2-3})$fluoroalkyl (especially 2-fluoro-ethyl), or $(C_{1-4})$alkoxy-$(C_{2-4})$alkyl (especially 2-methoxy-ethyl); and (R$^5$)$_n$ represents one to three optional substituents (i.e. n represents the integer 0, 1, 2, or 3) independently selected from $(C_{1-4})$alkyl (especially methyl), $(C_{1-4})$alkoxy (especially methoxy), halogen (especially fluorine, chlorine or bromine), $(C_{1-4})$alkyl-thio- (especially H$_3$C—S—), $(C_{1-3})$fluoroalkyl (especially trifluoromethyl), $(C_{1-3})$fluoroalkoxy (especially trifluoromethoxy), $(C_{1-3})$fluoroalkyl-thio- (especially F$_3$C—S—), hydroxy-$(C_{1-4})$alkyl- (especially HO—CH$_2$—), $(C_{1-4})$alkoxy-carbonyl- (especially H$_3$CO—CO—), nitro, hydroxy, and cyano; or (R$^5$)$_n$ represents a group —O—CH$_2$—CH$_2$—O—; or (R$^5$)$_n$ represents a fused phenyl group which, together with the benzimidazole moiety to which it is fused to, forms a 1H-naphtho[2,3-d]imidazol-2-yl group;

with the exception of

[(S)-2-(1H-benzimidazol-2-yl)-1-pyrrolidinyl][2-(1H-pyrazol-1-yl)phenyl]-methanone;

[(S)-2-(1H-benzimidazol-2-yl)-1-pyrrolidinyl][5-(2,5-dimethyl-1H-pyrrol-1-yl)-1-methyl-1H-pyrazol-4-yl]-methanone;

[(S)-2-(1H-benzimidazol-2-yl)-1-pyrrolidinyl][1,1'-biphenyl]-2-yl-methanone;

[(S)-2-(6-methyl-1H-benzimidazol-2-yl)-pyrrolidin-1-yl][3-phenyl-isoxazol-4-yl]-methanone;

[(S)-2-(1H-imidazol-2-yl)phenyl][2-(6-methyl-1H-benzimidazol-2-yl)-pyrrolidin-1-yl]-methanone;

[(S)-2-(6-methyl-1H-benzimidazol-2-yl)-pyrrolidin-1-yl][3-(thien-2-yl)-1H-pyrazol-4-yl]-methanone;

[(S)-2-(6-methyl-1H-benzimidazol-2-yl)-pyrrolidin-1-yl][3-phenyl-1H-pyrazol-4-yl]-methanone;

[(S)-2-(1H-benzimidazol-2-yl)-pyrrolidin-1-yl][3-cyclopropyl-1-phenyl-1H-pyrazol-5-yl]-methanone; and

[(S)-2-(1H-benzimidazol-2-yl)-pyrrolidin-1-yl][1-(2-fluorophenyl)-5-(1H-pyrrol-1-yl)-1H-pyrazol-4-yl]-methanone.

3) A third aspect of the invention relates to compounds of the formula (II) according to embodiment 2), which are also compounds of the formula (III); wherein the absolute configuration is as depicted in formula (III):

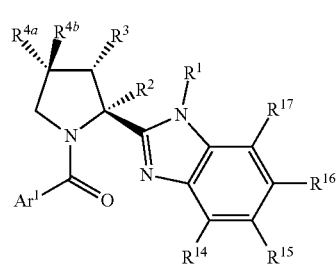

Formula (III)

wherein

Ar$^1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of Ar$^1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from $(C_{1-4})$alkyl, $(C_{1-4})$alkoxy, halogen, cyano, $(C_{1-3})$ fluoroalkyl, and $(C_{1-3})$fluoroalkoxy; or said ortho substituent is benzo[1,3]dioxolyl;

and the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$fluoroalkoxy; and —NR$^{10}$R$^{11}$, wherein R$^{10}$ and R$^{11}$ independently represent hydrogen or $(C_{1-4})$alkyl, or R$^{10}$ and R$^{11}$ together with the nitrogen to which they are attached to form a pyrrolidine ring;

one of R$^2$ and R$^3$ represents hydrogen, and the other represents hydrogen or $(C_{1-4})$alkyl (notably one of R$^2$ and R$^3$ represents hydrogen, and the other represents hydrogen or methyl); and R$^{4a}$ and R$^{4b}$ independently represent hydrogen or halogen (especially fluorine); or R$^{4a}$ represents $(C_{1-4})$alkoxy (especially methoxy) and R$^{4b}$ represents hydrogen; or R$^{4a}$ and R$^{4b}$ together represent a group H$_2$C=;

wherein, in case R$^3$ is different from hydrogen, both R$^{4a}$ and R$^{4b}$ represent hydrogen;

R$^1$ represents hydrogen, or $(C_{1-4})$alkyl (especially methyl or ethyl); and R$^{14}$, R$^{15}$, R$^{16}$ and R$^{17}$ together represent one to three optional substituents (i.e. at least one of R$^{14}$, R$^{15}$, R$^{16}$ and R$^{17}$ is hydrogen) [notably R$^{14}$, R$^{15}$, R$^{16}$ and R$^{17}$ together represent one to three substituents (i.e. at least one of R$^{14}$, R$^{15}$, R$^{16}$ and R$^{17}$ is hydrogen and at least one of R$^{14}$, R$^{15}$, R$^{16}$ and R$^{17}$ is different from hydrogen)], wherein R$^{14}$ and R$^{17}$ independently represent hydrogen, $(C_{1-4})$alkyl, $(C_{1-4})$alkoxy (especially methoxy), $(C_{1-4})$alkylthio- (especially H$_3$C—S—), halogen, $(C_{1-3})$fluoroalkyl (especially trifluoromethyl), $(C_{1-4})$alkoxycarbonyl- (especially H$_3$CO—CO—), hydroxy-$(C_{1-4})$alkyl-(especially HO—CH$_2$—), hydroxy, or nitro; and R$^{15}$ and R$^{16}$ independently represent hydrogen, $(C_{1-4})$alkyl, $(C_{1-4})$alkoxy (especially methoxy), $(C_{1-4})$alkylthio- (especially H$_3$C—S—), halogen, $(C_{1-3})$fluoroalkyl (especially trifluoromethyl), $(C_{1-3})$fluoroalkoxy (especially trifluoromethoxy), $(C_{1-3})$fluoroalkyl-thio- (especially F$_3$C—S—), hydroxy-$(C_{1-4})$alkyl- (especially HO—CH$_2$—), or cyano;

or R$^{14}$ and R$^{15}$ together, or R$^{16}$ and R$^{17}$ together, represent a group —O—CH$_2$—CH$_2$—O—;

or R$^{15}$ and R$^{16}$ together represent a fused phenyl group which, together with the benzimidazole moiety to which it is fused to, forms a 1H-naphtho[2,3-d]imidazol-2-yl group;

with the exception of

[(S)-2-(1H-benzimidazol-2-yl)-1-pyrrolidinyl][2-(1H-pyrazol-1-yl)phenyl]-methanone;

[(S)-2-(1H-benzimidazol-2-yl)-1-pyrrolidinyl][5-(2,5-dimethyl-1H-pyrrol-1-yl)-1-methyl-1H-pyrazol-4-yl]-methanone;

[(S)-2-(1H-benzimidazol-2-yl)-1-pyrrolidinyl][1,1'-biphenyl]-2-yl-methanone;

wherein, in a sub-embodiment, in addition to the above-listed three compounds also the following compounds are excluded from the scope of the compounds of embodiment 3):

[(S)-2-(6-methyl-1H-benzimidazol-2-yl)-pyrrolidin-1-yl][3-phenyl-isoxazol-4-yl]-methanone;

[(S)-2-(1H-imidazol-2-yl)phenyl][2-(6-methyl-1H-benzimidazol-2-yl)-pyrrolidin-1-yl]-methanone;

[(S)-2-(6-methyl-1H-benzimidazol-2-yl)-pyrrolidin-1-yl][3-(thien-2-yl)-1H-pyrazol-4-yl]-methanone;

[(S)-2-(6-methyl-1H-benzimidazol-2-yl)-pyrrolidin-1-yl][3-phenyl-1H-pyrazol-4-yl]-methanone;

[(S)-2-(1H-benzimidazol-2-yl)-pyrrolidin-1-yl][3-cyclopropyl-1-phenyl-1H-pyrazol-5-yl]-methanone; and

[(S)-2-(1H-benzimidazol-2-yl)-pyrrolidin-1-yl][1-(2-fluorophenyl)-5-(1H-pyrrol-1-yl)-1H-pyrazol-4-yl]-methanone.

The compounds of formula (I) contain at least one stereogenic center which is situated in position 2 of the pyrrolidine moiety. Preferably, the absolute configuration of the pyrrolidine moiety of the present compounds, especially the absolute configuration of said chiral center in position 2 of the pyrrolidine moiety, is as depicted in formula (II) and (III) of embodiments 2) or 3); i.e. for example for R$^2$ being the substituent of lowest priority (e.g. when R$^2$ is hydrogen or methyl), said chiral center is preferably in absolute (S) configuration. In addition, the compounds of formulae (I), (II), (III), and the compounds of formulae (IV), (V), and (VI) below, may contain one or more further stereogenic or asymmetric centers, such as one or more asymmetric carbon atoms. The compounds of formulae (I), (II), (III), (IV), (V), and (VI) may thus be present as mixtures of stereoisomers or preferably as pure stereoisomers. Mixtures of stereoisomers may be separated in a manner known to a person skilled in the art.

In addition, it is well understood that, in case the benzimidazole moiety of the present compounds is unsubstituted on the ring nitrogen having a free valency (i.e. R$^1$ represents hydrogen) such benzimidazole moiety represents tautomeric forms. Thus, substituents $(R^5)_n$ of the benzimidazole moiety may be attached in the position(s) ortho to the bridgehead atoms (i.e. attached in position(s) 4 and/or 7, corresponding to R$^{14}$ and/or R$^{17}$), and/or in the position(s) meta to the bridgehead atoms, (i.e. attached in position(s) 5 and/or 6, corresponding to R$^{15}$ and/or R$^{16}$). It is understood that the two ortho, and, respectively, the two meta positions are considered equivalent. For example, the group 4-methyl-1H-benzoimidazol-2-yl is understood to signify the same group as 7-methyl-1H-benzoimidazol-2-yl and 4-methyl-3H-benzoimidazol-2-yl and 7-methyl-3H-benzoimidazol-2-yl.

The present invention also includes isotopically labelled, especially $^2$H (deuterium) labelled compounds of formulae (I), (II), (III), (IV), (V), and (VI), which compounds are identical to the compounds of formulae (I), (II), (III), (IV), (V), and (VI) except that one or more atoms have each been replaced by an atom having the same atomic number but an atomic mass different from the atomic mass usually found in nature. Isotopically labelled, especially $^2$H (deuterium) labelled compounds of formulae (I), (II), (III), (IV), (V), and (VI) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formulae (I), (II), (III), (IV), (V), and (VI) are not isotopically labelled, or they are labelled only with one or more deuterium atoms. In a sub-embodiment, the compounds of formulae (I), (II), (III), (IV), (V), and (VI) are not isotopically labelled at all. Isotopically labelled compounds of formulae (I), (II), (III), (IV), (V), and (VI) be prepared in analogy to the methods described hereinafter, but using the appropriate isotopic variation of suitable reagents or starting materials.

In this patent application, a dotted line shows the point of attachment of the radical drawn. For example, the radical drawn below

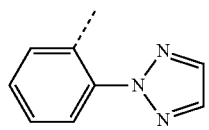

represents a 2-(2-triazolyl)-phenyl group.

Where the plural form is used for compounds, salts, pharmaceutical compositions, diseases and the like, this is intended to mean also a single compound, salt, or the like.

Any reference to compounds of formulae (I), (II), (III), (IV), (V), and (VI) according to any one of embodiments 1) to 57) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Salt selection for basic drugs", Int. J. Pharm. (1986), 33, 201-217; "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formulae (I), (II), (III), (IV), (V) and (VI) as defined in any one of embodiments 1) to 45), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "$(C_{1-4})$alkyl-thio-" used alone or in combination, refers to a group of the formula $(C_{1-4})$alkyl-S— in which the term "$(C_{1-4})$alkyl" has the previously given significance. An example is $CH_3$—S—.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$ fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "$(C_{1-3})$fluoroalkyl-thio-" refers to $(C_{1-3})$fluoroalkyl group as defined before, which is linked to the rest of the molecule through a sulfur atom. An example is $CF_3$—S—.

In case two of $(R^5)_n$ together form a group —O—$CH_2$—$CH_2$—O—, such group together with the benzimidazole moiety especially forms a 7,8-dihydro-3H-6,9-dioxa-1,3-diaza-cyclopenta[a]naphthalen-2-yl group.

Particular examples of $Ar^1$ representing a phenyl group, wherein said phenyl is mono-, di-, or tri-substituted; wherein one of said substituents is attached in ortho-position to the point of attachment of $Ar^1$ to the rest of the molecule; are such that the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$ fluoroalkoxy; unsubstituted pyridinyl; and phenyl which is unsubstituted, or mono- or di-substituted, wherein the substituents are independently selected from $(C_{1-4})$alkyl, $(C_{1-4})$alkoxy, cyano, and halogen [notably the other of said substituents, if present, is/are independently selected from $(C_{1-4})$alkyl, $(C_{1-4})$alkoxy, halogen, cyano, $(C_{1-3})$fluoroalkyl, and $(C_{1-3})$fluoroalkoxy; especially from $(C_{1-4})$alkyl, $(C_{1-4})$ alkoxy, and halogen]. Particular examples of such phenyl groups which are further substituted in ortho position as used for the group $Ar^1$ are 1,2-phenylene, 4-methyl-1,2-phenylene, 5-methyl-1,2-phenylene, 6-methyl-1,2-phenylene, 4,5-dimethyl-1,2-phenylene, 5-fluoro-1,2-phenylene, 6-fluoro-1,2-phenylene, 5-chloro-1,2-phenylene, 5-cyano-1,2-phenylene, 5-methoxy-1,2-phenylene, 4,5-dimethoxy-1,2-phenylene, 5-trifluoromethyl-1,2-phenylene, 5-trifluoromethoxy-1,2-phenylene, 6-fluoro-5-methyl-1,2-phenylene, and 6-fluoro-5-methoxy-1,2-phenylene; and in addition to the above listed groups: 5-bromo-1,2-phenylene, 3,4-dimethyl-1,2-phenylene, 5-(pyridine-3-yl)-1,2-phenylene, and 5-(3-cyano-phenyl)-1,2-phenylene; wherein in the above groups the carbonyl group is attached in position 1.

Examples of the particular phenyl groups which are substituents of the group $Ar^1$ are especially phenyl groups which are unsubstituted, mono-, or di-substituted, wherein the substituents are independently selected from $(C_{1-4})$alkyl, $(C_{1-4})$alkoxy, halogen, cyano, $(C_{1-3})$fluoroalkyl, and $(C_{1-3})$ fluoroalkoxy [notably from $(C_{1-4})$alkyl, $(C_{1-4})$alkoxy, halogen, and $(C_{1-3})$fluoroalkyl]. Particular examples are phenyl, 2-methyl-phenyl, 3-methyl-phenyl, 4-methyl-phenyl, 3,4-dimethyl-phenyl, 3-methoxy-phenyl, 2-fluoro-phenyl, 3-fluoro-phenyl, 4-fluoro-phenyl, 3,5-difluoro-phenyl, 4-fluoro-3-methyl-phenyl, 3-fluoro-4-methyl-phenyl, 3-chloro-phenyl, 4-chloro-phenyl, 2,3-dichloro-phenyl, 3,4-dichloro-phenyl, 4-bromo-phenyl, 3-trifluoromethyl-phenyl, 4-trifluoromethyl-phenyl; and in addition to the above-listed groups: 2-chloro-phenyl, 3,4-difluoro-phenyl, 2-methoxy-phenyl, 4-methoxy-phenyl, 3-cyano-phenyl, 4-cyano-phenyl, 3-trifluoromethoxy-phenyl, and 4-trifluoromethoxy-phenyl.

The term "heteroaryl", if not explicitly stated otherwise, means a 5- to 10-membered monocyclic, or bicyclic, aromatic ring containing 1 to a maximum of 3 heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; 6-membered monocyclic heteroaryl such as pyridyl, pyrimidyl, pyridazinyl, and pyrazinyl; and 8- to 10-membered bicyclic heteroaryl such as indolyl, isoindolyl, benzofuranyl, isobenzofuranyl, benzothiophenyl, indazolyl, benzimidazolyl, benzoxazolyl (or benzooxazolyl), benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrazolo[1,5-a]pyridyl, pyrazolo[1,5-a]pyrimidyl, imidazo[1,2-a]pyridyl, 1H-pyrrolo[3,2-b]pyridyl, 1H-pyrrolo[2,3-b]pyridyl, pyrrolo[3,2-d]pyrimidinyl, pyrrolo[2,3-d]pyrimidinyl, 4H-furo[3,2-b]pyrrolyl, pyrrolo[2,1-b]thiazolyl, imidazo[2,1-b]thiazolyl and purinyl.

Examples of the particular 5- or 6-membered heteroaryl groups which are further substituted in ortho position as used for the group $Ar^1$ are the above mentioned 5- or 6-membered heteroaryl groups, notably the 5-membered heteroaryl groups oxazolyl, isoxazolyl, thiophenyl, thiazolyl, isothiazolyl; and the 6-membered heteroaryl groups pyridyl, pyrimidyl and pyrazinyl. In a sub-embodiment, examples are oxazolyl (notably oxazol-4,5-diyl (in particular 2-methyl-oxazol-4,5-diyl), isoxazolyl (notably isoxazol-3,4-diyl, in particular 5-methyl-isoxazol-3,4-diyl), thiazolyl (notably thiazol-4,5-diyl, in particular 2-methyl-thiazol-4,5-diyl, 2-cyclopropyl-thiazol-4,5-diyl, 2-dimethylamino-thiazol-4,5-diyl, 2-(1-pyrrolidinyl)-thiazol-4,5-diyl) and thiophenyl (notably thiophen-2,3-diyl, in particular thiophen-2,3-diyl, 5-methyl-thiophen-2,3-diyl); as well as pyridyl (notably pyridin-2,3-diyl, in particular pyridin-2,3-diyl, 6-methyl-pyridin-2,3-diyl), pyrimidyl (notably pyrimidin-4,5-diyl, in particular pyrimidin-4,5-diyl, 2-methyl-pyrimidin-4,5-diyl), and pyrazinyl (notably pyrazin-2,3-diyl, in particular pyrazin-2,3-diyl). These groups are at least mono-substituted in ortho position, and preferably and independently carry no further substituent or one further substitutent as explicitly defined. In particular such optional further substituent may independently be selected from $(C_{1-4})$alkyl (especially methyl); $(C_{3-6})$cycloalkyl (especially cyclopropyl); —$NR^{10}R^{11}$, wherein $R^{10}$ and $R^{11}$ independently represent $(C_{1-4})$alkyl (especially methyl), or $R^{10}$ and $R^{11}$ together with the nitrogen to which they are attached to form a pyrrolidine ring; and phenyl which is unsubstituted, or mono- or di-substituted, wherein the substituents are independently selected from $(C_{1-4})$alkyl, $(C_{1-4})$alkoxy, cyano, and halogen. In a sub-embodiment, such optional further substituent may independently be selected from $(C_{1-4})$alkyl, $(C_{1-4})$alkoxy, $(C_{3-6})$cycloalkyl, halogen, cyano, $(C_{1-3})$fluoroalkyl, $(C_{1-3})$fluoroalkoxy, and —$NR^{10}R^{11}$ [wherein especially oxazolyl groups carry no further substituent or one further substitutent selected from $(C_{1-4})$alkyl, $(C_{3-6})$cycloalkyl, —$NR^{10}R^{11}$; thiazolyl groups carry no further substituent or one further substituent selected from $(C_{1-4})$alkyl, $(C_{3-6})$cycloalkyl, —$NR^{10}R^{11}$, and phenyl which is unsubstituted, or mono- or di-substituted, wherein the substituents are independently selected from $(C_{1-4})$alkyl, $(C_{1-4})$alkoxy, cyano, and halogen (notably methyl, cyclopropyl, and phenyl which is unsubstituted, or mono- or di-substituted, wherein the substituents are independently selected from $(C_{1-4})$alkyl, $(C_{1-4})$alkoxy, cyano, and halogen; especially methyl and cyclopropyl); thiophenyl, pyridinyl and pyrimidinyl groups carry no further substituent or one further substitutent selected from $(C_{1-4})$alkyl (especially methyl); and pyrazinyl group carry no further substitutent]. The above groups are preferably attached to the rest of the molecule (i.e. the carbonyl group) in position 4 of oxazolyl, isoxazolyl, or thiazolyl groups; in position 2 of pyridyl or pyrazinyl groups; in position 2 of thiophenyl groups; and in position 5 of pyrimidinyl groups. In a further sub-embodiment, particular examples of such groups are 2-methyl-thiazol-4,5-diyl, 2-cyclopropyl-thiazol-4,5-diyl, 2-dimethyl-amino-thiazol-4,5-diyl, thiophen-2,3-diyl; as well as 6-methyl-pyridin-2,3-diyl, 6-methyl-pyridin-3,4-diyl, 2-methyl-pyrimidin-4,5-diyl, pyrimidin-4,5-diyl, and pyrazin-2,3-diyl. Further particular examples are 2-(4-fluoro-2-methoxy-phenyl)-thiazol-4,5-diyl, 2-(2-methoxy-phenyl)-thiazol-4,5-diyl, 2-(3-methoxy-phenyl)-thiazol-4,5-diyl, 2-(4-methoxy-phenyl)-thiazol-4,5-diyl, 2-(3,4-dimethyl-phenyl)-thiazol-4,5-diyl, 2-(2,3-difluoro-phenyl)-thiazol-4,5-diyl, 2-(2,5-difluoro-phenyl)-thiazol-4,5-diyl, 2-(4-fluoro-2-methyl-phenyl)-thiazol-4,5-diyl, 2-(4-fluoro-3-methyl-phenyl)-thiazol-4,5-diyl, 2-(2-fluoro-4-methyl-phenyl)-thiazol-4,5-diyl, 2-(3-chloro-4-methyl-phenyl)-thiazol-4,5-diyl, 2-(3-cyano-phenyl)-thiazol-4,5-diyl, 2-(2-methyl-phenyl)-thiazol-4,5-diyl, 2-(3-methyl-phenyl)-thiazol-4,5-diyl, 2-(4-methyl-phenyl)-thiazol-4,5-diyl, 2-(2-fluoro-phenyl)-thiazol-4,5-diyl, 2-(3-fluoro-phenyl)-thiazol-4,5-diyl, 2-(4-fluoro-phenyl)-thiazol-4,5-diyl, 2-(2-chloro-phenyl)-thiazol-4,5-diyl, 2-(3-chloro-phenyl)-thiazol-4,5-diyl, and 2-phenyl)-thiazol-4,5-diyl.

Examples of the particular 5- or 6-membered heteroaryl groups which are substituents of the group $Ar^1$ are the above mentioned 5- or 6-membered heteroaryl groups; notably the 5-membered heteroaryl groups oxazolyl, isoxazolyl, oxadiazolyl, thienyl, thiazolyl, isothiazolyl, thiadiazolyl, imidazolyl, pyrazolyl, triazolyl, and the 6-membered heteroaryl groups pyridyl, pyrimidyl, pyrazinyl and pyridazinyl. In a sub-embodiment, such groups are especially pyrazolyl, triazolyl, pyridinyl and pyrimidinyl, notably pyrazol-1-yl, pyrimidin-2-yl, and [1,2,3]triazol-2-yl. The above mentioned groups may be unsubstituted or substituted as explicitly defined; wherein pyrazol-1-yl, and [1,2,3]triazol-2-yl groups are preferably unsubstituted. Particular examples are pyrazol-1-yl, [1,2,3]triazol-2-yl, 2-methyl-thiazol-4-yl, 3-methyl-[1,2,4]oxadiazol-5-yl, 6-methoxy-pyridin-3-yl, pyridin-2-yl, pyridin-3-yl, and pyrimidin-2-yl [notably the 5-membered heteroaryl group [1,2,3]triazol-2-yl; and the 6-membered heteroaryl group pyrimidin-2-yl].

Further embodiments of the invention are presented hereinafter:
4) Another embodiment relates to compounds according to any one of embodiments 1) to 3), wherein one of $R^2$ and $R^3$ represents hydrogen, and the other represents hydrogen or methyl (wherein especially $R^3$ represents hydrogen and $R^2$ represents hydrogen or methyl).

5) Another embodiment relates to compounds according to any one of embodiments 1) to 4), wherein $R^{4a}$ and $R^{4b}$ represent hydrogen; or $R^{4a}$ represents methoxy or fluorine, and $R^{4b}$ represents hydrogen; or $R^{4a}$ and $R^{4b}$ together represent a group $H_2C=$; wherein, in case $R^3$ is different from hydrogen, both $R^{4a}$ and $R^{4b}$ represent hydrogen.

6) Another embodiment relates to compounds according to any one of embodiments 1) to 3), wherein
one of $R^2$ and $R^3$ represents hydrogen, and the other represents hydrogen or methyl (wherein especially $R^3$ represents hydrogen and $R^2$ represents hydrogen or methyl); and
$R^{4a}$ and $R^{4b}$ represent hydrogen; or $R^{4a}$ represents methoxy or fluorine, and $R^{4b}$ represents hydrogen; or $R^{4a}$ and $R^{4b}$ together represent a group $H_2C=$; wherein, in case $R^3$ is methyl, both $R^{4a}$ and $R^{4b}$ represent hydrogen.

7) Another embodiment relates to compounds according to any one of embodiments 1) to 3), wherein
$R^3$ represents hydrogen;
$R^2$ represents hydrogen or methyl; and
$R^{4a}$ and $R^{4b}$ represent hydrogen; or $R^{4a}$ represents methoxy or fluorine, and $R^{4b}$ represents hydrogen; or $R^{4a}$ and $R^{4b}$ together represent a group $H_2C=$.

8) Another embodiment relates to compounds according to any one of embodiments 1) to 3), wherein $R^2$, $R^3$, $R^{4a}$ and $R^{4b}$ represent hydrogen.

9) Another embodiment relates to compounds according to any one of embodiments 1) to 3), wherein $R^2$ represents hydrogen or methyl; $R^3$ represents hydrogen; and $R^{4a}$ and $R^{4b}$ represent hydrogen, or $R^{4a}$ and $R^{4b}$ together represent a group $H_2C=$.

10) Another embodiment relates to compounds according to any one of embodiments 1) to 3), wherein $R^2$ represents hydrogen or methyl (especially methyl); and $R^3$, $R^{4a}$ and $R^{4b}$ represent hydrogen.

11) Another embodiment relates to compounds according to any one of embodiments 1) to 3), wherein $R^2$ represents hydrogen or methyl; $R^3$ represents hydrogen; and $R^{4a}$ and $R^{4b}$ together represent a group $H_2C=$.

12) Another embodiment relates to compounds according to any one of embodiments 1) to 3), wherein $R^2$ represents hydrogen or methyl; $R^3$ represents hydrogen; $R^{4a}$ represents methoxy or fluorine (especially $R^{4a}$ represents methoxy); and $R^{4b}$ represents hydrogen.

13) Another embodiment relates to compounds according to any one of embodiments 1) to 3), wherein $R^3$ represents methyl and $R^2$, $R^{4a}$ and $R^{4b}$ represent hydrogen.

14) Another embodiment relates to compounds according to any one of embodiments 1) to 3), wherein both $R^{4a}$ and $R^{4b}$ represent fluorine and $R^2$ and $R^3$ represent hydrogen.

15) Another embodiment relates to compounds of formula (I) or (II) according to any one of embodiments 1), 2), or 4) to 14), wherein $(R^5)_n$ represents one or two optional substituents (i.e. n represents the integer 0, 1, or 2) (especially $(R^5)_n$ represents one or two substituents; i.e. n represents the integer 1 or 2) independently selected from $(C_{1-4})$alkyl (especially methyl), $(C_{1-4})$alkoxy (especially methoxy), halogen (especially fluorine, chlorine or bromine), $(C_{1-4})$alkyl-thio- (especially $H_3C—S—$), $(C_{1-3})$ fluoroalkyl (especially trifluoromethyl), $(C_{1-3})$fluoroalkoxy (especially trifluoromethoxy), $(C_{1-3})$fluoroalkyl-thio- (especially $F_3C—S—$), and cyano.

16) Another embodiment relates to compounds of formula (III) according to any one of embodiments 3) to 14); or to compounds of formula (I) or (II) according to any one of embodiments 1) to 14), wherein the fragment

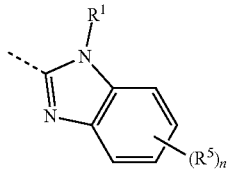

represents a fragment

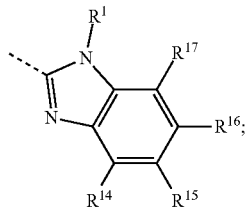

wherein
$R^{14}$, $R^{15}$, $R^{16}$ and $R^{17}$ together represent one or two optional substituents (i.e. at least two of $R^{14}$, $R^{15}$, $R^{16}$ and $R^{17}$ are hydrogen) [notably $R^{14}$, $R^{15}$, $R^{16}$ and $R^{17}$ together represent one or two substituents (i.e. at least two of $R^{14}$, $R^{15}$, $R^{16}$ and $R^{17}$ are hydrogen and at least one of $R^{14}$, $R^{15}$, $R^{16}$ and $R^{17}$ is different from hydrogen)], wherein
$R^{14}$ and $R^{17}$ independently represent hydrogen, $(C_{1-4})$alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-4})$alkoxycarbonyl- (especially $H_3CO—CO—$), hydroxy-$(C_{1-4})$alkyl-(especially $HO—CH_2—$), hydroxy, or nitro; and
$R^{15}$ and $R^{16}$ independently represent hydrogen, $(C_{1-4})$alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-3})$fluoroalkoxy (especially trifluoromethoxy), $(C_{1-3})$fluoroalkyl-thio- (especially $F_3C—S—$), hydroxy-$(C_{1-4})$alkyl- (especially $HO—CH_2—$), or cyano;
or $R^{14}$ and $R^{15}$ together, or $R^{16}$ and $R^{17}$ together, represent a group $—O—CH_2—CH_2—O—$;
or $R^{15}$ and $R^{16}$ together represent a fused phenyl group which, together with the benzimidazole moiety to which it is fused to, forms a 1H-naphtho[2,3-d]imidazol-2-yl group.

17) Another embodiment relates to compounds of formula (III) according to any one of embodiments 3) to 14); or to compounds of formula (I) or (II) according to any one of embodiments 1) to 14), wherein the fragment

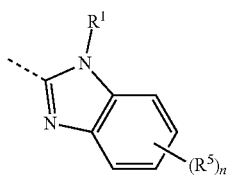

represents a fragment

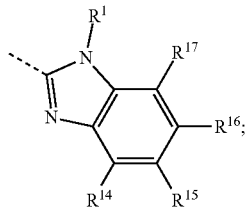

wherein
$R^{14}$, $R^{15}$, $R^{16}$ and $R^{17}$ together represent one or two optional substituents [notably $R^{14}$, $R^{15}$, $R^{16}$ and $R^{17}$ together represent one or two substituents (i.e. at least two of $R^{14}$, $R^{15}$, $R^{16}$ and $R^{17}$ are hydrogen and at least one of $R^{14}$, $R^{15}$, $R^{16}$ and $R^{17}$ is different from hydrogen)], wherein $R^{14}$ and $R^{17}$ independently represent hydrogen, $(C_{1-4})$alkyl, $(C_{1-4})$alkoxy (especially methoxy), $(C_{1-4})$alkyl-thio- (especially $H_3C—S—$), halogen, or $(C_{1-3})$fluoroalkyl (especially trifluoromethyl); and $R^{15}$ and $R^{16}$ independently represent hydrogen, $(C_{1-4})$alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-3})$fluoroalkoxy (especially trifluoromethoxy), $(C_{1-3})$fluoroalkyl-thio- (especially $F_3C—S—$), or cyano.

18) Another embodiment relates to compounds of formula (III) according to any one of embodiments 3) to 14); or to compounds of formula (I) or (II) according to any one of embodiments 1) to 14), wherein the fragment

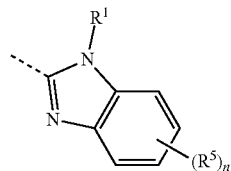

represents a fragment

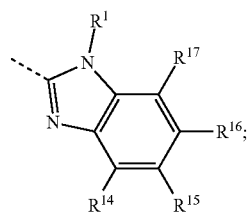

wherein $R^{14}$, $R^{15}$, $R^{16}$ and $R^{17}$ together represent one or two substituents (i.e. at least two of $R^{14}$, $R^{15}$, $R^{16}$ and $R^{17}$ are hydrogen and at least one of $R^{14}$, $R^{15}$, $R^{16}$ and $R^{17}$ is different from hydrogen), wherein one of $R^{15}$ and $R^{16}$ represents $(C_{1-4})$alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-3})$fluoroalkoxy (especially trifluoromethoxy), or cyano;

or one of $R^{14}$ and $R^{17}$ represents $(C_{1-4})$alkyl, $(C_{1-4})$alkoxy (especially methoxy), $(C_{1-4})$alkyl-thio- (especially $H_3C—S—$), halogen, or $(C_{1-3})$fluoroalkyl (especially trifluoromethyl);

and the remaining substituent, if present, is one of $R^{15}$ and $R^{16}$ representing $(C_{1-4})$alkyl, $(C_{1-4})$alkoxy (especially methoxy), or halogen.

19) Another embodiment relates to compounds according to any one of embodiments 1) to 18), wherein $R^1$ represents hydrogen.

20) Another embodiment relates to compounds according to any one of embodiments 1) to 18), wherein $R^1$ represents $(C_{1-4})$alkyl (especially methyl or ethyl, notably methyl).

21) Another embodiment relates to compounds according to any one of embodiments 1) to 20), wherein $Ar^1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $Ar^1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted (especially unsubstituted, mono-, or di-substituted), wherein the substituents are independently selected from $(C_{1-4})$alkyl, $(C_{1-4})$alkoxy, halogen, cyano, $(C_{1-3})$fluoroalkyl, and $(C_{1-3})$fluoroalkoxy; or said ortho substituent is benzo[1,3]dioxol-5-yl;

and the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$fluoroalkoxy; and $—NR^{10}R^{11}$, wherein $R^{10}$ and $R^{11}$ independently represent $(C_{1-4})$alkyl, or $R^{10}$ and $R^{11}$ together with the nitrogen to which they are attached to form a pyrrolidine ring.

22) Another embodiment relates to compounds of formula (I) or (II) according to any one of embodiments 1) to 20); or mutatis mutandis to compounds of formula (III) according to any one of embodiments 3) to 20); wherein $Ar^1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $Ar^1$ to the rest of the molecule; wherein said substituent is phenyl or 5- or 6-membered heteroaryl; wherein said phenyl or 5- or 6-membered heteroaryl substituent is independently unsubstituted, or mono-, or di-substituted, wherein the substituents are independently selected from $(C_{1-2})$alkyl, $(C_{1-2})$alkoxy, halogen, cyano, trifluoromethyl, and trifluoromethoxy; or said ortho substituent is benzo[1,3]dioxolyl; or said ortho substituent is 2-(3-methoxy-phenyl)-ethynyl and the other of said substituents, if present, is/are independently selected from methyl; methoxy; cyclopropyl; halogen; cyano; trifluoromethyl; trifluoromethoxy; dimethylamino; pyrrolidin-1-yl; unsubstituted pyridinyl; and phenyl which is unsubstituted, or mono- or di-substituted, wherein the substituents are independently selected from methyl, methoxy, cyano, and halogen.

23) Another embodiment relates to compounds according to any one of embodiments 1) to 20), wherein $Ar^1$ represents 5-membered heteroaryl, wherein the 5-membered heteroaryl is mono- or di-substituted; wherein one of said substituents is attached in ortho-position to the point of attachment of $Ar^1$ to the rest of the molecule; wherein said ortho-substituent is phenyl, or 6-membered heteroaryl (especially pyridyl), which phenyl or 6-membered heteroaryl is independently unsubstituted, mono-, di-, or tri-substituted (especially unsubstituted, mono-, or di-substituted), wherein the substituents are independently selected from $(C_{1-4})$alkyl, $(C_{1-4})$alkoxy, halogen, cyano, $(C_{1-3})$fluoroalkyl, and $(C_{1-3})$fluoroalkoxy [wherein phenyl is especially unsubstituted, or mono-, or di-substituted with $(C_{1-4})$alkyl, $(C_{1-4})$alkoxy, halogen, $(C_{1-3})$fluoroalkyl, or $(C_{1-3})$fluoroalkoxy; and 6-membered heteroaryl is notably pyridyl which is mono-substituted with $(C_{1-4})$alkoxy];

and the other of said substituents, if present, is/are independently selected from $(C_{1-4})$alkyl (especially methyl); (C$_{3-6}$)cycloalkyl (especially cyclopropyl); —NR$^{10}$R$^{11}$, wherein R$^{10}$ and R$^{11}$ independently represent (C$_{1-4}$)alkyl (especially methyl), or R$^{10}$ and R$^{11}$ together with the nitrogen to which they are attached to form a pyrrolidine ring; and phenyl which is unsubstituted, or mono- or di-substituted, wherein the substituents are independently selected from (C$_{1-4}$)alkyl, (C$_{1-4}$)alkoxy, cyano, and halogen (especially the other of said substituents represents methyl or cyclopropyl);

or Ar$^1$ represents 6-membered heteroaryl, wherein the 6-membered heteroaryl is mono-, di-, or tri-substituted (especially mono- or di-substituted); wherein
  one of said substituents is attached in ortho-position to the point of attachment of Ar$^1$ to the rest of the molecule; wherein
    said ortho-substituent is unsubstituted 5-membered heteroaryl (notably pyrazol-1-yl or [1,2,3]triazol-2-yl, especially in case Ar$^1$ represents pyridyl);
    or said ortho-substituent is phenyl which is unsubstituted, mono-, di-, or tri-substituted (especially unsubstituted, mono-, or di-substituted), wherein the substituents are independently selected from (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, halogen and (C$_{1-3}$)fluoroalkyl);
  and the other of said substituents, if present, is/are independently selected from (C$_{1-4}$)alkyl, (C$_{1-4}$)alkoxy, halogen, and (C$_{1-3}$)fluoroalkyl (especially (C$_{1-4}$)alkyl, and halogen; notably methyl);

or Ar$^1$ represents phenyl which is mono-, di-, or tri-substituted; wherein
  one of said substituents is attached in ortho-position to the point of attachment of Ar$^1$ to the rest of the molecule; wherein
    said ortho-substituent is phenyl which is unsubstituted, mono-, di-, or tri-substituted (especially unsubstituted, mono-, or di-substituted), wherein the substituents are independently selected from (C$_{1-4}$)alkyl, (C$_{1-4}$)alkoxy, halogen, cyano, (C$_{1-3}$)fluoroalkyl, and (C$_{1-3}$)fluoroalkoxy;
    or said ortho substituent is benzo[1,3]dioxol-5-yl;
    or said ortho-substituent is 6-membered heteroaryl which is unsubstituted, mono-, or di-substituted (especially unsubstituted or mono-substituted), wherein the substituents are independently selected from (C$_{1-4}$)alkyl, (C$_{1-4}$)alkoxy, halogen, and (C$_{1-3}$)fluoroalkyl (especially mono-substituted with (C$_{1-4}$)alkyl, or (C$_{1-4}$)alkoxy);
    or said ortho-substituent is 5-membered heteroaryl which is unsubstituted, mono-, or di-substituted (especially unsubstituted or mono-substituted), wherein the substituents are independently selected from (C$_{1-4}$)alkyl, (C$_{1-4}$)alkoxy, halogen, and (C$_{1-3}$)fluoroalkyl (especially (C$_{1-4}$)alkyl, notably methyl);
    or said ortho-substituent is 2-(3-methoxy-phenyl)-ethynyl;
  and the other of said substituents, if present, is/are independently selected from (C$_{1-4}$)alkyl; (C$_{1-4}$)alkoxy; (C$_{3-6}$)cycloalkyl; halogen; cyano; (C$_{1-3}$)fluoroalkyl; (C$_{1-3}$)fluoroalkoxy; unsubstituted pyridinyl; and phenyl which is unsubstituted, or mono- or di-substituted, wherein the substituents are independently selected from (C$_{1-4}$)alkyl, (C$_{1-4}$)alkoxy, cyano, and halogen [notably selected from (C$_{1-4}$)alkyl, (C$_{1-4}$)alkoxy, halogen, cyano, (C$_{1-3}$)fluoroalkyl, and (C$_{1-3}$)fluoroalkoxy; especially from (C$_{1-4}$)alkyl, (C$_{1-4}$)alkoxy, and halogen].

24) Another embodiment relates to compounds according to any one of embodiments 1) to 23), wherein one or both of the following characteristics are present:
  in case Ar$^1$ represents a 5-membered heteroaryl group, such group is an oxazolyl, thienyl, or thiazolyl group (especially a thiazolyl group); and/or
  in case Ar$^1$ represents a 6-membered heteroaryl group, such group is a pyridinyl, pyrazinyl, or pyrimidinyl group (especially a pyridinyl group);
wherein said groups independently are substituted as defined in any one of the preceeding embodiments.

25) Another embodiment relates to compounds according to any one of embodiments 1) to 24), wherein one or both of the following characteristics are present:
  in case said ortho substituent of Ar$^1$ represents a 5-membered heteroaryl group, such group is a triazolyl (especially unsubstituted [1,2,3]triazol-2-yl), a pyrazolyl (especially unsubstituted pyrazol-1-yl), an oxadiazolyl (especially 3-methyl-[1,2,4]oxadiazol-5-yl), or a thiazolyl group (especially 2-methyl-thiazol-4-yl); [notably such group is [1,2,3]triazol-2-yl or pyrazol-1-yl]; and/or
  in case said ortho substituent of Ar$^1$ represents a 6-membered heteroaryl group, such group is a pyridinyl or a pyrimidinyl group (especially 6-methoxy-pyridin-3-yl, pyridin-2-yl, pyridin-3-yl, or pyrimidin-2-yl; preferably 6-methoxy-pyridin-3-yl, pyridin-2-yl or pyrimidin-2-yl);
wherein said groups independently are unsubstituted or substituted as defined in any one of the preceeding embodiments, or as explicitly defined herein.

26) Another embodiment relates to compounds according to any one of the embodiments 1) to 20) wherein Ar$^1$ is a group independently selected from the following groups A, B, C, D, E, F, G, H, I, J, K, L, or M:

A.

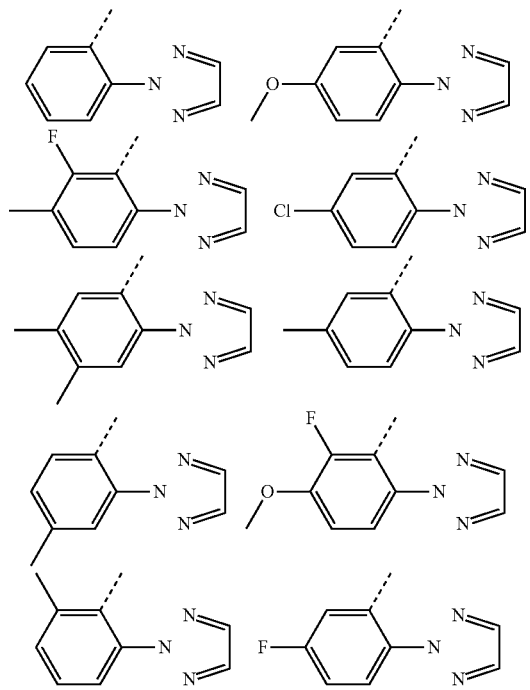

-continued
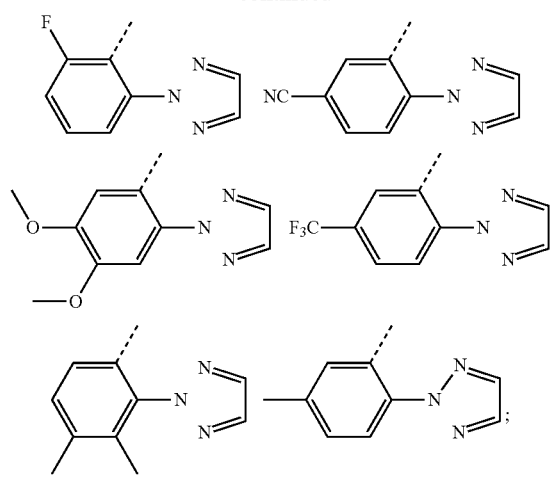
B.
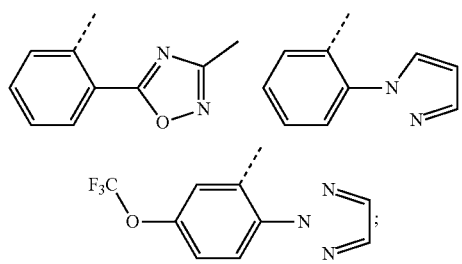
C.
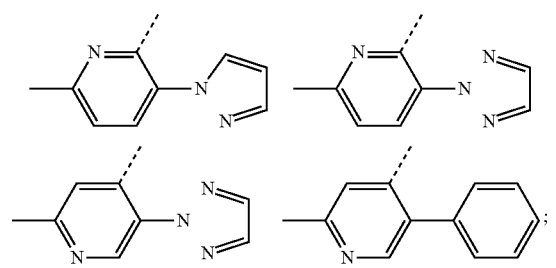
D.
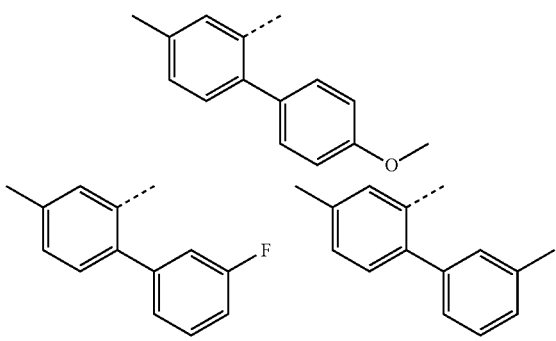
-continued
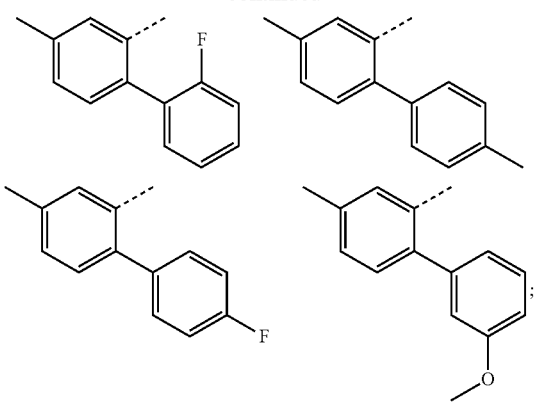
E.
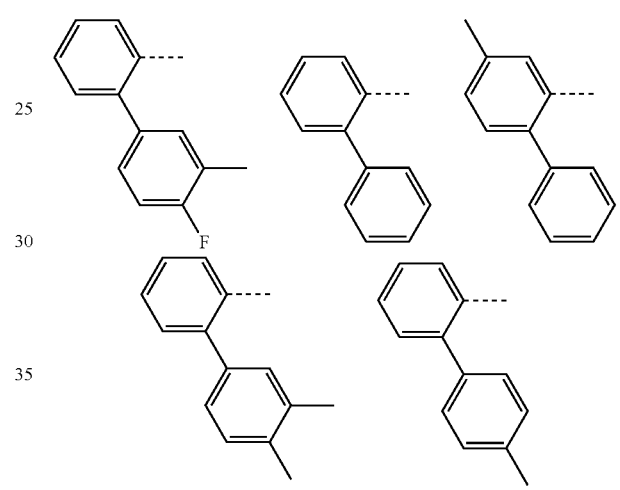
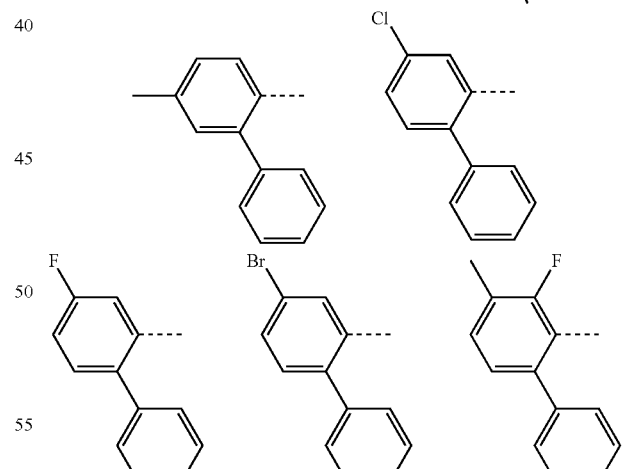
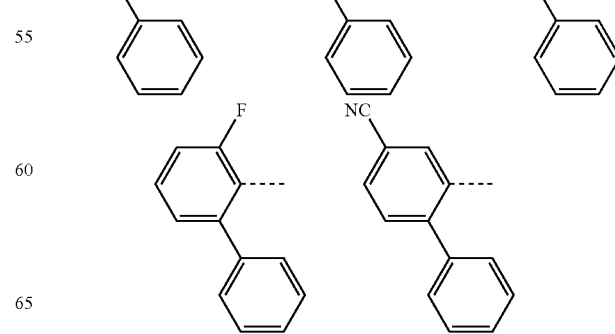

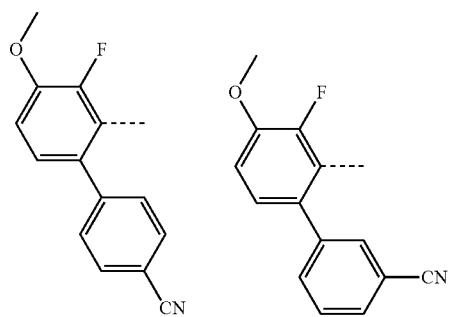
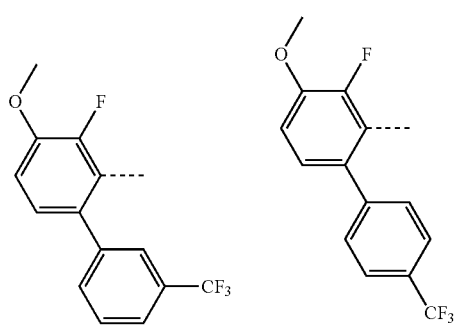
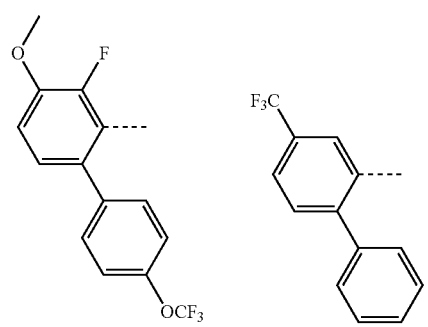
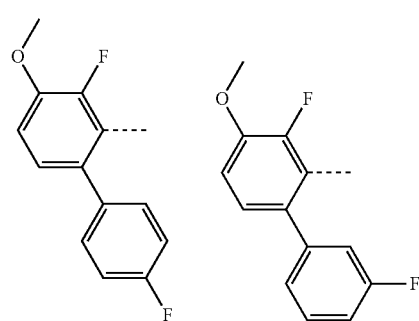
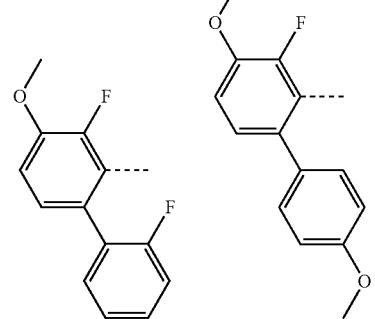
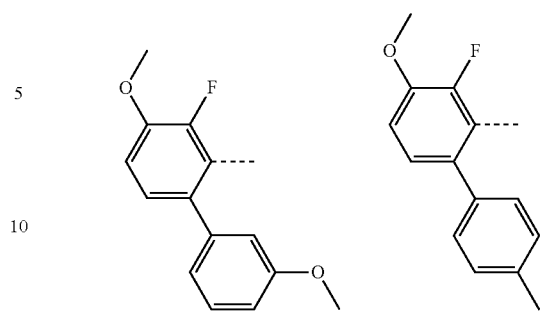
F.
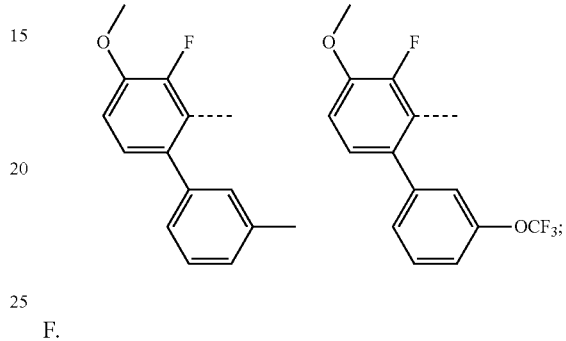
G.
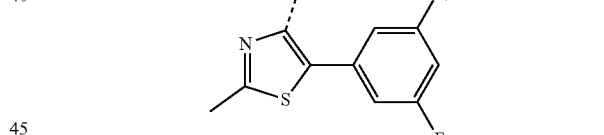
H.
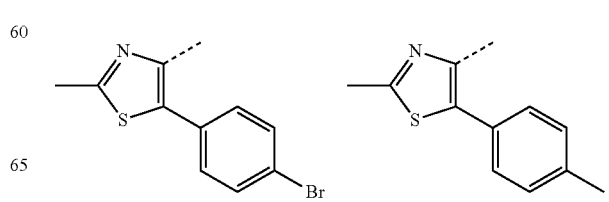

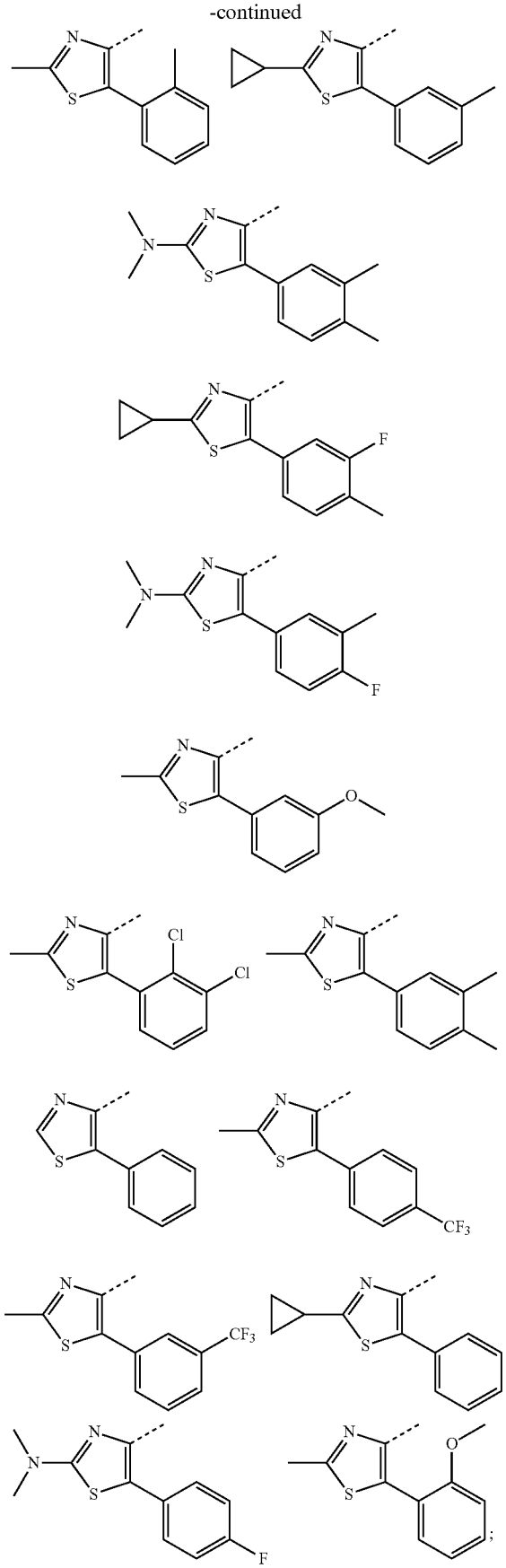
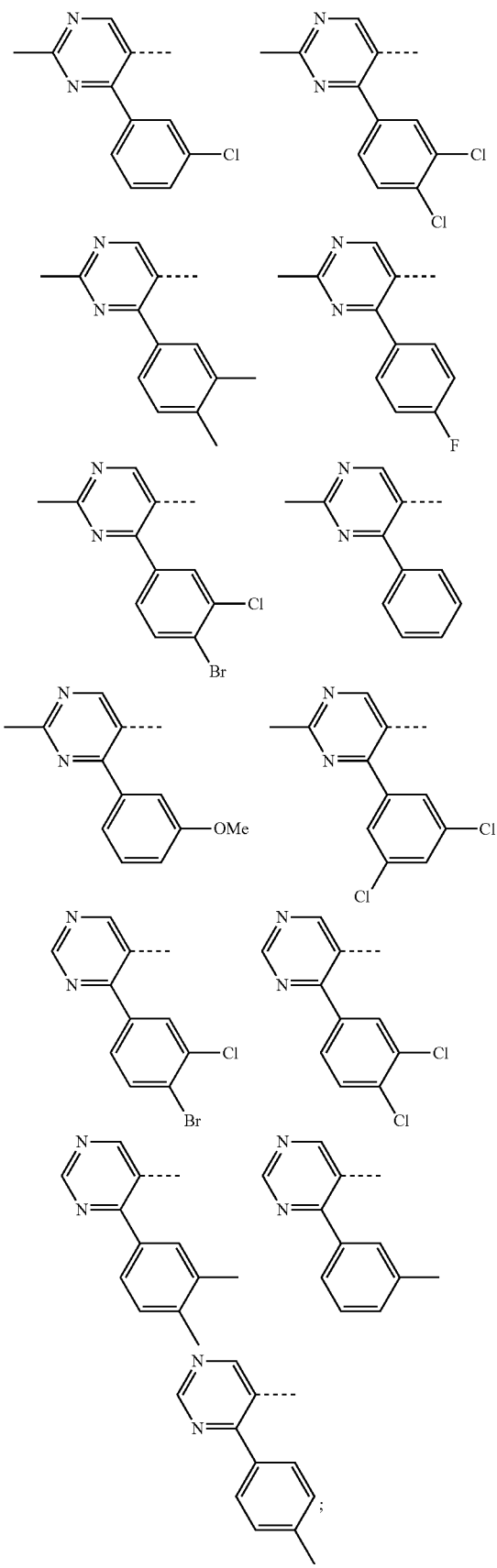
I.

J.

K.

L.

M.

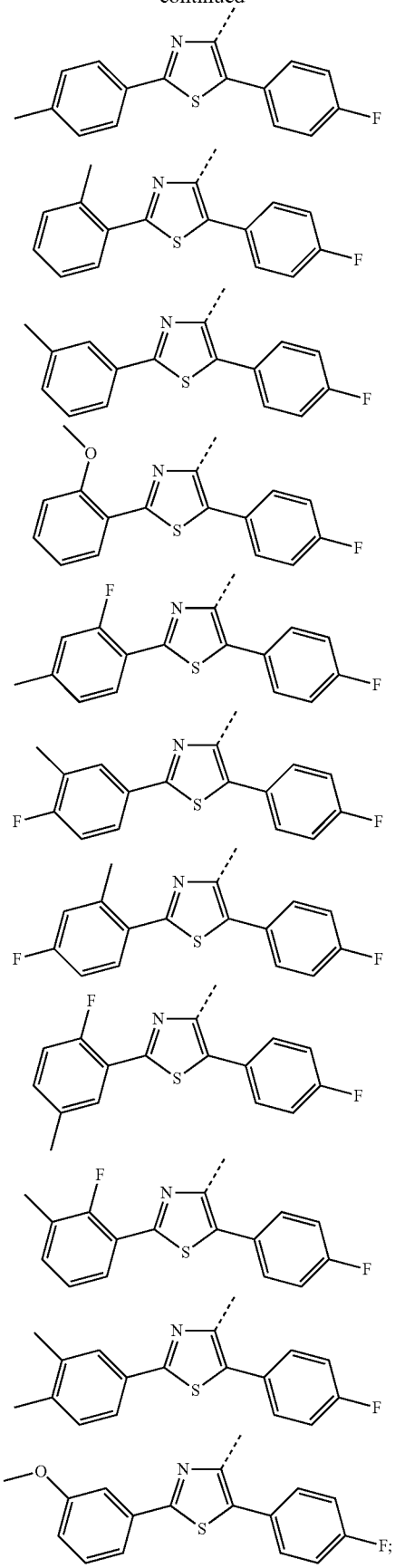

wherein the groups listed in A and L are preferred groups, and wherein each of the groups A to M forms a particular sub-embodiment.

27) Another embodiment relates to compounds of formula (III) according to any one of embodiments 3) to 14), or to compounds of formula (I) or (II) according to embodiment 16), wherein
$R^2$, $R^3$, $R^{4a}$, $R^{4b}$ represent hydrogen; $R^{15}$ represents chlorine and $R^{14}$ represents methyl, or $R^{16}$ represents chlorine and $R^{17}$ represents methyl, and the remaining represent hydrogen;
and $Ar^1$ is as defined in any one of embodiments 21) to 26);
wherein, in a sub-embodiment, a particular group for $Ar^1$ is:

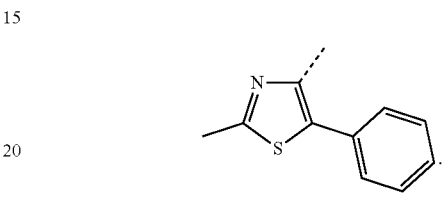

28) Another embodiment relates to compounds of formula (III) according to any one of embodiments 3) to 14), or to compounds of formula (I) or (II) according to embodiment 16), wherein $R^2$, $R^3$, $R^{4a}$, $R^{4b}$, $R^{14}$, $R^{15}$, $R^{16}$ and $R^{17}$ are characterized by one or more of the following characteristics:
$R^2$, $R^3$, $R^{4a}$, $R^{4b}$, $R^{15}$, and $R^{16}$ represent hydrogen; one of $R^{14}$ and $R^{17}$ represents —S—CH$_3$, and the remaining represents hydrogen; or
$R^2$, $R^3$, $R^{4a}$, $R^{4b}$, $R^{14}$, and $R^{17}$ represent hydrogen; one of $R^{15}$ and $R^{16}$ represents —O—CH$_3$ or —S—CH$_3$, and the remaining represents hydrogen;
and $Ar^1$ is as defined in any one of embodiments 21) to 26);
wherein, in a sub-embodiment, a particular group for $Ar^1$ is:

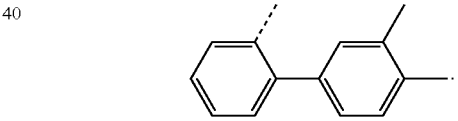

29) Another embodiment relates to compounds of formula (III) according to any one of embodiments 3) to 14), or to compounds of formula (I) or (II) according to embodiment 16), wherein
$R^2$, $R^3$, $R^{4a}$, $R^{4b}$, $R^{15}$, and $R^{16}$ represent hydrogen; one of $R^{14}$ and $R^{17}$ represents —S—CH$_3$, and the remaining represents hydrogen;
and $Ar^1$ is as defined in any one of embodiments 21) to 26);
wherein, in a sub-embodiment, particular groups for $Ar^1$ are:

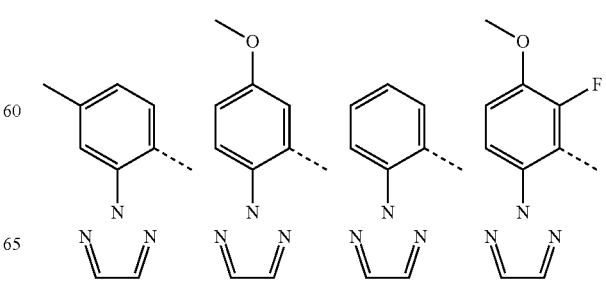

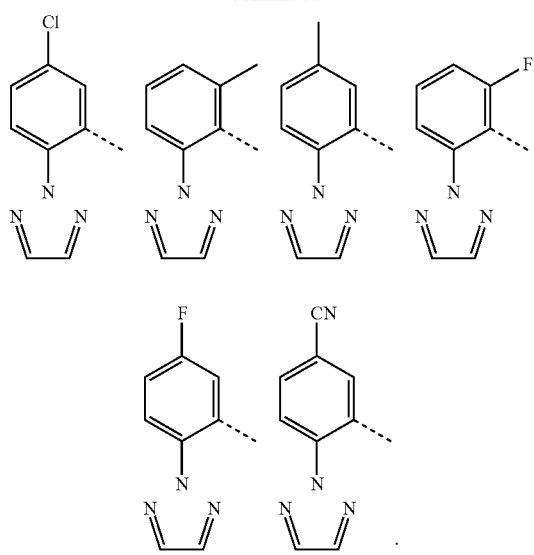

30) Another embodiment relates to compounds of formula (III) according to any one of embodiments 3) to 14), or to compounds of formula (I) or (II) according to embodiment 16), wherein $R^2$, $R^3$, $R^{4a}$, $R^{4b}$, $R^{14}$, $R^{15}$, $R^{16}$ and $R^{17}$ are characterized by one, or more (in any combination), or all of the following characteristics:

- $R^2$, $R^3$, $R^{4a}$, $R^{4b}$, $R^{17}$, and $R^{14}$ represent hydrogen, one of $R^{15}$ and $R^{16}$ represents —O—CH$_3$ or —S—CH$_3$, and the remaining represents hydrogen; or
- $R^2$ represents methyl; $R^3$, $R^{4a}$, and $R^{4b}$ represent hydrogen; $R^{15}$ represents chlorine and $R^{14}$ represents methyl, or $R^{16}$ represents chlorine and $R^{17}$ represents methyl, and the remaining represent hydrogen; or
- $R^2$ represents methyl; $R^3$, $R^{4a}$, $R^{4b}$, $R^{14}$ and $R^{17}$ represent hydrogen; $R^{16}$ and $R^{15}$ both represent methyl;

and Ar$^1$ is as defined in any one of embodiments 21) to 26); wherein, in a sub-embodiment, particular groups for Ar$^1$ are:

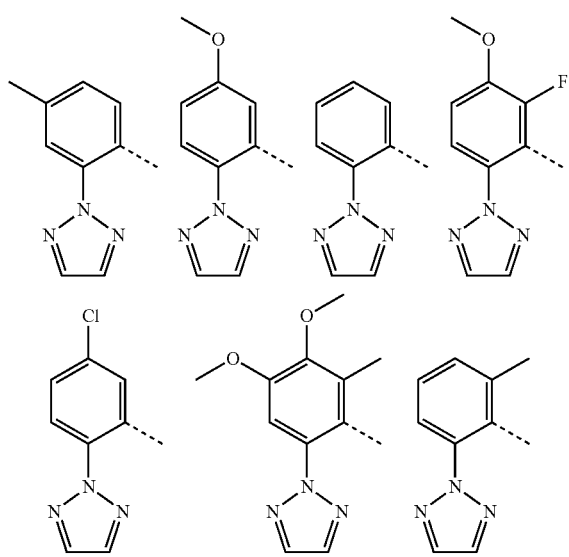

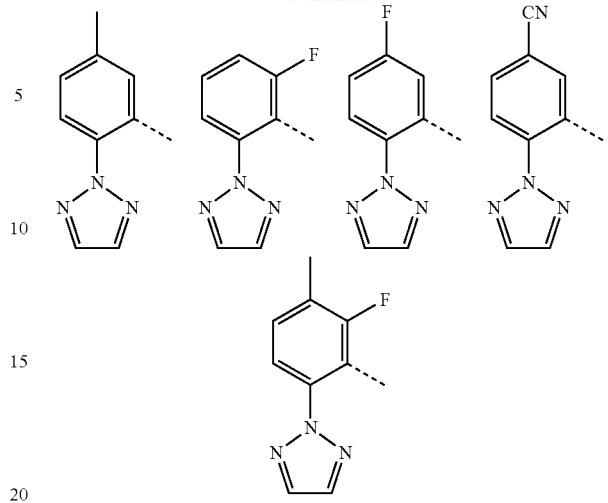

31) Another embodiment relates to compounds of formula (III) according to any one of embodiments 3) to 14), or to compounds of formula (I) or (II) according to embodiment 16), wherein
$R^2$ represents methyl; $R^3$, $R^{4a}$, $R^{4b}$, $R^{14}$ and $R^{17}$ represent hydrogen; $R^{15}$ and $R^{16}$ both represent methyl;
and Ar$^1$ is as defined in any one of embodiments 21) to 26); wherein, in a sub-embodiment, particular groups for Ar$^1$ are:

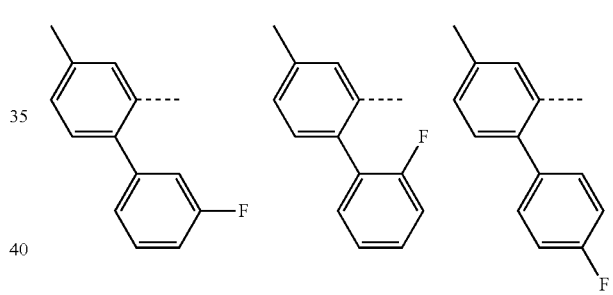

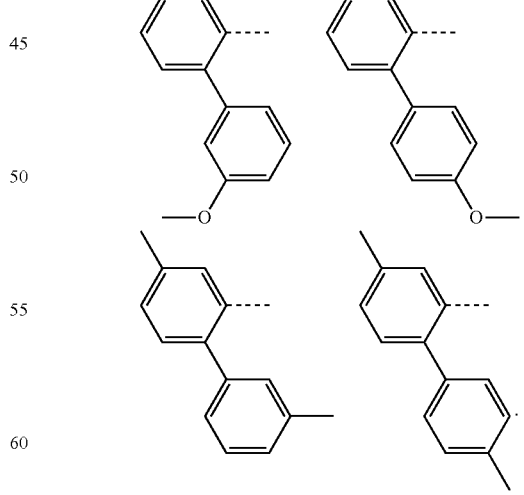

32) Another embodiment relates to compounds according of formula (III) according to any one of embodiments 3) to 14), or to compounds of formula (I) or (II) according to embodiment 16), wherein $R^2$ represents methyl; $R^3$, $R^{4a}$, $R^{4b}$, $R^{14}$ and $R^{17}$ represent hydrogen; $R^{15}$ and $R^{16}$ both represent methoxy;

and $Ar^1$ is as defined in any one of embodiments 21) to 26); wherein, in a sub-embodiment, particular groups for $Ar^1$ are:

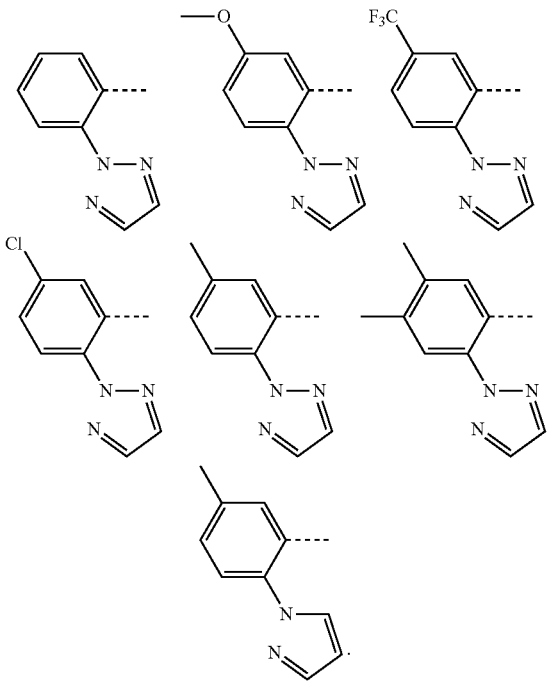

33) Another embodiment relates to compounds of formula (III) according to any one of embodiments 3) to 14), or to compounds of formula (I) or (II) according to embodiment 16), wherein $R^2$, $R^3$, $R^{4a}$, $R^{4b}$, $R^{14}$, $R^{15}$, $R^{16}$ and $R^{17}$ are characterized by one or more of the following characteristics:

$R^2$ represents methyl; $R^3$, $R^{4a}$, $R^{4b}$, $R^{14}$ and $R^{17}$ represent hydrogen; one of $R^{15}$ and $R^{16}$ represents trifluoromethyl, and the remaining represents hydrogen, chlorine or fluorine;

$R^2$ represents methyl; $R^3$, $R^{4a}$, and $R^{4b}$ represent hydrogen; $R^{14}$ represents chorine and $R^{16}$ represents trifluoromethyl, or $R^{17}$ represents chorine and $R^{15}$ represents trifluoromethyl, and the remaining represent hydrogen;

and $Ar^1$ is as defined in any one of embodiments 21) to 26); wherein, in a sub-embodiment, a particular group for $Ar^1$ is:

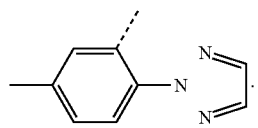

34) Another embodiment relates to compounds of formula (III) according to any one of embodiments 3) to 14), or to compounds of formula (I) or (II) according to embodiment 16), wherein $R^2$, $R^3$, $R^{4a}$, $R^{4b}$, $R^{14}$, $R^{15}$, $R^{16}$ and $R^{17}$ are characterized by one, or more (in any combination), or all of the following characteristics:

$R^3$ represents methyl; $R^2$, $R^{4a}$, and $R^{4b}$, represent hydrogen; $R^{14}$ represents methyl and $R^{15}$ represents chlorine, or $R^{17}$ represents methyl and $R^{16}$ represents chlorine, and the remaining represent hydrogen; or $R^3$ represents methyl; $R^2$, $R^{4a}$, $R^{4b}$, $R^{14}$ and $R^{17}$ represent hydrogen; one of $R^{15}$ and $R^{16}$ represents methyl, and the remaining represents chlorine; or $R^3$ represents methyl; $R^2$, $R^{4a}$, $R^{4b}$, $R^{14}$ and $R^{17}$ represent hydrogen; $R^{15}$ and $R^{16}$ both represent methyl; or $R^3$ represents methyl; $R^2$, $R^{4a}$, and $R^{4b}$ represent hydrogen; $R^{14}$ represents methyl and $R^{16}$ represents chlorine, or $R^{17}$ represents methyl and $R^{15}$ represents chlorine, and the remaining represent hydrogen; or $R^3$ represents methyl; $R^2$, $R^{4a}$, and $R^{4b}$ represent hydrogen; $R^{14}$ represents methyl and $R^{16}$ represents bromine, or $R^{17}$ represents methyl and $R^{15}$ represents bromine, and the remaining represent hydrogen; or $R^3$ represents methyl; $R^2$, $R^{4a}$, $R^{4b}$, $R^{14}$ and $R^{17}$ represent hydrogen; $R^{15}$ and $R^{16}$ both represent methoxy;

and $Ar^1$ is as defined in any one of embodiments 21) to 26); wherein, in a sub-embodiment, particular groups for $Ar^1$ are:

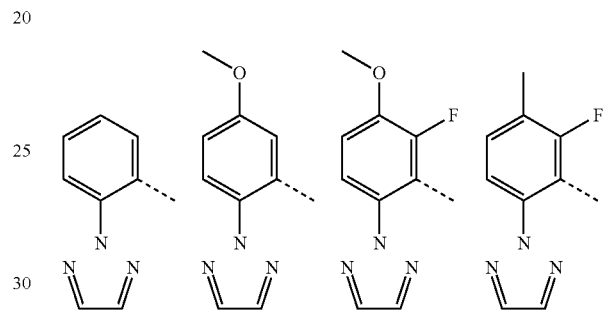

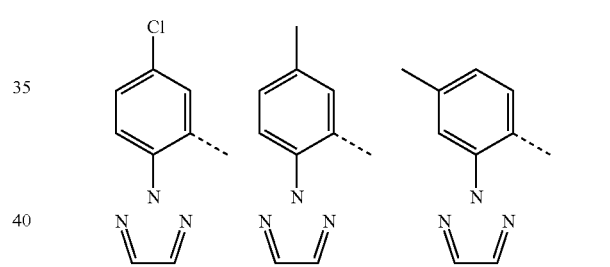

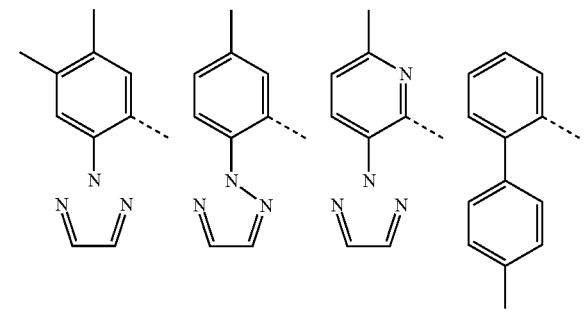

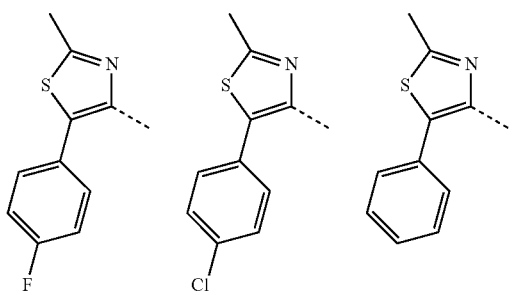

-continued

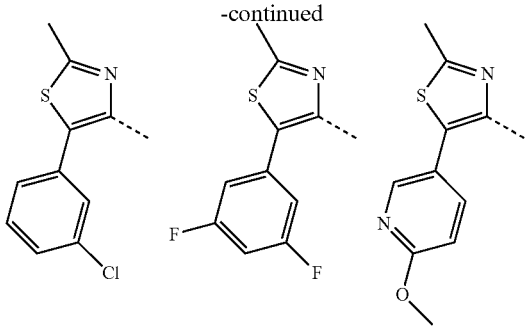

35) Another embodiment relates to compounds of formula (III) according to any one of embodiments 3) to 14), or to compounds of formula (I) or (II) according to embodiment 16), wherein $R^2$, $R^3$, $R^{4a}$, $R^{4b}$, $R^{14}$, $R^{15}$, $R^{16}$ and $R^{17}$ are characterized by one, or more (in any combination), or all of the following characteristics:

$R^2$, $R^3$, and $R^{4b}$ represent hydrogen; $R^{4a}$ represents methoxy; $R^{14}$ represents methyl and $R^{15}$ represents hydrogen or chlorine, or $R^{17}$ represents methyl and $R^{16}$ represents hydrogen or chlorine, and the remaining represent hydrogen; or $R^2$, $R^3$, and $R^{4a}$ represent hydrogen; $R^{4b}$ represents methoxy; $R^{14}$ represents methyl and $R^{15}$ represents hydrogen or chlorine, or $R^{17}$ represents methyl and $R^{16}$ represents hydrogen or chlorine, and the remaining represents hydrogen; or $R^2$, $R^3$, and $R^{4b}$ represent hydrogen; $R^{4a}$ represents fluorine; $R^{14}$ represents methyl and $R^{15}$ represents hydrogen or chlorine, or $R^{17}$ represents methyl and $R^{16}$ represents hydrogen or chlorine, and the remaining represents hydrogen; or $R^2$, $R^3$, and $R^{4a}$ represent hydrogen; $R^{4b}$ represents fluorine; $R^{14}$ represents methyl and $R^{15}$ represents hydrogen or chlorine, or $R^{17}$ represents methyl and $R^{16}$ represents hydrogen or chlorine, and the remaining represents hydrogen; or $R^2$ and $R^3$ represent hydrogen; $R^{4a}$ and $R^{4b}$ both represent fluorine; $R^{14}$ represents methyl and $R^{15}$ represents hydrogen or chlorine, or $R^{17}$ represents methyl and $R^{16}$ represents hydrogen or chlorine, and the remaining represents hydrogen;

and $Ar^1$ is as defined in any one of embodiments 21) to 26); wherein, in a sub-embodiment, particular groups for $Ar^1$ are:

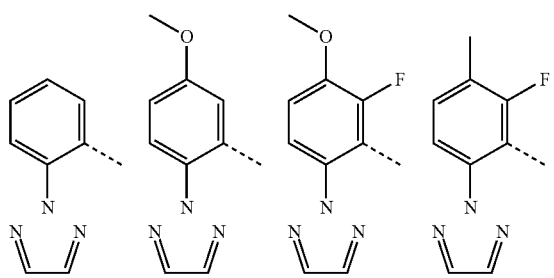

-continued

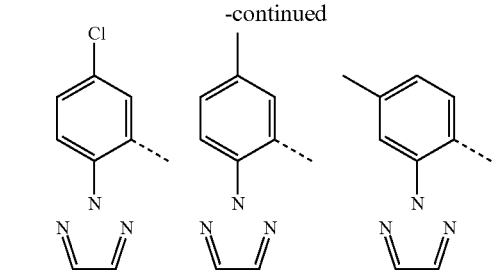

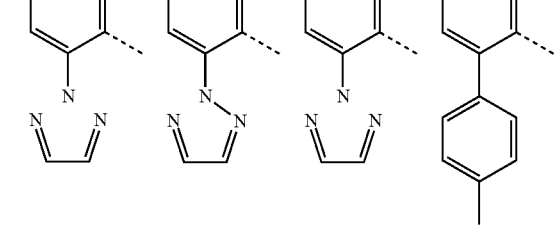

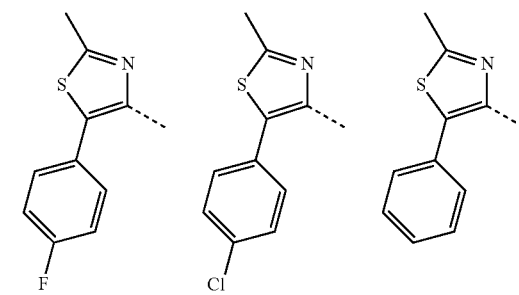

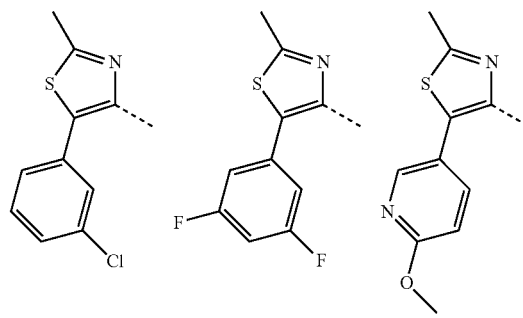

36) Another embodiment relates to compounds of formula (III) according to any one of embodiments 3) to 14), or to compounds of formula (I) or (II) according to embodiment 16), wherein $R^2$ and $R^3$ represent hydrogen, $R^{4a}$ and $R^{4b}$ together represent $H_2C=$, and $R^{14}$, $R^{15}$, $R^{16}$ and $R^{17}$ together represent one or two substituents (i.e. two or three of $R^{14}$, $R^{15}$, $R^{16}$ and $R^{17}$ are hydrogen), wherein $R^{14}$ represents hydrogen or methoxy;

$R^{15}$ represents hydrogen, chlorine, methyl or methoxy;

$R^{16}$ represents hydrogen, methyl, chlorine, methoxy, trifluoromethoxy, tert.-butyl or $-S-CH_3$; and $R^{17}$ represents hydrogen, methyl, methoxy, bromine or $-S-CH_3$;

and $Ar^1$ is as defined in any one of embodiments 21) to 26); wherein particular groups for $Ar^1$ are:

A.

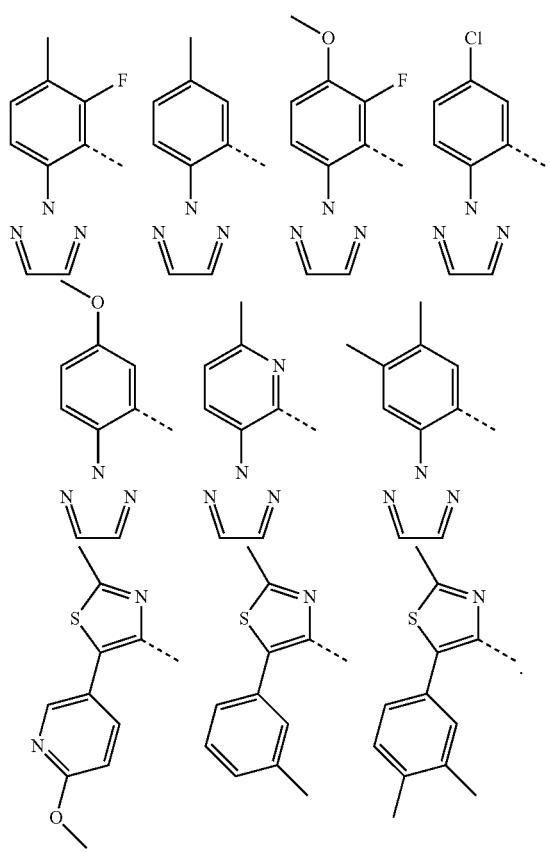
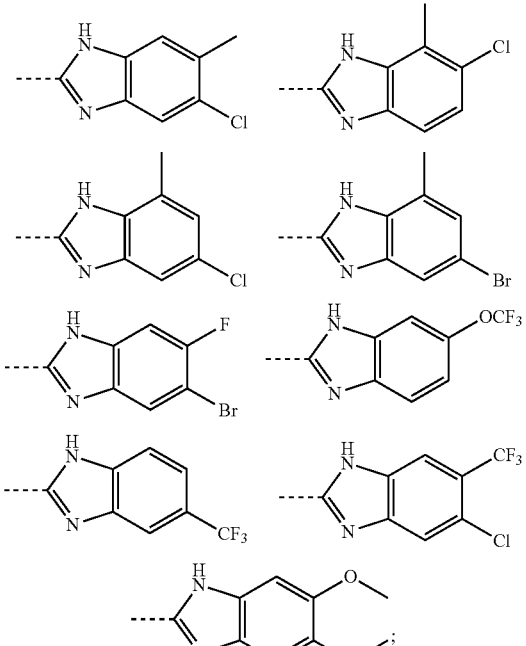

37) Another embodiment relates to compounds according to any one of embodiments 27) to 36), wherein $R^1$ represents hydrogen.
38) Another embodiment relates to compounds according to any one of embodiments 27) to 36), wherein $R^1$ represents $(C_{1-4})$alkyl (especially methyl or ethyl, notably methyl).
39) Another embodiment relates to compounds of formula (I) according to any one of embodiments 1) to 26); wherein the fragment

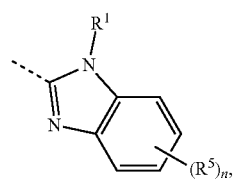

respectively the fragment

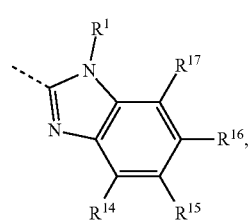

represents a group independently selected from the following groups A, B, or C:

B.

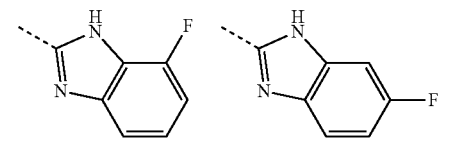
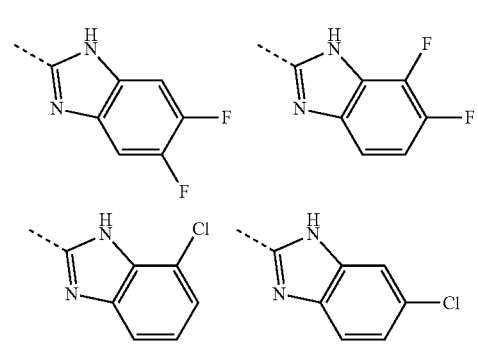
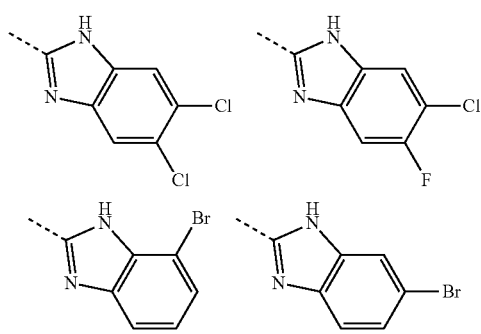

-continued
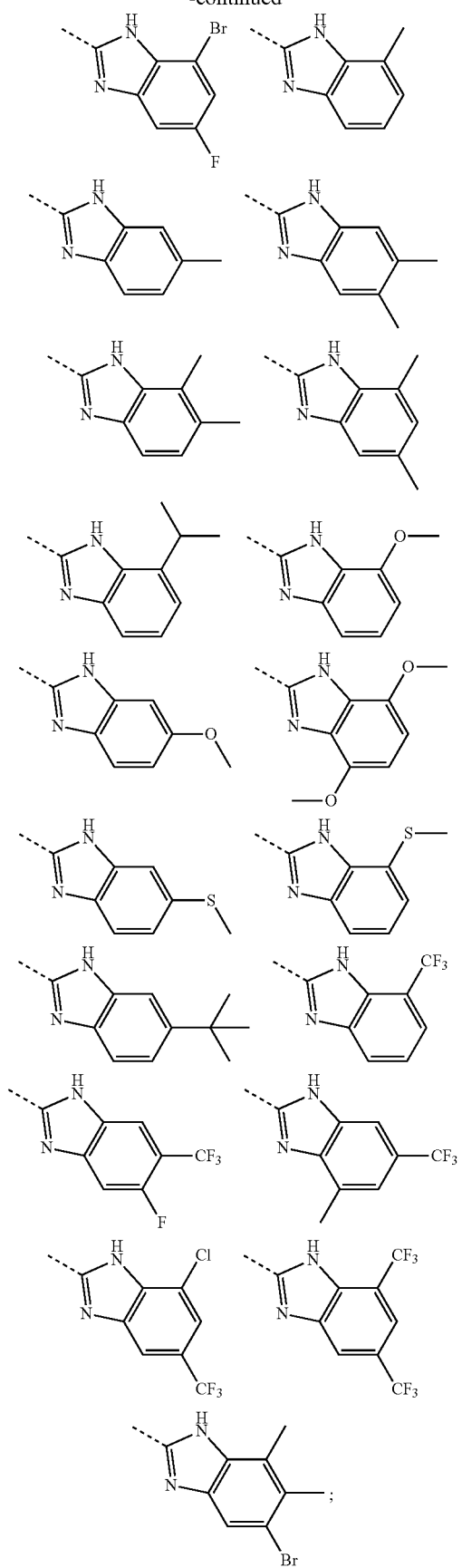
C.
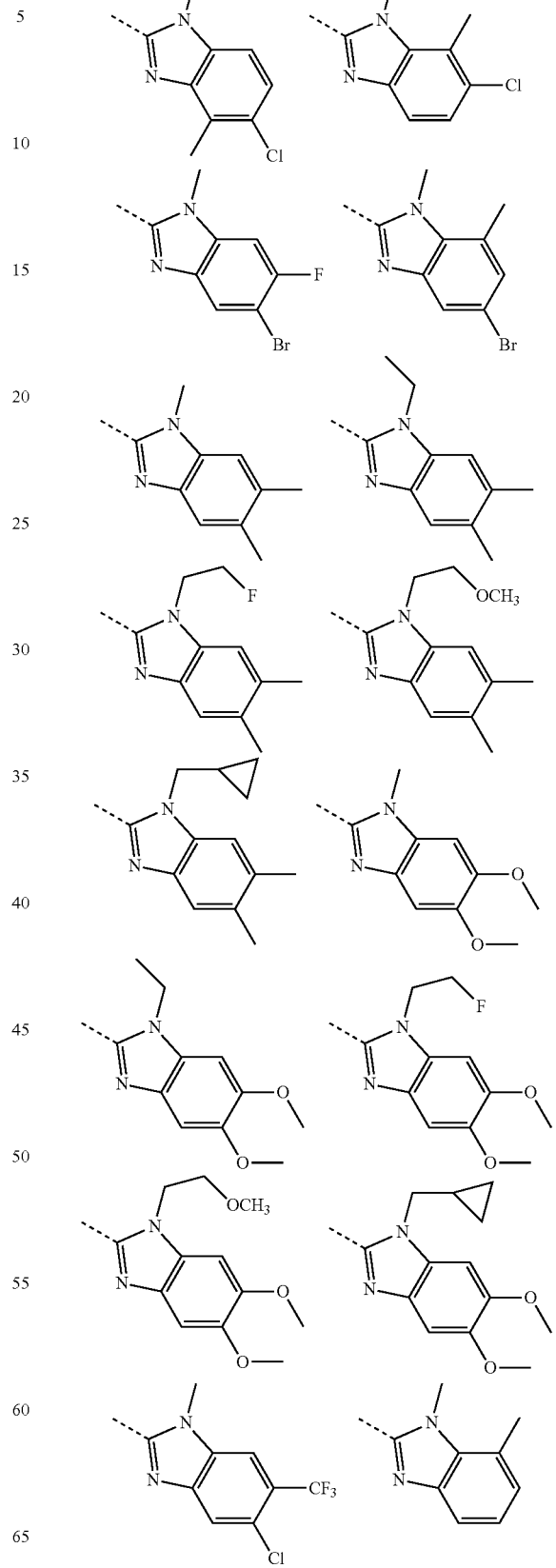

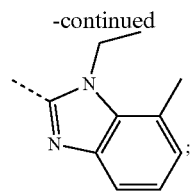

wherein it is understood that the benzimidazolyl moieties of groups A and B may be present in form of tautomers; and wherein the groups listed in group A are preferred groups.

40) Another embodiment relates to compounds of formula (I) according to any one of embodiments 1) to 14); wherein R² represents methyl; and R³, R⁴ᵃ, and R⁴ᵇ represent hydrogen (in which case the present embodiment is a particular embodiment for the compounds of formula (V) below); or R³ represents methyl; and R², R⁴ᵃ, and R⁴ᵇ represent hydrogen (in which case the present embodiment is a particular embodiment for the compounds of formula (VI) below);

the fragment

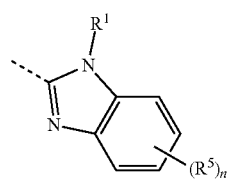

represents a fragment

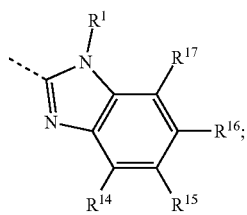

wherein

R¹ represents hydrogen; and

R¹⁴, R¹⁵, R¹⁶ and R¹⁷ together represent one or two substituents [i.e. at least two of R¹⁴, R¹⁵, R¹⁶ and R¹⁷ are hydrogen and at least one of R¹⁴, R¹⁵, R¹⁶ and R¹⁷ is different from hydrogen]; wherein one of R¹⁵ and R¹⁶ represents methyl, methoxy, fluorine, chlorine, bromine, trifluoromethyl, or trifluoromethoxy;

one of R¹⁴ and R¹⁷, or the remaining of R¹⁵ and R¹⁶, represents hydrogen, methyl, methoxy, fluorine, or chlorine;

and the remaining of R¹⁴, R¹⁵, R¹⁶ and R¹⁷ represent hydrogen;

wherein, in a sub-embodiment, particular benzimidazole fragments are independently selected from the following groups:

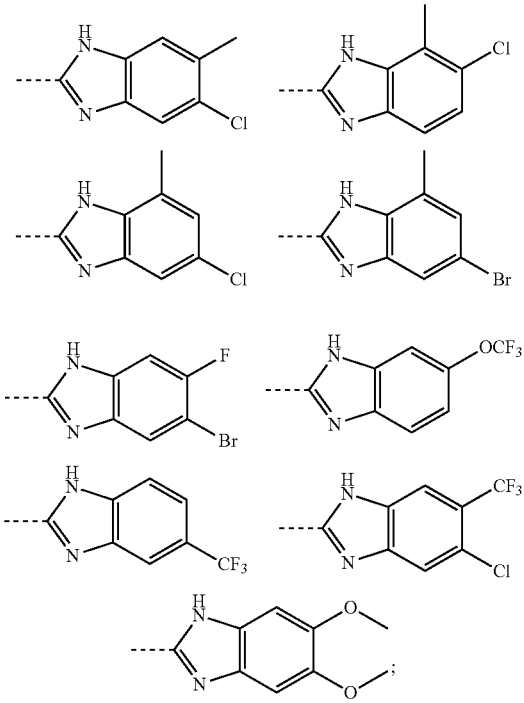

wherein it is understood that said benzimidazolyl moieties may be present in form of tautomers;

and

Ar¹ is as defined in any one of embodiments 21) to 26);

wherein, in a sub-embodiment, particular groups Ar¹ are independently selected from the following groups A, B, C, D, or E:

A.

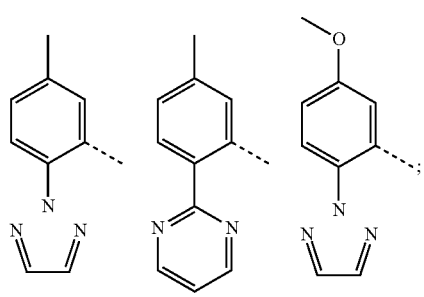

B.

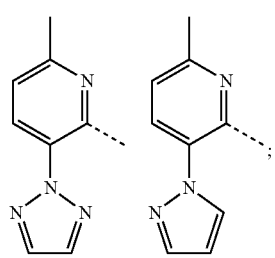

C.

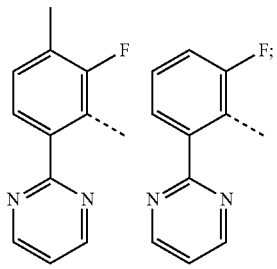

D.

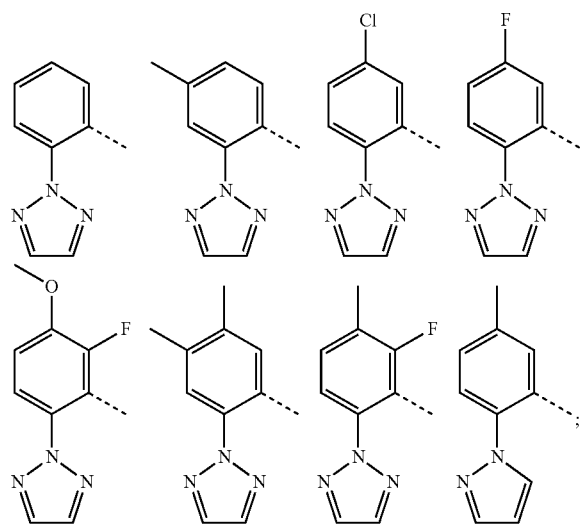

E.

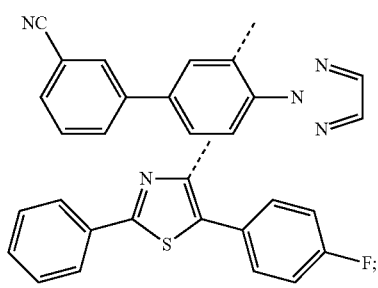

wherein, in a further sub-embodiment, Ar$^1$ is group is especially selected from the groups listed in group A.

41) Another embodiment relates to compounds of formula (I) according to any one of embodiments 1) to 14); wherein
R$^2$ represents methyl; and R$^3$, R$^{4a}$, and R$^{4b}$ represent hydrogen (in which case the present embodiment is a particular embodiment for the compounds of formula (V) below); or
R$^3$ represents methyl; and R$^2$, R$^{4a}$, and R$^{4b}$ represent hydrogen (in which case the present embodiment is a particular embodiment for the compounds of formula (VI) below);

the fragment

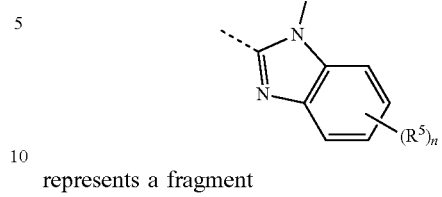

represents a fragment

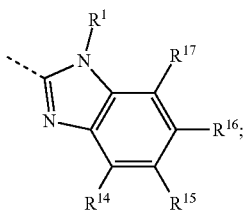

wherein
R$^1$ represents hydrogen; and
R$^{14}$, R$^{15}$, R$^{16}$ and R$^{17}$ are as follows:
  R$^{15}$ represents chlorine and R$^{16}$ represents methyl, or R$^{16}$ represents chlorine and R$^{15}$ represents methyl, and R$^{14}$ and R$^{17}$ represent hydrogen;
  or R$^{15}$ represents chlorine and R$^{14}$ represents methyl, or R$^{16}$ represents chlorine and R$^{17}$ represents methyl, and the remaining of R$^{14}$, R$^{15}$, R$^{16}$ and R$^{17}$ represent hydrogen;
  or R$^{16}$ represents chlorine and R$^{14}$ represents methyl, or R$^{15}$ represents chlorine and R$^{17}$ represents methyl, and the remaining of R$^{14}$, R$^{15}$, R$^{16}$ and R$^{17}$ represent hydrogen;
  R$^{15}$ represents bromine and R$^{16}$ represents fluorine, or R$^{16}$ represents bromine and R$^{15}$ represents fluorine, and R$^{14}$ and R$^{17}$ represent hydrogen;
  or R$^{16}$ represents bromine and R$^{14}$ represents methyl, or R$^{15}$ represents bromine and R$^{17}$ represents methyl, and the remaining of R$^{14}$, R$^{15}$, R$^{16}$ and R$^{17}$ represent hydrogen;
  or R$^{15}$ and R$^{16}$ both represent methoxy, and R$^{14}$ and R$^{17}$ represent hydrogen;
  or one of R$^{15}$ and R$^{16}$ represents trifluoromethyl, the remaining of R$^{15}$ and R$^{16}$ represents hydrogen or chlorine; and R$^{14}$ and R$^{17}$ represent hydrogen;
  or one of R$^{15}$ and R$^{16}$ represents trifluoromethoxy, and the remaining of R$^{15}$ and R$^{16}$, and R$^{14}$ and R$^{17}$ represent hydrogen;
wherein, in a sub-embodiment, particular benzimidazole fragments are independently selected from the following groups:

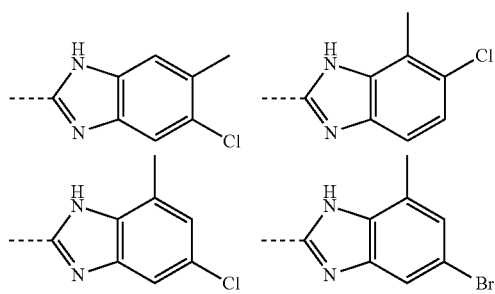

-continued

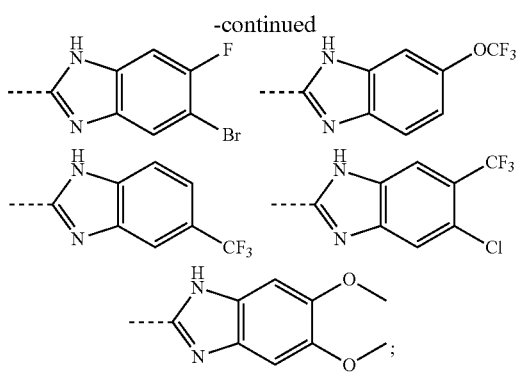

wherein it is understood that said benzimidazolyl moieties may be present in form of tautomers;

and

Ar¹ is as defined in any one of embodiments 21) to 26);

wherein, in a sub-embodiment, particular groups for Ar¹ are independently selected from the following groups A, B, C, D, or E:

A.

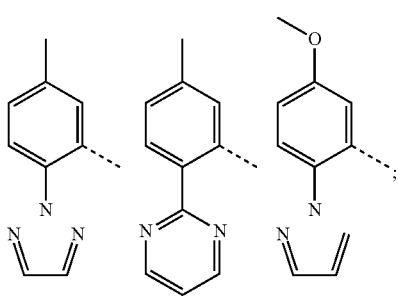

B.

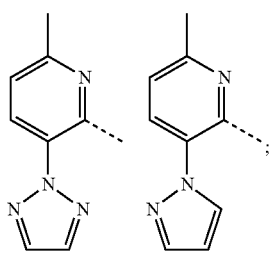

C.

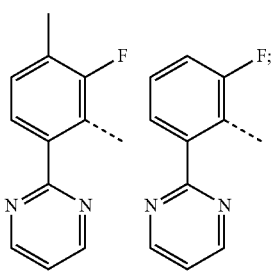

D.

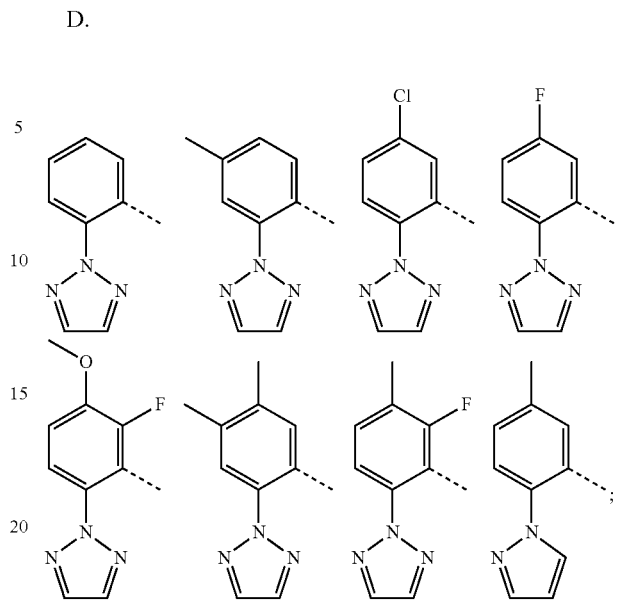

E.

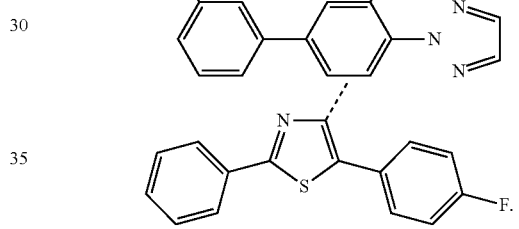

wherein, in a further sub-embodiment, Ar¹ is group is especially selected from the groups listed in group A.

42) The invention, thus, relates to compounds of the formula (I) as defined in embodiment 1), compounds of the formula (II) as defined in embodiment 2), compounds of the formula (III) as defined in embodiment 3); or to such compounds further limited by the characteristics of any one of embodiments 6) to 41), under consideration of their respective dependencies; to pharmaceutically acceptable salts thereof; and to the use of such compounds as medicaments especially in the treatment of mental health disorders relating to orexinergic dysfunctions, which disorders are as defined below and which are especially selected from sleep disorders, anxiety disorders, addiction disorders, cognitive dysfunctions, mood disorders, or appetite disorders. For avoidance of any doubt, especially the following embodiments relating to the compounds of formula (I), (II), and (III) are thus possible and intended and herewith specifically disclosed in individualized form:

1, 6+1, 17+1, 17+6+1, 18+1, 18+6+1, 19+1, 19+6+1, 19+17+1, 19+17+6+1, 19+18+1, 19+18+6+1, 22+1, 22+6+1, 22+17+1, 22+17+6+1, 22+18+1, 22+18+6+1, 22+19+1, 22+19+6+1, 22+19+17+1, 22+19+17+6+1, 22+19+18+1, 22+19+18+6+1, 23+1, 23+6+1, 23+17+1, 23+17+6+1, 23+18+1, 23+18+6+1, 23+19+1, 23+19+6+1, 23+19+17+1, 23+19+17+6+1, 23+19+18+1, 23+19+18+6+1, 24+1, 24+6+1, 24+17+1, 24+17+6+1, 24+18+1, 24+18+6+1, 24+19+1,

24+19+6+1, 24+19+17+1, 24+19+17+6+1, 24+19+18+1, 24+19+18+6+1, 24+22+1, 24+22+6+1, 24+22+17+1, 24+22+17+6+1, 24+22+18+1, 24+22+18+6+1, 24+22+19+1, 24+22+19+6+1, 24+22+19+17+1, 24+22+19+17+6+1, 24+22+19+18+1, 24+22+19+18+6+1, 24+23+1, 24+23+6+1, 24+23+17+1, 24+23+17+6+1, 24+23+18+1, 24+23+18+6+1, 24+23+19+1, 24+23+19+6+1, 24+23+19+17+1, 24+23+19+17+6+1, 24+23+19+18+1, 24+23+19+18+6+1, 25+1, 25+6+1, 25+17+1, 25+17+6+1, 25+18+1, 25+18+6+1, 25+19+1, 25+19+6+1, 25+19+17+1, 25+19+17+6+1, 25+19+18+1, 25+19+18+6+1, 25+22+1, 25+22+6+1, 25+22+17+1, 25+22+17+6+1, 25+22+18+1, 25+22+18+6+1, 25+22+19+1, 25+22+19+6+1, 25+22+19+17+1, 25+22+19+17+6+1, 25+22+19+18+1, 25+22+19+18+6+1, 25+23+1, 25+23+6+1, 25+23+17+1, 25+23+17+6+1, 25+23+18+1, 25+23+18+6+1, 25+23+19+1, 25+23+19+6+1, 25+23+19+17+1, 25+23+19+17+6+1, 25+23+19+18+1, 25+23+19+18+6+1, 25+24+1, 25+24+6+1, 25+24+17+1, 25+24+17+6+1, 25+24+18+1, 25+24+18+6+1, 25+24+19+1, 25+24+19+6+1, 25+24+19+17+1, 25+24+19+17+6+1, 25+24+19+18+1, 25+24+19+18+6+1, 25+24+22+1, 25+24+22+6+1, 25+24+22+17+1, 25+24+22+17+6+1, 25+24+22+18+1, 25+24+22+18+6+1, 25+24+22+19+1, 25+24+22+19+6+1, 25+24+22+19+17+1, 25+24+22+19+17+6+1, 25+24+22+19+18+1, 25+24+22+19+18+6+1, 25+24+23+1, 25+24+23+6+1, 25+24+23+17+1, 25+24+23+17+6+1, 25+24+23+18+1, 25+24+23+18+6+1, 25+24+23+19+1, 25+24+23+19+6+1, 25+24+23+19+17+1, 25+24+23+19+17+6+1, 25+24+23+19+18+1, 25+24+23+19+18+6+1, 26+1, 26+6+1, 26+17+1, 26+17+6+1, 26+18+1, 26+18+6+1, 26+19+1, 26+19+6+1, 26+19+17+1, 26+19+17+6+1, 26+19+18+1, 26+19+18+6+1, 39+1, 39+6+1, 39+22+1, 39+22+6+1, 39+23+1, 39+23+6+1, 39+24+1, 39+24+6+1, 39+24+22+1, 39+24+22+6+1, 39+24+23+1, 39+24+23+6+1, 39+25+1, 39+25+6+1, 39+25+22+1, 39+25+22+6+1, 39+25+23+1, 39+25+23+6+1, 39+25+24+1, 39+25+24+6+1, 39+25+24+22+1, 39+25+24+22+6+1, 39+25+24+23+1, 39+25+24+23+6+1, 39+26+1, 39+26+6+1, 39+26+10+1, 39+26+13+1, 40+1, 41+1;

2, 6+2, 17+2, 17+6+2, 18+2, 18+6+2, 19+2, 19+6+2, 19+17+2, 19+17+6+2, 19+18+2, 19+18+6+2, 22+2, 22+6+2, 22+17+2, 22+17+6+2, 22+18+2, 22+18+6+2, 22+19+2, 22+19+6+2, 22+19+17+2, 22+19+17+6+2, 22+19+18+2, 22+19+18+6+2, 23+2, 23+6+2, 23+17+2, 23+17+6+2, 23+18+2, 23+18+6+2, 23+19+2, 23+19+6+2, 23+19+17+2, 23+19+17+6+2, 23+19+18+2, 23+19+18+6+2, 24+2, 24+6+2, 24+17+2, 24+17+6+2, 24+18+2, 24+18+6+2, 24+19+2, 24+19+6+2, 24+19+17+2, 24+19+17+6+2, 24+19+18+2, 24+19+18+6+2, 24+22+2, 24+22+6+2, 24+22+17+2, 24+22+17+6+2, 24+22+18+2, 24+22+18+6+2, 24+22+19+2, 24+22+19+6+2, 24+22+19+17+2, 24+22+19+17+6+2, 24+22+19+18+2, 24+22+19+18+6+2, 24+23+2, 24+23+6+2, 24+23+17+2, 24+23+17+6+2, 24+23+18+2, 24+23+18+6+2, 24+23+19+2, 24+23+19+6+2, 24+23+19+17+2, 24+23+19+17+6+2, 24+23+19+18+2, 24+23+19+18+6+2, 25+2, 25+6+2, 25+17+2, 25+17+6+2, 25+18+2, 25+18+6+2, 25+19+2, 25+19+6+2, 25+19+17+2, 25+19+17+6+2, 25+19+18+2, 25+19+18+6+2, 25+22+2, 25+22+6+2, 25+22+17+2, 25+22+17+6+2, 25+22+18+2, 25+22+18+6+2, 25+22+19+2, 25+22+19+6+2, 25+22+19+17+2, 25+22+19+17+6+2, 25+22+19+18+2, 25+22+19+18+6+2, 25+23+2, 25+23+6+2, 25+23+17+2, 25+23+17+6+2, 25+23+18+2, 25+23+18+6+2, 25+23+19+2, 25+23+19+6+2, 25+23+19+17+2, 25+23+19+17+6+2, 25+23+19+18+2, 25+23+19+18+6+2, 25+24+2, 25+24+6+2, 25+24+17+2, 25+24+17+6+2, 25+24+18+2, 25+24+18+6+2, 25+24+19+2, 25+24+19+6+2, 25+24+19+17+2, 25+24+19+17+6+2, 25+24+19+18+2, 25+24+19+18+6+2, 25+24+22+2, 25+24+22+6+2, 25+24+22+17+2, 25+24+22+17+6+2, 25+24+22+18+2, 25+24+22+18+6+2, 25+24+22+19+2, 25+24+22+19+6+2, 25+24+22+19+17+2, 25+24+22+19+17+6+2, 25+24+22+19+18+2, 25+24+22+19+18+6+2, 25+24+23+2, 25+24+23+6+2, 25+24+23+17+2, 25+24+23+17+6+2, 25+24+23+18+2, 25+24+23+18+6+2, 25+24+23+19+2, 25+24+23+19+6+2, 25+24+23+19+17+2, 25+24+23+19+17+6+2, 25+24+23+19+18+2, 25+24+23+19+18+6+2, 26+2, 26+6+2, 26+17+2, 26+17+6+2, 26+18+2, 26+18+6+2, 26+19+2, 26+19+6+2, 26+19+17+2, 26+19+17+6+2, 26+19+18+2, 26+19+18+6+2, 37+34+26+10+2, 37+34+26+13+2, 39+2, 39+6+2, 39+22+2, 39+22+6+2, 39+23+2, 39+23+6+2, 39+24+2, 39+24+6+2, 39+24+22+2, 39+24+22+6+2, 39+24+23+2, 39+24+23+6+2, 39+25+2, 39+25+6+2, 39+25+22+2, 39+25+22+6+2, 39+25+23+2, 39+25+23+6+2, 39+25+24+2, 39+25+24+6+2, 39+25+24+22+2, 39+25+24+22+6+2, 39+25+24+23+2, 39+25+24+23+6+2, 39+26+2, 39+26+6+2, 39+26+10+2, 39+26+13+2, 40+2, 41+2;

3, 24+23+3, 25+23+3, 25+24+3, 25+24+23+3, 37+34+25+24+23+3.

In the list above the numbers refer to the embodiments according to their numbering provided hereinabove whereas "+" indicates the dependency from another embodiment. The different individualized embodiments are separated by commas. In other words, "39+26+6+2" for example refers to embodiment 39) depending on embodiment 26), depending on embodiment 6), depending on embodiment 2), i.e. embodiment "39+26+6+2" corresponds to the compounds of formula (II) according to embodiment 2) further limited by all the features of the embodiments 6), 26), and 39).

43) A further aspect of the invention relates to compounds of the formula (I) according to embodiment 1), which are also compounds of the formula (IV); wherein the absolute configuration is as depicted in formula (IV):

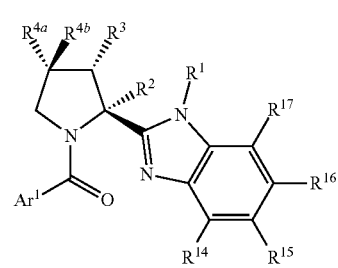

Formula (IV)

wherein
Ar$^1$ represents 5-membered heteroaryl selected from oxazolyl, thienyl, and thiazolyl (especially thiazolyl), wherein said 5-membered heteroaryl is mono- or di-substituted; wherein
one of said substituents is attached in ortho-position to the point of attachment of Ar$^1$ to the rest of the molecule; wherein said ortho-substituent is phenyl, or pyridyl, which phenyl or pyridyl is independently unsubstituted, mono-, or di-substituted, wherein the substituents are independently selected from $(C_{1-4})$alkyl, $(C_{1-4})$alkoxy, halogen, and $(C_{1-3})$fluoroalkyl, [wherein phenyl is especially unsubstituted, mono-, or di-substituted with methyl, ethyl, methoxy, halogen or trifluoromethyl; and pyridyl is mono-substituted with methoxy];
and the other of said substituents, if present, is independently selected from methyl; cyclopropyl; dimethylamino; pyrrolidin-1-yl; and phenyl which is unsubstituted, or mono- or di-substituted, wherein the substituents are independently selected from methyl, methoxy, cyano, and halogen (especially the other of said substituents represents methyl or cyclopropyl);

or $Ar^1$ represents 6-membered heteroaryl selected from pyridinyl, pyrazinyl, and pyrimidinyl (especially pyridinyl), wherein said 6-membered heteroaryl is mono- or di-substituted; wherein
one of said substituents is attached in ortho-position to the point of attachment of $Ar^1$ to the rest of the molecule; wherein
said ortho-substituent is pyrazol-1-yl or [1,2,3]triazol-2-yl;
or said ortho-substituent is phenyl which is unsubstituted, mono-, or di-substituted, wherein the substituents are independently selected from methyl, methoxy, halogen and trifluoromethyl;
and the other of said substituents, if present, is methyl;

or $Ar^1$ represents phenyl which is mono-, di-, or tri-substituted; wherein
one of said substituents is attached in ortho-position to the point of attachment of $Ar^1$ to the rest of the molecule; wherein
said ortho-substituent is phenyl which is unsubstituted, mono-, or di-substituted, wherein the substituents are independently selected from methyl, methoxy, halogen, cyano, trifluoromethyl, and trifluoromethoxy;
or said ortho substituent is benzo[1,3]dioxol-5-yl;
or said ortho substituent is 2-(3-methoxy-phenyl)-ethynyl
or said ortho-substituent is unsubstituted pyrimidinyl or pyridinyl;
or said ortho-substituent is unsubstituted pyrazol-1-yl or [1,2,3]triazol-2-yl; or oxadiazolyl or thiazolyl, optionally mono-substituted with methyl (especially unsubstituted pyrazol-1-yl or [1,2,3]triazol-2-yl);
and the other of said substituents, if present, is/are independently selected from methyl, methoxy, halogen, cyano, trifluoromethyl, trifluoromethoxy, unsubstituted pyridinyl, and phenyl optionally mono-substituted with cyano [especially methyl, methoxy, and halogen];

one of $R^2$ and $R^3$ represents hydrogen, the other of $R^2$ and $R^3$ represents hydrogen or methyl; and $R^{4a}$ and $R^{4b}$ independently represent hydrogen or fluorine; or $R^{4a}$ represents methoxy and $R^{4b}$ represents hydrogen; or $R^{4a}$ and $R^{4b}$ together represent a group $H_2C=$;

wherein, in case $R^3$ is different from hydrogen, both $R^{4a}$ and $R^{4b}$ represent hydrogen; (notably one of $R^2$ and $R^3$ represents hydrogen, the other of $R^2$ and $R^3$ represents methyl, and $R^{4a}$ and $R^{4b}$ both represent hydrogen)

$R^1$ represents hydrogen, methyl, ethyl, cyclopropyl-methyl, 2-fluoro-ethyl or 2-methoxy-ethyl (especially hydrogen); and $R^{14}$, $R^{15}$, $R^{16}$ and $R^{17}$ together represent one to three optional substituents (i.e. at least one of $R^{14}$, $R^{15}$, $R^{16}$ and $R^{17}$ is hydrogen) [notably $R^{14}$, $R^{15}$, $R^{16}$ and $R^{17}$ together represent one to three substituents (i.e. at least one of $R^{14}$, $R^{15}$, $R^{16}$ and $R^{17}$ is hydrogen and at least one of $R^{14}$, $R^{15}$, $R^{16}$ and $R^{17}$ is different from hydrogen)], wherein $R^{14}$ and $R^{17}$ independently represent hydrogen, $(C_{1-4})$ alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-4})$alkoxy-carbonyl- (especially $H_3CO—CO—$), hydroxy-$(C_{1-4})$ alkyl-(especially $HO—CH_2—$), hydroxy, or nitro; and $R^{15}$ and $R^{16}$ independently represent hydrogen, $(C_{1-4})$ alkyl, $(C_{1-4})$alkoxy (especially methoxy), $(C_{1-4})$alkyl-thio- (especially $H_3C—S—$), halogen, $(C_{1-3})$fluoroalkyl (especially trifluoromethyl), $(C_{1-3})$fluoroalkoxy (especially trifluoromethoxy), $(C_{1-3})$fluoroalkyl-thio- (especially $F_3C—S—$), hydroxy-$(C_{1-4})$alkyl- (especially $HO—CH_2—$), or cyano;

or $R^{14}$ and $R^{15}$ together, or $R^{16}$ and $R^{17}$ together, represent a group $—O—CH_2—CH_2—O—$;

or $R^{15}$ and $R^{16}$ together represent a fused phenyl group which, together with the benzimidazole moiety to which it is fused to, forms a 1H-naphtho[2,3-d]imidazol-2-yl group;

with the exception of
[(S)-2-(1H-benzimidazol-2-yl)-1-pyrrolidinyl][2-(1H-pyrazol-1-yl)phenyl]-methanone; and
[(S)-2-(1H-benzimidazol-2-yl)-1-pyrrolidinyl][1,1'-biphenyl]-2-yl-methanone;

wherein all characteristics disclosed in embodiments 4) to 42) are intended to apply mutatis mutandis also to the compounds formula (IV) according to embodiment 43); wherein especially the following embodiments are thus possible and intended and herewith specifically disclosed in individualized form:

43, 10+43, 13+43, 18+10+43, 18+13+43, 18+43, 19+10+43, 19+13+43, 19+18+10+43, 19+18+13+43, 19+18+43, 19+43, 26+10+43, 26+13+43, 26+18+10+43, 26+18+13+43, 26+18+43, 26+19+10+43, 26+19+13+43, 26+19+18+10+43, 26+19+18+13+43, 26+19+18+43, 26+19+43, 26+43, 39+10+43, 39+13+43, 39+18+10+43, 39+18+13+43, 39+18+43, 39+19+10+43, 39+19+13+43, 39+19+18+10+43, 39+19+18+13+43, 39+19+18+43, 39+19+43, 39+26+10+43, 39+26+13+43, 39+26+18+10+43, 39+26+18+13+43, 39+26+18+43, 39+26+19+10+43, 39+26+19+13+43, 39+26+19+18+10+43, 39+26+19+18+13+43, 39+26+19+18+43, 39+26+19+43, 39+26+43, 39+43.

In the list above the numbers refer to the embodiments according to their numbering provided hereinabove whereas "+" indicates the dependency from another embodiment as outlined above.

44) A preferred aspect of the invention relates to compounds of the formula (I) according to embodiment 1), which are also compounds of the formula (V); wherein the absolute configuration is as depicted in formula (V):

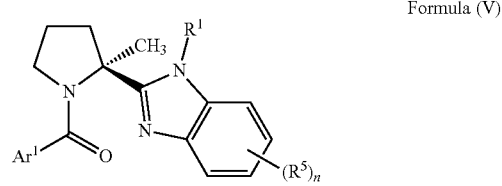

Formula (V)

wherein
$Ar^1$ represents
phenyl or 5- or 6-membered heteroaryl, wherein said phenyl or 5- or 6-membered heteroaryl independently is mono-, di-, or tri-substituted; wherein
one of said substituents is attached in ortho-position to the point of attachment of $Ar^1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from $(C_{1-4})$alkyl, $(C_{1-4})$alkoxy, halogen, cyano, $(C_{1-3})$fluoroalkyl, and $(C_{1-3})$fluoroalkoxy; or said ortho substituent is benzo[1,3]dioxolyl;

and the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$fluoroalkoxy; —$NR^{10}R^{11}$, wherein $R^{10}$ and $R^{11}$ independently represent hydrogen or $(C_{1-4})$alkyl, or $R^{10}$ and $R^{11}$ together with the nitrogen to which they are attached to form a pyrrolidine ring; unsubstituted pyridinyl; and phenyl which is unsubstituted, or mono- or di-substituted, wherein the substituents are independently selected from $(C_{1-4})$alkyl, $(C_{1-4})$alkoxy, cyano, and halogen;

$R^1$ represents hydrogen, $(C_{1-4})$alkyl (especially methyl or ethyl), $(C_{3-6})$cycloalkyl-($CH_2$)— (especially cyclopropylmethyl), $(C_{2-3})$fluoroalkyl (especially 2-fluoro-ethyl), or $(C_{1-4})$alkoxy-$(C_{2-4})$alkyl (especially 2-methoxy-ethyl); and $(R^5)_n$ represents one to three optional substituents (i.e. n represents the integer 0, 1, 2, or 3) independently selected from $(C_{1-4})$alkyl, $(C_{1-4})$alkoxy (especially methoxy), halogen, $(C_{1-4})$alkyl-thio- (especially $H_3C$—S—), $(C_{1-3})$fluoroalkyl (especially trifluoromethyl), $(C_{1-3})$fluoroalkoxy (especially trifluoromethoxy), $(C_{1-3})$fluoroalkyl-thio- (especially $F_3C$—S—), hydroxy-$(C_{1-4})$alkyl- (especially HO—$CH_2$—), $(C_{1-4})$alkoxy-carbonyl- (especially $H_3CO$—CO—), nitro, hydroxy, and cyano; or $(R^5)_n$ represents a group —O—$CH_2$—$CH_2$—O—.

wherein all characteristics disclosed in embodiments 15) to 42) are intended to apply mutatis mutandis also to the compounds formula (V) according to embodiment 44); wherein especially the following embodiments are thus possible and intended and herewith specifically disclosed in individualized form:
44, 17+44, 18+44, 19+17+44, 19+18+44, 19+44, 22+17+44, 22+18+44, 22+19+17+44, 22+19+18+44, 22+19+44, 22+44, 23+17+44, 23+18+44, 23+19+17+44, 23+19+18+44, 23+19+44, 23+44, 24+17+44, 24+18+44, 24+19+17+44, 24+19+18+44, 24+19+44, 24+22+17+44, 24+22+18+44, 24+22+19+17+44, 24+22+19+18+44, 24+22+19+44, 24+22+44, 24+23+17+44, 24+23+18+44, 24+23+19+17+44, 24+23+19+18+44, 24+23+19+44, 24+23+44, 24+44, 25+17+44, 25+18+44, 25+19+17+44, 25+19+18+44, 25+19+44, 25+22+17+44, 25+22+18+44, 25+22+19+17+44, 25+22+19+18+44, 25+22+19+44, 25+22+44, 25+23+17+44, 25+23+18+44, 25+23+19+17+44, 25+23+19+18+44, 25+23+19+44, 25+23+44, 25+24+17+44, 25+24+18+44, 25+24+19+17+44, 25+24+19+18+44, 25+24+19+44, 25+24+22+17+44, 25+24+22+18+44, 25+24+22+19+17+44, 25+24+22+19+18+44, 25+24+22+19+44, 25+24+22+44, 25+24+23+17+44, 25+24+23+18+44, 25+24+23+19+17+44, 25+24+23+19+18+44, 25+24+23+19+44, 25+24+23+44, 25+24+44, 25+44, 26+17+44, 26+18+44, 26+19+17+44, 26+19+18+44, 26+19+44, 26+44, 39+22+44, 39+23+44, 39+24+22+44, 39+24+23+44, 39+24+44, 39+25+22+44, 39+25+23+44, 39+25+24+22+44, 39+25+24+23+44, 39+25+24+44, 39+25+44, 39+26+44, 39+44, 40+44, 41+44.

In the list above the numbers refer to the embodiments according to their numbering provided hereinabove whereas "+" indicates the dependency from another embodiment as outlined above.

45) Another preferred aspect of the invention relates to compounds of the formula (I) according to embodiment 1), which are also compounds of the formula (VI); wherein the absolute configuration is as depicted in formula (VI):

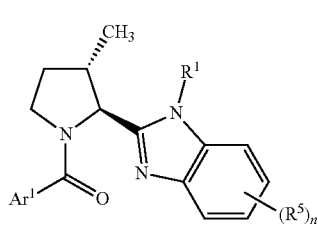

Formula (VI)

wherein $Ar^1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of $Ar^1$ to the rest of the molecule; wherein said substituent is phenyl or 5- or 6-membered heteroaryl, wherein said phenyl or 5- or 6-membered heteroaryl substituent is independently unsubstituted, mono-, di-, or tri-substituted, wherein the substituents are independently selected from $(C_{1-4})$alkyl, $(C_{1-4})$alkoxy, halogen, cyano, $(C_{1-3})$fluoroalkyl, and $(C_{1-3})$fluoroalkoxy; or said ortho substituent is benzo[1,3]dioxolyl;

and the other of said substituents, if present, is/are independently selected from $(C_{1-4})$alkyl; $(C_{1-4})$alkoxy; $(C_{3-6})$cycloalkyl; halogen; cyano; $(C_{1-3})$fluoroalkyl; $(C_{1-3})$fluoroalkoxy; —$NR^{10}R^{11}$, wherein $R^{10}$ and $R^{11}$ independently represent hydrogen or $(C_{1-4})$alkyl, or $R^{10}$ and $R^{11}$ together with the nitrogen to which they are attached to form a pyrrolidine ring; unsubstituted pyridinyl; and phenyl which is unsubstituted, or mono- or di-substituted, wherein the substituents are independently selected from $(C_{1-4})$alkyl, $(C_{1-4})$alkoxy, cyano, and halogen;

$R^1$ represents hydrogen, $(C_{1-4})$alkyl (especially methyl or ethyl), $(C_{3-6})$cycloalkyl-($CH_2$)— (especially cyclopropylmethyl), $(C_{2-3})$fluoroalkyl (especially 2-fluoro-ethyl), or $(C_{1-4})$alkoxy-$(C_{2-4})$alkyl (especially 2-methoxy-ethyl); and $(R^5)_n$ represents one to three optional substituents (i.e. n represents the integer 0, 1, 2, or 3) independently selected from $(C_{1-4})$alkyl, $(C_{1-4})$alkoxy (especially methoxy), halogen, $(C_{1-4})$alkyl-thio- (especially $H_3C$—S—), $(C_{1-3})$fluoroalkyl (especially trifluoromethyl), $(C_{1-3})$fluoroalkoxy (especially trifluoromethoxy), $(C_{1-3})$fluoroalkyl-thio- (especially $F_3C$—S—), hydroxy-$(C_{1-4})$alkyl- (especially HO—$CH_2$—), $(C_{1-4})$alkoxy-carbonyl- (especially $H_3CO$—CO—), nitro, hydroxy, and cyano; or $(R^5)_n$ represents a group —O—$CH_2$—$CH_2$—O—.

wherein all characteristics disclosed in embodiments 15) to 42) are intended to apply mutatis mutandis also to the compounds formula (VI) according to embodiment 45); wherein especially the following embodiments are thus possible and intended and herewith specifically disclosed in individualized form:
45, 17+45, 18+45, 19+17+45, 19+18+45, 19+45, 22+17+45, 22+18+45, 22+19+17+45, 22+19+18+45, 22+19+45, 22+45, 23+17+45, 23+18+45, 23+19+17+45, 23+19+18+45, 23+19+45, 23+45, 24+17+45, 24+18+45, 24+19+17+45, 24+19+18+45, 24+19+45, 24+22+17+45, 24+22+18+45, 24+22+19+17+45, 24+22+19+18+45, 24+22+19+45, 24+22+45, 24+23+17+45, 24+23+18+45, 24+23+19+17+45, 24+23+19+18+45, 24+23+19+45, 24+23+45, 24+45, 25+17+45, 25+18+45, 25+19+17+45, 25+19+18+45, 25+19+45, 25+22+17+45, 25+22+18+45, 25+22+19+17+45, 25+22+19+18+45, 25+22+19+45, 25+22+45, 25+23+17+45, 25+23+18+45, 25+23+19+17+45, 25+23+19+18+45, 25+23+19+45, 25+23+45, 25+24+17+45, 25+24+18+45, 25+24+19+17+45, 25+24+19+18+45, 25+24+19+45, 25+24+22+17+45, 25+24+22+18+45, 25+24+22+19+17+45, 25+24+22+19+18+45, 25+24+22+19+45, 25+24+22+45, 25+24+23+17+45, 25+24+23+18+45, 25+24+23+19+17+45, 25+24+23+19+18+45, 25+24+23+19+45, 25+24+23+45, 25+24+45, 25+45, 26+17+45, 26+18+45, 26+19+17+45, 26+19+18+45, 26+19+45, 26+45, 39+22+45, 39+23+45, 39+24+22+45, 39+24+23+45, 39+24+45, 39+25+22+45, 39+25+23+45, 39+25+24+22+45, 39+25+24+23+45, 39+25+24+45, 39+25+45, 39+26+45, 39+45, 40+45, 41+45.

In the list above the numbers refer to the embodiments according to their numbering provided hereinabove whereas "+" indicates the dependency from another embodiment as outlined above.

46) Another embodiment relates to compounds according to embodiment 1) selected from:

[2-(5-Chloro-6-methyl-1H-benzoimidazol-2-yl)-pyrrolidin-1-yl]-[5-(3-chloro-phenyl)-2-methyl-thiazol-4-yl]-methanone;

[5-(3-Chloro-phenyl)-2-methyl-thiazol-4-yl]-[2-(4,6-dimethyl-1H-benzoimidazol-2-yl)-pyrrolidin-1-yl]-methanone;

[2-(4-Bromo-1H-benzoimidazol-2-yl)-pyrrolidin-1-yl]-[5-(3-chloro-phenyl)-2-methyl-thiazol-4-yl]-methanone;

[2-(5-Bromo-7-methyl-1H-benzoimidazol-2-yl)-pyrrolidin-1-yl]-[5-(3-chloro-phenyl)-2-methyl-thiazol-4-yl]-methanone;

[2-(5-Chloro-4-methyl-1H-benzoimidazol-2-yl)-pyrrolidin-1-yl]-[5-(3-chloro-phenyl)-2-methyl-thiazol-4-yl]-methanone;

[5-(3-Chloro-phenyl)-2-methyl-thiazol-4-yl]-[2-(6-chloro-5-trifluoromethyl-1H-benzoimidazol-2-yl)-pyrrolidin-1-yl]-methanone;

[2-(4-Bromo-6-fluoro-1H-benzoimidazol-2-yl)-pyrrolidin-1-yl]-[5-(3-chloro-phenyl)-2-methyl-thiazol-4-yl]-methanone;

[5-(3-Chloro-phenyl)-2-methyl-thiazol-4-yl]-[2-(4,5-dimethyl-1H-benzoimidazol-2-yl)-pyrrolidin-1-yl]-methanone;

[2-(5,6-Dichloro-1H-benzoimidazol-2-yl)-pyrrolidin-1-yl]-(2-methyl-5-phenyl-thiazol-4-yl)-methanone;

[2-(5-Chloro-6-methyl-1H-benzoimidazol-2-yl)-pyrrolidin-1-yl]-(2-methyl-5-phenyl-thiazol-4-yl)-methanone;

[2-(4,6-Dimethyl-1H-benzoimidazol-2-yl)-pyrrolidin-1-yl]-(2-methyl-5-phenyl-thiazol-4-yl)-methanone;

[5-(3-Chloro-phenyl)-2-methyl-thiazol-4-yl]-[(S)-2-(7-methylsulfanyl-1H-benzoimidazol-2-yl)-pyrrolidin-1-yl]-methanone;

[2-(5-Chloro-4-methyl-1H-benzoimidazol-2-yl)-pyrrolidin-1-yl]-(2-methyl-5-phenyl-thiazol-4-yl)-methanone;

[2-(6-Chloro-5-trifluoromethyl-1H-benzoimidazol-2-yl)-pyrrolidin-1-yl]-(2-methyl-5-phenyl-thiazol-4-yl)-methanone;

[(S)-2-(4,6-Dimethyl-1H-benzoimidazol-2-yl)-pyrrolidin-1-yl]-(2-methyl-5-phenyl-thiazol-4-yl)-methanone;

[(S)-2-(5-Chloro-6-methyl-1H-benzoimidazol-2-yl)-pyrrolidin-1-yl]-(2-methyl-5-phenyl-thiazol-4-yl)-methanone;

[(S)-2-(6-Bromo-4-methyl-1H-benzoimidazol-2-yl)-pyrrolidin-1-yl]-(2-methyl-5-phenyl-thiazol-4-yl)-methanone;

[(S)-2-(5-Chloro-4-methyl-1H-benzoimidazol-2-yl)-pyrrolidin-1-yl]-(2-methyl-5-phenyl-thiazol-4-yl)-methanone;

[(S)-2-(5-Chloro-6-trifluoromethyl-1H-benzoimidazol-2-yl)-pyrrolidin-1-yl]-(2-methyl-5-phenyl-thiazol-4-yl)-methanone;

[(S)-2-(6-Methylsulfanyl-1H-benzoimidazol-2-yl)-pyrrolidin-1-yl]-(4-methyl-2-[1,2,3]triazol-2-yl-phenyl)-methanone;

(4,5-Dimethoxy-2-[1,2,3]triazol-2-yl-phenyl)-[(S)-2-(6-methylsulfanyl-1H-benzoimidazol-2-yl)-pyrrolidin-1-yl]-methanone;

(5-Methoxy-2-[1,2,3]triazol-2-yl-phenyl)-[(S)-2-(7-methylsulfanyl-1H-benzoimidazol-2-yl)-pyrrolidin-1-yl]-methanone;

(2-Fluoro-3-methoxy-6-[1,2,3]triazol-2-yl-phenyl)-[(S)-2-(7-methylsulfanyl-1H-benzoimidazol-2-yl)-pyrrolidin-1-yl]-methanone;

[(S)-2-(7-Methylsulfanyl-1H-benzoimidazol-2-yl)-pyrrolidin-1-yl]-(4-methyl-2-[1,2,3]triazol-2-yl-phenyl)-methanone;

[(S)-2-(6-Methylsulfanyl-1H-benzoimidazol-2-yl)-pyrrolidin-1-yl]-(2-methyl-5-p-tolyl-thiazol-4-yl)-methanone;

[(S)-2-(7-Methylsulfanyl-1H-benzoimidazol-2-yl)-pyrrolidin-1-yl]-(5-methyl-2-[1,2,3]triazol-2-yl-phenyl)-methanone;

[4-(3-Chloro-phenyl)-2-methyl-pyrimidin-5-yl]-[(S)-2-(6-methylsulfanyl-1H-benzoimidazol-2-yl)-pyrrolidin-1-yl]-methanone;

[4-(3,4-Dimethyl-phenyl)-2-methyl-pyrimidin-5-yl]-[(S)-2-(6-methylsulfanyl-1H-benzoimidazol-2-yl)-pyrrolidin-1-yl]-methanone;

(2-Methyl-4-phenyl-pyrimidin-5-yl)-[(S)-2-(6-methylsulfanyl-1H-benzoimidazol-2-yl)-pyrrolidin-1-yl]-methanone;

[4-(4-Bromo-3-chloro-phenyl)-2-methyl-pyrimidin-5-yl]-[(S)-2-(6-methylsulfanyl-1H-benzoimidazol-2-yl)-pyrrolidin-1-yl]-methanone;

(2-Cyclopropyl-5-phenyl-thiazol-4-yl)-[(S)-2-(7-methylsulfanyl-1H-benzoimidazol-2-yl)-pyrrolidin-1-yl]-methanone;

[5-(3-Methoxy-phenyl)-2-methyl-thiazol-4-yl]-[(S)-2-(7-methylsulfanyl-1H-benzoimidazol-2-yl)-pyrrolidin-1-yl]-methanone;

[(S)-2-(7-Methylsulfanyl-1H-benzoimidazol-2-yl)-pyrrolidin-1-yl]-[2-methyl-5-(3-trifluoromethyl-phenyl)-thiazol-4-yl]-methanone;

[(S)-2-(7-Methylsulfanyl-1H-benzoimidazol-2-yl)-pyrrolidin-1-yl]-(2-methyl-5-p-tolyl-thiazol-4-yl)-methanone;

(2-Cyclopropyl-5-p-tolyl-thiazol-4-yl)-[(S)-2-(7-methylsulfanyl-1H-benzoimidazol-2-yl)-pyrrolidin-1-yl]-methanone;

[2-Cyclopropyl-5-(4-fluoro-phenyl)-thiazol-4-yl]-[(S)-2-(7-methylsulfanyl-1H-benzoimidazol-2-yl)-pyrrolidin-1-yl]-methanone;

(3',4'-Dimethyl-biphenyl-2-yl)-[(S)-2-(7-methylsulfanyl-1H-benzoimidazol-2-yl)-pyrrolidin-1-yl]-methanone;

[4-(3,4-Dichloro-phenyl)-2-methyl-pyrimidin-5-yl]-[(S)-2-(7-methylsulfanyl-1H-benzoimidazol-2-yl)-pyrrolidin-1-yl]-methanone;

[4-(3,4-Dichloro-phenyl)-pyrimidin-5-yl]-[(S)-2-(7-methylsulfanyl-1H-benzoimidazol-2-yl)-pyrrolidin-1-yl]-methanone;

[4-(3,4-Dimethyl-phenyl)-pyrimidin-5-yl]-[(S)-2-(7-methylsulfanyl-1H-benzoimidazol-2-yl)-pyrrolidin-1-yl]-methanone;

[4-(4-Bromo-3-chloro-phenyl)-pyrimidin-5-yl]-[(S)-2-(7-methylsulfanyl-1H-benzoimidazol-2-yl)-pyrrolidin-1-yl]-methanone;

[4-(3,4-Dimethyl-phenyl)-2-methyl-pyrimidin-5-yl]-[(S)-2-(7-methylsulfanyl-1H-benzoimidazol-2-yl)-pyrrolidin-1-yl]-methanone;

(2-Methyl-4-phenyl-pyrimidin-5-yl)-[(S)-2-(7-methylsulfanyl-1H-benzoimidazol-2-yl)-pyrrolidin-1-yl]-methanone;

[4-(4-Bromo-3-chloro-phenyl)-2-methyl-pyrimidin-5-yl]-[(S)-2-(7-methylsulfanyl-1H-benzoimidazol-2-yl)-pyrrolidin-1-yl]-methanone;

[4-(3,5-Dichloro-phenyl)-2-methyl-pyrimidin-5-yl]-[(S)-2-(7-methylsulfanyl-1H-benzoimidazol-2-yl)-pyrrolidin-1-yl]-methanone;

[5-(3-Chloro-phenyl)-2-methyl-thiazol-4-yl]-[2-(5,6-dichloro-1H-benzoimidazol-2-yl)-pyrrolidin-1-yl]-methanone;

[5-(3-Chloro-phenyl)-2-methyl-thiazol-4-yl]-[2-(5,6-dimethyl-1H-benzoimidazol-2-yl)-pyrrolidin-1-yl]-methanone;

[(2S,4R)-2-(5-Chloro-4-methyl-1H-benzoimidazol-2-yl)-4-fluoro-pyrrolidin-1-yl]-[5-(3-chloro-phenyl)-2-methyl-thiazol-4-yl]-methanone;

[(2S,4R)-2-(5-Chloro-4-methyl-1H-benzoimidazol-2-yl)-4-fluoro-pyrrolidin-1-yl]-(5-methyl-2-[1,2,3]triazol-2-yl-phenyl)-methanone;

[5-(3-Chloro-phenyl)-2-methyl-thiazol-4-yl]-[(2S,4R)-4-fluoro-2-(4-methyl-1H-benzoimidazol-2-yl)-pyrrolidin-1-yl]-methanone;

[(2S,4R)-2-(6-Chloro-7-methyl-1H-benzoimidazol-2-yl)-4-methoxy-pyrrolidin-1-yl]-(5-chloro-2-[1,2,3]triazol-2-yl-phenyl)-methanone;

[(2S,4R)-2-(6-Chloro-7-methyl-1H-benzoimidazol-2-yl)-4-methoxy-pyrrolidin-1-yl]-(2-fluoro-3-methoxy-6-[1,2,3]triazol-2-yl-phenyl)-methanone;

[(2S,4R)-2-(6-Chloro-7-methyl-1H-benzoimidazol-2-yl)-4-methoxy-pyrrolidin-1-yl]-(5-methoxy-2-[1,2,3]triazol-2-yl-phenyl)-methanone;

[(2S,4R)-2-(6-Chloro-7-methyl-1H-benzoimidazol-2-yl)-4-methoxy-pyrrolidin-1-yl]-(2-fluoro-3-methyl-6-[1,2,3]triazol-2-yl-phenyl)-methanone;

[(2S,4R)-2-(6-Chloro-7-methyl-1H-benzoimidazol-2-yl)-4-methoxy-pyrrolidin-1-yl]-(4,5-dimethyl-2-[1,2,3]triazol-2-yl-phenyl)-methanone;

[(2S,4R)-2-(5-Chloro-4-methyl-1H-benzoimidazol-2-yl)-4-methoxy-pyrrolidin-1-yl]-(5-methyl-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(2-methyl-5-phenyl-thiazol-4-yl)-methanone;

[(4R)-2-(5-Chloro-4-methyl-1H-benzoimidazol-2-yl)-4-methoxy-2-methyl-pyrrolidin-1-yl]-(5-methyl-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-[5-(3-chloro-phenyl)-2-methyl-thiazol-4-yl]-methanone;

[5-(3-Chloro-phenyl)-2-methyl-thiazol-4-yl]-[(4R)-4-methoxy-2-methyl-2-(4-methyl-1H-benzoimidazol-2-yl)-pyrrolidin-1-yl]-methanone;

[(4R)-4-Methoxy-2-methyl-2-(4-methyl-1H-benzoimidazol-2-yl)-pyrrolidin-1-yl]-(2-methyl-5-phenyl-thiazol-4-yl)-methanone;

[(2S,4R)-2-(5-Chloro-4-methyl-1H-benzoimidazol-2-yl)-4-methoxy-2-methyl-pyrrolidin-1-yl]-(5-methyl-2-[1,2,3]triazol-2-yl-phenyl)-methanone;

[(2S,4R)-2-(5-Chloro-4-methyl-1H-benzoimidazol-2-yl)-4-methoxy-2-methyl-pyrrolidin-1-yl]-[5-(3-chloro-phenyl)-2-methyl-thiazol-4-yl]-methanone;

[(2S,4R)-2-(6-Chloro-7-methyl-1H-benzoimidazol-2-yl)-4-methoxy-pyrrolidin-1-yl]-(2-methyl-5-m-tolyl-thiazol-4-yl)-methanone;

[(2S,4R)-2-(6-Chloro-7-methyl-1H-benzoimidazol-2-yl)-4-methoxy-pyrrolidin-1-yl]-[2-dimethylamino-5-(3,4-dimethyl-phenyl)-thiazol-4-yl]-methanone;

[(2S,4R)-2-(6-Chloro-7-methyl-1H-benzoimidazol-2-yl)-4-methoxy-pyrrolidin-1-yl]-[5-(3,4-dimethyl-phenyl)-2-methyl-thiazol-4-yl]-methanone;

[(2S,4R)-2-(6-Chloro-7-methyl-1H-benzoimidazol-2-yl)-4-methoxy-pyrrolidin-1-yl]-[5-(4-chloro-phenyl)-2-methyl-thiazol-4-yl]-methanone;

[(2S,4R)-2-(6-Chloro-7-methyl-1H-benzoimidazol-2-yl)-4-methoxy-pyrrolidin-1-yl]-(2-methyl-5-p-tolyl-thiazol-4-yl)-methanone;

[(2S,4R)-2-(6-Chloro-7-methyl-1H-benzoimidazol-2-yl)-4-methoxy-pyrrolidin-1-yl]-[5-(4-methoxy-phenyl)-2-methyl-thiazol-4-yl]-methanone;

[(2S,4R)-2-(6-Chloro-7-methyl-1H-benzoimidazol-2-yl)-4-methoxy-pyrrolidin-1-yl]-(3',4'-dimethyl-biphenyl-2-yl)-methanone;

[(2S,4R)-4-Methoxy-2-(4-methyl-1H-benzoimidazol-2-yl)-pyrrolidin-1-yl]-(2-methyl-5-phenyl-thiazol-4-yl)-methanone;

[(2S,4R)-2-(6-Chloro-7-methyl-1H-benzoimidazol-2-yl)-4-methoxy-pyrrolidin-1-yl]-(4'-fluoro-3'-methyl-biphenyl-2-yl)-methanone;

[(2S,4R)-2-(6-Chloro-7-methyl-1H-benzoimidazol-2-yl)-4-methoxy-pyrrolidin-1-yl]-[5-(3-chloro-phenyl)-2-dimethylamino-thiazol-4-yl]-methanone;

[(4R)-2-(5-Chloro-4-methyl-1H-benzoimidazol-2-yl)-4-methoxy-2-methyl-pyrrolidin-1-yl]-(5-fluoro-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(5-chloro-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(4,5-dimethyl-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(4-methyl-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(4,5-dimethoxy-2-[1,2,3]triazol-2-yl-phenyl)-methanone;

[(4R)-2-(5-Chloro-4-methyl-1H-benzoimidazol-2-yl)-4-methoxy-2-methyl-pyrrolidin-1-yl]-(5-methyl-2-pyrazol-1-yl-phenyl)-methanone;

[(4R)-2-(5-Chloro-4-methyl-1H-benzoimidazol-2-yl)-4-methoxy-2-methyl-pyrrolidin-1-yl]-(6-methyl-3-pyrazol-1-yl-pyridin-2-yl)-methanone;

[(4R)-2-(5-Chloro-4-methyl-1H-benzoimidazol-2-yl)-4-methoxy-2-methyl-pyrrolidin-1-yl]-(6-methyl-3-[1,2,3]triazol-2-yl-pyridin-2-yl)-methanone;

[(2S,4R)-2-(5-Chloro-4-methyl-1H-benzoimidazol-2-yl)-4-methoxy-pyrrolidin-1-yl]-(2-methyl-5-phenyl-thiazol-4-yl)-methanone;

[5-(3-Chloro-phenyl)-2-methyl-thiazol-4-yl]-[(2S,4R)-4-methoxy-2-(4-methyl-1H-benzoimidazol-2-yl)-pyrrolidin-1-yl]-methanone;

[(2S,4S)-2-(5-Chloro-4-methyl-1H-benzoimidazol-2-yl)-4-methoxy-pyrrolidin-1-yl]-[5-(3-chloro-phenyl)-2-methyl-thiazol-4-yl]-methanone;

[(2S,4R)-2-(5-Chloro-4-methyl-1H-benzoimidazol-2-yl)-4-methoxy-pyrrolidin-1-yl]-[5-(3-chloro-phenyl)-2-methyl-thiazol-4-yl]-methanone;

(5-Chloro-2-[1,2,3]triazol-2-yl-phenyl)-[(2S,3S)-2-(5,6-dimethoxy-1H-benzoimidazol-2-yl)-3-methyl-pyrrolidin-1-yl]-methanone;

[(2S,3S)-2-(5,6-Dimethoxy-1H-benzoimidazol-2-yl)-3-methyl-pyrrolidin-1-yl]-(4-methyl-2-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-(4-methyl-2-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-(5-methoxy-2-[1,2,3]triazol-2-yl-phenyl)-methanone;

[(2S,3S)-2-(5,6-Dimethyl-1H-benzoimidazol-2-yl)-3-methyl-pyrrolidin-1-yl]-(4-methyl-2-[1,2,3]triazol-2-yl-phenyl)-methanone;

[(2S,3S)-2-(5,6-Dimethyl-1H-benzoimidazol-2-yl)-3-methyl-pyrrolidin-1-yl]-(5-methoxy-2-[1,2,3]triazol-2-yl-phenyl)-methanone;

[(2S,3S)-2-(5,6-Dimethyl-1H-benzoimidazol-2-yl)-3-methyl-pyrrolidin-1-yl]-(2-[1,2,3]triazol-2-yl-phenyl)-methanone;

[(S)-2-Methyl-2-(4-methyl-1H-benzoimidazol-2-yl)-pyrrolidin-1-yl]-(2-methyl-5-phenyl-thiazol-4-yl)-methanone;

[(S)-2-(5,6-Dimethyl-1H-benzoimidazol-2-yl)-2-methyl-pyrrolidin-1-yl]-(5-methyl-2-[1,2,3]triazol-2-yl-phenyl)-methanone;

[(S)-2-(5,6-Dimethyl-1H-benzoimidazol-2-yl)-2-methyl-pyrrolidin-1-yl]-(4,4'-dimethyl-biphenyl-2-yl)-methanone;

[(S)-2-(5,6-Dimethyl-1H-benzoimidazol-2-yl)-2-methyl-pyrrolidin-1-yl]-(3'-fluoro-biphenyl-2-yl)-methanone;

[(S)-2-(5,6-Dimethyl-1H-benzoimidazol-2-yl)-2-methyl-pyrrolidin-1-yl]-(3'-methyl-biphenyl-2-yl)-methanone;

[(S)-2-(4,5-Dimethyl-1H-benzoimidazol-2-yl)-2-methyl-pyrrolidin-1-yl]-(3'-fluoro-4-methyl-biphenyl-2-yl)-methanone;

[(S)-2-(4,5-Dimethyl-1H-benzoimidazol-2-yl)-2-methyl-pyrrolidin-1-yl]-(3'-methoxy-4-methyl-biphenyl-2-yl)-methanone;

[(S)-2-(4,5-Dimethyl-1H-benzoimidazol-2-yl)-2-methyl-pyrrolidin-1-yl]-(4,3'-dimethyl-biphenyl-2-yl)-methanone;

[(S)-2-(4,5-Dimethyl-1H-benzoimidazol-2-yl)-2-methyl-pyrrolidin-1-yl]-(4'-methoxy-4-methyl-biphenyl-2-yl)-methanone;

[(S)-2-(4,5-Dimethyl-1H-benzoimidazol-2-yl)-2-methyl-pyrrolidin-1-yl]-(4,4'-dimethyl-biphenyl-2-yl)-methanone;

[(S)-2-(4,5-Dimethyl-1H-benzoimidazol-2-yl)-2-methyl-pyrrolidin-1-yl]-(2'-fluoro-4-methyl-biphenyl-2-yl)-methanone;

[(S)-2-(4,5-Dimethyl-1H-benzoimidazol-2-yl)-2-methyl-pyrrolidin-1-yl]-(4'-fluoro-4-methyl-biphenyl-2-yl)-methanone;

[(S)-2-(4,5-Dimethyl-1H-benzoimidazol-2-yl)-2-methyl-pyrrolidin-1-yl]-(3'-fluoro-biphenyl-2-yl)-methanone;

[(S)-2-(4,5-Dimethyl-1H-benzoimidazol-2-yl)-2-methyl-pyrrolidin-1-yl]-(3'-methyl-biphenyl-2-yl)-methanone;

[(S)-2-(4,5-Dimethyl-1H-benzoimidazol-2-yl)-2-methyl-pyrrolidin-1-yl]-(4-methoxy-biphenyl-2-yl)-methanone;

[(S)-2-(4,5-Dimethyl-1H-benzoimidazol-2-yl)-2-methyl-pyrrolidin-1-yl]-(4'-methyl-biphenyl-2-yl)-methanone;

[(S)-2-(6-Bromo-5-fluoro-1H-benzoimidazol-2-yl)-2-methyl-pyrrolidin-1-yl]-(4,5-dimethyl-2-[1,2,3]triazol-2-yl-phenyl)-methanone;

[(S)-2-(6-Bromo-5-fluoro-1H-benzoimidazol-2-yl)-2-methyl-pyrrolidin-1-yl]-(5-chloro-2-[1,2,3]triazol-2-yl-phenyl)-methanone;

[(S)-2-(5-tert-Butyl-1H-benzoimidazol-2-yl)-2-methyl-pyrrolidin-1-yl]-(5-methyl-2-[1,2,3]triazol-2-yl-phenyl)-methanone;

[(S)-2-(6-Bromo-5-fluoro-1H-benzoimidazol-2-yl)-2-methyl-pyrrolidin-1-yl]-(4-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(2-fluoro-6-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(2-fluoro-3-methyl-6-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(4,5-dimethoxy-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(5-fluoro-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(4,5-dimethyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(5-methyl-2-pyrazol-1-yl-phenyl)-methanone;

(5-Chloro-2-[1,2,3]triazol-2-yl-phenyl)-[(S)-2-(6-chloro-5-trifluoromethyl-1H-benzoimidazol-2-yl)-2-methyl-pyrrolidin-1-yl]-methanone;

[(S)-2-(4-Chloro-6-trifluoromethyl-1H-benzoimidazol-2-yl)-2-methyl-pyrrolidin-1-yl]-(5-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(4-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(6-methyl-3-[1,2,3]triazol-2-yl-pyridin-2-yl)-methanone;

[(S)-2-(6-Chloro-5-trifluoromethyl-1H-benzoimidazol-2-yl)-2-methyl-pyrrolidin-1-yl]-(2-fluoro-3-methoxy-6-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(3'-methoxy-4-methyl-biphenyl-2-yl)-methanone;

[(S)-2-(5-Chloro-6-methyl-1H-benzoimidazol-2-yl)-2-methyl-pyrrolidin-1-yl]-(5-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(2'-fluoro-4-methyl-biphenyl-2-yl)-methanone;

[(S)-2-(6-Chloro-5-trifluoromethyl-1H-benzoimidazol-2-yl)-2-methyl-pyrrolidin-1-yl]-(4'-fluoro-4-methyl-biphenyl-2-yl)-methanone;

[(S)-2-(6-Chloro-5-trifluoromethyl-1H-benzoimidazol-2-yl)-2-methyl-pyrrolidin-1-yl]-(3'-fluoro-4-methyl-biphenyl-2-yl)-methanone;

2'-[(S)-2-(6-Chloro-5-trifluoromethyl-1H-benzoimidazol-2-yl)-2-methyl-pyrrolidine-1-carbonyl]-4'-methyl-biphenyl-3-carbonitrile;

[(S)-2-(4,6-Dimethyl-1H-benzoimidazol-2-yl)-2-methyl-pyrrolidin-1-yl]-(5-methyl-2-[1,2,3]triazol-2-yl-phenyl)-methanone;

(5-Chloro-2-[1,2,3]triazol-2-yl-phenyl)-[(S)-2-methyl-2-(5-trifluoromethyl-1H-benzoimidazol-2-yl)-pyrrolidin-1-yl]-methanone;

(4,5-Dimethyl-2-[1,2,3]triazol-2-yl-phenyl)-[(S)-2-methyl-2-(5-trifluoromethyl-1H-benzoimidazol-2-yl)-pyrrolidin-1-yl]-methanone;

(4-Methyl-2-[1,2,3]triazol-2-yl-phenyl)-[(S)-2-methyl-2-(5-trifluoromethyl-1H-benzoimidazol-2-yl)-pyrrolidin-1-yl]-methanone;

[(S)-2-(4-Bromo-1H-benzoimidazol-2-yl)-2-methyl-pyrrolidin-1-yl]-(5-methyl-2-[1,2,3]triazol-2-yl-phenyl)-methanone;

(3'-Fluoro-4-methyl-biphenyl-2-yl)-[(S)-2-methyl-2-(5-trifluoromethyl-1H-benzoimidazol-2-yl)-pyrrolidin-1-yl]-methanone;

(4,3'-Dimethyl-biphenyl-2-yl)-[(S)-2-methyl-2-(5-trifluoromethyl-1H-benzoimidazol-2-yl)-pyrrolidin-1-yl]-methanone;

[(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone;

(4'-Methoxy-4-methyl-biphenyl-2-yl)-[(S)-2-methyl-2-(5-trifluoromethyl-1H-benzoimidazol-2-yl)-pyrrolidin-1-yl]-methanone;

(4,4'-Dimethyl-biphenyl-2-yl)-[(S)-2-methyl-2-(5-trifluoromethyl-1H-benzoimidazol-2-yl)-pyrrolidin-1-yl]-methanone;

(2-Benzo[1,3]dioxol-5-yl-5-methyl-phenyl)-[(S)-2-methyl-2-(5-trifluoromethyl-1H-benzoimidazol-2-yl)-pyrrolidin-1-yl]-methanone;

[(S)-2-(5-Chloro-4-methyl-1H-benzoimidazol-2-yl)-2-methyl-pyrrolidin-1-yl]-(5-methyl-2-[1,2,3]triazol-2-yl-phenyl)-methanone;

[5-(3-Chloro-phenyl)-2-methyl-thiazol-4-yl]-[(S)-2-(4,5-difluoro-1H-benzoimidazol-2-yl)-2-methyl-pyrrolidin-1-yl]-methanone;

[(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone;

[(S)-2-(4,5-Difluoro-1H-benzoimidazol-2-yl)-2-methyl-pyrrolidin-1-yl]-(2-methyl-5-m-tolyl-thiazol-4-yl)-methanone;

[(S)-2-(4,5-Difluoro-1H-benzoimidazol-2-yl)-2-methyl-pyrrolidin-1-yl]-[5-(3-methoxy-phenyl)-2-methyl-thiazol-4-yl]-methanone;

[(S)-2-(5-Chloro-4-methyl-1H-benzoimidazol-2-yl)-2-methyl-pyrrolidin-1-yl]-(5-methyl-2-pyrimidin-2-yl-phenyl)-methanone;

[(S)-2-(5-Chloro-4-methyl-1H-benzoimidazol-2-yl)-2-methyl-pyrrolidin-1-yl]-(5-methyl-2-pyridin-2-yl-phenyl)-methanone;

[(S)-2-(5-Chloro-4-methyl-1H-benzoimidazol-2-yl)-2-methyl-pyrrolidin-1-yl]-(5-methyl-2-pyridin-3-yl-phenyl)-methanone;

[(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone;

[(S)-2-(4-Bromo-6-fluoro-1H-benzoimidazol-2-yl)-2-methyl-pyrrolidin-1-yl]-(5-methyl-2-[1,2,3]triazol-2-yl-phenyl)-methanone;

[(S)-2-(4,5-Dimethyl-1H-benzoimidazol-2-yl)-2-methyl-pyrrolidin-1-yl]-(5-methyl-2-[1,2,3]triazol-2-yl-phenyl)-methanone;

[(S)-2-(4-Isopropyl-1H-benzoimidazol-2-yl)-2-methyl-pyrrolidin-1-yl]-(5-methyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(2-methyl-5-phenyl-thiazol-4-yl)-methanone;

[(S)-2-(7,8-Dihydro-3H-6,9-dioxa-1,3-diaza-cyclopenta[a]naphthalen-2-yl)-2-methyl-pyrrolidin-1-yl]-(5-methyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(5-chloro-2-[1,2,3]triazol-2-yl-phenyl)-methanone;

[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone;

[(S)-2-(5-Chloro-4-methyl-1H-benzoimidazol-2-yl)-2-methyl-pyrrolidin-1-yl]-(2-fluoro-3-methoxy-6-[1,2,3]triazol-2-yl-phenyl)-methanone;

[(S)-2-(5-Chloro-4-methyl-1H-benzoimidazol-2-yl)-2-methyl-pyrrolidin-1-yl]-(4-methyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(4,5-dimethoxy-2-[1,2,3]triazol-2-yl-phenyl)-methanone;

[5-(3-Chloro-phenyl)-2-methyl-thiazol-4-yl]-[(S)-2-methyl-2-(4-methyl-1H-benzoimidazol-2-yl)-pyrrolidin-1-yl]-methanone;

[(S)-2-(5-Chloro-4-methyl-1H-benzoimidazol-2-yl)-2-methyl-pyrrolidin-1-yl]-(4,5-dimethyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(5-methyl-2-pyrazol-1-yl-phenyl)-methanone;

[(S)-2-(5-Chloro-4-methyl-1H-benzoimidazol-2-yl)-2-methyl-pyrrolidin-1-yl]-(6-methyl-3-pyrazol-1-yl-pyridin-2-yl)-methanone;

[(S)-2-(5-Chloro-4-methyl-1H-benzoimidazol-2-yl)-2-methyl-pyrrolidin-1-yl]-(5-fluoro-2-[1,2,3]triazol-2-yl-phenyl)-methanone;

[(S)-2-(5-Chloro-4-methyl-1H-benzoimidazol-2-yl)-2-methyl-pyrrolidin-1-yl]-(2-[1,2,3]triazol-2-yl-phenyl)-methanone;

[(S)-2-(5-Chloro-4-methyl-1H-benzoimidazol-2-yl)-2-methyl-pyrrolidin-1-yl]-(6-methyl-3-[1,2,3]triazol-2-yl-pyridin-2-yl)-methanone;

[(S)-2-(5-Chloro-4-methyl-1H-benzoimidazol-2-yl)-2-methyl-pyrrolidin-1-yl]-(2-fluoro-6-[1,2,3]triazol-2-yl-phenyl)-methanone;

[(S)-2-(5-Chloro-4-methyl-1H-benzoimidazol-2-yl)-2-methyl-pyrrolidin-1-yl]-[5-(3-chloro-phenyl)-2-methyl-thiazol-4-yl]-methanone;

(4,5-Dimethyl-2-[1,2,3]triazol-2-yl-phenyl)-[(S)-2-methyl-2-(4-methyl-1H-benzoimidazol-2-yl)-pyrrolidin-1-yl]-methanone;

(5-Chloro-2-[1,2,3]triazol-2-yl-phenyl)-[(S)-2-(5,6-dimethyl-1H-benzoimidazol-2-yl)-2-methyl-pyrrolidin-1-yl]-methanone;

[(S)-2-(5,6-Dimethyl-1H-benzoimidazol-2-yl)-2-methyl-pyrrolidin-1-yl]-(5-methoxy-2-[1,2,3]triazol-2-yl-phenyl)-methanone;

[(S)-2-(5,6-Dimethyl-1H-benzoimidazol-2-yl)-2-methyl-pyrrolidin-1-yl]-(4-methyl-2-[1,2,3]triazol-2-yl-phenyl)-methanone;

[(S)-2-(5,6-Dimethyl-1H-benzoimidazol-2-yl)-2-methyl-pyrrolidin-1-yl]-(4,5-dimethyl-2-[1,2,3]triazol-2-yl-phenyl)-methanone;

(5-Chloro-2-[1,2,3]triazol-2-yl-phenyl)-[(S)-2-(5,6-dimethoxy-1H-benzoimidazol-2-yl)-2-methyl-pyrrolidin-1-yl]-methanone;

[(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone;

[(S)-2-(5,6-Dichloro-1H-benzoimidazol-2-yl)-2-methyl-pyrrolidin-1-yl]-(5-methyl-2-[1,2,3]triazol-2-yl-phenyl)-methanone;

[(S)-2-(5,6-Dimethoxy-1H-benzoimidazol-2-yl)-2-methyl-pyrrolidin-1-yl]-(2-[1,2,3]triazol-2-yl-5-trifluoromethyl-phenyl)-methanone;

[(S)-2-(5,6-Dimethoxy-1H-benzoimidazol-2-yl)-2-methyl-pyrrolidin-1-yl]-(4,5-dimethyl-2-[1,2,3]triazol-2-yl-phenyl)-methanone;

[(S)-2-(5,6-Dimethoxy-1H-benzoimidazol-2-yl)-2-methyl-pyrrolidin-1-yl]-(5-methyl-2-pyrazol-1-yl-phenyl)-methanone;

[(S)-2-(5,6-Dimethyl-1H-benzoimidazol-2-yl)-2-methyl-pyrrolidin-1-yl]-(3'-methoxy-4-methyl-biphenyl-2-yl)-methanone;

[(S)-2-(5,6-Dimethyl-1H-benzoimidazol-2-yl)-2-methyl-pyrrolidin-1-yl]-(4'-methoxy-4-methyl-biphenyl-2-yl)-methanone;

[(S)-2-(5,6-Dimethyl-1H-benzoimidazol-2-yl)-2-methyl-pyrrolidin-1-yl]-(2'-fluoro-4-methyl-biphenyl-2-yl)-methanone;

[(S)-2-(5,6-Dimethyl-1H-benzoimidazol-2-yl)-2-methyl-pyrrolidin-1-yl]-(4'-fluoro-4-methyl-biphenyl-2-yl)-methanone;

[(S)-2-(5,6-Dimethyl-1H-benzoimidazol-2-yl)-2-methyl-pyrrolidin-1-yl]-(3'-fluoro-4-methyl-biphenyl-2-yl)-methanone;

[(S)-2-(5,6-Dimethyl-1H-benzoimidazol-2-yl)-2-methyl-pyrrolidin-1-yl]-(4,3'-dimethyl-biphenyl-2-yl)-methanone;

[5-(4-Bromo-phenyl)-2-methyl-thiazol-4-yl]-[(S)-2-(7-methyl-1H-benzoimidazol-2-yl)-4-methylene-pyrrolidin-1-yl]-methanone;

[(S)-2-(7-Methyl-1H-benzoimidazol-2-yl)-4-methylene-pyrrolidin-1-yl]-(2-methyl-5-m-tolyl-thiazol-4-yl)-methanone;

[5-(3-Bromo-phenyl)-2-methyl-thiazol-4-yl]-[(S)-2-(7-methyl-1H-benzoimidazol-2-yl)-4-methylene-pyrrolidin-1-yl]-methanone;

[5-(3,5-Dimethyl-phenyl)-2-methyl-thiazol-4-yl]-[(S)-2-(7-methyl-1H-benzoimidazol-2-yl)-4-methylene-pyrrolidin-1-yl]-methanone;

[5-(3-Bromo-4-fluoro-phenyl)-2-methyl-thiazol-4-yl]-[(S)-2-(7-methyl-1H-benzoimidazol-2-yl)-4-methylene-pyrrolidin-1-yl]-methanone;

[(S)-2-(7-Methyl-1H-benzoimidazol-2-yl)-4-methylene-pyrrolidin-1-yl]-[2-methyl-5-(3-trifluoromethyl-phenyl)-thiazol-4-yl]-methanone;

[5-(3,4-Dichloro-phenyl)-2-methyl-thiazol-4-yl]-[(S)-2-(7-methyl-1H-benzoimidazol-2-yl)-4-methylene-pyrrolidin-1-yl]-methanone;

[5-(3-Methoxy-phenyl)-2-methyl-thiazol-4-yl]-[(S)-2-(7-methyl-1H-benzoimidazol-2-yl)-4-methylene-pyrrolidin-1-yl]-methanone;

[5-(4-Bromo-phenyl)-2-methyl-thiazol-4-yl]-[(S)-2-(6-chloro-7-methyl-1H-benzoimidazol-2-yl)-4-methylene-pyrrolidin-1-yl]-methanone;

[(S)-2-(6-Chloro-7-methyl-1H-benzoimidazol-2-yl)-4-methylene-pyrrolidin-1-yl]-[5-(6-methoxy-pyridin-3-yl)-2-methyl-thiazol-4-yl]-methanone;

[(S)-2-(6-Chloro-7-methyl-1H-benzoimidazol-2-yl)-4-methylene-pyrrolidin-1-yl]-[5-(4-fluoro-phenyl)-2-methyl-thiazol-4-yl]-methanone;

[(S)-2-(6-Chloro-7-methyl-1H-benzoimidazol-2-yl)-4-methylene-pyrrolidin-1-yl]-[5-(4-chloro-phenyl)-2-methyl-thiazol-4-yl]-methanone;

[(S)-2-(6-Chloro-7-methyl-1H-benzoimidazol-2-yl)-4-methylene-pyrrolidin-1-yl]-[2-methyl-5-(3-trifluoromethyl-phenyl)-thiazol-4-yl]-methanone;

[(S)-2-(6-Chloro-7-methyl-1H-benzoimidazol-2-yl)-4-methylene-pyrrolidin-1-yl]-[5-(3-methoxy-phenyl)-2-methyl-thiazol-4-yl]-methanone;

[(S)-2-(6-Chloro-7-methyl-1H-benzoimidazol-2-yl)-4-methylene-pyrrolidin-1-yl]-(2-methyl-5-m-tolyl-thiazol-4-yl)-methanone;

[5-(3-Bromo-phenyl)-2-methyl-thiazol-4-yl]-[(S)-2-(6-chloro-7-methyl-1H-benzoimidazol-2-yl)-4-methylene-pyrrolidin-1-yl]-methanone;

[(S)-2-(6-Chloro-7-methyl-1H-benzoimidazol-2-yl)-4-methylene-pyrrolidin-1-yl]-[5-(3,5-dimethyl-phenyl)-2-methyl-thiazol-4-yl]-methanone;

[5-(3-Bromo-4-fluoro-phenyl)-2-methyl-thiazol-4-yl]-[(S)-2-(6-chloro-7-methyl-1H-benzoimidazol-2-yl)-4-methylene-pyrrolidin-1-yl]-methanone;

[(S)-2-(6-Chloro-7-methyl-1H-benzoimidazol-2-yl)-4-methylene-pyrrolidin-1-yl]-[5-(3,4-dichloro-phenyl)-2-methyl-thiazol-4-yl]-methanone;

[(S)-2-(6-Chloro-7-methyl-1H-benzoimidazol-2-yl)-4-methylene-pyrrolidin-1-yl]-(6-methyl-3-[1,2,3]triazol-2-yl-pyridin-2-yl)-methanone;

[(S)-2-(6-Chloro-7-methyl-1H-benzoimidazol-2-yl)-4-methylene-pyrrolidin-1-yl]-(5-chloro-2-[1,2,3]triazol-2-yl-phenyl)-methanone;

[(S)-2-(6-Chloro-7-methyl-1H-benzoimidazol-2-yl)-4-methylene-pyrrolidin-1-yl]-(4,5-dimethyl-2-[1,2,3]triazol-2-yl-phenyl)-methanone;

[(S)-2-(6-Chloro-7-methyl-1H-benzoimidazol-2-yl)-4-methylene-pyrrolidin-1-yl]-(5-methoxy-2-[1,2,3]triazol-2-yl-phenyl)-methanone;

[(S)-2-(6-Chloro-7-methyl-1H-benzoimidazol-2-yl)-4-methylene-pyrrolidin-1-yl]-(2-fluoro-3-methyl-6-[1,2,3]triazol-2-yl-phenyl)-methanone;

[(S)-2-(6-Chloro-7-methyl-1H-benzoimidazol-2-yl)-4-methylene-pyrrolidin-1-yl]-(2-fluoro-3-methoxy-6-[1,2,3]triazol-2-yl-phenyl)-methanone;

[(S)-2-(6-Chloro-5-trifluoromethyl-1H-benzoimidazol-2-yl)-4-methylene-pyrrolidin-1-yl]-[5-(3,4-dimethyl-phenyl)-2-methyl-thiazol-4-yl]-methanone;

[2-(5-Methoxy-1H-benzoimidazol-2-yl)-2-methyl-4-methylene-pyrrolidin-1-yl]-(2-methyl-5-m-tolyl-thiazol-4-yl)-methanone;

[2-Dimethylamino-5-(3,4-dimethyl-phenyl)-thiazol-4-yl]-[2-(5-methoxy-1H-benzoimidazol-2-yl)-2-methyl-4-methylene-pyrrolidin-1-yl]-methanone;

[5-(3,4-Dimethyl-phenyl)-2-methyl-thiazol-4-yl]-[2-(5-methoxy-1H-benzoimidazol-2-yl)-2-methyl-4-methylene-pyrrolidin-1-yl]-methanone;

[5-(4-Chloro-phenyl)-2-methyl-thiazol-4-yl]-[2-(5-methoxy-1H-benzoimidazol-2-yl)-2-methyl-4-methylene-pyrrolidin-1-yl]-methanone;

[2-(5-Methoxy-1H-benzoimidazol-2-yl)-2-methyl-4-methylene-pyrrolidin-1-yl]-[5-(4-methoxy-phenyl)-2-methyl-thiazol-4-yl]-methanone;
[2-(5-Methoxy-1H-benzoimidazol-2-yl)-2-methyl-4-methylene-pyrrolidin-1-yl]-(2-methyl-5-p-tolyl-thiazol-4-yl)-methanone;
[5-(3-Chloro-phenyl)-2-dimethylamino-thiazol-4-yl]-[2-(5-methoxy-1H-benzoimidazol-2-yl)-2-methyl-4-methylene-pyrrolidin-1-yl]-methanone;
[5-(3-Chloro-phenyl)-2-methyl-thiazol-4-yl]-[2-(5-methoxy-1H-benzoimidazol-2-yl)-2-methyl-4-methylene-pyrrolidin-1-yl]-methanone;
[2-(5-Methoxy-1H-benzoimidazol-2-yl)-2-methyl-4-methylene-pyrrolidin-1-yl]-(5-methyl-2-[1,2,3]triazol-2-yl-phenyl)-methanone;
(5-Chloro-2-[1,2,3]triazol-2-yl-phenyl)-[2-(5-methoxy-1H-benzoimidazol-2-yl)-2-methyl-4-methylene-pyrrolidin-1-yl]-methanone;
(4,5-Dimethyl-2-[1,2,3]triazol-2-yl-phenyl)-[2-(5-methoxy-1H-benzoimidazol-2-yl)-2-methyl-4-methylene-pyrrolidin-1-yl]-methanone;
[(S)-2-(5-tert-Butyl-1H-benzoimidazol-2-yl)-4-methylene-pyrrolidin-1-yl]-(4,5-dimethyl-2-[1,2,3]triazol-2-yl-phenyl)-methanone;
[(S)-2-(5-tert-Butyl-1H-benzoimidazol-2-yl)-4-methylene-pyrrolidin-1-yl]-(4-methyl-2-[1,2,3]triazol-2-yl-phenyl)-methanone;
[(S)-2-(5-tert-Butyl-1H-benzoimidazol-2-yl)-4-methylene-pyrrolidin-1-yl]-(4,5-dimethoxy-2-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(2-fluoro-6-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(5-fluoro-2-[1,2,3]triazol-2-yl-phenyl)-methanone;
(5-Chloro-2-[1,2,3]triazol-2-yl-phenyl)-[(S)-2-(5-chloro-6-trifluoromethyl-1H-benzoimidazol-2-yl)-4-methylene-pyrrolidin-1-yl]-methanone;
[(S)-2-(5-Chloro-6-trifluoromethyl-1H-benzoimidazol-2-yl)-4-methylene-pyrrolidin-1-yl]-(2-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(2-fluoro-3-methoxy-6-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(2-fluoro-3-methyl-6-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(4,5-dimethyl-2-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(4-methyl-2-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(4,5-dimethoxy-2-[1,2,3]triazol-2-yl-phenyl)-methanone;
[(S)-2-(5-Chloro-6-trifluoromethyl-1H-benzoimidazol-2-yl)-4-methylene-pyrrolidin-1-yl]-(5-methyl-2-pyrazol-1-yl-phenyl)-methanone;
[(S)-2-(5-Chloro-6-trifluoromethyl-1H-benzoimidazol-2-yl)-4-methylene-pyrrolidin-1-yl]-(6-methyl-3-pyrazol-1-yl-pyridin-2-yl)-methanone;
[(S)-2-(5-Chloro-6-trifluoromethyl-1H-benzoimidazol-2-yl)-4-methylene-pyrrolidin-1-yl]-(6-methyl-3-[1,2,3]triazol-2-yl-pyridin-2-yl)-methanone;
[(S)-2-(5,6-Dimethyl-1H-benzoimidazol-2-yl)-4-methylene-pyrrolidin-1-yl]-(5-fluoro-2-[1,2,3]triazol-2-yl-phenyl)-methanone;
(5-Chloro-2-[1,2,3]triazol-2-yl-phenyl)-[(S)-2-(5,6-dimethyl-1H-benzoimidazol-2-yl)-4-methylene-pyrrolidin-1-yl]-methanone;
[(S)-2-(5,6-Dimethyl-1H-benzoimidazol-2-yl)-4-methylene-pyrrolidin-1-yl]-(2-[1,2,3]triazol-2-yl-phenyl)-methanone;
[(S)-2-(5,6-Dimethyl-1H-benzoimidazol-2-yl)-4-methylene-pyrrolidin-1-yl]-(2-fluoro-3-methoxy-6-[1,2,3]triazol-2-yl-phenyl)-methanone;
[(S)-2-(5,6-Dimethyl-1H-benzoimidazol-2-yl)-4-methylene-pyrrolidin-1-yl]-(2-fluoro-3-methyl-6-[1,2,3]triazol-2-yl-phenyl)-methanone;
[(S)-2-(5,6-Dimethyl-1H-benzoimidazol-2-yl)-4-methylene-pyrrolidin-1-yl]-(4,5-dimethyl-2-[1,2,3]triazol-2-yl-phenyl)-methanone;
[5-(3-Bromo-4-fluoro-phenyl)-2-methyl-thiazol-4-yl]-[(S)-2-(5-methoxy-1H-benzoimidazol-2-yl)-4-methylene-pyrrolidin-1-yl]-methanone;
(2-Cyclopropyl-5-m-tolyl-thiazol-4-yl)-[(S)-2-(5-methoxy-1H-benzoimidazol-2-yl)-4-methylene-pyrrolidin-1-yl]-methanone;
[2-Dimethylamino-5-(3,4-dimethyl-phenyl)-thiazol-4-yl]-[(S)-2-(5-methoxy-1H-benzoimidazol-2-yl)-4-methylene-pyrrolidin-1-yl]-methanone;
[5-(3-Bromo-phenyl)-2-cyclopropyl-thiazol-4-yl]-[(S)-2-(5-methoxy-1H-benzoimidazol-2-yl)-4-methylene-pyrrolidin-1-yl]-methanone;
[2-Cyclopropyl-5-(3-methoxy-phenyl)-thiazol-4-yl]-[(S)-2-(5-methoxy-1H-benzoimidazol-2-yl)-4-methylene-pyrrolidin-1-yl]-methanone;
[2-(3,4-Dimethyl-phenyl)-5-methyl-thiophen-3-yl]-[(S)-2-(5-methoxy-1H-benzoimidazol-2-yl)-4-methylene-pyrrolidin-1-yl]-methanone;
[(S)-2-(5-Chloro-4-methyl-1H-benzoimidazol-2-yl)-4-methylene-pyrrolidin-1-yl]-(2-methyl-5-phenyl-thiazol-4-yl)-methanone;
[(S)-2-(5-Chloro-4-methyl-1H-benzoimidazol-2-yl)-4-methylene-pyrrolidin-1-yl]-(5-methyl-2-[1,2,3]triazol-2-yl-phenyl)-methanone;
[5-(3-Chloro-phenyl)-2-methyl-thiazol-4-yl]-[(S)-2-(4-methyl-1H-benzoimidazol-2-yl)-4-methylene-pyrrolidin-1-yl]-methanone;
[(S)-2-(5-Chloro-4-methyl-1H-benzoimidazol-2-yl)-4-methylene-pyrrolidin-1-yl]-[5-(3-chloro-phenyl)-2-methyl-thiazol-4-yl]-methanone;
[5-(3,4-Dimethyl-phenyl)-2-methyl-thiazol-4-yl]-[(S)-2-(6-methoxy-1H-benzoimidazol-2-yl)-4-methylene-pyrrolidin-1-yl]-methanone;
[(S)-2-(4,5-Dimethyl-1H-benzoimidazol-2-yl)-4-methylene-pyrrolidin-1-yl]-[5-(3,4-dimethyl-phenyl)-2-methyl-thiazol-4-yl]-methanone;
[(S)-2-(4,7-Dimethoxy-1H-benzoimidazol-2-yl)-4-methylene-pyrrolidin-1-yl]-[5-(3,4-dimethyl-phenyl)-2-methyl-thiazol-4-yl]-methanone;
[5-(3,4-Dimethyl-phenyl)-2-methyl-thiazol-4-yl]-[(S)-4-methylene-2-(4-methylsulfanyl-1H-benzoimidazol-2-yl)-pyrrolidin-1-yl]-methanone;
[(S)-2-(4-Bromo-1H-benzoimidazol-2-yl)-4-methylene-pyrrolidin-1-yl]-[5-(3,4-dimethyl-phenyl)-2-methyl-thiazol-4-yl]-methanone;
[(S)-2-(4-Chloro-1H-benzoimidazol-2-yl)-4-methylene-pyrrolidin-1-yl]-[5-(3,4-dimethyl-phenyl)-2-methyl-thiazol-4-yl]-methanone;

[5-(3,4-Dimethyl-phenyl)-2-methyl-thiazol-4-yl]-[(S)-4-methylene-2-(5-methylsulfanyl-1H-benzoimidazol-2-yl)-pyrrolidin-1-yl]-methanone;

[5-(3,4-Dimethyl-phenyl)-2-methyl-thiazol-4-yl]-[(S)-2-(4-methyl-1H-benzoimidazol-2-yl)-4-methylene-pyrrolidin-1-yl]-methanone;

[(S)-2-(5-Chloro-4-methyl-1H-benzoimidazol-2-yl)-4-methylene-pyrrolidin-1-yl]-[5-(3,4-dimethyl-phenyl)-2-methyl-thiazol-4-yl]-methanone;

[(S)-2-(5-Chloro-6-methyl-1H-benzoimidazol-2-yl)-4-methylene-pyrrolidin-1-yl]-[5-(3,4-dimethyl-phenyl)-2-methyl-thiazol-4-yl]-methanone;

[(S)-2-(5,6-Dimethyl-1H-benzoimidazol-2-yl)-4-methylene-pyrrolidin-1-yl]-[5-(3,4-dimethyl-phenyl)-2-methyl-thiazol-4-yl]-methanone;

[(S)-2-(5-tert-Butyl-1H-benzoimidazol-2-yl)-4-methylene-pyrrolidin-1-yl]-[5-(3,4-dimethyl-phenyl)-2-methyl-thiazol-4-yl]-methanone;

[(S)-2-(4,6-Dimethyl-1H-benzoimidazol-2-yl)-4-methylene-pyrrolidin-1-yl]-[5-(3,4-dimethyl-phenyl)-2-methyl-thiazol-4-yl]-methanone;

[(S)-2-(5,6-Dimethyl-1H-benzoimidazol-2-yl)-4-methylene-pyrrolidin-1-yl]-(5-methyl-2-[1,2,3]triazol-2-yl-phenyl)-methanone;

[(S)-2-(4,6-Dimethyl-1H-benzoimidazol-2-yl)-4-methylene-pyrrolidin-1-yl]-(5-methyl-2-[1,2,3]triazol-2-yl-phenyl)-methanone;

[(S)-2-(5-Chloro-6-methyl-1H-benzoimidazol-2-yl)-4-methylene-pyrrolidin-1-yl]-(5-methyl-2-[1,2,3]triazol-2-yl-phenyl)-methanone;

[(S)-2-(5-Chloro-6-trifluoromethyl-1H-benzoimidazol-2-yl)-4-methylene-pyrrolidin-1-yl]-(5-methyl-2-[1,2,3]triazol-2-yl-phenyl)-methanone;

[(S)-2-(5-Methoxy-1H-benzoimidazol-2-yl)-4-methylene-pyrrolidin-1-yl]-(2-methyl-5-m-tolyl-thiazol-4-yl)-methanone;

[2-(3,4-Dimethyl-phenyl)-5-methyl-thiophen-3-yl]-[2-(5-methoxy-1H-benzoimidazol-2-yl)-4-methylene-pyrrolidin-1-yl]-methanone;

[2-(3,4-Dimethyl-phenyl)-5-methyl-thiophen-3-yl]-[4-methylene-2-(7-methylsulfanyl-1H-benzoimidazol-2-yl)-pyrrolidin-1-yl]-methanone;

[2-(3,4-Dimethyl-phenyl)-5-methyl-thiophen-3-yl]-[4-methylene-2-(5-methylsulfanyl-1H-benzoimidazol-2-yl)-pyrrolidin-1-yl]-methanone;

[2-(5-Chloro-4-methyl-1H-benzoimidazol-2-yl)-4-methylene-pyrrolidin-1-yl]-[2-(3,4-dimethyl-phenyl)-5-methyl-thiophen-3-yl]-methanone;

[2-(5,6-Dimethyl-1H-benzoimidazol-2-yl)-4-methylene-pyrrolidin-1-yl]-[2-(3,4-dimethyl-phenyl)-5-methyl-thiophen-3-yl]-methanone;

[2-(4,6-Dimethyl-1H-benzoimidazol-2-yl)-4-methylene-pyrrolidin-1-yl]-[2-(3,4-dimethyl-phenyl)-5-methyl-thiophen-3-yl]-methanone;

[2-(4,5-Dimethyl-1H-benzoimidazol-2-yl)-4-methylene-pyrrolidin-1-yl]-[2-(3,4-dimethyl-phenyl)-5-methyl-thiophen-3-yl]-methanone;

[2-(4-Bromo-1H-benzoimidazol-2-yl)-4-methylene-pyrrolidin-1-yl]-[2-(3,4-dimethyl-phenyl)-5-methyl-thiophen-3-yl]-methanone;

[2-(3,4-Dimethyl-phenyl)-5-methyl-thiophen-3-yl]-[2-(4-methyl-1H-benzoimidazol-2-yl)-4-methylene-pyrrolidin-1-yl]-methanone;

[5-(3-Chloro-phenyl)-2-methyl-thiazol-4-yl]-[(S)-2-(5-methoxy-1H-benzoimidazol-2-yl)-4-methylene-pyrrolidin-1-yl]-methanone;

[2-(5-Chloro-6-methyl-1H-benzoimidazol-2-yl)-4-methylene-pyrrolidin-1-yl]-[2-(3,4-dimethyl-phenyl)-5-methyl-thiophen-3-yl]-methanone;

[2-(5-tert-Butyl-1H-benzoimidazol-2-yl)-4-methylene-pyrrolidin-1-yl]-[2-(3,4-dimethyl-phenyl)-5-methyl-thiophen-3-yl]-methanone;

[2-(4,7-Dimethoxy-1H-benzoimidazol-2-yl)-4-methylene-pyrrolidin-1-yl]-[2-(3,4-dimethyl-phenyl)-5-methyl-thiophen-3-yl]-methanone;

[2-(7-Chloro-1H-benzoimidazol-2-yl)-4-methylene-pyrrolidin-1-yl]-[2-(3,4-dimethyl-phenyl)-5-methyl-thiophen-3-yl]-methanone;

(2-Cyclopropyl-5-m-tolyl-thiazol-4-yl)-[2-(5-methoxy-1H-benzoimidazol-2-yl)-4-methylene-pyrrolidin-1-yl]-methanone;

(2-Cyclopropyl-5-m-tolyl-thiazol-4-yl)-[4-methylene-2-(7-methylsulfanyl-1H-benzoimidazol-2-yl)-pyrrolidin-1-yl]-methanone;

(2-Cyclopropyl-5-m-tolyl-thiazol-4-yl)-[4-methylene-2-(5-methylsulfanyl-1H-benzoimidazol-2-yl)-pyrrolidin-1-yl]-methanone;

[2-(5-Chloro-4-methyl-1H-benzoimidazol-2-yl)-4-methylene-pyrrolidin-1-yl]-(2-cyclopropyl-5-m-tolyl-thiazol-4-yl)-methanone;

[5-(3,4-Dimethyl-phenyl)-2-methyl-thiazol-4-yl]-[(S)-2-(5-methoxy-1H-benzoimidazol-2-yl)-4-methylene-pyrrolidin-1-yl]-methanone;

(2-Cyclopropyl-5-m-tolyl-thiazol-4-yl)-[2-(5,6-dimethyl-1H-benzoimidazol-2-yl)-4-methylene-pyrrolidin-1-yl]-methanone;

(2-Cyclopropyl-5-m-tolyl-thiazol-4-yl)-[2-(4,6-dimethyl-1H-benzoimidazol-2-yl)-4-methylene-pyrrolidin-1-yl]-methanone;

(2-Cyclopropyl-5-m-tolyl-thiazol-4-yl)-[2-(4,5-dimethyl-1H-benzoimidazol-2-yl)-4-methylene-pyrrolidin-1-yl]-methanone;

[2-(4-Bromo-1H-benzoimidazol-2-yl)-4-methylene-pyrrolidin-1-yl]-(2-cyclopropyl-5-m-tolyl-thiazol-4-yl)-methanone;

(2-Cyclopropyl-5-m-tolyl-thiazol-4-yl)-[2-(4-methyl-1H-benzoimidazol-2-yl)-4-methylene-pyrrolidin-1-yl]-methanone;

[2-(5-Chloro-6-methyl-1H-benzoimidazol-2-yl)-4-methylene-pyrrolidin-1-yl]-(2-cyclopropyl-5-m-tolyl-thiazol-4-yl)-methanone;

[2-(5-Chloro-6-trifluoromethyl-1H-benzoimidazol-2-yl)-4-methylene-pyrrolidin-1-yl]-(2-cyclopropyl-5-m-tolyl-thiazol-4-yl)-methanone;

(2-Cyclopropyl-5-m-tolyl-thiazol-4-yl)-[2-(4,7-dimethoxy-1H-benzoimidazol-2-yl)-4-methylene-pyrrolidin-1-yl]-methanone;

[2-(7-Chloro-1H-benzoimidazol-2-yl)-4-methylene-pyrrolidin-1-yl]-(2-cyclopropyl-5-m-tolyl-thiazol-4-yl)-methanone;

[(S)-2-(5-Chloro-1,4-dimethyl-1H-benzoimidazol-2-yl)-2-methyl-pyrrolidin-1-yl]-(5-methyl-2-[1,2,3]triazol-2-yl-phenyl)-methanone;

[(S)-2-(6-Chloro-1,7-dimethyl-1H-benzoimidazol-2-yl)-2-methyl-pyrrolidin-1-yl]-(5-methyl-2-[1,2,3]triazol-2-yl-phenyl)-methanone;

[(S)-2-(5-Bromo-1,7-dimethyl-1H-benzoimidazol-2-yl)-2-methyl-pyrrolidin-1-yl]-(5-methyl-2-[1,2,3]triazol-2-yl-phenyl)-methanone;

[(S)-2-(6-Bromo-1,4-dimethyl-1H-benzoimidazol-2-yl)-2-methyl-pyrrolidin-1-yl]-(5-methyl-2-[1,2,3]triazol-2-yl-phenyl)-methanone;

(S)-(5-(3-chlorophenyl)-2-methylthiazol-4-yl)(2-(1,4-dimethyl-1H-benzo[d]imidazol-2-yl)-2-methylpyrrolidin-1-yl)methanone;

(S)-(5-(3-chlorophenyl)-2-methylthiazol-4-yl)(2-(1,7-dimethyl-1H-benzo[d]imidazol-2-yl)-2-methylpyrrolidin-1-yl)methanone;

(S)-(5-(3-chlorophenyl)-2-methylthiazol-4-yl)(2-(1-ethyl-4-methyl-1H-benzo[d]imidazol-2-yl)-2-methylpyrrolidin-1-yl)methanone;

(S)-(5-(3-chlorophenyl)-2-methylthiazol-4-yl)(2-(1-ethyl-7-methyl-1H-benzo[d]imidazol-2-yl)-2-methylpyrrolidin-1-yl)methanone;

(S)-(2-(5-chloro-1,4-dimethyl-1H-benzo[d]imidazol-2-yl)-2-methylpyrrolidin-1-yl)(2-methyl-5-phenylthiazol-4-yl)methanone;

(S)-(2-(6-chloro-1,7-dimethyl-1H-benzo[d]imidazol-2-yl)-2-methylpyrrolidin-1-yl)(2-methyl-5-phenylthiazol-4-yl)methanone;

(S)-(2-(5-chloro-1-ethyl-4-methyl-1H-benzo[d]imidazol-2-yl)-2-methylpyrrolidin-1-yl)(2-methyl-5-phenylthiazol-4-yl)methanone; and (S)-(2-(6-chloro-1-ethyl-7-methyl-1H-benzo[d]imidazol-2-yl)-2-methylpyrrolidin-1-yl)(2-methyl-5-phenylthiazol-4-yl)methanone.

47) In addition to the above-listed compounds, further compounds according to embodiment 1) are selected from:

[5-(3-Chloro-phenyl)-2-methyl-thiazol-4-yl]-[2-(4-chloro-6-trifluoromethyl-1H-benzoimidazol-2-yl)-pyrrolidin-1-yl]-methanone;

[4-(3-Chloro-phenyl)-2-methyl-pyrimidin-5-yl]-[(S)-2-(7-methylsulfanyl-1H-benzoimidazol-2-yl)-pyrrolidin-1-yl]-methanone;

[(2S,3S)-3-Methyl-2-(4-methyl-1H-benzoimidazol-2-yl)-pyrrolidin-1-yl]-(5-methyl-2-[1,2,3]triazol-2-yl-phenyl)-methanone;

[5-(3-Chloro-phenyl)-2-methyl-thiazol-4-yl]-[(2S,3S)-2-(5,6-dimethyl-1H-benzoimidazol-2-yl)-3-methyl-pyrrolidin-1-yl]-methanone;

[(2S,3S)-2-(6-Chloro-4-methyl-1H-benzoimidazol-2-yl)-3-methyl-pyrrolidin-1-yl]-[5-(4-fluoro-phenyl)-2-methyl-thiazol-4-yl]-methanone;

[(2S,3S)-2-(6-Chloro-4-methyl-1H-benzoimidazol-2-yl)-3-methyl-pyrrolidin-1-yl]-(2-[1,2,3]triazol-2-yl-phenyl)-methanone;

[(2S,3S)-2-(5-Chloro-1H-benzoimidazol-2-yl)-3-methyl-pyrrolidin-1-yl]-[5-(3-chloro-phenyl)-2-methyl-thiazol-4-yl]-methanone;

[5-(3-Chloro-phenyl)-2-methyl-thiazol-4-yl]-[(2S,3S)-2-(5,6-difluoro-1H-benzoimidazol-2-yl)-3-methyl-pyrrolidin-1-yl]-methanone;

2-{(2S,3S)-1-[5-(3-Chloro-phenyl)-2-methyl-thiazole-4-carbonyl]-3-methyl-pyrrolidin-2-yl}-1H-benzoimidazole-4-carboxylic acid methyl ester;

[5-(3-Chloro-phenyl)-2-methyl-thiazol-4-yl]-[(2S,3S)-2-(4-methoxy-1H-benzoimidazol-2-yl)-3-methyl-pyrrolidin-1-yl]-methanone;

[(2S,3S)-2-(5-Chloro-6-methyl-1H-benzoimidazol-2-yl)-3-methyl-pyrrolidin-1-yl]-[5-(3-chloro-phenyl)-2-methyl-thiazol-4-yl]-methanone;

[5-(3-Chloro-phenyl)-2-methyl-thiazol-4-yl]-[(2S,3S)-2-(4,6-dimethyl-1H-benzoimidazol-2-yl)-3-methyl-pyrrolidin-1-yl]-methanone;

[5-(3-Chloro-phenyl)-2-methyl-thiazol-4-yl]-[(2S,3S)-2-(4-hydroxymethyl-1H-benzoimidazol-2-yl)-3-methyl-pyrrolidin-1-yl]-methanone;

[5-(3-Chloro-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[5-(3-Chloro-phenyl)-2-methyl-thiazol-4-yl]-[(2S,3S)-2-(5-fluoro-1H-benzoimidazol-2-yl)-3-methyl-pyrrolidin-1-yl]-methanone;

[(2S,3S)-2-(5-Chloro-4-methyl-1H-benzoimidazol-2-yl)-3-methyl-pyrrolidin-1-yl]-[5-(3-chloro-phenyl)-2-methyl-thiazol-4-yl]-methanone;

[(2S,3S)-2-(4-Chloro-1H-benzoimidazol-2-yl)-3-methyl-pyrrolidin-1-yl]-[5-(3-chloro-phenyl)-2-methyl-thiazol-4-yl]-methanone;

[5-(3-Chloro-phenyl)-2-methyl-thiazol-4-yl]-[(2S,3S)-2-(4,5-difluoro-1H-benzoimidazol-2-yl)-3-methyl-pyrrolidin-1-yl]-methanone;

[5-(3-Chloro-phenyl)-2-methyl-thiazol-4-yl]-[(2S,3S)-2-(4,5-dimethyl-1H-benzoimidazol-2-yl)-3-methyl-pyrrolidin-1-yl]-methanone;

[5-(3-Chloro-phenyl)-2-methyl-thiazol-4-yl]-[(2S,3S)-2-(4-isopropyl-1H-benzoimidazol-2-yl)-3-methyl-pyrrolidin-1-yl]-methanone;

[5-(3-Chloro-phenyl)-2-methyl-thiazol-4-yl]-[(2S,3S)-2-(5-methoxy-1H-benzoimidazol-2-yl)-3-methyl-pyrrolidin-1-yl]-methanone;

[(2S,3S)-2-(5-Chloro-7-methyl-1H-benzoimidazol-2-yl)-3-methyl-pyrrolidin-1-yl]-[5-(3-chloro-phenyl)-2-methyl-thiazol-4-yl]-methanone;

(5-Methyl-2-[1,2,3]triazol-2-yl-phenyl)-[(2S,3S)-3-methyl-2-(5-trifluoromethyl-1H-benzoimidazol-2-yl)-pyrrolidin-1-yl]-methanone;

[5-(3-Chloro-phenyl)-2-methyl-thiazol-4-yl]-[(2S,3S)-3-methyl-2-(5-methyl-1H-benzoimidazol-2-yl)-pyrrolidin-1-yl]-methanone;

[(2S,3S)-2-(5,6-Dimethyl-1H-benzoimidazol-2-yl)-3-methyl-pyrrolidin-1-yl]-(5-methyl-2-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(5-methyl-2-[1,2,3]triazol-2-yl-phenyl)-methanone;

[(2S,3S)-2-(4,6-Dimethyl-1H-benzoimidazol-2-yl)-3-methyl-pyrrolidin-1-yl]-(5-methyl-2-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-(5-methyl-2-[1,2,3]triazol-2-yl-phenyl)-methanone;

[(2S,3S)-2-(4,5-Dimethyl-1H-benzoimidazol-2-yl)-3-methyl-pyrrolidin-1-yl]-(5-methyl-2-[1,2,3]triazol-2-yl-phenyl)-methanone;

[(2S,3S)-2-(5-Chloro-7-methyl-1H-benzoimidazol-2-yl)-3-methyl-pyrrolidin-1-yl]-(5-methyl-2-[1,2,3]triazol-2-yl-phenyl)-methanone;

[(2S,3S)-3-Methyl-2-(4-methyl-1H-benzoimidazol-2-yl)-pyrrolidin-1-yl]-(2-methyl-5-phenyl-thiazol-4-yl)-methanone;

[(2S,3S)-3-Methyl-2-(5-methyl-1H-benzoimidazol-2-yl)-pyrrolidin-1-yl]-(2-methyl-5-phenyl-thiazol-4-yl)-methanone;

[5-(3,5-Difluoro-phenyl)-2-methyl-thiazol-4-yl]-[(2S,3S)-2-(5,6-dimethoxy-1H-benzoimidazol-2-yl)-3-methyl-pyrrolidin-1-yl]-methanone;

[(2S,3S)-2-(5,6-Dimethoxy-1H-benzoimidazol-2-yl)-3-methyl-pyrrolidin-1-yl]-[5-(4-fluoro-phenyl)-2-methyl-thiazol-4-yl]-methanone;

[(2S,3S)-2-(5-Chloro-4-methyl-1H-benzoimidazol-2-yl)-3-methyl-pyrrolidin-1-yl]-(2-[1,2,3]triazol-2-yl-phenyl)-methanone;

[(2S,3S)-2-(1H-Benzoimidazol-2-yl)-3-methyl-pyrrolidin-1-yl]-[5-(3-chloro-phenyl)-2-methyl-thiazol-4-yl]-methanone;

[(2S,3S)-2-(5-Chloro-4-methyl-1H-benzoimidazol-2-yl)-3-methyl-pyrrolidin-1-yl]-(5-chloro-2-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-(4'-methyl-biphenyl-2-yl)-methanone;

[(2S,3S)-2-(5-Chloro-4-methyl-1H-benzoimidazol-2-yl)-3-methyl-pyrrolidin-1-yl]-[5-(4-chloro-phenyl)-2-methyl-thiazol-4-yl]-methanone;

[(2S,3S)-2-(5-Chloro-4-methyl-1H-benzoimidazol-2-yl)-3-methyl-pyrrolidin-1-yl]-(5-methyl-2-pyrazol-1-yl-phenyl)-methanone;

[(2S,3S)-2-(5-Chloro-4-methyl-1H-benzoimidazol-2-yl)-3-methyl-pyrrolidin-1-yl]-(2-methyl-4-p-tolyl-thiazol-5-yl)-methanone;

[(2S,3S)-2-(5-Chloro-4-methyl-1H-benzoimidazol-2-yl)-3-methyl-pyrrolidin-1-yl]-[5-(3,5-difluoro-phenyl)-2-methyl-thiazol-4-yl]-methanone;

[(2S,3S)-2-(5-Chloro-4-methyl-1H-benzoimidazol-2-yl)-3-methyl-pyrrolidin-1-yl]-(2-fluoro-3-methyl-6-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-[5-(6-methoxy-pyridin-3-yl)-2-methyl-thiazol-4-yl]-methanone;

[5-(3-Chloro-phenyl)-2-methyl-thiazol-4-yl]-[(2S,3S)-3-methyl-2-(4-methyl-1H-benzoimidazol-2-yl)-pyrrolidin-1-yl]-methanone;

[(2S,3S)-2-(5-Chloro-4-methyl-1H-benzoimidazol-2-yl)-3-methyl-pyrrolidin-1-yl]-[5-(4-fluoro-phenyl)-2-methyl-thiazol-4-yl]-methanone;

[(2S,3S)-2-(5-Chloro-6-methyl-1H-benzoimidazol-2-yl)-3-methyl-pyrrolidin-1-yl]-(5-chloro-2-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(4-methyl-2-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(5-methyl-2-pyrazol-1-yl-phenyl)-methanone;

[(2S,3S)-2-(5-Chloro-6-methyl-1H-benzoimidazol-2-yl)-3-methyl-pyrrolidin-1-yl]-(5-methoxy-2-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(2-fluoro-3-methyl-6-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(2-[1,2,3]triazol-2-yl-phenyl)-methanone;

[(2S,3S)-2-(5-Chloro-6-methyl-1H-benzoimidazol-2-yl)-3-methyl-pyrrolidin-1-yl]-(4'-methyl-biphenyl-2-yl)-methanone;

[(2S,3S)-2-(5-Chloro-6-methyl-1H-benzoimidazol-2-yl)-3-methyl-pyrrolidin-1-yl]-[5-(4-chloro-phenyl)-2-methyl-thiazol-4-yl]-methanone;

[(2S,3S)-2-(5-Chloro-6-methyl-1H-benzoimidazol-2-yl)-3-methyl-pyrrolidin-1-yl]-(2-methyl-4-p-tolyl-thiazol-5-yl)-methanone;

[(2S,3S)-2-(5-Chloro-6-methyl-1H-benzoimidazol-2-yl)-3-methyl-pyrrolidin-1-yl]-[5-(3,5-difluoro-phenyl)-2-methyl-thiazol-4-yl]-methanone;

(5-Chloro-2-[1,2,3]triazol-2-yl-phenyl)-[(2S,3S)-2-(5,6-dimethyl-1H-benzoimidazol-2-yl)-3-methyl-pyrrolidin-1-yl]-methanone;

[(2S,3S)-2-(5,6-Dimethyl-1H-benzoimidazol-2-yl)-3-methyl-pyrrolidin-1-yl]-(5-methyl-2-pyrazol-1-yl-phenyl)-methanone;

[(2S,3S)-2-(5,6-Dimethyl-1H-benzoimidazol-2-yl)-3-methyl-pyrrolidin-1-yl]-(4'-methyl-biphenyl-2-yl)-methanone;

[5-(4-Chloro-phenyl)-2-methyl-thiazol-4-yl]-[(2S,3S)-2-(5,6-dimethyl-1H-benzoimidazol-2-yl)-3-methyl-pyrrolidin-1-yl]-methanone;

[(2S,3S)-2-(5,6-Dimethyl-1H-benzoimidazol-2-yl)-3-methyl-pyrrolidin-1-yl]-(2-methyl-4-p-tolyl-thiazol-5-yl)-methanone;

[5-(3,5-Difluoro-phenyl)-2-methyl-thiazol-4-yl]-[(2S,3S)-2-(5,6-dimethyl-1H-benzoimidazol-2-yl)-3-methyl-pyrrolidin-1-yl]-methanone;

[5-(3-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[(2S,3S)-2-(5,6-Dimethyl-1H-benzoimidazol-2-yl)-3-methyl-pyrrolidin-1-yl]-[5-(4-fluoro-phenyl)-2-methyl-thiazol-4-yl]-methanone;

[(2S,3S)-2-(6-Chloro-4-methyl-1H-benzoimidazol-2-yl)-3-methyl-pyrrolidin-1-yl]-(5-chloro-2-[1,2,3]triazol-2-yl-phenyl)-methanone;

[(2S,3S)-2-(6-Chloro-4-methyl-1H-benzoimidazol-2-yl)-3-methyl-pyrrolidin-1-yl]-(4'-methyl-biphenyl-2-yl)-methanone;

[(2S,3S)-2-(6-Chloro-4-methyl-1H-benzoimidazol-2-yl)-3-methyl-pyrrolidin-1-yl]-(4-methyl-2-[1,2,3]triazol-2-yl-phenyl)-methanone;

[(2S,3S)-2-(6-Chloro-4-methyl-1H-benzoimidazol-2-yl)-3-methyl-pyrrolidin-1-yl]-[5-(4-chloro-phenyl)-2-methyl-thiazol-4-yl]-methanone;

[(2S,3S)-2-(6-Chloro-4-methyl-1H-benzoimidazol-2-yl)-3-methyl-pyrrolidin-1-yl]-(5-methyl-2-pyrazol-1-yl-phenyl)-methanone;

[(2S,3S)-2-(6-Chloro-4-methyl-1H-benzoimidazol-2-yl)-3-methyl-pyrrolidin-1-yl]-(2-methyl-4-p-tolyl-thiazol-5-yl)-methanone;

[(2S,3S)-2-(6-Chloro-4-methyl-1H-benzoimidazol-2-yl)-3-methyl-pyrrolidin-1-yl]-(5-methoxy-2-[1,2,3]triazol-2-yl-phenyl)-methanone;

[(2S,3S)-2-(6-Chloro-4-methyl-1H-benzoimidazol-2-yl)-3-methyl-pyrrolidin-1-yl]-[5-(3,5-difluoro-phenyl)-2-methyl-thiazol-4-yl]-methanone;

[(2S,3S)-2-(6-Chloro-4-methyl-1H-benzoimidazol-2-yl)-3-methyl-pyrrolidin-1-yl]-(2-fluoro-3-methyl-6-[1,2,3]triazol-2-yl-phenyl)-methanone;

[(S)-2-(5-Chloro-1H-benzoimidazol-2-yl)-2-methyl-pyrrolidin-1-yl]-(5-methyl-2-[1,2,3]triazol-2-yl-phenyl)-methanone;

[(S)-2-(6-Chloro-5-fluoro-1H-benzoimidazol-2-yl)-2-methyl-pyrrolidin-1-yl]-(5-methyl-2-[1,2,3]triazol-2-yl-phenyl)-methanone;

[(S)-2-(6-Bromo-5-fluoro-1H-benzoimidazol-2-yl)-2-methyl-pyrrolidin-1-yl]-(5-methyl-2-pyrazol-1-yl-phenyl)-methanone;

[(S)-2-(6-Bromo-5-fluoro-1H-benzoimidazol-2-yl)-2-methyl-pyrrolidin-1-yl]-(6-methyl-3-[1,2,3]triazol-2-yl-pyridin-2-yl)-methanone;

[(S)-2-(6-Chloro-5-trifluoromethyl-1H-benzoimidazol-2-yl)-2-methyl-pyrrolidin-1-yl]-(2-pyrazol-1-yl-phenyl)-methanone;

[(S)-2-(6-Chloro-5-trifluoromethyl-1H-benzoimidazol-2-yl)-2-methyl-pyrrolidin-1-yl]-(6-methyl-3-pyrazol-1-yl-pyridin-2-yl)-methanone;

[(S)-2-(6-Chloro-5-trifluoromethyl-1H-benzoimidazol-2-yl)-2-methyl-pyrrolidin-1-yl]-(2-[1,2,3]triazol-2-yl-5-trifluoromethyl-phenyl)-methanone;
[(S)-2-(6-Chloro-5-trifluoromethyl-1H-benzoimidazol-2-yl)-2-methyl-pyrrolidin-1-yl]-(2-[1,2,3]triazol-2-yl-5-trifluoromethoxy-phenyl)-methanone;
(5-Methyl-2-[1,2,3]triazol-2-yl-phenyl)-[(S)-2-methyl-2-(4-trifluoromethyl-1H-benzoimidazol-2-yl)-pyrrolidin-1-yl]-methanone;
(5-Methyl-2-pyrazol-1-yl-phenyl)-[(S)-2-methyl-2-(5-trifluoromethyl-1H-benzoimidazol-2-yl)-pyrrolidin-1-yl]-methanone;
(6-Methyl-3-[1,2,3]triazol-2-yl-pyridin-2-yl)-[(S)-2-methyl-2-(5-trifluoromethyl-1H-benzoimidazol-2-yl)-pyrrolidin-1-yl]-methanone;
(3'-Methoxy-4-methyl-biphenyl-2-yl)-[(S)-2-methyl-2-(5-trifluoromethyl-1H-benzoimidazol-2-yl)-pyrrolidin-1-yl]-methanone;
4'-Methyl-2'-[(S)-2-methyl-2-(5-trifluoromethyl-1H-benzoimidazol-2-yl)-pyrrolidine-1-carbonyl]-biphenyl-4-carbonitrile;
(2'-Fluoro-4-methyl-biphenyl-2-yl)-[(S)-2-methyl-2-(5-trifluoromethyl-1H-benzoimidazol-2-yl)-pyrrolidin-1-yl]-methanone;
(4'-Fluoro-4-methyl-biphenyl-2-yl)-[(S)-2-methyl-2-(5-trifluoromethyl-1H-benzoimidazol-2-yl)-pyrrolidin-1-yl]-methanone;
[(S)-2-(4,5-Difluoro-1H-benzoimidazol-2-yl)-2-methyl-pyrrolidin-1-yl]-(4,5-dimethyl-2-[1,2,3]triazol-2-yl-phenyl)-methanone;
(5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone;
[(S)-2-(4,5-Difluoro-1H-benzoimidazol-2-yl)-2-methyl-pyrrolidin-1-yl]-(2-methyl-5-phenyl-thiazol-4-yl)-methanone;
[(S)-2-(4,5-Difluoro-1H-benzoimidazol-2-yl)-2-methyl-pyrrolidin-1-yl]-(2-methyl-5-p-tolyl-thiazol-4-yl)-methanone;
[5-(4-Chloro-phenyl)-2-methyl-thiazol-4-yl]-[(S)-2-(4,5-difluoro-1H-benzoimidazol-2-yl)-2-methyl-pyrrolidin-1-yl]-methanone;
[(S)-2-(4,5-Difluoro-1H-benzoimidazol-2-yl)-2-methyl-pyrrolidin-1-yl]-[5-(3-fluoro-phenyl)-2-methyl-thiazol-4-yl]-methanone;
[(S)-2-(6-Fluoro-5-trifluoromethyl-1H-benzoimidazol-2-yl)-2-methyl-pyrrolidin-1-yl]-(5-methyl-2-[1,2,3]triazol-2-yl-phenyl)-methanone;
[(S)-2-(5-Bromo-1H-benzoimidazol-2-yl)-2-methyl-pyrrolidin-1-yl]-(5-methyl-2-[1,2,3]triazol-2-yl-phenyl)-methanone;
(5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone;
[(2S,4R)-2-(6-Chloro-1,7-dimethyl-1H-benzoimidazol-2-yl)-4-methoxy-pyrrolidin-1-yl]-(5-methoxy-2-[1,2,3]triazol-2-yl-phenyl)-methanone; and
[(2S,4R)-2-(5-Chloro-1,4-dimethyl-1H-benzoimidazol-2-yl)-4-methoxy-pyrrolidin-1-yl]-(5-methoxy-2-[1,2,3]triazol-2-yl-phenyl)-methanone.

48) In addition to the above-listed compounds, further compounds according to embodiment 1) are selected from:

[2-(5,6-Dimethoxy-1H-benzoimidazol-2-yl)-pyrrolidin-1-yl]-(2-methyl-5-phenyl-thiazol-4-yl)-methanone;
[2-(4,5-Dimethyl-1H-benzoimidazol-2-yl)-pyrrolidin-1-yl]-(2-methyl-5-phenyl-thiazol-4-yl)-methanone;
[2-(5-Methoxy-1H-benzoimidazol-2-yl)-pyrrolidin-1-yl]-(5-methyl-2-[1,2,3]triazol-2-yl-phenyl)-methanone;
(5-Fluoro-2-[1,2,3]triazol-2-yl-phenyl)-[(S)-2-(6-methylsulfanyl-1H-benzoimidazol-2-yl)-pyrrolidin-1-yl]-methanone;
(5-Chloro-2-[1,2,3]triazol-2-yl-phenyl)-[(S)-2-(6-methylsulfanyl-1H-benzoimidazol-2-yl)-pyrrolidin-1-yl]-methanone;
(5-Methoxy-2-[1,2,3]triazol-2-yl-phenyl)-[(S)-2-(6-methylsulfanyl-1H-benzoimidazol-2-yl)-pyrrolidin-1-yl]-methanone;
3-[(S)-2-(6-Methylsulfanyl-1H-benzoimidazol-2-yl)-pyrrolidine-1-carbonyl]-4-[1,2,3]triazol-2-yl-benzonitrile;
[(S)-2-(6-Methylsulfanyl-1H-benzoimidazol-2-yl)-pyrrolidin-1-yl]-(2-methyl-6-[1,2,3]triazol-2-yl-phenyl)-methanone;
(5-Fluoro-2-[1,2,3]triazol-2-yl-phenyl)-[(S)-2-(6-methoxy-1H-benzoimidazol-2-yl)-pyrrolidin-1-yl]-methanone;
(5-Chloro-2-[1,2,3]triazol-2-yl-phenyl)-[(S)-2-(6-methoxy-1H-benzoimidazol-2-yl)-pyrrolidin-1-yl]-methanone;
[(S)-2-(6-Methoxy-1H-benzoimidazol-2-yl)-pyrrolidin-1-yl]-(5-methoxy-2-[1,2,3]triazol-2-yl-phenyl)-methanone;
3-[(S)-2-(6-Methoxy-1H-benzoimidazol-2-yl)-pyrrolidine-1-carbonyl]-4-[1,2,3]triazol-2-yl-benzonitrile;
[(S)-2-(6-Methoxy-1H-benzoimidazol-2-yl)-pyrrolidin-1-yl]-(5-methyl-2-[1,2,3]triazol-2-yl-phenyl)-methanone;
[(S)-2-(6-Methoxy-1H-benzoimidazol-2-yl)-pyrrolidin-1-yl]-(4-methyl-2-[1,2,3]triazol-2-yl-phenyl)-methanone;
[(S)-2-(6-Methoxy-1H-benzoimidazol-2-yl)-pyrrolidin-1-yl]-(2-methyl-6-[1,2,3]triazol-2-yl-phenyl)-methanone;
(4,5-Dimethoxy-2-[1,2,3]triazol-2-yl-phenyl)-[(S)-2-(6-methoxy-1H-benzoimidazol-2-yl)-pyrrolidin-1-yl]-methanone;
(5-Fluoro-2-[1,2,3]triazol-2-yl-phenyl)-[(S)-2-(7-methylsulfanyl-1H-benzoimidazol-2-yl)-pyrrolidin-1-yl]-methanone;
(2-Fluoro-6-[1,2,3]triazol-2-yl-phenyl)-[(S)-2-(7-methylsulfanyl-1H-benzoimidazol-2-yl)-pyrrolidin-1-yl]-methanone;
(5-Chloro-2-[1,2,3]triazol-2-yl-phenyl)-[(S)-2-(7-methylsulfanyl-1H-benzoimidazol-2-yl)-pyrrolidin-1-yl]-methanone;
3-[(S)-2-(7-Methylsulfanyl-1H-benzoimidazol-2-yl)-pyrrolidine-1-carbonyl]-4-[1,2,3]triazol-2-yl-benzonitrile;
[(S)-2-(6-Methylsulfanyl-1H-benzoimidazol-2-yl)-pyrrolidin-1-yl]-(5-methyl-2-[1,2,3]triazol-2-yl-phenyl)-methanone;
[(S)-2-(7-Methylsulfanyl-1H-benzoimidazol-2-yl)-pyrrolidin-1-yl]-(2-methyl-6-[1,2,3]triazol-2-yl-phenyl)-methanone;
(2-Fluoro-3-methyl-6-[1,2,3]triazol-2-yl-phenyl)-[(S)-2-(5-methoxy-1H-benzoimidazol-2-yl)-pyrrolidin-1-yl]-methanone;
(5-Methyl-2-pyrazol-1-yl-phenyl)-[(S)-2-(5-methylsulfanyl-1H-benzoimidazol-2-yl)-pyrrolidin-1-yl]-methanone;
(2-Fluoro-3-methyl-6-[1,2,3]triazol-2-yl-phenyl)-[(S)-2-(5-methylsulfanyl-1H-benzoimidazol-2-yl)-pyrrolidin-1-yl]-methanone;
[(S)-2-(5-Methoxy-1H-benzoimidazol-2-yl)-pyrrolidin-1-yl]-(5-methyl-2-[1,2,3]triazol-2-yl-phenyl)-methanone;
(3',4-Dimethyl-biphenyl-2-yl)-[(S)-2-(6-methoxy-1H-benzoimidazol-2-yl)-pyrrolidin-1-yl]-methanone;
[5-(2,3-Dichloro-phenyl)-2-methyl-thiazol-4-yl]-[(S)-2-(6-methylsulfanyl-1H-benzoimidazol-2-yl)-pyrrolidin-1-yl]-methanone;
[(S)-2-(7-Methoxy-1H-benzoimidazol-2-yl)-pyrrolidin-1-yl]-(5-methyl-2-[1,2,3]triazol-2-yl-phenyl)-methanone;

(3',4-Dimethyl-biphenyl-2-yl)-[(S)-2-(6-methylsulfanyl-1H-benzoimidazol-2-yl)-pyrrolidin-1-yl]-methanone;
[(S)-2-(6-Methylsulfanyl-1H-benzoimidazol-2-yl)-pyrrolidin-1-yl]-(2-[1,2,3]triazol-2-yl-phenyl)-methanone;
[(S)-2-(5-Methylsulfanyl-1H-benzoimidazol-2-yl)-pyrrolidin-1-yl]-(5-methyl-2-[1,2,3]triazol-2-yl-phenyl)-methanone;
[(S)-2-(7-Methylsulfanyl-1H-benzoimidazol-2-yl)-pyrrolidin-1-yl]-(2-[1,2,3]triazol-2-yl-phenyl)-methanone;
[(2S,4R)-2-(6-Chloro-7-methyl-1H-benzoimidazol-2-yl)-4-methoxy-pyrrolidin-1-yl]-(2-methyl-6-[1,2,3]triazol-2-yl-phenyl)-methanone;
[(2S,4R)-2-(6-Chloro-7-methyl-1H-benzoimidazol-2-yl)-4-methoxy-pyrrolidin-1-yl]-(4-methyl-2-[1,2,3]triazol-2-yl-phenyl)-methanone;
[(2S,4R)-2-(6-Chloro-7-methyl-1H-benzoimidazol-2-yl)-4-methoxy-pyrrolidin-1-yl]-(5-fluoro-2-[1,2,3]triazol-2-yl-phenyl)-methanone;
(5-Chloro-2-[1,2,3]triazol-2-yl-phenyl)-[(2S,4R)-4-methoxy-2-(6-methoxy-1H-benzoimidazol-2-yl)-pyrrolidin-1-yl]-methanone;
(4,5-Dimethyl-2-[1,2,3]triazol-2-yl-phenyl)-[(2S,4R)-4-methoxy-2-(6-methoxy-1H-benzoimidazol-2-yl)-pyrrolidin-1-yl]-methanone;
[(S)-2-(5,6-Dimethyl-1H-benzoimidazol-2-yl)-2-methyl-pyrrolidin-1-yl]-(2-[1,2,3]triazol-2-yl-phenyl)-methanone;
[5-(6-Methoxy-pyridin-3-yl)-2-methyl-thiazol-4-yl]-[(S)-2-(7-methyl-1H-benzoimidazol-2-yl)-4-methylene-pyrrolidin-1-yl]-methanone;
[5-(4-Fluoro-phenyl)-2-methyl-thiazol-4-yl]-[(S)-2-(7-methyl-1H-benzoimidazol-2-yl)-4-methylene-pyrrolidin-1-yl]-methanone;
(4,5-Dimethyl-2-[1,2,3]triazol-2-yl-phenyl)-[(S)-2-(7-methyl-1H-benzoimidazol-2-yl)-4-methylene-pyrrolidin-1-yl]-methanone;
[5-(4-Chloro-phenyl)-2-methyl-thiazol-4-yl]-[(S)-2-(7-methyl-1H-benzoimidazol-2-yl)-4-methylene-pyrrolidin-1-yl]-methanone;
(5-Methoxy-2-[1,2,3]triazol-2-yl-phenyl)-[(S)-2-(7-methyl-1H-benzoimidazol-2-yl)-4-methylene-pyrrolidin-1-yl]-methanone;
[(S)-2-(7-Methyl-1H-benzoimidazol-2-yl)-4-methylene-pyrrolidin-1-yl]-(6-methyl-3-[1,2,3]triazol-2-yl-pyridin-2-yl)-methanone;
[(S)-2-(5-Methoxy-1H-benzoimidazol-2-yl)-4-methylene-pyrrolidin-1-yl]-(5-methyl-2-[1,2,3]triazol-2-yl-phenyl)-methanone;
[(S)-2-(5-Methoxy-1H-benzoimidazol-2-yl)-4-methylene-pyrrolidin-1-yl]-(2-[1,2,3]triazol-2-yl-phenyl)-methanone;
[(S)-2-(6-Chloro-7-methyl-1H-benzoimidazol-2-yl)-4-methylene-pyrrolidin-1-yl]-(5-methyl-2-pyrazol-1-yl-phenyl)-methanone;
[(S)-2-(6-Chloro-7-methyl-1H-benzoimidazol-2-yl)-4-methylene-pyrrolidin-1-yl]-(6-methyl-3-pyrazol-1-yl-pyridin-2-yl)-methanone;
(5-Chloro-2-[1,2,3]triazol-2-yl-phenyl)-[(S)-2-(6-methoxy-1H-benzoimidazol-2-yl)-4-methylene-pyrrolidin-1-yl]-methanone;
[(S)-2-(6-Methoxy-1H-benzoimidazol-2-yl)-4-methylene-pyrrolidin-1-yl]-(5-methyl-2-pyrazol-1-yl-phenyl)-methanone;
(4,5-Dimethyl-2-[1,2,3]triazol-2-yl-phenyl)-[(S)-2-(6-methoxy-1H-benzoimidazol-2-yl)-4-methylene-pyrrolidin-1-yl]-methanone;
[(S)-2-(5-Methoxy-1H-benzoimidazol-2-yl)-4-methylene-pyrrolidin-1-yl]-(3'-methyl-biphenyl-2-yl)-methanone;
[(S)-2-(6-Methoxy-1H-benzoimidazol-2-yl)-4-methylene-pyrrolidin-1-yl]-(5-methoxy-2-[1,2,3]triazol-2-yl-phenyl)-methanone;
(2-Fluoro-3-methyl-6-[1,2,3]triazol-2-yl-phenyl)-[(S)-2-(6-methoxy-1H-benzoimidazol-2-yl)-4-methylene-pyrrolidin-1-yl]-methanone;
[(S)-2-(5-tert-Butyl-1H-benzoimidazol-2-yl)-4-methylene-pyrrolidin-1-yl]-(5-fluoro-2-[1,2,3]triazol-2-yl-phenyl)-methanone;
[(S)-2-(5-tert-Butyl-1H-benzoimidazol-2-yl)-4-methylene-pyrrolidin-1-yl]-(5-chloro-2-[1,2,3]triazol-2-yl-phenyl)-methanone;
[(S)-2-(5-tert-Butyl-1H-benzoimidazol-2-yl)-4-methylene-pyrrolidin-1-yl]-(2-[1,2,3]triazol-2-yl-phenyl)-methanone;
[(S)-2-(5-tert-Butyl-1H-benzoimidazol-2-yl)-4-methylene-pyrrolidin-1-yl]-(2-fluoro-3-methyl-6-[1,2,3]triazol-2-yl-phenyl)-methanone;
[(S)-2-(5-tert-Butyl-1H-benzoimidazol-2-yl)-4-methylene-pyrrolidin-1-yl]-(2-methyl-6-[1,2,3]triazol-2-yl-phenyl)-methanone;
[(S)-2-(5-tert-Butyl-1H-benzoimidazol-2-yl)-4-methylene-pyrrolidin-1-yl]-(5-methyl-2-pyrazol-1-yl-phenyl)-methanone;
[(S)-2-(5-tert-Butyl-1H-benzoimidazol-2-yl)-4-methylene-pyrrolidin-1-yl]-(6-methyl-3-[1,2,3]triazol-2-yl-pyridin-2-yl)-methanone;
(5-Fluoro-2-[1,2,3]triazol-2-yl-phenyl)-[(S)-2-(5-methoxy-1H-benzoimidazol-2-yl)-4-methylene-pyrrolidin-1-yl]-methanone;
[(S)-2-(5-Chloro-6-trifluoromethyl-1H-benzoimidazol-2-yl)-4-methylene-pyrrolidin-1-yl]-(2-methyl-6-[1,2,3]triazol-2-yl-phenyl)-methanone;
[(S)-2-(5,6-Dimethyl-1H-benzoimidazol-2-yl)-4-methylene-pyrrolidin-1-yl]-(2-fluoro-6-[1,2,3]triazol-2-yl-phenyl)-methanone;
[(S)-2-(5-Methoxy-1H-benzoimidazol-2-yl)-4-methylene-pyrrolidin-1-yl]-[5-(4-methoxy-phenyl)-2-methyl-thiazol-4-yl]-methanone;
[5-(4-Bromo-phenyl)-2-methyl-thiazol-4-yl]-[(S)-2-(5-methoxy-1H-benzoimidazol-2-yl)-4-methylene-pyrrolidin-1-yl]-methanone;
[(S)-2-(5-Methoxy-1H-benzoimidazol-2-yl)-4-methylene-pyrrolidin-1-yl]-(2-methyl-5-phenyl-thiazol-4-yl)-methanone;
[5-(3-Fluoro-phenyl)-2-methyl-thiazol-4-yl]-[(S)-2-(5-methoxy-1H-benzoimidazol-2-yl)-4-methylene-pyrrolidin-1-yl]-methanone;
[(S)-2-(5-Methoxy-1H-benzoimidazol-2-yl)-4-methylene-pyrrolidin-1-yl]-(2-m-tolyl-thiophen-3-yl)-methanone;
[2-(3,4-Dimethyl-phenyl)-thiophen-3-yl]-[(S)-2-(5-methoxy-1H-benzoimidazol-2-yl)-4-methylene-pyrrolidin-1-yl]-methanone;
[(S)-2-(4-Methyl-1H-benzoimidazol-2-yl)-4-methylene-pyrrolidin-1-yl]-(2-methyl-5-phenyl-thiazol-4-yl)-methanone;
[5-(4-Chloro-phenyl)-2-methyl-thiazol-4-yl]-[(S)-2-(5-methoxy-1H-benzoimidazol-2-yl)-4-methylene-pyrrolidin-1-yl]-methanone;
[(S)-4-Methylene-2-(7-methylsulfanyl-1H-benzoimidazol-2-yl)-pyrrolidin-1-yl]-(5-methyl-2-[1,2,3]triazol-2-yl-phenyl)-methanone;
[(S)-4-Methylene-2-(5-methylsulfanyl-1H-benzoimidazol-2-yl)-pyrrolidin-1-yl]-(5-methyl-2-[1,2,3]triazol-2-yl-phenyl)-methanone;

[(S)-2-(4,5-Dimethyl-1H-benzoimidazol-2-yl)-4-methyl-ene-pyrrolidin-1-yl]-(5-methyl-2-[1,2,3]triazol-2-yl-phenyl)-methanone; and

[(S)-2-(5-tert-Butyl-1H-benzoimidazol-2-yl)-4-methylene-pyrrolidin-1-yl]-(5-methyl-2-[1,2,3]triazol-2-yl-phenyl)-methanone.

49) In addition to the above-listed compounds, further compounds according to embodiment 1) are selected from:

[(2S,3S)-2-(4-Chloro-1H-benzoimidazol-2-yl)-3-methyl-pyrrolidin-1-yl]-[2-(3,4-dimethyl-phenyl)-thiophen-3-yl]-methanone;

[5-(3,4-Dimethyl-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[2-(3,4-Dimethyl-phenyl)-thiophen-3-yl]-[(2S,3S)-3-methyl-2-(4-trifluoromethyl-1H-benzoimidazol-2-yl)-pyrrolidin-1-yl]-methanone;

[(2S,3S)-2-(5,6-Dimethoxy-1H-benzoimidazol-2-yl)-3-methyl-pyrrolidin-1-yl]-(5-methyl-2-pyrimidin-2-yl-phenyl)-methanone;

[(S)-2-(5-Chloro-4-methyl-1H-benzoimidazol-2-yl)-2-methyl-pyrrolidin-1-yl]-(4-fluoro-biphenyl-2-yl)-methanone;

[(S)-2-(5-Chloro-4-methyl-1H-benzoimidazol-2-yl)-2-methyl-pyrrolidin-1-yl]-(5-fluoro-2-pyridin-2-yl-phenyl)-methanone;

[(S)-2-(5-Chloro-4-methyl-1H-benzoimidazol-2-yl)-2-methyl-pyrrolidin-1-yl]-(2-fluoro-6-pyridin-2-yl-phenyl)-methanone;

[(S)-2-(5-Chloro-4-methyl-1H-benzoimidazol-2-yl)-2-methyl-pyrrolidin-1-yl]-(2-fluoro-6-pyrimidin-2-yl-phenyl)-methanone;

[(S)-2-(5-Chloro-4-methyl-1H-benzoimidazol-2-yl)-2-methyl-pyrrolidin-1-yl]-(4-methyl-biphenyl-2-yl)-methanone;

[(S)-2-(5-Chloro-4-methyl-1H-benzoimidazol-2-yl)-2-methyl-pyrrolidin-1-yl]-(5-fluoro-2-pyrimidin-2-yl-phenyl)-methanone;

[(S)-2-(5-Chloro-4-methyl-1H-benzoimidazol-2-yl)-2-methyl-pyrrolidin-1-yl]-(3-fluoro-biphenyl-2-yl)-methanone;

(4,5-Dimethyl-2-[1,2,3]triazol-2-yl-phenyl)-[(S)-2-methyl-2-(5-trifluoromethoxy-1H-benzoimidazol-2-yl)-pyrrolidin-1-yl]-methanone;

(4-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone;

[5-(3,4-Dimethyl-phenyl)-2-methyl-thiazol-4-yl]-[(S)-2-methyl-2-(5-trifluoromethoxy-1H-benzoimidazol-2-yl)-pyrrolidin-1-yl]-methanone;

[(S)-2-(5-Chloro-4-methyl-1H-benzoimidazol-2-yl)-2-methyl-pyrrolidin-1-yl]-(2-methyl-5-phenyl-pyridin-4-yl)-methanone;

[(S)-2-Methyl-2-(5-trifluoromethyl-1H-benzoimidazol-2-yl)-pyrrolidin-1-yl]-(4-pyridin-3-yl-biphenyl-2-yl)-methanone;

[(S)-2-(6-Bromo-4,5-dimethyl-1H-benzoimidazol-2-yl)-2-methyl-pyrrolidin-1-yl]-(5-methyl-2-[1,2,3]triazol-2-yl-phenyl)-methanone;

[(S)-2-(6-Bromo-4,5-dimethyl-1H-benzoimidazol-2-yl)-2-methyl-pyrrolidin-1-yl]-(2-fluoro-6-[1,2,3]triazol-2-yl-phenyl)-methanone;

Biphenyl-2-yl-[(S)-2-(6-bromo-4,5-dimethyl-1H-benzoimidazol-2-yl)-2-methyl-pyrrolidin-1-yl]-methanone;

[(S)-2-(6-Bromo-4,5-dimethyl-1H-benzoimidazol-2-yl)-2-methyl-pyrrolidin-1-yl]-(4-methyl-biphenyl-2-yl)-methanone;

[(S)-2-(6-Bromo-4,5-dimethyl-1H-benzoimidazol-2-yl)-2-methyl-pyrrolidin-1-yl]-(2-methyl-5-o-tolyl-thiazol-4-yl)-methanone;

[(S)-2-(6-Bromo-4,5-dimethyl-1H-benzoimidazol-2-yl)-2-methyl-pyrrolidin-1-yl]-[5-(2,3-dichloro-phenyl)-2-methyl-thiazol-4-yl]-methanone;

[(S)-2-(6-Bromo-4,5-dimethyl-1H-benzoimidazol-2-yl)-2-methyl-pyrrolidin-1-yl]-[5-(3,4-dimethyl-phenyl)-2-methyl-thiazol-4-yl]-methanone;

[(S)-2-(6-Bromo-4,5-dimethyl-1H-benzoimidazol-2-yl)-2-methyl-pyrrolidin-1-yl]-[5-(3,5-difluoro-phenyl)-2-methyl-thiazol-4-yl]-methanone;

[(S)-2-(6-Bromo-4,5-dimethyl-1H-benzoimidazol-2-yl)-2-methyl-pyrrolidin-1-yl]-[5-(3-methoxy-phenyl)-2-methyl-thiazol-4-yl]-methanone;

[(S)-2-(6-Bromo-4,5-dimethyl-1H-benzoimidazol-2-yl)-2-methyl-pyrrolidin-1-yl]-[5-(4-fluoro-phenyl)-2-methyl-thiazol-4-yl]-methanone;

[(S)-2-(5-Bromo-7-methyl-1H-benzoimidazol-2-yl)-2-methyl-pyrrolidin-1-yl]-(5-methyl-2-pyrimidin-2-yl-phenyl)-methanone;

[(S)-2-Methyl-2-(7-methyl-1H-benzoimidazol-2-yl)-pyrrolidin-1-yl]-(5-methyl-2-pyrimidin-2-yl-phenyl)-methanone;

[(S)-2-(6-Chloro-5-trifluoromethyl-1H-benzoimidazol-2-yl)-2-methyl-pyrrolidin-1-yl]-(5-methyl-2-pyrimidin-2-yl-phenyl)-methanone;

[(S)-2-(5,6-Dimethoxy-1H-benzoimidazol-2-yl)-2-methyl-pyrrolidin-1-yl]-(5-methyl-2-pyrimidin-2-yl-phenyl)-methanone;

[(S)-2-(5,6-Dimethyl-1H-benzoimidazol-2-yl)-2-methyl-pyrrolidin-1-yl]-(5-methyl-2-pyrimidin-2-yl-phenyl)-methanone;

[(S)-2-(5-Chloro-4-methyl-1H-benzoimidazol-2-yl)-2-methyl-pyrrolidin-1-yl]-(3-fluoro-4,3'-dimethoxy-biphenyl-2-yl)-methanone;

[(S)-2-(5-Chloro-4-methyl-1H-benzoimidazol-2-yl)-2-methyl-pyrrolidin-1-yl]-(3,2'-difluoro-4-methoxy-biphenyl-2-yl)-methanone;

[(S)-2-(5-Chloro-4-methyl-1H-benzoimidazol-2-yl)-2-methyl-pyrrolidin-1-yl]-(3,4'-difluoro-4-methoxy-biphenyl-2-yl)-methanone;

[(S)-2-(5-Chloro-4-methyl-1H-benzoimidazol-2-yl)-2-methyl-pyrrolidin-1-yl]-(3,3'-difluoro-4-methoxy-biphenyl-2-yl)-methanone;

[(S)-2-(5-Chloro-4-methyl-1H-benzoimidazol-2-yl)-2-methyl-pyrrolidin-1-yl]-(3-fluoro-4-methoxy-3'-methyl-biphenyl-2-yl)-methanone;

[(S)-2-(5-Chloro-4-methyl-1H-benzoimidazol-2-yl)-2-methyl-pyrrolidin-1-yl]-(3-fluoro-4-methoxy-4'-methyl-biphenyl-2-yl)-methanone;

[(S)-2-(5-Chloro-4-methyl-1H-benzoimidazol-2-yl)-2-methyl-pyrrolidin-1-yl]-(3-fluoro-4-methoxy-3'-trifluoromethyl-biphenyl-2-yl)-methanone;

(6-Benzo[1,3]dioxol-5-yl-2-fluoro-3-methoxy-phenyl)-[(S)-2-(5-chloro-4-methyl-1H-benzoimidazol-2-yl)-2-methyl-pyrrolidin-1-yl]-methanone;

2'-[(S)-2-(5-Chloro-4-methyl-1H-benzoimidazol-2-yl)-2-methyl-pyrrolidine-1-carbonyl]-3'-fluoro-4'-methoxy-biphenyl-3-carbonitrile;

[(S)-2-(5-Chloro-4-methyl-1H-benzoimidazol-2-yl)-2-methyl-pyrrolidin-1-yl]-(3-fluoro-4-methoxy-3'-trifluoromethoxy-biphenyl-2-yl)-methanone;

[(S)-2-(5,6-Dimethyl-1H-benzoimidazol-2-yl)-4-methylene-pyrrolidin-1-yl]-(4-methyl-2-[1,2,3]triazol-2-yl-phenyl)-methanone;
(4,5-Dimethoxy-2-[1,2,3]triazol-2-yl-phenyl)-[(S)-2-(5,6-dimethyl-1H-benzoimidazol-2-yl)-4-methylene-pyrrolidin-1-yl]-methanone;
(4-Methyl-2-[1,2,3]triazol-2-yl-phenyl)-[(S)-2-methyl-2-(1,5,6-trimethyl-1H-benzoimidazol-2-yl)-pyrrolidin-1-yl]-methanone;
[(S)-2-(1-Ethyl-5,6-dimethyl-1H-benzoimidazol-2-yl)-2-methyl-pyrrolidin-1-yl]-(4-methyl-2-[1,2,3]triazol-2-yl-phenyl)-methanone;
[(S)-2-(5,6-Dimethoxy-1-methyl-1H-benzoimidazol-2-yl)-2-methyl-pyrrolidin-1-yl]-(4,5-dimethyl-2-[1,2,3]triazol-2-yl-phenyl)-methanone;
(4,5-Dimethyl-2-[1,2,3]triazol-2-yl-phenyl)-[(S)-2-(1-ethyl-5,6-dimethoxy-1H-benzoimidazol-2-yl)-2-methyl-pyrrolidin-1-yl]-methanone;
(4'-Fluoro-4-methyl-biphenyl-2-yl)-[(S)-2-methyl-2-(1,5,6-trimethyl-1H-benzoimidazol-2-yl)-pyrrolidin-1-yl]-methanone;
[(S)-2-(1-Ethyl-5,6-dimethyl-1H-benzoimidazol-2-yl)-2-methyl-pyrrolidin-1-yl]-(4'-fluoro-4-methyl-biphenyl-2-yl)-methanone;
(4,5-Dimethyl-2-[1,2,3]triazol-2-yl-phenyl)-[(S)-2-methyl-2-(1,5,6-trimethyl-1H-benzoimidazol-2-yl)-pyrrolidin-1-yl]-methanone;
[(S)-2-(5-Chloro-1,4-dimethyl-1H-benzoimidazol-2-yl)-2-methyl-pyrrolidin-1-yl]-(6-methyl-3-[1,2,3]triazol-2-yl-pyridin-2-yl)-methanone;
[(S)-2-(5-Chloro-1,4-dimethyl-1H-benzoimidazol-2-yl)-2-methyl-pyrrolidin-1-yl]-(2-[1,2,3]triazol-2-yl-phenyl)-methanone;
[(S)-2-(6-Chloro-1-methyl-5-trifluoromethyl-1H-benzoimidazol-2-yl)-2-methyl-pyrrolidin-1-yl]-(5-methyl-2-[1,2,3]triazol-2-yl-phenyl)-methanone;
[(S)-2-(5-Chloro-1-ethyl-4-methyl-1H-benzoimidazol-2-yl)-2-methyl-pyrrolidin-1-yl]-(5-methyl-2-[1,2,3]triazol-2-yl-phenyl)-methanone;
[(S)-2-(5-Chloro-1,4-dimethyl-1H-benzoimidazol-2-yl)-2-methyl-pyrrolidin-1-yl]-(5-chloro-2-[1,2,3]triazol-2-yl-phenyl)-methanone;
[(S)-2-(5-Chloro-1,4-dimethyl-1H-benzoimidazol-2-yl)-2-methyl-pyrrolidin-1-yl]-(5-methoxy-2-[1,2,3]triazol-2-yl-phenyl)-methanone;
(4,3'-Dimethyl-biphenyl-2-yl)-[(S)-2-methyl-2-(1,5,6-trimethyl-1H-benzoimidazol-2-yl)-pyrrolidin-1-yl]-methanone;
(4,3'-Dimethyl-biphenyl-2-yl)-[(S)-2-(1-ethyl-5,6-dimethyl-1H-benzoimidazol-2-yl)-2-methyl-pyrrolidin-1-yl]-methanone;
(4,3'-Dimethyl-biphenyl-2-yl)-{(S)-2-[1-(2-fluoro-ethyl)-5,6-dimethyl-1H-benzoimidazol-2-yl]-2-methyl-pyrrolidin-1-yl}-methanone;
(4,3'-Dimethyl-biphenyl-2-yl)-{(S)-2-[1-(2-methoxy-ethyl)-5,6-dimethyl-1H-benzoimidazol-2-yl]-2-methyl-pyrrolidin-1-yl}-methanone;
(3'-Fluoro-4-methyl-biphenyl-2-yl)-[(S)-2-methyl-2-(1,5,6-trimethyl-1H-benzoimidazol-2-yl)-pyrrolidin-1-yl]-methanone;
[(S)-2-(1-Ethyl-5,6-dimethyl-1H-benzoimidazol-2-yl)-2-methyl-pyrrolidin-1-yl]-(3'-fluoro-4-methyl-biphenyl-2-yl)-methanone;
[(S)-2-(5-Chloro-1,4-dimethyl-1H-benzoimidazol-2-yl)-2-methyl-pyrrolidin-1-yl]-[5-(3-chloro-phenyl)-2-methyl-thiazol-4-yl]-methanone;
[(S)-2-(1-Cyclopropylmethyl-5,6-dimethyl-1H-benzoimidazol-2-yl)-2-methyl-pyrrolidin-1-yl]-(3'-fluoro-4-methyl-biphenyl-2-yl)-methanone;
{(S)-2-[1-(2-Fluoro-ethyl)-5,6-dimethyl-1H-benzoimidazol-2-yl]-2-methyl-pyrrolidin-1-yl}-(3-fluoro-4-methyl-biphenyl-2-yl)-methanone;
(4,4'-Dimethyl-biphenyl-2-yl)-[(S)-2-methyl-2-(1,5,6-trimethyl-1H-benzoimidazol-2-yl)-pyrrolidin-1-yl]-methanone;
(4,4'-Dimethyl-biphenyl-2-yl)-[(S)-2-(1-ethyl-5,6-dimethyl-1H-benzoimidazol-2-yl)-2-methyl-pyrrolidin-1-yl]-methanone;
(4,4'-Dimethyl-biphenyl-2-yl)-{(S)-2-[1-(2-fluoro-ethyl)-5,6-dimethyl-1H-benzoimidazol-2-yl]-2-methyl-pyrrolidin-1-yl}-methanone;
(3'-Methoxy-4-methyl-biphenyl-2-yl)-[(S)-2-methyl-2-(1,5,6-trimethyl-1H-benzoimidazol-2-yl)-pyrrolidin-1-yl]-methanone;
(2'-Fluoro-4-methyl-biphenyl-2-yl)-[(S)-2-methyl-2-(1,5,6-trimethyl-1H-benzoimidazol-2-yl)-pyrrolidin-1-yl]-methanone;
[(S)-2-(1-Ethyl-5,6-dimethyl-1H-benzoimidazol-2-yl)-2-methyl-pyrrolidin-1-yl]-(3'-methoxy-4-methyl-biphenyl-2-yl)-methanone;
{(S)-2-[1-(2-Fluoro-ethyl)-5,6-dimethyl-1H-benzoimidazol-2-yl]-2-methyl-pyrrolidin-1-yl}-(3'-methoxy-4-methyl-biphenyl-2-yl)-methanone;
{(S)-2-[1-(2-Fluoro-ethyl)-5,6-dimethyl-1H-benzoimidazol-2-yl]-2-methyl-pyrrolidin-1-yl}-(2'-fluoro-4-methyl-biphenyl-2-yl)-methanone; and
[(S)-2-(5,6-Dimethoxy-1-methyl-1H-benzoimidazol-2-yl)-2-methyl-pyrrolidin-1-yl]-(5-methyl-2-[1,2,3]triazol-2-yl-phenyl)-methanone.

50) In addition to the above-listed compounds, further compounds according to embodiment 1) are selected from:
[(2S,3S)-2-(5-Chloro-6-methyl-1H-benzoimidazol-2-yl)-3-methyl-pyrrolidin-1-yl]-(5-methyl-2-pyridin-2-yl-phenyl)-methanone;
(4-Chloro-biphenyl-2-yl)-[(2S,3S)-2-(5-chloro-6-methyl-1H-benzoimidazol-2-yl)-3-methyl-pyrrolidin-1-yl]-methanone;
[(2S,3S)-2-(5-Chloro-6-methyl-1H-benzoimidazol-2-yl)-3-methyl-pyrrolidin-1-yl]-(5-methyl-2-pyridin-3-yl-phenyl)-methanone;
[(2S,3S)-2-(5-Chloro-6-methyl-1H-benzoimidazol-2-yl)-3-methyl-pyrrolidin-1-yl]-(4-fluoro-biphenyl-2-yl)-methanone;
[(2S,3S)-2-(5-Chloro-6-methyl-1H-benzoimidazol-2-yl)-3-methyl-pyrrolidin-1-yl]-(5-fluoro-2-pyridin-2-yl-phenyl)-methanone;
2-[(2S,3S)-2-(5-Chloro-6-methyl-1H-benzoimidazol-2-yl)-3-methyl-pyrrolidine-1-carbonyl]-biphenyl-4-carbonitrile;
[(2S,3S)-2-(5-Chloro-6-methyl-1H-benzoimidazol-2-yl)-3-methyl-pyrrolidin-1-yl]-(4-methyl-2-pyridin-2-yl-phenyl)-methanone;
[(2S,3S)-2-(5-Chloro-6-methyl-1H-benzoimidazol-2-yl)-3-methyl-pyrrolidin-1-yl]-(4-methyl-2-pyridin-3-yl-phenyl)-methanone;
[(2S,3S)-2-(5-Chloro-6-methyl-1H-benzoimidazol-2-yl)-3-methyl-pyrrolidin-1-yl]-(5-methyl-biphenyl-2-yl)-methanone;
[(2S,3S)-2-(5-Chloro-6-methyl-1H-benzoimidazol-2-yl)-3-methyl-pyrrolidin-1-yl]-(3-fluoro-biphenyl-2-yl)-methanone;

[(2S,3S)-2-(5-Chloro-6-methyl-1H-benzoimidazol-2-yl)-3-methyl-pyrrolidin-1-yl]-(2-fluoro-3-methyl-6-pyridin-2-yl-phenyl)-methanone;

[(2S,3S)-2-(5-Chloro-6-methyl-1H-benzoimidazol-2-yl)-3-methyl-pyrrolidin-1-yl]-(3-fluoro-4-methyl-biphenyl-2-yl)-methanone;

[(2S,3S)-2-(5-Chloro-6-methyl-1H-benzoimidazol-2-yl)-3-methyl-pyrrolidin-1-yl]-(4-methyl-biphenyl-2-yl)-methanone;

[(2S,3S)-2-(5-Chloro-6-methyl-1H-benzoimidazol-2-yl)-3-methyl-pyrrolidin-1-yl]-(2-fluoro-3-methyl-6-pyridin-3-yl-phenyl)-methanone;

[(2S,3S)-2-(4-Chloro-1H-benzoimidazol-2-yl)-3-methyl-pyrrolidin-1-yl]-[5-(3,5-difluoro-phenyl)-2-methyl-thiazol-4-yl]-methanone;

[(2S,3S)-2-(4-Chloro-1H-benzoimidazol-2-yl)-3-methyl-pyrrolidin-1-yl]-[5-(4-chloro-phenyl)-2-methyl-thiazol-4-yl]-methanone;

[(2S,3S)-2-(4-Chloro-1H-benzoimidazol-2-yl)-3-methyl-pyrrolidin-1-yl]-[5-(3-methoxy-phenyl)-2-methyl-thiazol-4-yl]-methanone;

[(2S,3S)-2-(4-Chloro-1H-benzoimidazol-2-yl)-3-methyl-pyrrolidin-1-yl]-(2-methyl-5-m-tolyl-thiazol-4-yl)-methanone;

[5-(4-Bromo-phenyl)-2-methyl-thiazol-4-yl]-[(2S,3S)-2-(4-chloro-1H-benzoimidazol-2-yl)-3-methyl-pyrrolidin-1-yl]-methanone;

[(2S,3S)-2-(4-Chloro-1H-benzoimidazol-2-yl)-3-methyl-pyrrolidin-1-yl]-(2-methyl-5-p-tolyl-thiazol-4-yl)-methanone;

[(2S,3S)-2-(4-Chloro-1H-benzoimidazol-2-yl)-3-methyl-pyrrolidin-1-yl]-[5-(3,4-dimethyl-phenyl)-2-methyl-thiazol-4-yl]-methanone;

[(2S,3S)-2-(4-Chloro-1H-benzoimidazol-2-yl)-3-methyl-pyrrolidin-1-yl]-[2-dimethylamino-5-(3,4-dimethyl-phenyl)-thiazol-4-yl]-methanone;

[(2S,3S)-2-(5-Chloro-6-methyl-1H-benzoimidazol-2-yl)-3-methyl-pyrrolidin-1-yl]-(4-methyl-2-pyrimidin-2-yl-phenyl)-methanone;

[(2S,3S)-2-(5-Chloro-6-methyl-1H-benzoimidazol-2-yl)-3-methyl-pyrrolidin-1-yl]-(5-fluoro-2-pyrimidin-2-yl-phenyl)-methanone;

[(2S,3S)-2-(5-Chloro-6-methyl-1H-benzoimidazol-2-yl)-3-methyl-pyrrolidin-1-yl]-(2-fluoro-6-pyrimidin-2-yl-phenyl)-methanone;

[(2S,3S)-2-(5-Chloro-4-methyl-1H-benzoimidazol-2-yl)-3-methyl-pyrrolidin-1-yl]-[2-(3-methoxy-phenylethynyl)-phenyl]-methanone;

[(2S,3S)-2-(5-Chloro-6-methyl-1H-benzoimidazol-2-yl)-3-methyl-pyrrolidin-1-yl]-[2-(3-methoxy-phenylethynyl)-phenyl]-methanone;

[5-(4-Fluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(3-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone;

(2-Methyl-5-m-tolyl-thiazol-4-yl)-[(2S,3S)-3-methyl-2-(5-trifluoromethyl-1H-benzoimidazol-2-yl)-pyrrolidin-1-yl]-methanone;

[5-(4-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

(2-Methyl-5-p-tolyl-thiazol-4-yl)-[(2S,3S)-3-methyl-2-(5-trifluoromethyl-1H-benzoimidazol-2-yl)-pyrrolidin-1-yl]-methanone;

[5-(4-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(4-Bromo-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(3,4-Difluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[2-(3,4-Dimethyl-phenyl)-thiophen-3-yl]-[(2S,3S)-3-methyl-2-(5-trifluoromethyl-1H-benzoimidazol-2-yl)-pyrrolidin-1-yl]-methanone;

[5-(3,4-Dimethyl-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(2-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(2-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(3,5-Difluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone;

[5-(4-Fluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[5-(4-Chloro-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[5-(4-Bromo-phenyl)-2-methyl-thiazol-4-yl]-[(2S,3S)-3-methyl-2-(4-trifluoromethyl-1H-benzoimidazol-2-yl)-pyrrolidin-1-yl]-methanone;

(2-Methyl-5-p-tolyl-thiazol-4-yl)-[(2S,3S)-3-methyl-2-(4-trifluoromethyl-1H-benzoimidazol-2-yl)-pyrrolidin-1-yl]-methanone;

[5-(3,4-Difluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[5-(2-Methoxy-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[5-(3,5-Difluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone;

(2-Methyl-5-m-tolyl-thiazol-4-yl)-[(2S,3S)-3-methyl-2-(4-trifluoromethyl-1H-benzoimidazol-2-yl)-pyrrolidin-1-yl]-methanone;

[5-(4-Methoxy-phenyl)-2-methyl-thiazol-4-yl]-[(2S,3S)-3-methyl-2-(4-trifluoromethyl-1H-benzoimidazol-2-yl)-pyrrolidin-1-yl]-methanone;

[(2S,3S)-2-(5-Chloro-4-methyl-1H-benzoimidazol-2-yl)-3-methyl-pyrrolidin-1-yl]-(5-methyl-2-pyridin-2-yl-phenyl)-methanone;

(4-Chloro-biphenyl-2-yl)-[(2S,3S)-2-(5-chloro-4-methyl-1H-benzoimidazol-2-yl)-3-methyl-pyrrolidin-1-yl]-methanone;

[(2S,3S)-2-(5-Chloro-4-methyl-1H-benzoimidazol-2-yl)-3-methyl-pyrrolidin-1-yl]-(5-methyl-2-pyridin-3-yl-phenyl)-methanone;

[(2S,3S)-2-(5-Chloro-4-methyl-1H-benzoimidazol-2-yl)-3-methyl-pyrrolidin-1-yl]-(4-fluoro-biphenyl-2-yl)-methanone;

[(2S,3S)-2-(5-Chloro-4-methyl-1H-benzoimidazol-2-yl)-3-methyl-pyrrolidin-1-yl]-(5-fluoro-2-pyridin-2-yl-phenyl)-methanone;

2-[(2S,3S)-2-(5-Chloro-4-methyl-1H-benzoimidazol-2-yl)-3-methyl-pyrrolidine-1-carbonyl]-biphenyl-4-carbonitrile;

[(2S,3S)-2-(5-Chloro-4-methyl-1H-benzoimidazol-2-yl)-3-methyl-pyrrolidin-1-yl]-(4-methyl-2-pyridin-2-yl-phenyl)-methanone;

[(2S,3S)-2-(5-Chloro-4-methyl-1H-benzoimidazol-2-yl)-3-methyl-pyrrolidin-1-yl]-(5-methyl-biphenyl-2-yl)-methanone;

[(2S,3S)-2-(5-Chloro-4-methyl-1H-benzoimidazol-2-yl)-3-methyl-pyrrolidin-1-yl]-(3-fluoro-biphenyl-2-yl)-methanone;

[(2S,3S)-2-(5-Chloro-4-methyl-1H-benzoimidazol-2-yl)-3-methyl-pyrrolidin-1-yl]-(4-trifluoromethyl-biphenyl-2-yl)-methanone;

[(2S,3S)-2-(5-Chloro-4-methyl-1H-benzoimidazol-2-yl)-3-methyl-pyrrolidin-1-yl]-(3-fluoro-4-methyl-biphenyl-2-yl)-methanone;

[(2S,3S)-2-(5-Chloro-4-methyl-1H-benzoimidazol-2-yl)-3-methyl-pyrrolidin-1-yl]-(4-methyl-biphenyl-2-yl)-methanone;

[(2S,3S)-2-(5-Chloro-4-methyl-1H-benzoimidazol-2-yl)-3-methyl-pyrrolidin-1-yl]-(2-fluoro-3-methyl-6-pyridin-3-yl-phenyl)-methanone;

[(2S,3S)-2-(5-Chloro-4-methyl-1H-benzoimidazol-2-yl)-3-methyl-pyrrolidin-1-yl]-(4-methyl-2-pyrimidin-2-yl-phenyl)-methanone;

[(2S,3S)-2-(5-Chloro-4-methyl-1H-benzoimidazol-2-yl)-3-methyl-pyrrolidin-1-yl]-(5-fluoro-2-pyrimidin-2-yl-phenyl)-methanone;

[(2S,3S)-2-(5-Chloro-4-methyl-1H-benzoimidazol-2-yl)-3-methyl-pyrrolidin-1-yl]-(2-fluoro-3-methyl-6-pyrimidin-2-yl-phenyl)-methanone;

[(2S,3S)-2-(5-Chloro-4-methyl-1H-benzoimidazol-2-yl)-3-methyl-pyrrolidin-1-yl]-(2-fluoro-6-pyrimidin-2-yl-phenyl)-methanone;

[(2S,3S)-2-(5-Chloro-4-methyl-1H-benzoimidazol-2-yl)-3-methyl-pyrrolidin-1-yl]-(5-methyl-2-pyrimidin-2-yl-phenyl)-methanone;

[(2S,3S)-2-(5-Chloro-6-methyl-1H-benzoimidazol-2-yl)-3-methyl-pyrrolidin-1-yl]-(5-methyl-2-pyrimidin-2-yl-phenyl)-methanone;

[(2S,3S)-2-(6-Chloro-7-methyl-1H-benzoimidazol-2-yl)-3-methyl-pyrrolidin-1-yl]-(5-methyl-2-pyrimidin-2-yl-phenyl)-methanone;

[(2S,3S)-2-(5-Chloro-7-methyl-1H-benzoimidazol-2-yl)-3-methyl-pyrrolidin-1-yl]-(5-methyl-2-pyrimidin-2-yl-phenyl)-methanone;

[(S)-2-(5-Chloro-4-methyl-1H-benzoimidazol-2-yl)-2-methyl-pyrrolidin-1-yl]-[5-(4-fluoro-phenyl)-2-phenyl-thiazol-4-yl]-methanone;

[2,5-Bis-(4-fluoro-phenyl)-thiazol-4-yl]-[(S)-2-(5-chloro-4-methyl-1H-benzoimidazol-2-yl)-2-methyl-pyrrolidin-1-yl]-methanone;

[(S)-2-(5-Chloro-4-methyl-1H-benzoimidazol-2-yl)-2-methyl-pyrrolidin-1-yl]-[5-(4-fluoro-phenyl)-2-m-tolyl-thiazol-4-yl]-methanone;

[(S)-2-(5-Chloro-4-methyl-1H-benzoimidazol-2-yl)-2-methyl-pyrrolidin-1-yl]-[5-(4-fluoro-phenyl)-2-(3-methoxy-phenyl)-thiazol-4-yl]-methanone;

[(S)-2-(5-Chloro-4-methyl-1H-benzoimidazol-2-yl)-2-methyl-pyrrolidin-1-yl]-[5-(4-fluoro-phenyl)-2-p-tolyl-thiazol-4-yl]-methanone;

[(S)-2-(5-Chloro-4-methyl-1H-benzoimidazol-2-yl)-2-methyl-pyrrolidin-1-yl]-[5-(4-fluoro-phenyl)-2-(2-fluoro-phenyl)-thiazol-4-yl]-methanone;

[(S)-2-(5-Chloro-4-methyl-1H-benzoimidazol-2-yl)-2-methyl-pyrrolidin-1-yl]-[5-(4-fluoro-phenyl)-2-(3-fluoro-phenyl)-thiazol-4-yl]-methanone;

(4-Methyl-biphenyl-2-yl)-[(S)-2-methyl-2-(5-trifluoromethoxy-1H-benzoimidazol-2-yl)-pyrrolidin-1-yl]-methanone;

[5-(3,5-Difluoro-phenyl)-2-methyl-thiazol-4-yl]-[(S)-2-methyl-2-(5-trifluoromethoxy-1H-benzoimidazol-2-yl)-pyrrolidin-1-yl]-methanone;

[5-(3-Methoxy-phenyl)-2-methyl-thiazol-4-yl]-[(S)-2-methyl-2-(5-trifluoromethoxy-1H-benzoimidazol-2-yl)-pyrrolidin-1-yl]-methanone;

[5-(4-Fluoro-phenyl)-2-methyl-thiazol-4-yl]-[(S)-2-methyl-2-(5-trifluoromethoxy-1H-benzoimidazol-2-yl)-pyrrolidin-1-yl]-methanone;

[(S)-2-(5-Chloro-4-methyl-1H-benzoimidazol-2-yl)-2-methyl-pyrrolidin-1-yl]-[2-(2,3-difluoro-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(4-fluoro-3-methyl-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(2-fluoro-4-methyl-phenyl)-5-(4-fluoro-phenyl)-thiazol-4-yl]-methanone;

3-[4-[(S)-2-(5-Chloro-4-methyl-1H-benzoimidazol-2-yl)-2-methyl-pyrrolidine-1-carbonyl]-5-(4-fluoro-phenyl)-thiazol-2-yl]-benzonitrile;

[(S)-2-(5-Chloro-4-methyl-1H-benzoimidazol-2-yl)-2-methyl-pyrrolidin-1-yl]-[2-(2-chloro-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(3-chloro-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(4-fluoro-2-methyl-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(4-fluoro-2-methoxy-phenyl)-5-(4-fluoro-phenyl)-thiazol-4-yl]-methanone;

[(S)-2-(5-Chloro-4-methyl-1H-benzoimidazol-2-yl)-2-methyl-pyrrolidin-1-yl]-[2-(2,5-difluoro-phenyl)-5-(4-fluoro-phenyl)-thiazol-4-yl]-methanone;

[(S)-2-(6-Bromo-4,5-dimethyl-1H-benzoimidazol-2-yl)-2-methyl-pyrrolidin-1-yl]-(3,4-dimethyl-2-[1,2,3]triazol-2-yl-phenyl)-methanone;

3'-[(S)-2-Methyl-2-(5-trifluoromethyl-1H-benzoimidazol-2-yl)-pyrrolidine-1-carbonyl]-4'-[1,2,3]triazol-2-yl-biphenyl-3-carbonitrile;

2'-[(S)-2-(5-Chloro-4-methyl-1H-benzoimidazol-2-yl)-2-methyl-pyrrolidine-1-carbonyl]-3'-fluoro-4'-methoxy-biphenyl-4-carbonitrile;

[(S)-2-(6-Bromo-5-fluoro-1-methyl-1H-benzoimidazol-2-yl)-2-methyl-pyrrolidin-1-yl]-(5-methyl-2-[1,2,3]triazol-2-yl-phenyl)-methanone;

(3'-Fluoro-4-methyl-biphenyl-2-yl)-{(S)-2-[1-(2-methoxy-ethyl)-5,6-dimethyl-1H-benzoimidazol-2-yl]-2-methyl-pyrrolidin-1-yl}-methanone; and

[(2S,3S)-2-(5-Chloro-6-methyl-1H-benzoimidazol-2-yl)-3-methyl-pyrrolidin-1-yl]-(2-fluoro-3-methyl-6-pyrimidin-2-yl-phenyl)-methanone.

51) In addition to the above-listed compounds, further compounds according to embodiment 1) are selected from:

(4-Bromo-biphenyl-2-yl)-[(S)-2-methyl-2-(5-trifluoromethyl-1H-benzoimidazol-2-yl)-pyrrolidin-1-yl]-methanone;

[(S)-2-(5,6-Dimethyl-1H-benzoimidazol-2-yl)-4-methylene-pyrrolidin-1-yl]-(2-methyl-6-[1,2,3]triazol-2-yl-phenyl)-methanone;

[(S)-2-(5,6-Dimethyl-1H-benzoimidazol-2-yl)-4-methylene-pyrrolidin-1-yl]-(5-methyl-2-pyrazol-1-yl-phenyl)-methanone; and

[(S)-2-(5,6-Dimethyl-1H-benzoimidazol-2-yl)-4-methylene-pyrrolidin-1-yl]-(6-methyl-3-[1,2,3]triazol-2-yl-pyridin-2-yl)-methanone.

52) In another embodiment, preferred compounds according to embodiment 1) are selected from:

[(2S,3S)-2-(5-Chloro-4-methyl-1H-benzoimidazol-2-yl)-3-methyl-pyrrolidin-1-yl]-(2-fluoro-6-pyrimidin-2-yl-phenyl)-methanone;

[(2S,3S)-2-(5-Chloro-4-methyl-1H-benzoimidazol-2-yl)-3-methyl-pyrrolidin-1-yl]-(2-fluoro-3-methyl-6-pyrimidin-2-yl-phenyl)-methanone;

[(2S,3S)-2-(5-Chloro-6-methyl-1H-benzoimidazol-2-yl)-3-methyl-pyrrolidin-1-yl]-(2-fluoro-3-methyl-6-pyrimidin-2-yl-phenyl)-methanone;

[(2S,3S)-2-(5-Chloro-4-methyl-1H-benzoimidazol-2-yl)-3-methyl-pyrrolidin-1-yl]-(5-chloro-2-[1,2,3]triazol-2-yl-phenyl)-methanone;

[(2S,3S)-2-(5-Chloro-4-methyl-1H-benzoimidazol-2-yl)-3-methyl-pyrrolidin-1-yl]-(2-fluoro-3-methyl-6-[1,2,3]triazol-2-yl-phenyl)-methanone;

3'-[(S)-2-Methyl-2-(5-trifluoromethyl-1H-benzoimidazol-2-yl)-pyrrolidine-1-carbonyl]-4'-[1,2,3]triazol-2-yl-biphenyl-3-carbonitrile; and

[(S)-2-(5-Chloro-4-methyl-1H-benzoimidazol-2-yl)-2-methyl-pyrrolidin-1-yl]-[5-(4-fluoro-phenyl)-2-phenyl-thiazol-4-yl]-methanone.

53) In another embodiment, preferred compounds according to embodiment 1) are selected from:

(5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone;

(5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone;

[(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone;

[(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone;

[(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(5-chloro-2-[1,2,3]triazol-2-yl-phenyl)-methanone;

[(S)-2-(5-Chloro-4-methyl-1H-benzoimidazol-2-yl)-2-methyl-pyrrolidin-1-yl]-(2-fluoro-3-methoxy-6-[1,2,3]triazol-2-yl-phenyl)-methanone;

[(S)-2-(5-Chloro-4-methyl-1H-benzoimidazol-2-yl)-2-methyl-pyrrolidin-1-yl]-(4-methyl-2-[1,2,3]triazol-2-yl-phenyl)-methanone;

[(S)-2-(5-Chloro-4-methyl-1H-benzoimidazol-2-yl)-2-methyl-pyrrolidin-1-yl]-(5-methyl-2-pyrazol-1-yl-phenyl)-methanone;

[(S)-2-(5-Chloro-4-methyl-1H-benzoimidazol-2-yl)-2-methyl-pyrrolidin-1-yl]-(6-methyl-3-pyrazol-1-yl-pyridin-2-yl)-methanone;

[(S)-2-(5-Chloro-4-methyl-1H-benzoimidazol-2-yl)-2-methyl-pyrrolidin-1-yl]-(5-fluoro-2-[1,2,3]triazol-2-yl-phenyl)-methanone;

[(S)-2-(5-Chloro-4-methyl-1H-benzoimidazol-2-yl)-2-methyl-pyrrolidin-1-yl]-(2-[1,2,3]triazol-2-yl-phenyl)-methanone;

(5-Chloro-2-[1,2,3]triazol-2-yl-phenyl)-[(S)-2-(5,6-dimethoxy-1H-benzoimidazol-2-yl)-2-methyl-pyrrolidin-1-yl]-methanone;

[(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone;

[(S)-2-(5,6-Dimethoxy-1H-benzoimidazol-2-yl)-2-methyl-pyrrolidin-1-yl]-(5-methyl-2-pyrazol-1-yl-phenyl)-methanone;

[(S)-2-(6-Chloro-5-trifluoromethyl-1H-benzoimidazol-2-yl)-2-methyl-pyrrolidin-1-yl]-(4,5-dimethyl-2-[1,2,3]triazol-2-yl-phenyl)-methanone; and (4,5-Dimethyl-2-[1,2,3]triazol-2-yl-phenyl)-[(S)-2-methyl-2-(5-trifluoromethyl-1H-benzoimidazol-2-yl)-pyrrolidin-1-yl]-methanone.

54) In another embodiment, further preferred compounds according to embodiment 1) are:

[(S)-2-(5-Chloro-4-methyl-1H-benzoimidazol-2-yl)-2-methyl-pyrrolidin-1-yl]-(6-methyl-3-[1,2,3]triazol-2-yl-pyridin-2-yl)-methanone; and

[(S)-2-(5-Chloro-4-methyl-1H-benzoimidazol-2-yl)-2-methyl-pyrrolidin-1-yl]-(5-methyl-2-pyrimidin-2-yl-phenyl)-methanone.

55) A particularly preferred compound according to embodiment 1) is:

[(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone.

56) Another particularly preferred compound according to embodiment 1) is:

[(S)-2-(5-Bromo-7-methyl-1H-benzoimidazol-2-yl)-2-methyl-pyrrolidin-1-yl]-(5-methyl-2-pyrimidin-2-yl-phenyl)-methanone.

57) Another particularly preferred compound according to embodiment 1) is:

[(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone.

The compounds of formulae (I), (II), (III), (IV), (V), and (VI) according to any one of embodiments 1) to 57) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formulae (I), (II) and (III) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formulae (I), (II), (III), (IV), (V), and (VI) according to any one of embodiments 1) to 57).

In a preferred embodiment of the invention, the administered amount of such a compound of formulae (I), (II), (III), (IV), (V), and (VI) according to any one of embodiments 1) to 57) is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

The compounds according to formulae (I), (II), (III), (IV), (V), and (VI) according to any one of embodiments 1) to 57) are useful for the prevention or treatment of disorders relating to orexinergic dysfunctions.

Such disorders relating to orexinergic dysfunctions are diseases or disorders where an antagonist of a human orexin receptor is required, notably mental health disorders relating to orexinergic dysfunctions. The above mentioned disorders may in particular be defined as comprising sleep disorders, anxiety disorders, addiction disorders, cognitive dysfunctions, mood disorders, or appetite disorders. In one sub-embodiment, the above mentioned disorders comprise especially anxiety disorders, addiction disorders and mood disorders, notably anxiety disorders and addiction disorders. In another sub-embodiment, the above mentioned disorders comprise especially sleep disorders.

In addition, further disorders relating to orexinergic dysfunctions are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; and treating or controlling agitation, in isolation or co-morbid with another medical condition.

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, posttraumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], cannabis, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including over-eating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rhythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleep-walking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

Preparation of Compounds of Formula (I):

The compounds of formulae (I), (II), (III), (IV), (V), and (VI) can be prepared by the methods given below, by the methods given in the experimental part below or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products.

Compounds of formulae (I), (II), (III), (IV), (V), and (VI) of the present invention can be prepared according to the general sequence of reactions outlined below wherein $Ar^1$, $R^1$, $R^2$, $R^3$, $R^{4a}$, $R^{4b}$ and $(R^5)_n$ are as defined for formula (I).

The synthesis of compound of formulae (I), wherein $R^1$ represents hydrogen, starts from proline-derivatives (a) which are commercially available or prepared as described below.

There are two general synthetic approaches of equal importance towards compounds of formulae (I).

Synthetic approach 1 starts with a Boc-protection of the respective proline derivative a under standard conditions by for example dissolving the proline a in a solvent such as DCM or THF and adding a base to the solution, for example DIPEA, TEA or aqueous $Na_2CO_3$ followed by the addition of $Boc_2O$. The reaction is performed at room temperature and is usually complete within a few hours and results in the Boc-protected proline derivative b which is then coupled with the appropriate phenylene-diamine- or pyridine-diamine derivative in solvents such as THF, DCM or DMF in the presence of a coupling agent such as HBTU or TBTU or the like and a base, for example DIPEA or TEA to give compound c. To obtain the benzimidazole derivative d the precursor c is dissolved in AcOH and heated to 100° C. for 1 h. Compound d is Boc-deprotected under acidic conditions such as 4M HCl in dioxane (preferred method) or TFA in DCM to give precursor e which is converted into final compound f by an amide coupling reaction with $Ar^1$—COOH in a solvent such as THF, DMF or DCM in the presence of a coupling agent such as TBTU, HBTU, HATU, EDC or the like and a base such as DIPEA, TEA or N-methylmorpholine.

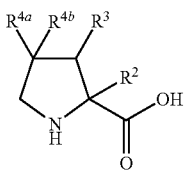

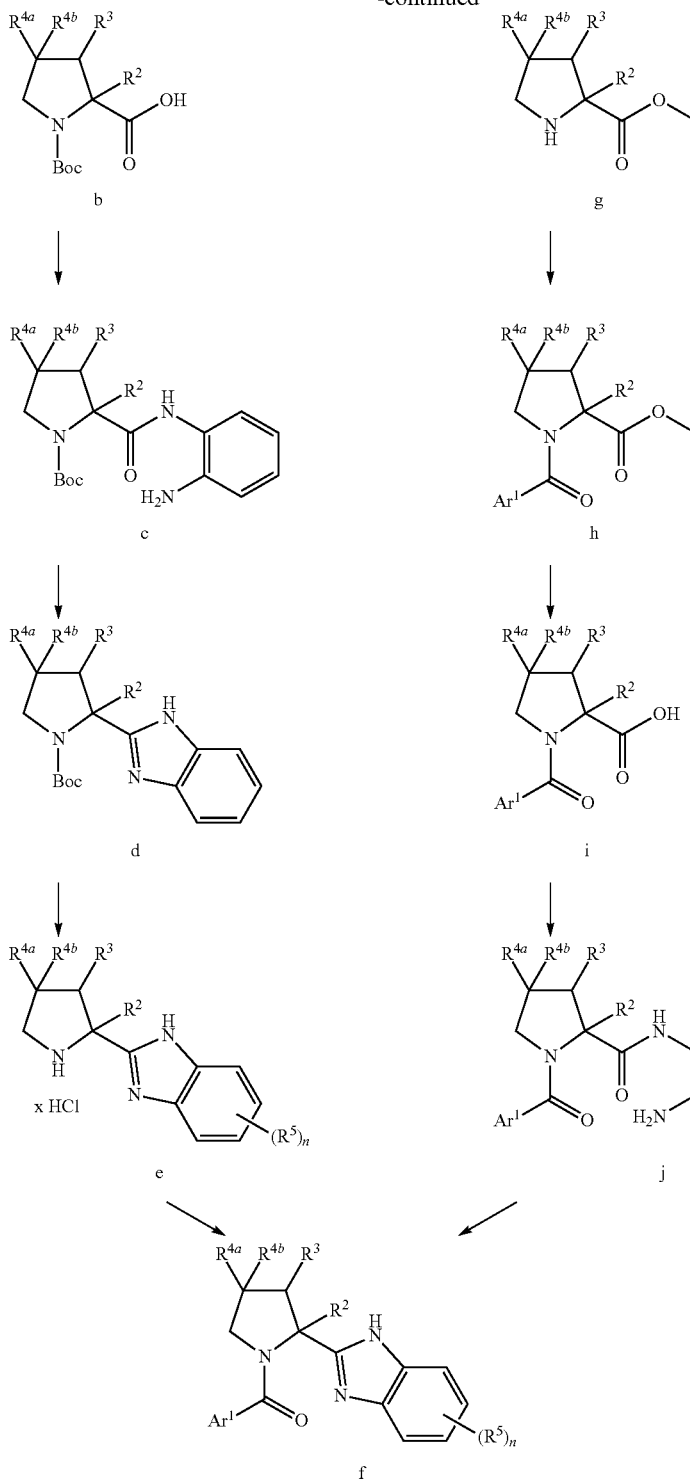

Synthetic approach 2 starts with an esterification (usually methyl ester formation) of the proline derivative a by dissolving the starting material in THF and adding 5 equivalents of the respective alcohol (usually MeOH) followed by the addition of EDC and DMAP. The reaction is run at RT and is usually complete within a few hours. The methyl-ester derivative g is acylated with Ar¹—COOH under conditions described above to result in intermediate h. Esterhydrolysis under standard conditions by dissolving the ester derivative h in THF/MeOH=1/1 followed by the addition of 2 equivalents of aq. 1M NaOH solution. The reaction runs at RT and is usually complete after a few hours to result in the carboxylic acid derivative i. The final compounds f are obtained via precursor j by applying the same conditions as described for the amide-coupling and the cyclization in synthetic approach 1.

The following scheme depicts the methodology to prepare N-methylated benzimidazolo-derivatives of formula (I), wherein $R^1$ represents methyl:

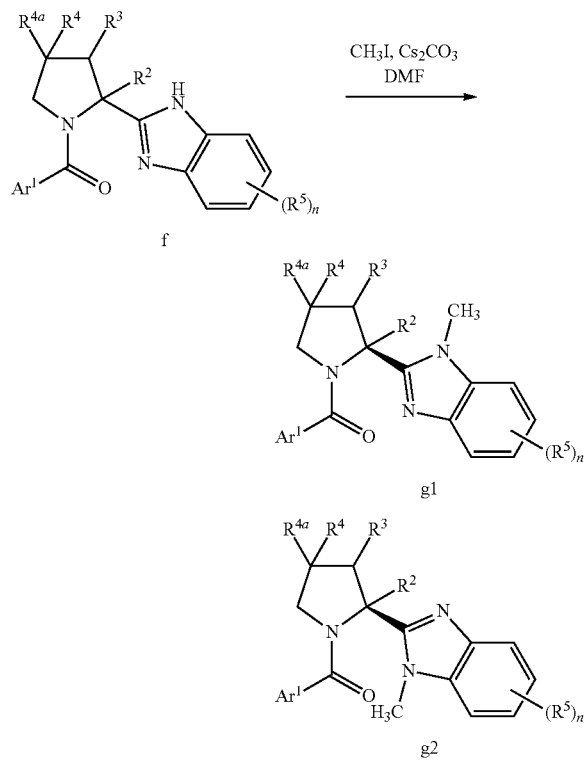

Final compounds g1 and g2 are prepared by simple alkylation of compounds f (compounds of formula (I) wherein $R^1$ is H) with an alkyl halide (for example MeI) in the presence of a carbonate base (e.g. $Cs_2CO_3$) in a polar, aprotic solvent (e.g. DMF) at RT. In case the phenylring of the benzimidazole-system is unsymmetrically substituted with respect to $R^{14}$, $R^{15}$, $R^{16}$, and $R^{17}$ the alkylation (methylation) reaction results in two isomeric products g1 and g2 as depicted above.

The following proline derivatives are commercially available and were purchased and used as starting materials according to the methods described herein:

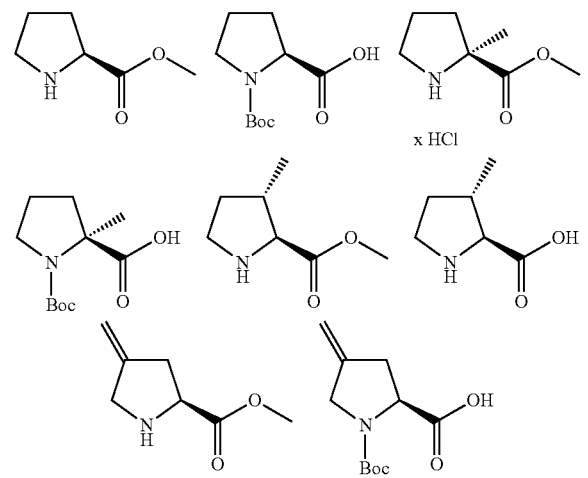

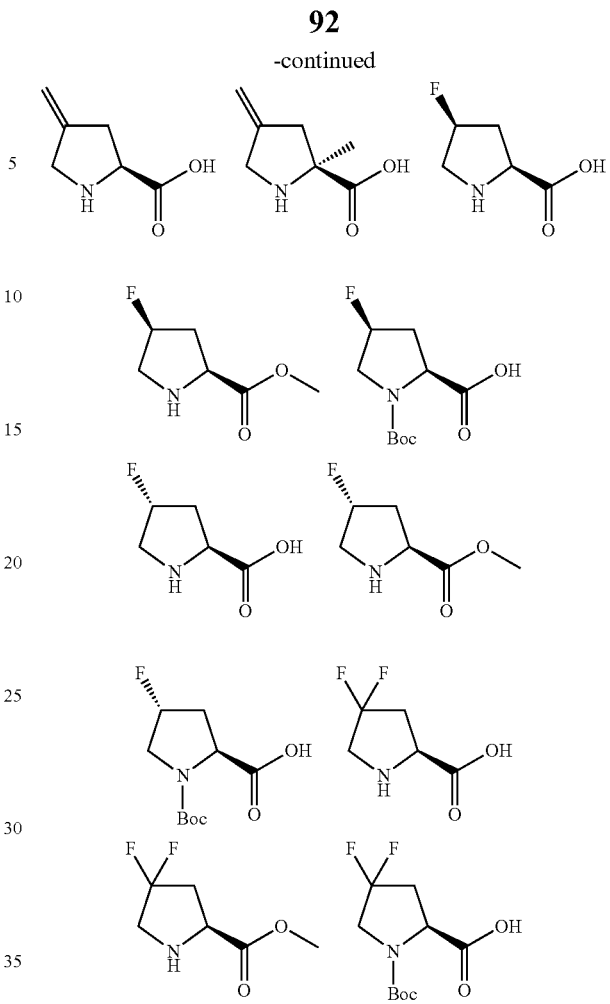

The following proline derivatives may be prepared according to the procedures outlined in the following scheme:

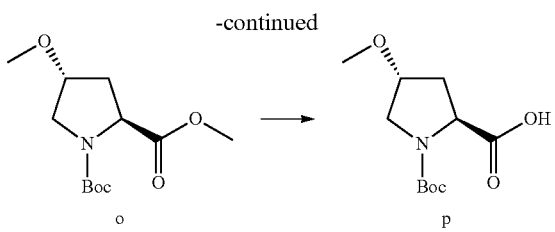

The diastereomeric 4-hydroxy-proline derivatives k and n are commercially available starting points. Both compounds may be fully deprotonated with NaH in DMF followed by the addition of an excess of MeI to give the 4-methoxy-proline-methylester derivatives l and o which can be transformed into the carboxylic acid derivatives m and p by standard ester hydrolysis (e.g. 1M NaOH, MeOH, THF, rt).

Whenever the compounds of formulae (I), (II), (III), (IV), (V), or (VI) are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 μm) column, a Daicel ChiralCel OD-H (5 μm) column, a Daicel ChiralCel OD (10 μm) column, a Daicel ChiralPak IA (5 μm) column, a Daicel ChiralPak IB (5 μm) column, a Daicel ChiralPak IC (5 μm) column, or a (R,R)-Whelk-01 (5 μm) column. Typical conditions of chiral HPLC are an isocratic mixture of eluent A (EtOH, in presence or absence of a base like TEA and/or diethylamine or of an acid like TFA) and eluent B (heptane).

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given. Racemates can be separated into their enantiomers by preparative HPLC (column: ChiralPaK IC 250×4.6 mm, 5 μm, 45% ethanol in heptane).

LC-MS with Acidic Conditions

Method A: Agilent 1100 series with mass spectrometry detection (MS: Finnigan single quadrupole). Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method B: Agilent 1100 series with mass spectrometry detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

LC-MS with Basic Conditions

Method C: Agilent 1100 series with mass spectrometry detection (MS: Finnigan single quadrupole). Column: Zorbax Extend C18 (5 μm, 4.6×50 mm). Conditions: MeCN [eluent A]; 13 mmol/L NH$_3$ in water [eluent B]. Gradient: 95% B→5% B over 1.5 min (flow: 4.5 mL/min). Detection: UV/Vis+MS.

Method D: Agilent 1100 series with mass spectrometry detection (MS: Finnigan single quadrupole). Column: Waters XBridge C18 (5 m, 4.6×50 mm). Conditions: MeCN [eluent A]; 13 mmol/L NH$_3$ in water [eluent B]. Gradient: 95% B→5% B over 1.5 min (flow: 4.5 mL/min). Detection: UV/Vis+MS.

Preparative HPLC with Acidic Conditions

Method E: Column: Waters XBridge (10 m, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Preparative HPLC with Basic Conditions

Method F: Column: Waters XBridge (10 m, 75×30 mm). Conditions: MeCN [eluent A]; water+0.5% NH$_4$OH (25% aq.) [eluent B]; Gradient: 90% B→5% B over 6.5 min (flow: 75 mL/min). Detection: UV/Vis+MS Abbreviations (As Used Hereinbefore Or Hereinafter)

Abbrevations (as used herein and in the description above):

Ac Acetyl (such as in OAc=acetate, AcOH=acetic acid)
AcOH Acetic acid
anh. Anhydrous
aq. aqueous
atm Atmosphere
tBME tert-Butylmethylether
Boc tert-Butoxycarbonyl
Boc$_2$O di-tert-Butyl dicarbonate
BSA Bovine serum albumine
Bu Butyl such as in tBu=tert-butyl=tertiary butyl
CC Column Chromatography on silica gel
CHO Chinese Hamster Ovary
conc. Concentrated
DCE 1,2-Dichloroethane
DCM Dichloromethane
DEA Diethylamine
DIPEA Diisopropylethylamine
DMF N,N-Dimethylformamide
DMSO Dimethyl sulfoxide
EDC
ELSD Evaporative Light-Scattering Detection
eq Equivalent(s)
ES Electron spray
Et Ethyl
Et$_2$O Diethyl ether
EtOAc Ethyl acetate
EtOH Ethanol
Ex. Example
FC Flash Chromatography on silica gel
FCS Foatal calf serum
FLIPR Fluorescent imaging plate reader
h Hour(s)
HATU
HBSS Hank's balanced salt solution
HBTU
HEPES 4-(2-Hydroxyethyl)-piperazine-1-ethanesulfonic acid
$^1$H-NMR Nuclear magnetic resonance of the proton
HPLC High performance liquid chromatography
LC-MS Liquid chromatography—Mass Spectroscopy
Lit. Literature
M Exact mass (as used for LC-MS)
Me Methyl
MeCN Acetonitrile MeOH Methanol
MeI Methyl iodide
MHz Megahertz
μl microliter
min Minute(s)
MS Mass spectroscopy
N Normality
Pd(OAc)$_2$ Palladium diacetate
Pd(PPh$_3$)$_4$ Tetrakis(triphenylphosphine)palladium(0)
PL-HCO$_3$ Polymer supported hydrogen carbonate
Ph Phenyl
PPh$_3$ Triphenylphosphine
prep. Preparative
RT Room temperature
sat. Saturated
TBTU O-(Benzotriazol-1-yl)-N,N,N',N'-tetramethyluronium tetrafluoroborate
TEA Triethylamine
TFA trifluoroacetic acid
Tf Trifluoromethansulfonyl
THF Tetrahydrofuran
$t_R$ Retention time
UV Ultra violet I—Chemistry All temperatures are stated in ° C. The commercially available starting materials were used as received without further purification. Compounds are purified by flash column chromatography on silica gel (FC) or by preparative HPLC. Compounds described in the invention are characterized by LC-MS (retention time $t_R$ is given in min.; molecular weight obtained from the mass spectrum is given in g/mol, using the conditions listed below). If the mass is not detectable the compounds are also characterized by $^1$H-NMR (400 MHz: Bruker; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz).

LC-MS with Acidic Conditions (Conditions A)

Apparatus: Agilent 1100 series with mass spectroscopy detection (MS: Finnigan single quadrupole). Column: Waters XBridge C18 (2.5 m, 4.6×30 mm). Conditions: MeCN [eluent A]; water+0.04% TFA [eluent B]. Gradient: 95% B→5% B over 1.5 min. (flow: 4.5 ml/min.). Detection: UV/Vis+MS.

LC-MS with Basic Conditions (Conditions B)

Apparatus: Agilent 1100 series with mass spectroscopy detection (MS: Finnigan single quadrupole). Column: Waters XBridge C18 (5 m, 4.6×50 mm). Conditions: MeCN [eluent A]; 13 mmol/l NH$_3$ in water [eluent B]. Gradient: 95% B→5% B over 1.5 min. (flow: 4.5 ml/min.). Detection: UV/Vis+MS.

Preparative HPLC for Purification of Compounds (Conditions C)

Column: Waters XBridge (10 m, 75×30 mm). Conditions: MeCN [eluent A]; water+0.5% NH$_4$OH (25% aq.) [eluent B]; Gradient: 90% B→5% B over 6.5 min. (flow: 75 ml/min.). Detection: UV+ELSD.

Preparative HPLC for Purification of Compounds (Conditions D)

Column: Waters Atlantis T3 OBD (10 m, 75×30 mm). Conditions: MeCN [eluent A]; water+0.5% HCOOH [eluent B]; Gradient: 90% B→5% B over 6.4 min. (flow: 75 ml/min.). Detection: UV+ELSD.

LC-MS with Basic Conditions (Conditions E)

Apparatus: Agilent 1100 series with mass spectroscopy detection (MS: Finnigan single quadrupole). Column: Agilent Zorbax Extend-C18 (5 um, 4.6×50 mm). Conditions: MeCN [eluent A]; 13 mmol/l NH$_3$ in water [eluent B]. Gradient: 95% B→5% B over 1.5 min. (flow: 4.5 ml/min.). Detection: UV+MS.

LC-MS with Acidic Conditions (Conditions F)

Apparatus: Agilent 1100 series with mass spectroscopy detection (MS: Finnigan single quadrupole). Column: Agilent Zorbax SB-Aq, (3.5 um, 4.6×50 mm). Conditions: MeCN [eluent A]; water+0.04% TFA [eluent B]. Gradient: 95% B→5% B over 1.5 min. (flow: 4.5 ml/min.). Detection: UV+MS.

The following examples illustrate the preparation of compounds of the invention but do not at all limit the scope thereof.

Preparation of Precursors and Intermediates:

A Preparation of Building Blocks of Formula Ar$^1$—CO—OH:

The preparation of these acids is described in detail for example in the following documents: WO 2008/020405; WO 2008/038251; WO 2008/081399; WO 2008/139416. All other carboxylic acids used in the experimental part which are not described in the following section are either commercially available or fully described in the literature listed above and in the introduction part.

In addition to commercially available building blocks, further particular building blocks of formula Ar$^1$—CO—OH are prepared as follows:

39

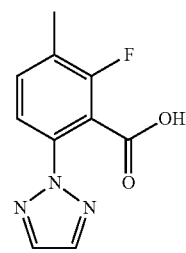

40

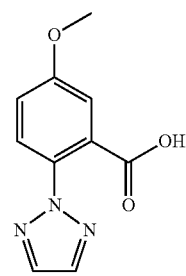

41

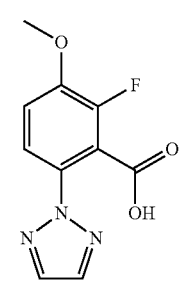

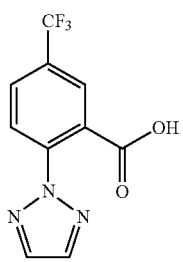

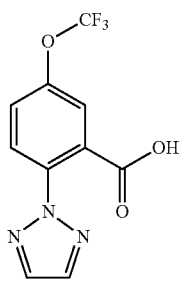

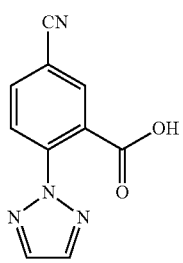

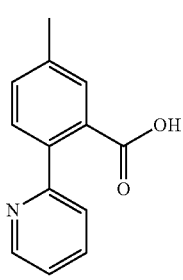

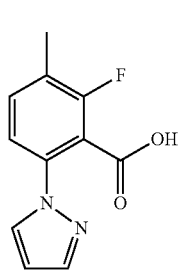

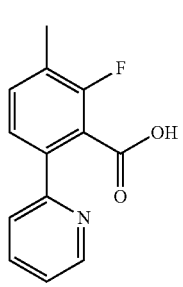

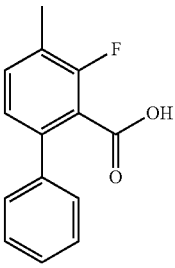

A.1 2-Fluoro-3-methyl-6-(2H-1,2,3-triazol-2-yl)benzoic acid 39

2-Fluoro-3-methyl-6-(2H-1,2,3-triazol-2-yl)benzoic acid 39 is synthesized in analogy to procedures reported in WO2008/069997.

In a dry Schlenk Tube at RT under nitrogen are successively charged 2-fluoro-6-iodo-3-methyl-benzoic acid (1.786 mmol, 1 eq), CuI (0.089 mmol, 0.05 eq), 1H-1,2,3-triazole (3.571 mmol, 2 eq), $Cs_2CO_3$ (3.571 mmol, 2 eq) and DMF (2.5 mL). The resulting blue suspension is stirred at 80° C. overnight. The obtained reaction mixture is taken up in 1 M aq. HCl and extracted twice with EtOAc. The combined organic layers are dried over $Na_2SO_4$, filtered and concentrated under reduced pressure. Purification is achieved by preparative HPLC (conditions D) to give the titled compound (246 mg) as a pale yellow solid. LC-MS (conditions A): $t_R$=0.55 min, $[M+1]^+$=222.19.

A.2 5-Methoxy-2-(2H-1,2,3-triazol-2-yl)benzoic acid 40

The title compound is prepared in analogy to compound 39 starting from 2-iodo-5-methoxybenzoic acid (1.798 mmol, 1 eq). 40 (313 mg) is obtained as a yellow solid. LC-MS (conditions A): $t_R$=0.49 min, $[M+1]^+$=220.07.

A.3 2-Fluoro-3-methoxy-6-(2H-1,2,3-triazol-2-yl)benzoic acid 41

The title compound is prepared in analogy to compound 39 starting from 2-fluoro-6-iodo-3-methoxy-benzoic acid (1.689 mmol, 1 eq). 41 (221 mg) is obtained as a pale yellow solid. LC-MS (conditions A): $t_R$=0.48 min, $[M+1]^+$=238.18.

A.4 2-(2H-1,2,3-Triazol-2-yl)-5-(trifluoromethyl)benzoic acid 42

The title compound is prepared in analogy to compound 39 starting from 2-iodo-5-trifluorobenzoic acid (1.582 mmol, 1 eq). 42 (268 mg, 66%) is obtained as a white solid. LC-MS (conditions A): $t_R$=0.64 min, $[M+1]^+$=257.91.

A.5 2-(2H-1,2,3-Triazol-2-yl)-5-(trifluoromethoxy)benzoic acid 43

The title compound is prepared in analogy to compound 39 starting from 2-iodo-5-(trifluoromethoxy)benzoic acid (1.506 mmol, 1 eq). 43 (243 mg) is obtained as an off-white solid. LC-MS (conditions A): $t_R$=0.66 min, $[M+1]^+$=273.69.

A.6 5-Cyano-2-(2H-1,2,3-triazol-2-yl)benzoic acid 44

The title compound is prepared in analogy to compound 39 starting from 5-cyano-2-iodobenzoic acid (1.831 mmol, 1 eq). 44 (214 mg) is obtained as a grey solid. LC-MS (conditions A): $t_R$=0.46 min, $[M+1]^+$=not detectable. $^1$H NMR ($D_6$-DMSO): ☐☐ 13.49 (m, 1H), 8.21 (m, 1 H), 8.18 (m, 2 H), 8.15 (m, 1 H), 8.03 (m, 1 H).

A.7 5-Methyl-2-(pyridin-2-yl)benzoic acid 45 a) In a dry Schlenk Tube at RT under nitrogen are successively charged 2-iodo-5-methylbenzoic acid methyl ester (13.765 mmol, 1 eq), CuI (2.753 mmol, 0.2 eq), CsF (27.529 mmol, 2 eq), 2-tributylstannylpyridine (20.647 mmol, 1.5 eq), $Pd(PPh_3)_4$ (1.376 mmol, 0.1 eq) and DMF (60 mL). The resulting suspension is stirred at 90° C. overnight. The obtained reaction mixture is diluted with EtOAc and filtered through a short pad of Celite®. A solution of sat. aq. NaHCO$_3$ is then added to the filtrate and the aq. phase extracted with EtOAc (3 times). The combined organic layers are washed with H$_2$O and brine, dried over Na$_2$SO$_4$, filtered and concentrated under reduced pressure. Purification is achieved by FC (EtOAc/Heptane 1:4 to 3:7) to give methyl 5-methyl-2-(pyridin-2-yl)benzoate (2.64 g) as a brown oil. LC-MS (conditions A): t$_R$=0.67 min, [M+1]$^+$=228.07.

b) To a solution of methyl 5-methyl-2-(pyridin-2-yl)benzoate (11.617 mmol, 1 eq) in MeOH (15 mL) and THF (17 mL) is added 1 M NaOH (23.233 mL, 2 eq). The resulting mixture is stirred at RT overnight. The volatiles are evaporated under reduced pressure and the remaining aq. phase is acidified with 2 M HCl to pH=1-2 and extracted with DCM (3 times). The combined organic layers are dried over Na$_2$SO$_4$, filtered and concentrated under reduced pressure to give 5-methyl-2-(pyridin-2-yl)benzoic acid 45 (2.65 g) as a pale brown foam. LC-MS (conditions A): t$_R$=0.39 min, [M+1]$^+$=214.25.

A.8 2-Fluoro-3-methyl-6-(1H-pyrazol-1-yl)benzoic acid 46

The title compound is prepared in analogy to compound 39 replacing the 1H-1,2,3-triazole with 1H-pyrazole (25 mmol, 2 eq). 46 (1.86 g) is obtained as a light yellow solid. LC-MS (conditions F): t$_R$=0.63 min, [M+1]$^+$=221.16.

A.9 2-Fluoro-3-methyl-6-(pyridin-2-yl)benzoic acid 47 a) In a dry Schlenk Tube at RT under nitrogen are successively charged methyl 2-fluoro-6-iodo-3-methylbenzoate (9.18 mmol, 1 eq), CuI (1.84 mmol, 0.2 eq), CsF (18.4 mmol, 2 eq), 2-tributylstannylpyridine (9.18 mmol, 1 eq), Pd(PPh$_3$)$_4$ (0.918 mmol, 0.1 eq) and DMF (40 mL). The resulting suspension is stirred at 90° C. overnight. The obtained reaction mixture is diluted with EtOAc and filtered through a short pad of Celite®. A solution of sat. aq. NaHCO$_3$ is then added to the filtrate and the aq. phase extracted with EtOAc (3 times). The combined organic layers are washed with H$_2$O and brine, dried over Na$_2$SO$_4$, filtered and concentrated under reduced pressure. Purification is achieved by FC (Teledyne Isco Combiflash Rf, SiO$_2$ cartridge 120 g; Heptane to EtOAc/Heptane 3:7) to give methyl 2-fluoro-3-methyl-6-(pyridin-2-yl)benzoate as a brown oil. LC-MS (conditions F): t$_R$=0.74 min, [M+1]$^+$=246.15.

b) To a solution of methyl 2-fluoro-3-methyl-6-(pyridin-2-yl)benzoate (6.36 mmol, 1 eq) in MeOH (11.3 mL) is added NaOH 32% (6.27 mL). The resulting mixture is stirred at 60° C. for 1 hour. The volatiles are evaporated under reduced pressure and the remaining aq. phase is acidified with 7 M HCl to pH=1-2. The pink suspension is concentrated under reduced pressure and the obtained solid is purified by preparative HPLC (conditions D) to give 2-fluoro-3-methyl-6-(pyridin-2-yl)benzoic acid 47 (1.14 g) as a light pink solid. LC-MS (conditions F): t$_R$=0.47 min, [M+1]$^+$=232.17.

A.10 3-fluoro-4-methyl-[1,1'-biphenyl]-2-carboxylic acid 48 a) In a dry Schlenk Tube at RT under nitrogen are successively charged methyl 2-fluoro-6-iodo-3-methylbenzoate (23.5 mmol, 1 eq), Pd(PPh$_3$)$_4$ (1.17 mmol, 0.05 eq) and toluene (60 mL). The resulting mixture is stirred at RT for 15 minutes before a solution of phenyloronic acid (25.8 mmol, 1.1 eq) in EtOH (26 mL) and 2 M Na$_2$CO$_3$ (54 mL) are successively added. The resulting mixture is stirred at reflux overnight. The obtained reaction mixture is diluted with Et$_2$O and the solvents are removed under reduced pressure. The residue is purified by FC (Teledyne Isco Combiflash Rf, SiO$_2$ cartridge 120 g; heptane to EtOAc/heptane 3:97) to give methyl 3-fluoro-4-methyl-[1,1'-biphenyl]-2-carboxylate as a light yellow oil. LC-MS (conditions F): t$_R$=0.94 min, [M+1]$^+$=245.19.

b) To a solution of methyl 3-fluoro-4-methyl-[1,1'-biphenyl]-2-carboxylate (23 mmol, 1 eq) in MeOH (42 mL) is added NaOH 32% (24 mL). The resulting mixture is stirred at 65° C. for 2 hour. The volatiles are evaporated under reduced pressure and the remaining aq. phase is acidified with 7 M HCl to pH=1-2. The resulting suspension is filtered under vacuum and the obtained solid dried under hight vacuum. 3-Fluoro-4-methyl-[1,1'-biphenyl]-2-carboxylic acid 48 (4.35 g) is obtained as a white solid. LC-MS (conditions F): t$_R$=0.81 min, [M+1]$^+$=not detectable.

5-Aryl-2-methyl-thiazole-4-carboxylic acids

These acids were prepared by a three-step sequence depicted in the scheme below, e.g. Darzens condensation of 4-fluoro-benzaldehyde 49 with methyl dichloroacetate to give the methyl keto-ester 50 (Hamamoto H. et al *Tetrahedron Asymmetry* 2000, 11, 4485-4497) which is converted to the desired 5-(4-fluoro-phenyl)-2-methyl-4-carboxylic acid 51 by reaction with thioamide (U.S. Pat. No. 3,282,927) followed by ester hydrolysis under basic conditions.

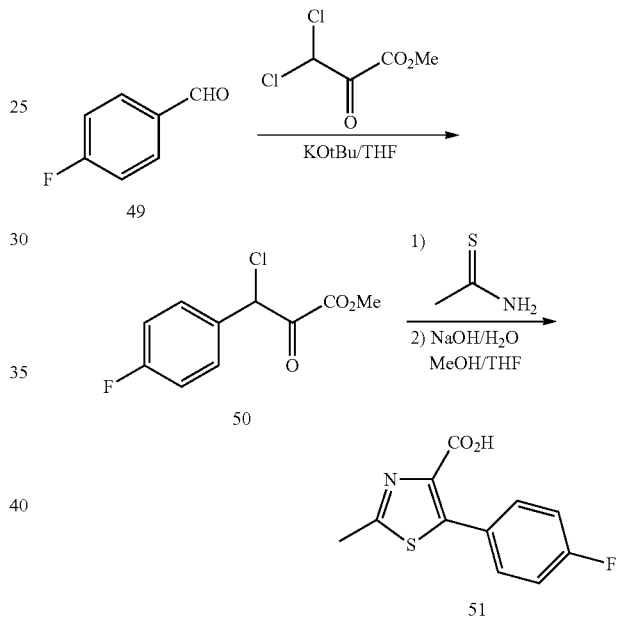

The following compounds were prepared according to the same sequence:

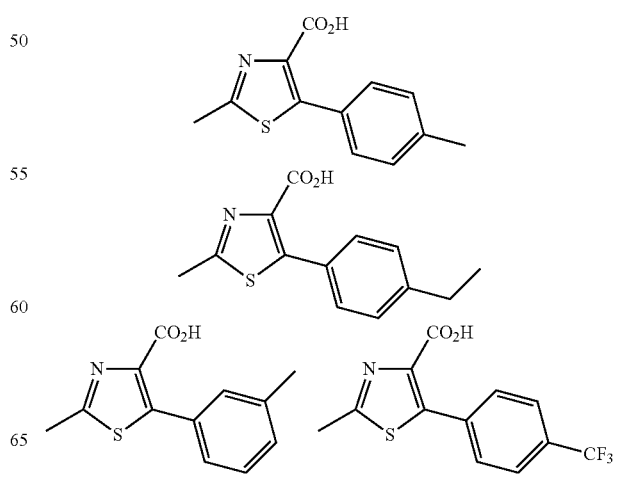

101
-continued
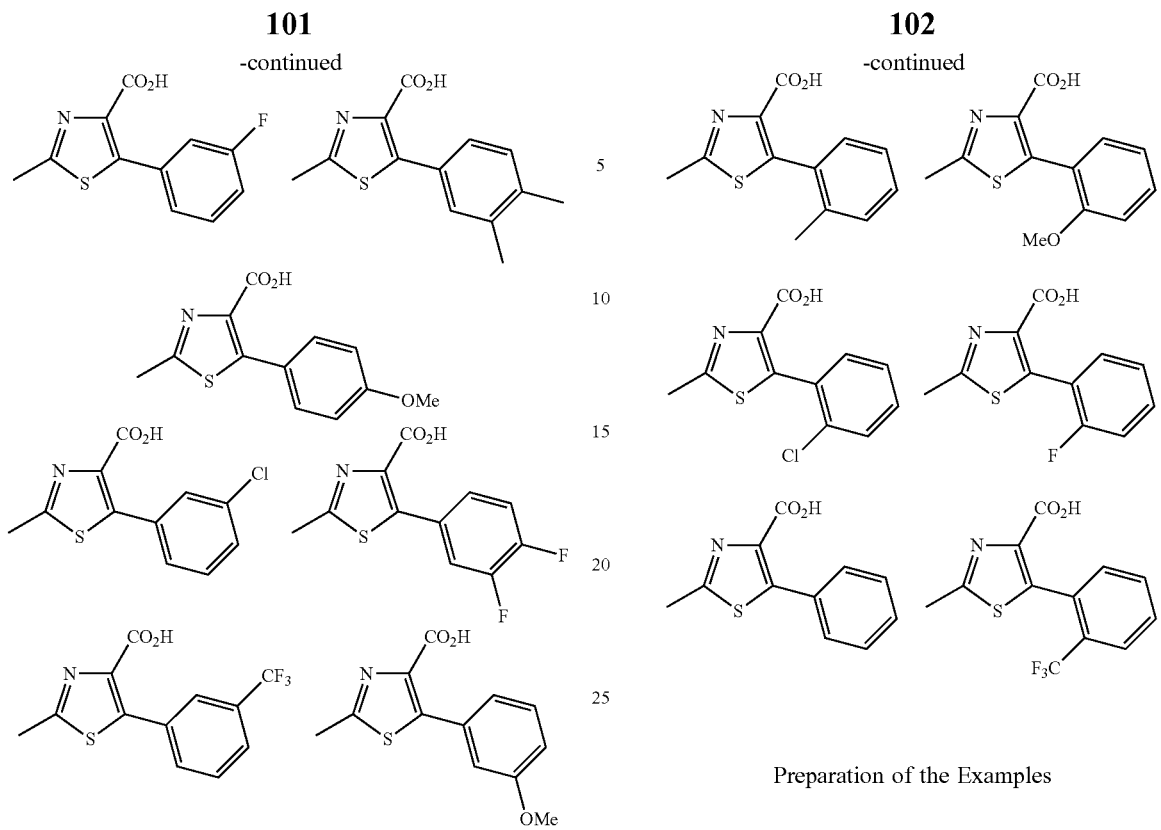
102
-continued
Preparation of the Examples
Synthesis of Example 1.1
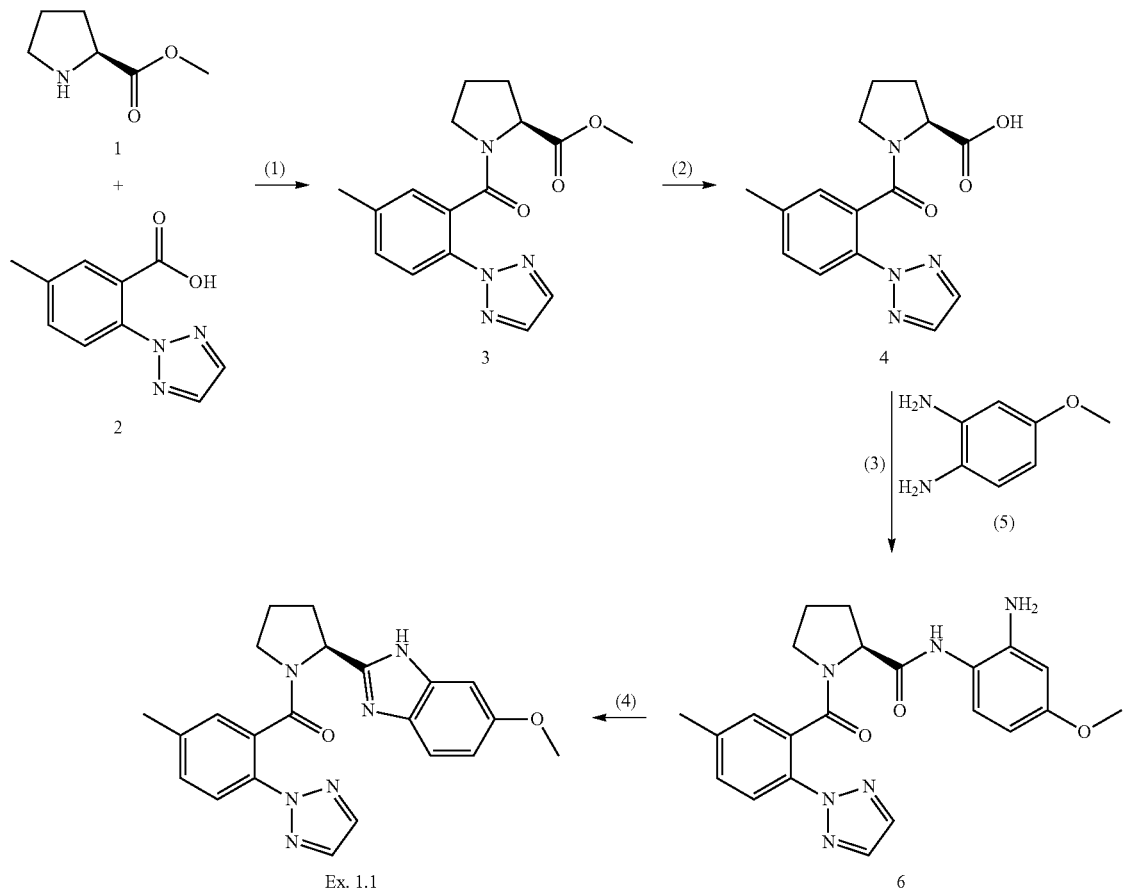

Step 1: 5-Methyl-2-(2H-1,2,3-triazol-2-yl)benzoic acid (2; 12.27 g, 60.4 mmol) and L-proline methylester hydrochloride (1; 10.20 g, 60.4 mmol) are dissolved in DCM (250 ml) followed by the addition of DIPEA (23.42 g, 31 ml, 181 mmol) and HATU (22.95 g, 60.4 mmol). Stirring at room temperature is continued for 1 h, the DCM is evaporated under reduced pressure and EtOAc (750 ml) is added. The reaction mixture is extracted with brine (3×300 ml). The organic layer is dried with MgSO$_4$, filtered and the solvent is evaporated under reduced pressure to give (S)-methyl 1-(5-methyl-2-(2H-1,2,3-triazol-2-yl)benzoyl)pyrrolidine-2-carboxylate (3) which is used in the next step without further purification. LC-MS: $t_R$=0.66 min; [M+H]$^+$=315.09.

Step 2: (S)-Methyl 1-(5-methyl-2-(2H-1,2,3-triazol-2-yl)benzoyl)pyrrolidine-2-carboxylate (3, 18.81 g, 60.4 mmol) is dissolved in a mixture of MeOH (180 ml) and THF (210 ml) followed by the addition of aq. NaOH solution (1 M; 150 ml). Stirring is continued for 1 h. The reaction mixture is concentrated (removal of the organic solvents) under reduced pressure and acidified to pH 1 by the addition of aq. HCl (1M). The product is extracted with EtOAc (3×250 ml). The combined organic layers are dried with MgSO$_4$, filtered and the solvent is evaporated under reduced pressure to give 17.14 g (87%) (S)-1-(5-methyl-2-(2H-1,2,3-triazol-2-yl)benzoyl)pyrrolidine-2-carboxylic acid (4). LC-MS: $t_R$=0.57 min; [M+H]$^+$=301.17.

Step 3: (S)-1-(5-Methyl-2-(2H-1,2,3-triazol-2-yl)benzoyl)pyrrolidine-2-carboxylic acid (4; 17.11 g, 51.3 mmol) is dissolved in DCM (250 ml) at RT followed by the addition of 3,4-diaminoanisole dihydrochloride (5; 10.83 g, 51.3 mmol). To this reaction mixture DIPEA (23.2 g, 180 mmol) is then slowly added followed by the addition of HATU (19.7 g, 51.8 mmol). Stirring is continued for 1 h at RT. The reaction mixture is concentrated under reduced pressure. The residue is taken up in EtOAc (750 ml) and washed with brine (2×500 ml). The organic layer is dried with MgSO$_4$, filtered and concentrated under reduced pressure. The crude product is purified by flash master chromatography (Silicagel; EtOAc/MeOH=95/5) to give (S)—N-(2-amino-4-methoxyphenyl)-1-(5-methyl-2-(2H-1,2,3-triazol-2-yl)benzoyl)pyrrolidine-2-carboxamide (6). LC-MS: $t_R$=0.64 min; [M+H]$^+$=421.17.

Step 4: (S)—N-(2-amino-4-methoxyphenyl)-1-(5-methyl-2-(2H-1,2,3-triazol-2-yl)benzoyl) pyrrolidine-2-carboxamide (6; 21.57 g, 51.3 mmol) is dissolved in pure AcOH (390 ml) and heated to 100° C. for 30 minutes. The reaction mixture is cooled to rt and the acetic acid is removed under reduced pressure. The residual material is carefully diluted with sat. aq. NaHCO$_3$ solution (600 ml). The product precipitated and is filtered off and purified by flash master chromatography (Silicagel, DCM/MeOH=98/2) to give (S)-(2-(6-methoxy-1H-benzo[d]imidazol-2-yl)pyrrolidin-1-yl)(5-methyl-2-(2H-1,2,3-triazol-2-yl)phenyl) methanone (Example 1.1) as a colorless powder. LC-MS: $t_R$=0.55 min; [M+H]$^+$=403.16.

Synthesis of Example 2.1

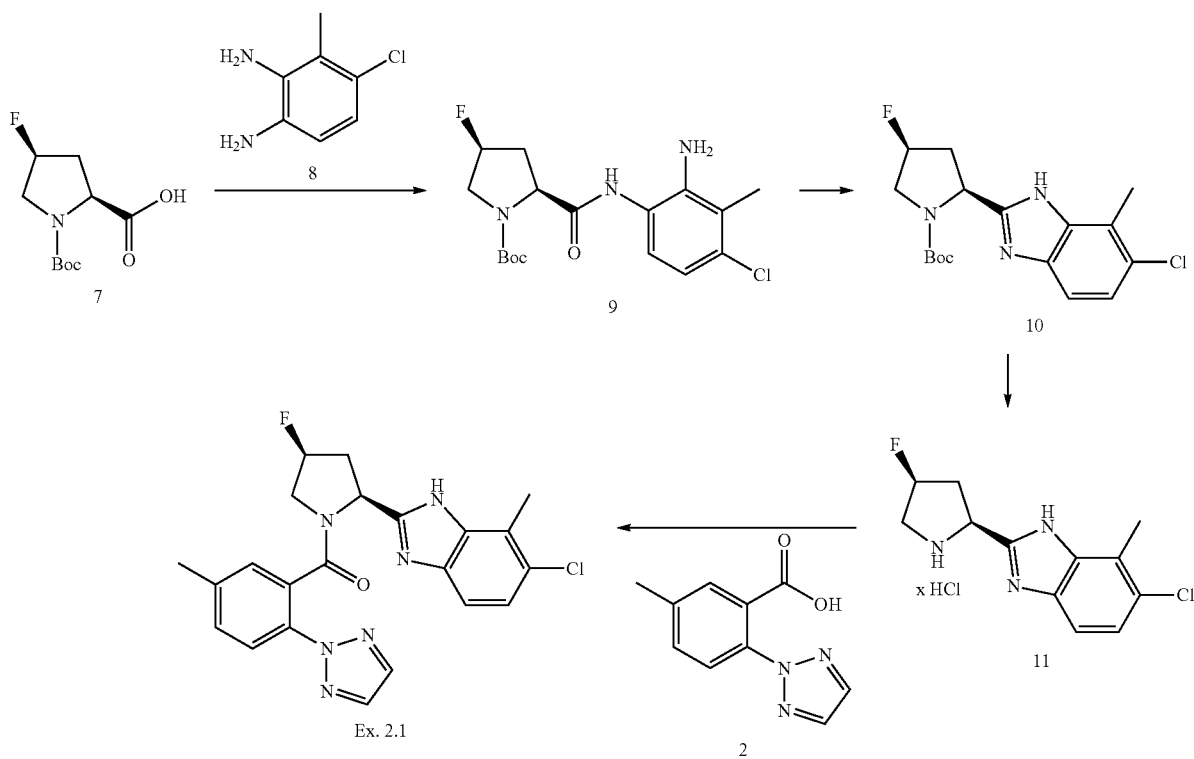

Step 1: (2S,4S)-1-(tert-Butoxycarbonyl)-4-fluoropyrrolidine-2-carboxylic acid (7; 144.27 mg, 0.6 mmol) is dissolved in a 1/1 mixture of DMF/DCM (1.2 ml) followed by the addition of DIPEA (0.44 ml, 2.52 mmol) and 4-chloro-3-methylbenzene-1,2-diamine (8; 121.95 mg, 0.6 mmol) dissolved in a 1/1 mixture of DMF/DCM (1.2 ml) and finally by the addition of HATU (240 mg, 0.63 mmol) dissolved in DMF (1 ml). The reaction mixture is stirred at RT for 15 h then passed through PL-HCO$_3$ packed filter syringe (1 g) with a 1/1-mixture of DMF/DCM (4 ml). The solvent is removed under reduced pressure to give (2S,4)-tert-butyl 2-((2-amino-4-chloro-3-methylphenyl)carbamoyl)-4-fluoropyrrolidine-1-carboxylate (9) which is used in the next step without further purification. LC-MS: $t_R$=0.79 min; [M+H]$^+$=372.26.

Step 2: (2S,4S)-tert-Butyl 2-((2-amino-4-chloro-3-methylphenyl)carbamoyl)-4-fluoropyrrolidine-1-carboxylate (9; 220 mg, 0.6 mmol) is dissolved in 100% AcOH (3 ml, 52.5 mmol) and heated to 60° C. for 3 h. Toluene (3 ml) is added to the reaction mixture and the solvents are removed under reduced pressure to give (2S,4S)-tert-butyl 2-(6-chloro-7-methyl-1H-benzo[d]imidazol-2-yl)-4-fluoropyrrolidine-1-carboxylate (10), which is used in the next step without further purification. LC-MS: $t_R$=0.8 min; [M+H]$^+$=354.25.

Step 3: (2S,4S)-tert-Butyl 2-(6-chloro-7-methyl-1H-benzo[d]imidazol-2-yl)-4-fluoropyrrolidine-1-carboxylate (10; 210 mg, 0.6 mmol) is dissolved in dioxane (0.5 ml) and a solution of HCl in dioxane (4M, 3 ml, 12 mmol) is carefully added. The reaction mixture turns into a suspension. To solubilize the reaction mixture MeOH (1 ml) is added. Stirring is continued for 2 h. The solvents are removed under reduced pressure to give 6-chloro-2-((2S,4S)-4-fluoropyrrolidin-2-yl)-7-methyl-1H-benzo[d]imidazole hydrochloride (11) which is used in the next step without further purification. LC-MS: $t_R$=0.61 min; [M+H]$^+$=254.14.

Step 4: 6-Chloro-2-((2S,4S)-4-fluoropyrrolidin-2-yl)-7-methyl-1H-benzo[d]imidazole hydrochloride (11; 30 mg, 0.1 mmol) is dissolved in DCM (0.2 ml) and DIPEA (0.072 ml, 0.42 mmol) is added, followed by the addition of a solution of 5-methyl-2-(2H-1,2,3-triazol-2-yl)benzoic acid (2; 20.3 mg, 0.1 mmol), HATU (40 mg, 0.105 mmol) and DIPEA (80 mg, 0.62 mmol) in 0.5 ml DMF. Stirring is continued at room temperature for 16 h. The reaction mixture is diluted with DCM/MeOH=1/1 (1 ml) followed by the addition of PL-HCO$_3$-resin (213 mg, 0.4 mmol) and stirring is continued for 2 h. The resin is filtered off, the solvent is evaporated under reduced pressure and the product is purified by preparative HPLC to give ((2S,4S)-2-(6-chloro-7-methyl-1H-benzo[d]imidazol-2-yl)-4-fluoropyrrolidin-1-yl)(5-methyl-2-(2H-1,2,3-triazol-2-yl)phenyl)methanone (Example 2.1) as a colorless powder. LC-MS: $t_R$=1.14 min; [M+H]$^+$=439.25.

Synthesis of Example 3.1

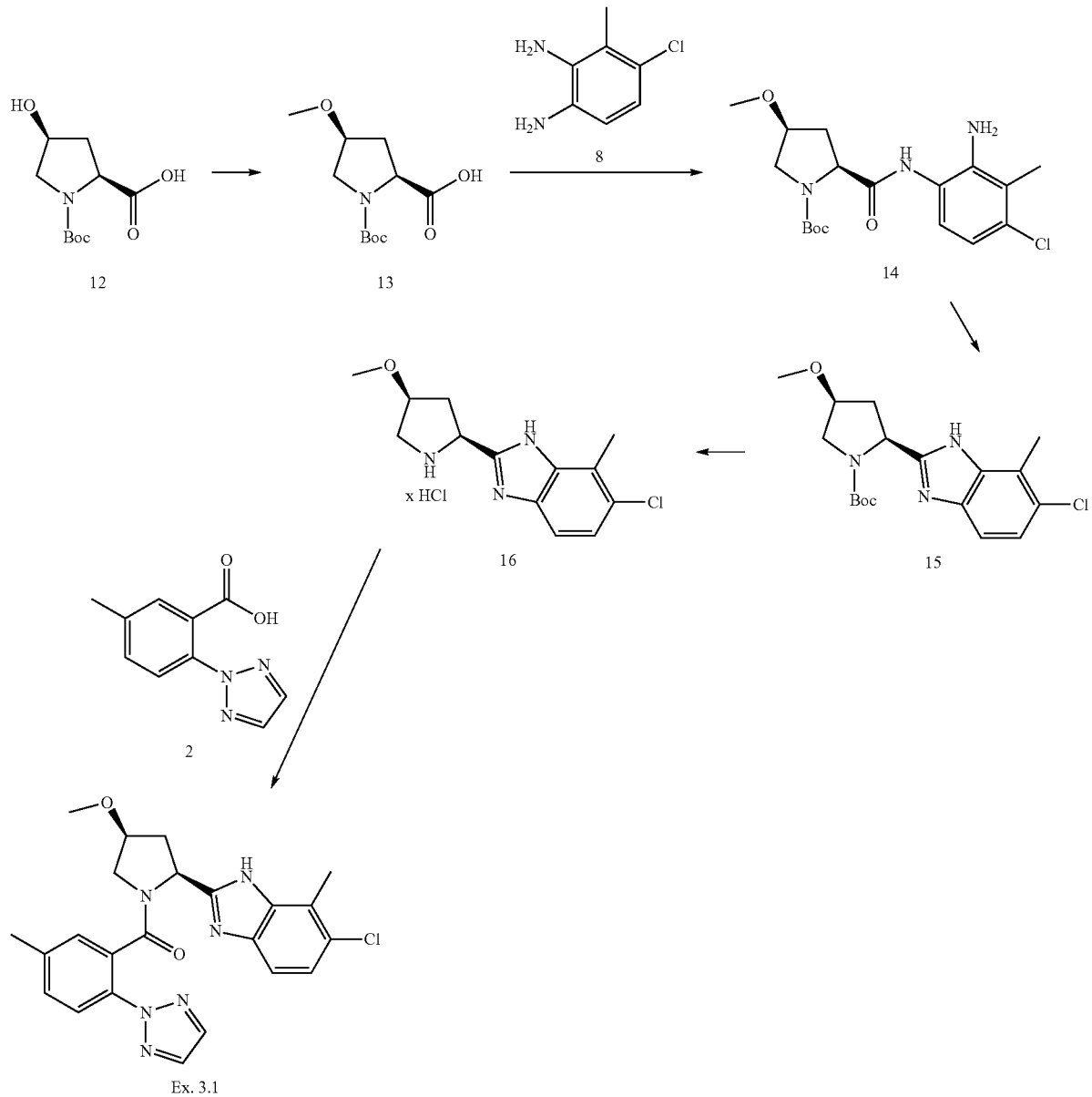

Ex. 3.1

Step 1: (2S,4S)-1-(tert-Butoxycarbonyl)-4-hydroxypyrrolidine-2-carboxylic acid (12, 1.503 g, 6.5 mmol) is dissolved in DMF (9.06 ml) and added to a suspension of NaH (60% dispersion in mineral oil, 676 mg, 16.9 mmol) in DMF (9.06 ml) in an argon atmosphere at RT and stirring is continued for 30 minutes followed by the addition of MeI (3.14 g, 22.14 mmol). Stirring is continued for 23 h. An aq., sat. solution of $KH_2PO_4$ (30 ml) is added followed by the addition of solid $KH_2PO_4$ (400 mg) and another portion of an aq., sat. solution of $KH_2PO_4$ (10 ml). The product is extracted with $Et_2O$ (3×40 ml). The combined organic layers are dried with $MgSO_4$, filtered and the solvent is removed under reduced pressure to give the 3-methoxy-proline methylester-intermediate, which is dissolved in MeOH (4.5 ml) followed by the addition of an aq. NaOH solution (3M, 3.76 ml, 11.3 mmol). Stirring is continued for 12 h. The reaction mixture is neutralized to pH=9, by the addition of a sat. solution of $KH_2PO_4$ and extracted with $Et_2O$ (3×8 ml). The combined ether layers are discarded and the aq. layer is acidified to pH=4.5 with aq. HCl. The product is extracted with EtOAc (3×40 ml). The combined organic layers are dried with $MgSO_4$, filtered and the solvent is removed under reduced pressure to give (2S,4S)-1-(tert-butoxycarbonyl)-4-methoxypyrrolidine-2-carboxylic acid (13).

Step 2: (2S,4S)-1-(tert-Butoxycarbonyl)-4-methoxypyrrolidine-2-carboxylic acid (13; 147.1 mg, 0.6 mmol) is dissolved in a 1/1 mixture of DMF/DCM (1.2 ml) followed by the addition of DIPEA (0.44 ml, 2.52 mmol) and 4-chloro-3-methylbenzene-1,2-diamine (8; 121.95 mg, 0.6 mmol) dissolved in a 1/1 mixture of DMF/DCM (1.2 ml) and finally by the addition of HATU (240 mg, 0.63 mmol) dissolved in DMF (1 ml). The reaction mixture is stirred at RT for 15 h then passed through $PL-HCO_3$ packed filter syringe (1 g) with a 1/1-mixture of DMF/DCM (4 ml). The solvent is removed under reduced pressure to give (2S,4S)-tert-butyl 2-((2-amino-4-chloro-3-methylphenyl)carbamoyl)-4-methoxypyrrolidine-1-carboxylate (14) which is used in the next step without further purification. LC-MS: $t_R$=0.8 min; $[M+H]^+$=384.28.

Step 3: (2S,4S)-tert-Butyl 2-((2-amino-4-chloro-3-methylphenyl)carbamoyl)-4-methoxypyrrolidine-1-carboxylate (14; 230 mg, 0.6 mmol) is dissolved in 100% AcOH (3 ml, 52.5 mmol) and heated to 60° C. for 3 h. Toluene (3 ml) is added to the reaction mixture and the solvents are removed under reduced pressure to give (2S,4S)-tert-butyl 2-(6-chloro-7-methyl-1H-benzo[d]imidazol-2-yl)-4-methoxypyrrolidine-1-carboxylate (15), which is used in the next step without further purification. LC-MS: $t_R$=0.80 min; $[M+H]^+$=366.27.

Step 4: (2S,4S)-tert-Butyl 2-(6-chloro-7-methyl-1H-benzo[d]imidazol-2-yl)-4-methoxypyrrolidine-1-carboxylate (15; 220 mg, 0.6 mmol) is dissolved in dioxane (0.5 ml) and a solution of HCl in dioxane (4M, 3 ml, 12 mmol) is carefully added. The reaction mixture turns into a suspension. To solubilize the reaction mixture MeOH (1 ml) is added. Stirring is continued for 2 h. The solvents are removed under reduced pressure to give 6-chloro-2-((2S,4S)-4-methoxypyrrolidin-2-yl)-7-methyl-1H-benzo[d]imidazole hydrochloride (16) which is used in the next step without further purification. LC-MS: $t_R$=0.61 min; $[M+H]^+$=266.16.

Step 5: 6-Chloro-2-((2S,4S)-4-methoxypyrrolidin-2-yl)-7-methyl-1H-benzo[d]imidazole (16; 30 mg, 0.1 mmol) is dissolved in DCM (0.2 ml) and DIPEA (0.072 ml, 0.42 mmol) is added, followed by the addition of a solution of 5-methyl-2-(2H-1,2,3-triazol-2-yl)benzoic acid (2; 20.3 mg, 0.1 mmol), HATU (40 mg, 0.105 mmol) and DIPEA (80 mg, 0.62 mmol) in 0.5 ml DMF. Stirring is continued at room temperature for 16 h. The reaction mixture is diluted with DCM/MeOH=1/1 (1 ml) followed by the addition of $PL-HCO_3$-resin (213 mg, 0.4 mmol) and stirring is continued for 2 h. The resin is filtered off, the solvent is evaporated under reduced pressure and the product is purified by preparative HPLC to give ((2S,4S)-2-(6-chloro-7-methyl-1H-benzo[d]imidazol-2-yl)-4-methoxypyrrolidin-1-yl)(5-methyl-2-(2H-1,2,3-triazol-2-yl)phenyl)methanone (Ex. 3.1) as a colorless powder. LC-MS: tR=1.16 min; $[M+H]^+$=451.29.

Synthesis of Example 4.1

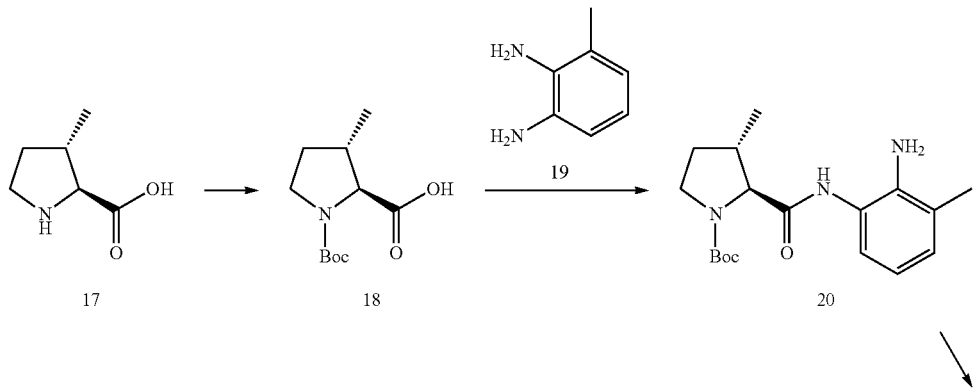

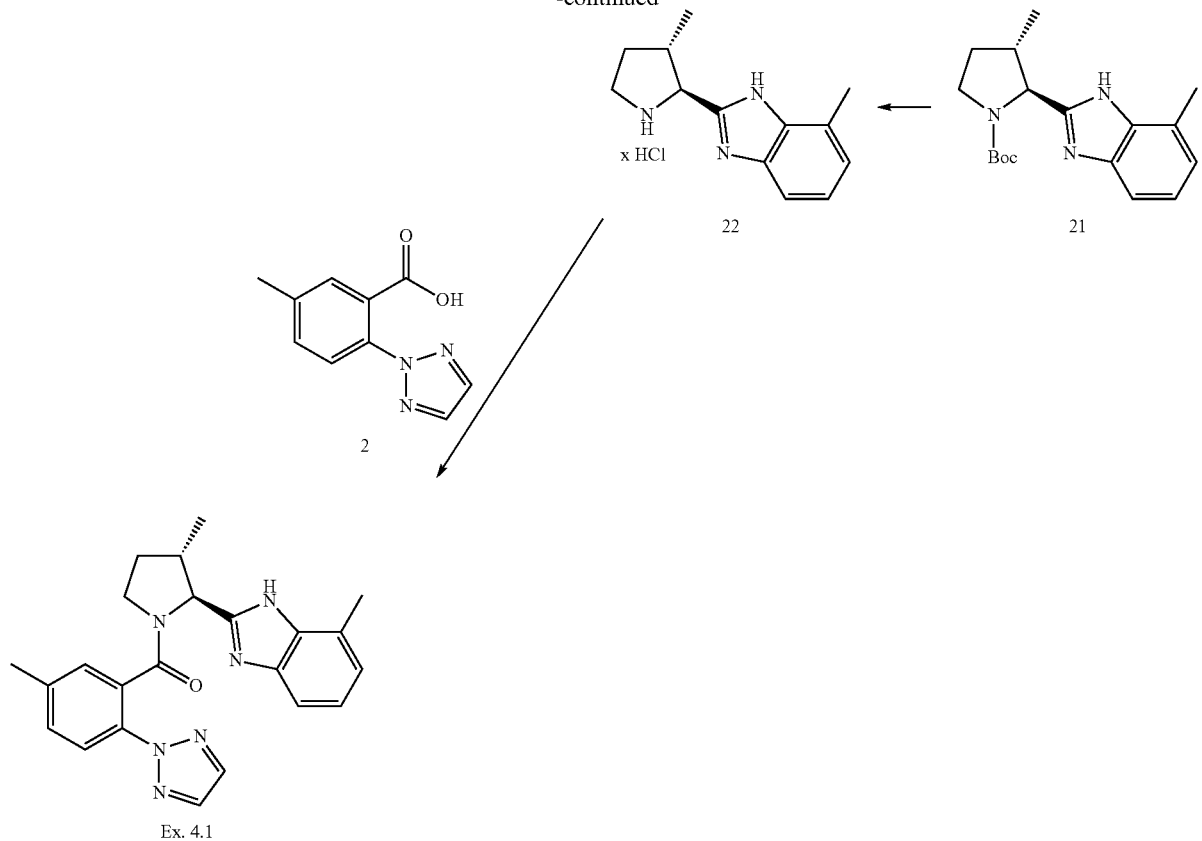

Ex. 4.1

Step 1: (2S,3S)-3-Methylpyrrolidine-2-carboxylic acid (17; 2.45 g, 19 mmol) is dissolved in a 1/1-mixture of MeCN/water (66.5 ml) and TEA (13.6 ml; 69.9 mmol) is added followed by the addition of Boc$_2$O (6.22 g, 28.5 mmol) dissolved in MeCN (14.25 ml). The reaction mixture is stirred at RT for 90 minutes. The organic solvents are evaporated under reduced pressure and water (24 ml) is added to the residue followed by the addition of aq. NaOH solution (1M, 28.5 ml, 28.5 mmol). The product is extracted with Et$_2$O (5×60 ml). The combined organic layers are dried with MgSO$_4$, filtered and the solvent is evaporated under reduced pressure to give (2S,3S)-1-(tert-butoxycarbonyl)-3-methylpyrrolidine-2-carboxylic acid (18). LC-MS: $t_R$=0.64 min; [M+H]$^+$=230.16.

Step 2: (2S,3S)-1-(tert-Butoxycarbonyl)-3-methylpyrrolidine-2-carboxylic acid (18; 69 mg, 0.3 mmol) is dissolved in a 1/1 mixture of DMF/DCM (0.6 ml) followed by the addition of DIPEA (0.22 ml, 1.26 mmol) and 3-methylbenzene-1,2-diamine (19; 36.9 mg, 0.3 mmol) dissolved in a 1/1 mixture of DMF/DCM (0.6 ml) and finally by the addition of HATU (120 mg, 0.315 mmol) dissolved in DMF (0.63 ml). The reaction mixture is stirred at RT for 17 h then passed through PL-HCO$_3$ packed filter syringe (640 mg) with a 1/1-mixture of DMF/DCM (6 ml). The solvent is removed under reduced pressure to give (2S,3S)-tert-butyl 2-((2-amino-3-methylphenyl)carbamoyl)-3-methylpyrrolidine-1-carboxylate (20) which is used in the next step without further purification. LC-MS: $t_R$=0.75 min; [M+H]$^+$=334.11.

Step 3: (2S,3S)-tert-Butyl 2-((2-amino-3-methylphenyl)carbamoyl)-3-methylpyrrolidine-1-carboxylate (20; 100 mg, 0.3 mmol) is dissolved in 100% AcOH (3 ml, 52.5 mmol) and heated to 60° C. for 3 h. Toluene (3 ml) is added to the reaction mixture and the solvents are removed under reduced pressure to give (2S,3S)-tert-butyl 3-methyl-2-(7-methyl-1H-benzo[d]imidazol-2-yl)pyrrolidine-1-carboxylate (21), which is used in the next step without further purification. LC-MS: $t_R$=0.75 min; [M+H]$^+$=316.11.

Step 4: (2S,3S)-tert-Butyl 3-methyl-2-(7-methyl-1H-benzo[d]imidazol-2-yl)pyrrolidine-1-carboxylate (21; 94.5 mg, 0.3 mmol) is dissolved in methanol (0.75 ml) and a solution of HCl in dioxane (4M, 1.5 ml, 6 mmol) is carefully added. Stirring is continued for 2 h. The solvents are removed under reduced pressure to give 7-methyl-2-((2S,3S)-3-methylpyrrolidin-2-yl)-1H-benzo[d]imidazole hydrochloride (22) which is used in the next step without further purification. LC-MS: $t_R$=0.58 min; [M+H]$^+$=216.14.

Step 5: 7-Methyl-2-((2S,3S)-3-methylpyrrolidin-2-yl)-1H-benzo[d]imidazole hydrochloride (22; 25.2 mg, 0.1 mmol) is dissolved in DCM (0.2 ml) and DIPEA (0.072 ml, 0.42 mmol) is added, followed by the addition of a solution of 5-methyl-2-(2H-1,2,3-triazol-2-yl)benzoic acid (2; 20.3 mg, 0.1 mmol), HATU (40 mg, 0.105 mmol) and DIPEA (80 mg, 0.62 mmol) in 0.5 ml DMF. Stirring is continued at room temperature for 16 h. The reaction mixture is diluted with DCM/MeOH=1/1 (1 ml) followed by the addition of PL-HCO$_3$-resin (213 mg, 0.4 mmol) and stirring is continued for 2 h. The resin is filtered off, the solvent is evaporated under reduced pressure and the product is purified by preparative HPLC to give (5-methyl-2-(2H-1,2,3-triazol-2-yl)phenyl)((2S,3S)-3-methyl-2-(7-methyl-1H-benzo[d]imidazol-2-yl)pyrrolidin-1-yl)methanone (Ex. 4.1) as a colorless powder. LC-MS: $t_R$=0.96 min; [M+H]$^+$=401.16.

Synthesis of Example 5.1

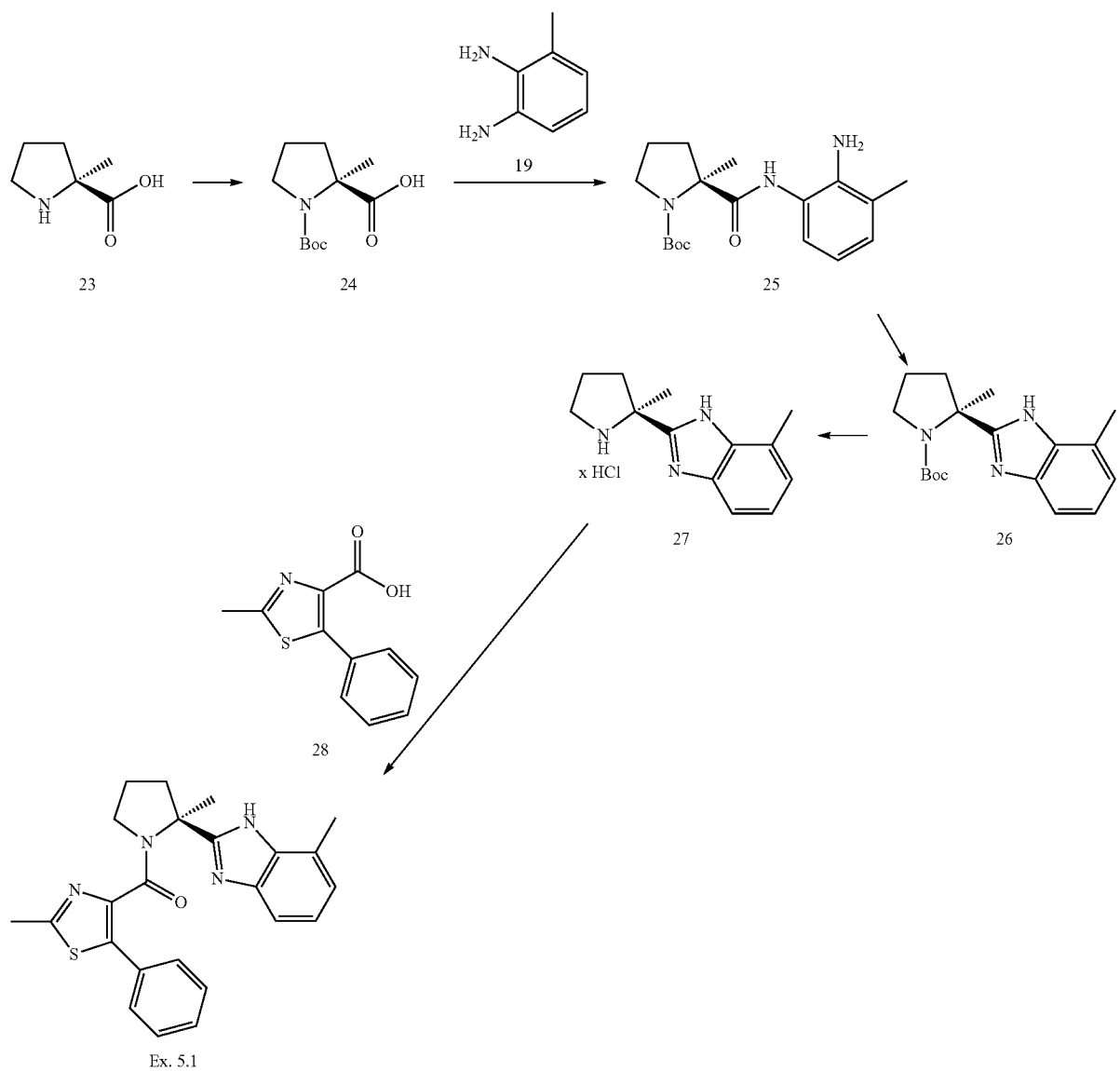

Step 1: (S)-2-Methylpyrrolidine-2-carboxylic acid hydrochloride (23; 82.5 g, 498 mmol) is dissolved in a 1/1-mixture of MeCN/water (1000 ml) and TEA (210 ml; 1490 mmol) is added followed by the addition of Boc$_2$O (120 g, 548 mmol) dissolved in MeCN (200 ml). The reaction mixture is stirred at RT for 3 hours. The organic solvents are evaporated under reduced pressure and 2M aqueous sodium hydroxide (300 ml) is added to the residue The aqueous phase is extracted with Et$_2$O (400 ml). and cooled to 10° C. followed by slow addition of 25% aqueous hydrochloric acid until the pH=5-6 followed by careful addition of aqueous 1M hydrochloric acid to pH=2. The product precipitates and is filtered off, washed with water (300 ml) and dried at high vacuum to give 90.7 g of (S)-1-(tert-butoxycarbonyl)-2-methylpyrrolidine-2-carboxylic acid (24) as a slightly grey solid. LC-MS: $t_R$=0.63 min; [M+H]$^+$=230.24.

Step 2: (S)-1-(tert-Butoxycarbonyl)-2-methylpyrrolidine-2-carboxylic acid (24; 137.6 mg, 0.6 mmol) is dissolved in a 1/1 mixture of DMF/DCM (1.2 ml) followed by the addition of DIPEA (0.44 ml, 2.52 mmol) and 3-methylbenzene-1,2-diamine (19; 73.8 mg, 0.6 mmol) dissolved in a 1/1 mixture of DMF/DCM (1.2 ml) and finally by the addition of HATU (240 mg, 0.63 mmol) dissolved in DMF (1.26 ml). The reaction mixture is stirred at RT for 17 h then passed through PL-HCO$_3$ packed filter syringe (1 g) with a 1/1-mixture of DMF/DCM (6 ml). The solvent is removed under reduced pressure to give (S)-tert-butyl 2-((2-amino-3-methylphenyl)carbamoyl)-2-methylpyrrolidine-1-carboxylate (25) which is used in the next step without further purification. LC-MS: $t_R$=0.78 min; [M+H]$^+$=334.3.

Step 3: (S)-tert-Butyl 2-((2-amino-3-methylphenyl)carbamoyl)-2-methylpyrrolidine-1-carboxylate (25; 200 mg, 0.6 mmol) is dissolved in 100% AcOH (3 ml, 52.5 mmol) and heated to 60° C. for 3 h. Toluene (3 ml) is added to the reaction mixture and the solvents are removed under reduced pressure to give (S)-tert-butyl 2-methyl-2-(7-methyl-1H-benzo[d]imidazol-2-yl)pyrrolidine-1-carboxylate (26), which is used in the next step without further purification. LC-MS: $t_R$=0.76 min; [M+H]$^+$=316.24.

Step 4: (S)-tert-Butyl 2-methyl-2-(7-methyl-1H-benzo[d]imidazol-2-yl)pyrrolidine-1-carboxylate (26; 189.7 mg, 0.6 mmol) is dissolved in MeOH (1.5 ml) and a solution of HCl in dioxane (4M, 3 ml, 12 mmol) is carefully added. Stirring is continued for 2 h. The solvents are removed under reduced pressure to give (S)-7-methyl-2-(2-methylpyrrolidin-2-yl)-1H-benzo[d]imidazole hydrochloride (27) which is used in the next step without further purification. LC-MS: $t_R$=0.57 min; [M+H]$^+$=216.31.

Step 5: (S)-7-Methyl-2-(2-methylpyrrolidin-2-yl)-1H-benzo[d]imidazole hydrochloride (27; 25.2 mg, 0.1 mmol) is dissolved in DCM (0.2 ml) and DIPEA (0.072 ml, 0.42 mmol) is added, followed by the addition of a solution of 2-methyl-5-phenylthiazole-4-carboxylic acid (28; 22 mg, 0.1 mmol), HATU (40 mg, 0.105 mmol) and DIPEA (80 mg, 0.62 mmol) in 0.5 ml DMF. Stirring is continued at RT for 16 h. The reaction mixture is diluted with DCM/MeOH=1/1 (1 ml) followed by the addition of PL-HCO$_3$-resin (213 mg, 0.4 mmol) and stirring is continued for 2 h. The resin is filtered off, the solvent is evaporated under reduced pressure and the product is purified by preparative HPLC to give (S)-(2-methyl-2-(7-methyl-1H-benzo[d]imidazol-2-yl)pyrrolidin-1-yl)(2-methyl-5-phenylthiazol-4-yl)methanone (Ex. 5.1) as a colorless powder. LC-MS: $t_R$=1.19 min; [M+H]$^+$=417.31.

Synthesis of Example 6.1

The reaction mixture is stirred at RT for 16 h. The mixture is then poured onto brine (100 ml) and extracted with DCM (2×100 ml). The combined organic layers are dried over MgSO$_4$, filtered and the solvent is removed under reduced pressure. The crude product is purified by FC (ethyl acetate) to give (S)-tert-butyl 2-((2-amino-4-methoxyphenyl)carbamoyl)-4-methylenepyrrolidine-1-carboxylate (30) as a slightly yellow amorphous solid. LC-MS: $t_R$=0.65 min; [M+H]$^+$=348.03.

Step 2: (S)-tert-Butyl 2-((2-amino-4-methoxyphenyl)carbamoyl)-4-methylenepyrrolidine-1-carboxylate (30; 1.52 g, 4.38 mmol) is dissolved in 100% AcOH (43.8 ml, 766 mmol) and heated to 100° C. for 30 minutes. The reaction mixture is concentrated under reduced pressure followed by the addition of DCM (150 ml) to the residue. The organic layer is washed with sat. aq. NaHCO$_3$ solution (150 ml) and brine (150 ml) and dried over MgSO$_4$, filtered and the solvent is evaporated to give (S)-tert-butyl 2-(6-methoxy-1H-benzo[d]imidazol-2-yl)-4-methylenepyrrolidine-1-carboxylate (31) as a slightly yellow, amorphous solid. LC-MS: $t_R$=0.55 min; [M+H]$^+$=330.22.

Step 3: (S)-tert-Butyl 2-(6-methoxy-1H-benzo[d]imidazol-2-yl)-4-methylenepyrrolidine-1-carboxylate (31; 1.21 g, 3.67 mmol) is dissolved in dioxane (19 ml) and a solution of HCl in dioxane (4M, 19 ml, 73.5 mmol) is carefully added. Stirring is continued for 2 h. The solvents are removed under reduced pressure and the product is dried at HV to give

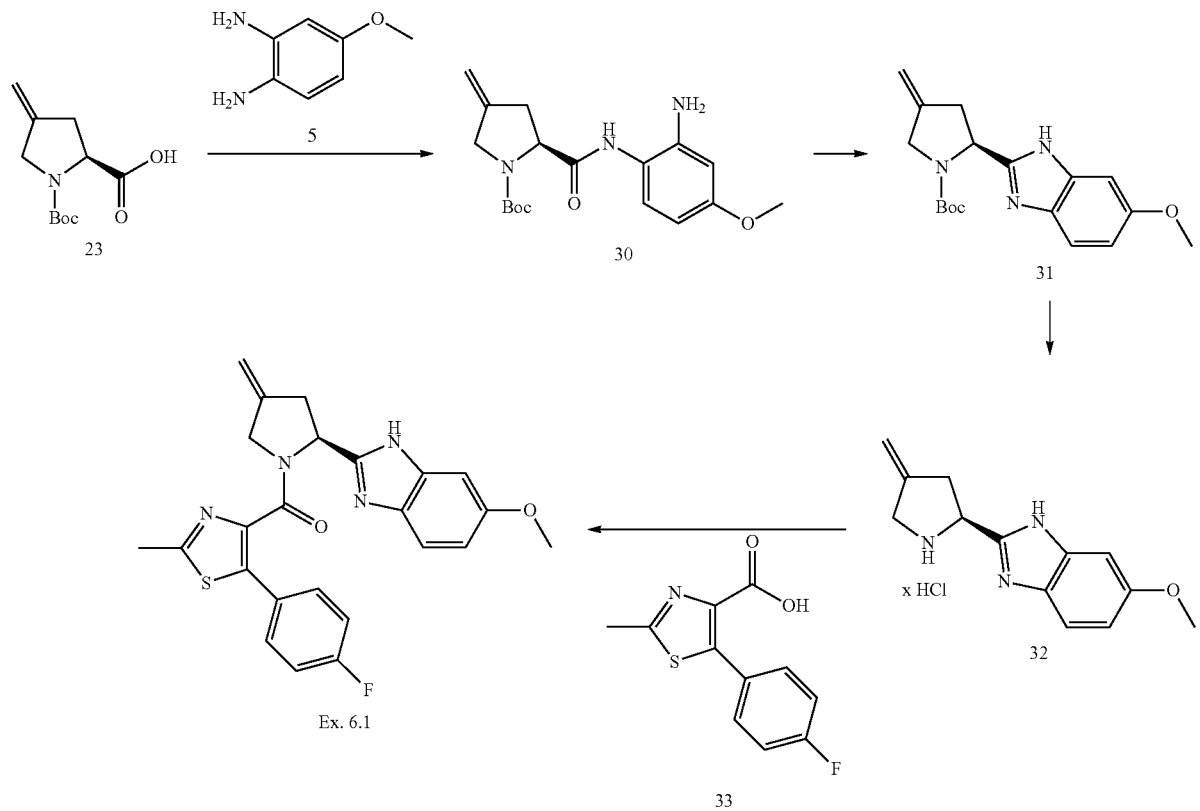

Ex. 6.1

Step 1: (S)-1-(tert-Butoxycarbonyl)-4-methylenepyrrolidine-2-carboxylic acid (29; 1.0 g, 4.4 mmol) and HATU (1.84 g, 4.84 mmol) is suspended in DCM (30 ml) followed by the addition of DIPEA (3.8 ml, 22 mmol) and 4-methoxybenzene-1,2-diamine hydrochloride (5; 960 mg, 4.4 mmol).

(S)-6-methoxy-2-(4-methylenepyrrolidin-2-yl)-1H-benzo[d]imidazole hydrochloride (32), as a slightly beige solid. LC-MS: $t_R$=0.37 min; [M+H]$^+$=230.22.

Step 4: 5-(4-Fluorophenyl)-2-methylthiazole-4-carboxylic acid (33; 12.4 mg, 0.207 mmol) is dissolved in MeCN (1 ml) and TBTU (66.5 mg, 0.207 mmol) and DIPEA (0.161 ml, 122 mg, 0.941 mmol) are added, followed by the addition of a solution of (S)-6-methoxy-2-(4-methylenepyrrolidin-2-yl)-1H-benzo[d]imidazole hydrochloride (32; 50 mg, 0.188 mmol) and DIPEA (8 mg, 0.6 mmol, 0.05 ml) in 0.5 ml MeCN. Stirring is continued at RT for 16 h. The product is directly purified by preparative HPLC to give (S)-(5-(4-fluorophenyl)-2-methylthiazol-4-yl)(2-(6-methoxy-1H-benzo[d]imidazol-2-yl)-4-methylenepyrrolidin-1-yl)methanone (Ex. 6.1) as a colorless powder. LC-MS: $t_R$=0.63 min; $[M+H]^+$=448.97.

Synthesis of Example 7.4

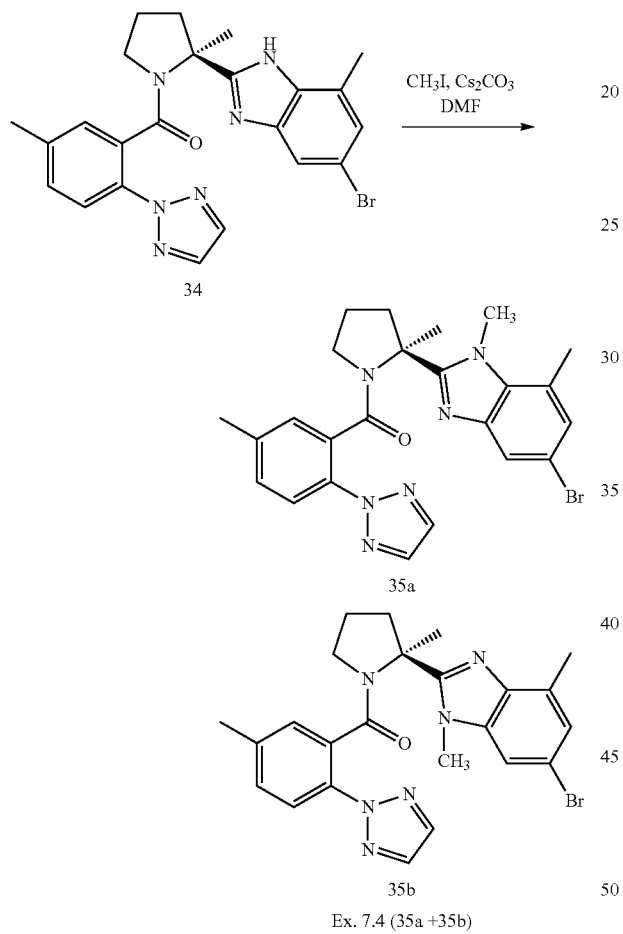

(S)-(2-(5-bromo-7-methyl-1H-benzo[d]imidazol-2-yl)-2-methylpyrrolidin-1-yl)(5-methyl-2-(2H-1,2,3-triazol-2-yl)phenyl)methanone (34; 157 mg, 0.329 mmol) is dissolved in DMF (2 ml) and $Cs_2CO_3$ (161 mg, 0.493 mmol) is added followed by the slow addition of a solution of MeI (58.3 mg, 0.411 mmol) in DMF (1 ml) at 0° C. Stirring is continued for 60 min at 0° C. The reaction mixture is poured onto water (100 ml). The precipitated product is filtered off, washed with water (10 ml), dried at HV to give an isomeric mixture of Ex. 7.4 consisting of (S)-(2-(5-bromo-1,7-dimethyl-1H-benzo[d]imidazol-2-yl)-2-methylpyrrolidin-1-yl)(5-methyl-2-(2H-1,2,3-triazol-2-yl)phenyl)methanone (35a) and (S)-(2-(6-bromo-1,4-dimethyl-1H-benzo[d]imidazol-2-yl)-2-methylpyrrolidin-1-yl)(5-methyl-2-(2H-1,2,3-triazol-2-yl)phenyl)methanone (35b) as a slightly grey powder. LC-MS: $t_R$=0.79 min; $[M+H]^+$=495.11.

According to the procedures described herein before, the following examples are prepared:

| Example | Compound name. LC-MS data |
|---|---|
| 1.1 | (5-Methyl-2-[1,2,3]triazol-2-yl-phenyl)-[(S)-2-(4-nitro-1H-benzoimidazol-2-yl)-pyrrolidin-1-yl]-methanone. LC-MS: $t_R$ = 0.84; $[M + H]^+$ = 418.2 |
| 1.2 | [(S)-2-(5-Methoxy-1H-benzoimidazol-2-yl)-pyrrolidin-1-yl]-(5-methyl-2-[1,2,3]triazol-2-yl-phenyl)-methanone. LC-MS: $t_R$ = 0.63; $[M + H]^+$ = 403.2 |
| 1.3 | [(S)-2-(5-Chloro-1H-benzoimidazol-2-yl)-pyrrolidin-1-yl]-(5-methyl-2-[1,2,3]triazol-2-yl-phenyl)-methanone. LC-MS: $t_R$ = 0.71; $[M + H]^+$ = 407.1 |
| 1.4 | [(S)-2-(7-Methoxy-1H-benzoimidazol-2-yl)-pyrrolidin-1-yl]-(5-methyl-2-[1,2,3]triazol-2-yl-phenyl)-methanone. LC-MS: $t_R$ = 0.64; $[M + H]^+$ = 403.2 |
| 1.5 | [(S)-2-(7-Methylsulfanyl-1H-benzoimidazol-2-yl)-pyrrolidin-1-yl]-(5-methyl-2-[1,2,3]triazol-2-yl-phenyl)-methanone. LC-MS: $t_R$ = 0.68; $[M + H]^+$ = 419.2 |
| 1.6 | [(S)-2-(7-Chloro-1H-benzoimidazol-2-yl)-pyrrolidin-1-yl]-(5-methyl-2-[1,2,3]triazol-2-yl-phenyl)-methanone. LC-MS: $t_R$ = 0.74; $[M + H]^+$ = 407.2 |
| 1.7 | [(S)-2-(5-Methylsulfanyl-1H-benzoimidazol-2-yl)-pyrrolidin-1-yl]-(5-methyl-2-[1,2,3]triazol-2-yl-phenyl)-methanone. LC-MS: $t_R$ = 0.68; $[M + H]^+$ = 419.2 |
| 1.9 | [5-(3-Chloro-phenyl)-2-methyl-thiazol-4-yl]-[(S)-2-(5-methoxy-1H-benzoimidazol-2-yl)-pyrrolidin-1-yl]-methanone. LC-MS: $t_R$ = 0.76; $[M + H]^+$ = 453.2 |
| 1.10 | [(S)-2-(5-Chloro-1H-benzoimidazol-2-yl)-pyrrolidin-1-yl]-[5-(3-chloro-phenyl)-2-methyl-thiazol-4-yl]-methanone. LC-MS: $t_R$ = 0.84; $[M + H]^+$ = 457.1 |
| 1.11 | [5-(3-Chloro-phenyl)-2-methyl-thiazol-4-yl]-[(S)-2-(7-methoxy-1H-benzoimidazol-2-yl)-pyrrolidin-1-yl]-methanone. LC-MS: $t_R$ = 0.77; $[M + H]^+$ = 453.1 |
| 1.12 | [5-(3-Chloro-phenyl)-2-methyl-thiazol-4-yl]-[(S)-2-(4-hydroxy-1H-benzoimidazol-2-yl)-pyrrolidin-1-yl]-methanone. LC-MS: $t_R$ = 0.71; $[M + H]^+$ = 439.1 |
| 1.13 | [5-(3-Chloro-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.82; $[M + H]^+$ = 469.1 |
| 1.14 | [(S)-2-(7-Chloro-1H-benzoimidazol-2-yl)-pyrrolidin-1-yl]-[5-(3-chloro-phenyl)-2-methyl-thiazol-4-yl]-methanone. LC-MS: $t_R$ = 0.87; $[M + H]^+$ = 457.1 |
| 1.15 | [5-(3-Chloro-phenyl)-2-methyl-thiazol-4-yl]-[(S)-2-(5-methylsulfanyl-1H-benzoimidazol-2-yl)-pyrrolidin-1-yl]-methanone. LC-MS: $t_R$ = 0.81; $[M + H]^+$ = 469.1 |
| 1.16 | [(S)-2-(6-Methoxy-1H-benzoimidazol-2-yl)-pyrrolidin-1-yl]-(5-methyl-2-[1,2,3]triazol-2-yl-phenyl)-methanone. LC-MS: $t_R$ = 0.63; $[M + H]^+$ = 403.2 |
| 1.17 | [(S)-2-(6-Methylsulfanyl-1H-benzoimidazol-2-yl)-pyrrolidin-1-yl]-(5-methyl-2-[1,2,3]triazol-2-yl-phenyl)-methanone. LC-MS: $t_R$ = 0.69; $[M + H]^+$ = 419.2 |
| 1.18 | [5-(4-Bromo-phenyl)-2-methyl-thiazol-4-yl]-[(S)-2-(6-methoxy-1H-benzoimidazol-2-yl)-pyrrolidin-1-yl]-methanone. LC-MS: $t_R$ = 0.77; $[M + H]^+$ = 497.1 |
| 1.19 | [5-(2,3-Dichloro-phenyl)-2-methyl-thiazol-4-yl]-[(S)-2-(6-methoxy-1H-benzoimidazol-2-yl)-pyrrolidin-1-yl]-methanone. LC-MS: $t_R$ = 0.81; $[M + H]^+$ = 487.1 |
| 1.20 | [(S)-2-(6-Methoxy-1H-benzoimidazol-2-yl)-pyrrolidin-1-yl]-[5-(3-methoxy-phenyl)-2-methyl-thiazol-4-yl]-methanone. LC-MS: $t_R$ = 0.70; $[M + H]^+$ = 449.2 |
| 1.21 | [5-(3-Fluoro-phenyl)-2-methyl-thiazol-4-yl]-[(S)-2-(6-methoxy-1H-benzoimidazol-2-yl)-pyrrolidin-1-yl]-methanone. LC-MS: $t_R$ = 0.71; $[M + H]^+$ = 437.2 |
| 1.22 | [(S)-2-(6-Methoxy-1H-benzoimidazol-2-yl)-pyrrolidin-1-yl]-(2-methyl-5-p-tolyl-thiazol-4-yl)-methanone. LC-MS: $t_R$ = 0.75; $[M + H]^+$ = 433.2 |
| 1.23 | (2-Cyclopropyl-5-p-tolyl-thiazol-4-yl)-[(S)-2-(6-methoxy-1H-benzoimidazol-2-yl)-pyrrolidin-1-yl]-methanone. LC-MS: $t_R$ = 0.83; $[M + H]^+$ = 459.3 |
| 1.24 | [5-(4-Ethyl-phenyl)-2-methyl-thiazol-4-yl]-[(S)-2-(6-methoxy-1H-benzoimidazol-2-yl)-pyrrolidin-1-yl]-methanone. LC-MS: $t_R$ = 0.81; $[M + H]^+$ = 447.2 |
| 1.25 | [5-(3-Chloro-phenyl)-2-methyl-thiazol-4-yl]-[(S)-2-(6-methoxy-1H-benzoimidazol-2-yl)-pyrrolidin-1-yl]-methanone. LC-MS: $t_R$ = 0.76; $[M + H]^+$ = 453.2 |

| Example | Compound name. LC-MS data |
|---|---|
| 1.26 | (3',4'-Dimethyl-biphenyl-2-yl)-[(S)-2-(6-methoxy-1H-benzoimidazol-2-yl)-pyrrolidin-1-yl]-methanone. LC-MS: $t_R$ = 0.80; [M + H]$^+$ = 426.3 |
| 1.27 | [(S)-2-(6-Methoxy-1H-benzoimidazol-2-yl)-pyrrolidin-1-yl]-(2-[1,2,3]triazol-2-yl-phenyl)-methanone. LC-MS: $t_R$ = 0.58; [M + H]$^+$ = 389.2 |
| 1.28 | [4-(3,4-Dichloro-phenyl)-2-methyl-pyrimidin-5-yl]-[(S)-2-(6-methoxy-1H-benzoimidazol-2-yl)-pyrrolidin-1-yl]-methanone. LC-MS: $t_R$ = 0.76; [M + H]$^+$ = 482.2 |
| 1.29 | [4-(3-Chloro-phenyl)-2-methyl-pyrimidin-5-yl]-[(S)-2-(6-methoxy-1H-benzoimidazol-2-yl)-pyrrolidin-1-yl]-methanone. LC-MS: $t_R$ = 0.68; [M + H]$^+$ = 448.2 |
| 1.30 | [4-(4-Bromo-3-chloro-phenyl)-pyrimidin-5-yl]-[(S)-2-(6-methoxy-1H-benzoimidazol-2-yl)-pyrrolidin-1-yl]-methanone. LC-MS: $t_R$ = 0.73; [M + H]$^+$ = 512.1 |
| 1.31 | [4-(3,4-Dimethyl-phenyl)-2-methyl-pyrimidin-5-yl]-[(S)-2-(6-methoxy-1H-benzoimidazol-2-yl)-pyrrolidin-1-yl]-methanone. LC-MS: $t_R$ = 0.69; [M + H]$^+$ = 442.3 |
| 1.32 | [(S)-2-(6-Methoxy-1H-benzoimidazol-2-yl)-pyrrolidin-1-yl]-(2-methyl-4-phenyl-pyrimidin-5-yl)-methanone. LC-MS: $t_R$ = 0.59; [M + H]$^+$ = 414.2 |
| 1.33 | [4-(4-Bromo-3-chloro-phenyl)-2-methyl-pyrimidin-5-yl]-[(S)-2-(6-methoxy-1H-benzoimidazol-2-yl)-pyrrolidin-1-yl]-methanone. LC-MS: $t_R$ = 0.77; [M + H]$^+$ = 526.1 |
| 1.34 | [5-(4-Bromo-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.83; [M + H]$^+$ = 513.1 |
| 1.35 | (2-Cyclopropyl-5-phenyl-thiazol-4-yl)-[(S)-2-(6-methylsulfanyl-1H-benzoimidazol-2-yl)-pyrrolidin-1-yl]-methanone. LC-MS: $t_R$ = 0.82; [M + H]$^+$ = 461.2 |
| 1.36 | [5-(2,3-Dichloro-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.86; [M + H]$^+$ = 503.1 |
| 1.37 | [5-(3-Methoxy-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.75; [M + H]$^+$ = 465.2 |
| 1.38 | [(S)-2-(6-Methylsulfanyl-1H-benzoimidazol-2-yl)-pyrrolidin-1-yl]-[2-methyl-5-(3-trifluoromethyl-phenyl)-thiazol-4-yl]-methanone. LC-MS: $t_R$ = 0.85; [M + H]$^+$ = 503.2 |
| 1.39 | [5-(3-Fluoro-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.76; [M + H]$^+$ = 453.2 |
| 1.40 | [(S)-2-(6-Methylsulfanyl-1H-benzoimidazol-2-yl)-pyrrolidin-1-yl]-(2-methyl-5-p-tolyl-thiazol-4-yl)-methanone. LC-MS: $t_R$ = 0.80; [M + H]$^+$ = 449.2 |
| 1.41 | (2-Cyclopropyl-5-p-tolyl-thiazol-4-yl)-[(S)-2-(6-methylsulfanyl-1H-benzoimidazol-2-yl)-pyrrolidin-1-yl]-methanone. LC-MS: $t_R$ = 0.87; [M + H]$^+$ = 475.3 |
| 1.42 | [5-(4-Ethyl-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.85; [M + H]$^+$ = 463.2 |
| 1.43 | [5-(3-Chloro-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.81; [M + H]$^+$ = 469.2 |
| 1.44 | [5-(3,5-Difluoro-phenyl)-2-methyl-thiazol-4-yl]-[(S)-2-(6-methylsulfanyl-1H-benzoimidazol-2-yl)-pyrrolidin-1-yl]-methanone. LC-MS: $t_R$ = 0.79; [M + H]$^+$ = 471.2 |
| 1.45 | [3-(3-Fluoro-5-methyl-phenyl)-pyrazin-2-yl]-[(S)-2-(6-methylsulfanyl-1H-benzoimidazol-2-yl)-pyrrolidin-1-yl]-methanone. LC-MS: $t_R$ = 0.73; [M + H]$^+$ = 448.2 |
| 1.46 | (3',4'-Dimethyl-biphenyl-2-yl)-[(S)-2-(6-methylsulfanyl-1H-benzoimidazol-2-yl)-pyrrolidin-1-yl]-methanone. LC-MS: $t_R$ = 0.85; [M + H]$^+$ = 442.2 |
| 1.47 | [(S)-2-(6-Methylsulfanyl-1H-benzoimidazol-2-yl)-pyrrolidin-1-yl]-(2-[1,2,3]triazol-2-yl-phenyl)-methanone. LC-MS: $t_R$ = 0.63; [M + H]$^+$ = 405.2 |
| 1.49 | [4-(3,4-Dichloro-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.82; [M + H]$^+$ = 498.1 |
| 1.50 | [4-(4-Fluoro-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.69; [M + H]$^+$ = 448.2 |
| 1.51 | [4-(3-Chloro-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.74; [M + H]$^+$ = 464.2 |
| 1.52 | [4-(3,4-Dichloro-phenyl)-pyrimidin-5-yl]-[(S)-2-(6-methylsulfanyl-1H-benzoimidazol-2-yl)-pyrrolidin-1-yl]-methanone. LC-MS: $t_R$ = 0.78; [M + H]$^+$ = 484.1 |
| 1.53 | 4-(3,4-Dimethyl-phenyl)-pyrimidin-5-yl]-[(S)-2-(6-methylsulfanyl-1H-benzoimidazol-2-yl)-pyrrolidin-1-yl]-methanone. LC-MS: $t_R$ = 0.72; [M + H]$^+$ = 444.2 |
| 1.54 | [4-(4-Bromo-3-chloro-phenyl)-pyrimidin-5-yl]-[(S)-2-(6-methylsulfanyl-1H-benzoimidazol-2-yl)-pyrrolidin-1-yl]-methanone. LC-MS: $t_R$ = 0.79; [M + H]$^+$ = 528.1 |
| 1.55 | [4-(3,4-Dimethyl-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.75; [M + H]$^+$ = 458.3 |
| 1.56 | [4-(3-Methoxy-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.67; [M + H]$^+$ = 460.3 |
| 1.57 | (2-Methyl-4-phenyl-pyrimidin-5-yl)-[(S)-2-(6-methylsulfanyl-1H-benzoimidazol-2-yl)-pyrrolidin-1-yl]-methanone. LC-MS: $t_R$ = 0.66; [M + H]$^+$ = 430.2 |
| 1.58 | [4-(4-Bromo-3-chloro-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.83; [M + H]$^+$ = 542.0 |
| 1.59 | [4-(3,5-Dichloro-phenyl)-2-methyl-pyrimidin-5-yl]-[(S)-2-(6-methylsulfanyl-1H-benzoimidazol-2-yl)-pyrrolidin-1-yl]-methanone. LC-MS: $t_R$ = 0.82; [M + H]$^+$ = 498.2 |
| 1.60 | [5-(4-Bromo-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.84; [M + H]$^+$ = 513.1 |
| 1.61 | (2-Cyclopropyl-5-phenyl-thiazol-4-yl)-[(S)-2-(7-methylsulfanyl-1H-benzoimidazol-2-yl)-pyrrolidin-1-yl]-methanone. LC-MS: $t_R$ = 0.83; [M + H]$^+$ = 461.2 |
| 1.62 | [5-(2,3-Dichloro-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.86; [M + H]$^+$ = 503.1 |
| 1.63 | [5-(3-Methoxy-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.76; [M + H]$^+$ = 465.2 |
| 1.64 | [(S)-2-(7-Methylsulfanyl-1H-benzoimidazol-2-yl)-pyrrolidin-1-yl]-[2-methyl-5-(3-trifluoromethyl-phenyl)-thiazol-4-yl]-methanone. LC-MS: $t_R$ = 0.86; [M + H]$^+$ = 503.2 |
| 1.65 | [5-(3-Fluoro-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.77; [M + H]$^+$ = 453.2 |
| 1.66 | [(S)-2-(7-Methylsulfanyl-1H-benzoimidazol-2-yl)-pyrrolidin-1-yl]-(2-methyl-5-p-tolyl-thiazol-4-yl)-methanone. LC-MS: $t_R$ = 0.80; [M + H]$^+$ = 449.2 |
| 1.67 | [5-(3,4-Difluoro-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.80; [M + H]$^+$ = 471.1 |
| 1.68 | (2-Cyclopropyl-5-p-tolyl-thiazol-4-yl)-[(S)-2-(7-methylsulfanyl-1H-benzoimidazol-2-yl)-pyrrolidin-1-yl]-methanone. LC-MS: $t_R$ = 0.88; [M + H]$^+$ = 475.3 |
| 1.69 | [5-(4-Ethyl-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.86; [M + H]$^+$ = 463.2 |
| 1.70 | [2-Cyclopropyl-5-(4-fluoro-phenyl)-thiazol-4-yl]-[(S)-2-(7-methylsulfanyl-1H-benzoimidazol-2-yl)-pyrrolidin-1-yl]-methanone. LC-MS: $t_R$ = 0.84; [M + H]$^+$ = 479.2 |
| 1.71 | [5-(3,5-Difluoro-phenyl)-2-methyl-thiazol-4-yl]-[(S)-2-(7-methylsulfanyl-1H-benzoimidazol-2-yl)-pyrrolidin-1-yl]-methanone. LC-MS: $t_R$ = 0.79; [M + H]$^+$ = 471.2 |
| 1.72 | [3-(4-Methoxy-phenyl)-pyrazin-2-yl]-[(S)-2-(6-methylsulfanyl-1H-benzoimidazol-2-yl)-pyrrolidin-1-yl]-methanone. LC-MS: $t_R$ = 0.68; [M + H]$^+$ = 446.2 |
| 1.73 | [(S)-2-(7-Methylsulfanyl-1H-benzoimidazol-2-yl)-pyrrolidin-1-yl]-[3-(3-trifluoromethyl-phenyl)-pyrazin-2-yl]-methanone. LC-MS: $t_R$ = 0.80; [M + H]$^+$ = 484.2 |
| 1.74 | [3-(3-Fluoro-5-methyl-phenyl)-pyrazin-2-yl]-[(S)-2-(7-methylsulfanyl-1H-benzoimidazol-2-yl)-pyrrolidin-1-yl]-methanone. LC-MS: $t_R$ = 0.74; [M + H]$^+$ = 448.2 |
| 1.75 | (3',4'-Dimethyl-biphenyl-2-yl)-[(S)-2-(7-methylsulfanyl-1H-benzoimidazol-2-yl)-pyrrolidin-1-yl]-methanone. LC-MS: $t_R$ = 0.87; [M + H]$^+$ = 442.2 |
| 1.76 | [(S)-2-(7-Methylsulfanyl-1H-benzoimidazol-2-yl)-pyrrolidin-1-yl]-(2-[1,2,3]triazol-2-yl-phenyl)-methanone. LC-MS: $t_R$ = 0.63; [M + H]$^+$ = 405.2 |

-continued

| Example | Compound name. LC-MS data |
|---|---|
| 1.78 | [(S)-2-(7-Methylsulfanyl-1H-benzoimidazol-2-yl)-pyrrolidin-1-yl]-(4-p-tolyl-pyrimidin-5-yl)-methanone. LC-MS: $t_R$ = 0.70; $[M + H]^+$ = 430.2 |
| 1.79 | [4-(3,4-Dichloro-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.86; $[M + H]^+$ = 498.2 |
| 1.80 | [4-(4-Fluoro-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.71; $[M + H]^+$ = 448.2 |
| 1.81 | [4-(3-Chloro-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.77; $[M + H]^+$ = 464.2 |
| 1.82 | [4-(3,4-Dichloro-phenyl)-pyrimidin-5-yl]-[(S)-2-(7-methylsulfanyl-1H-benzoimidazol-2-yl)-pyrrolidin-1-yl]-methanone. LC-MS: $t_R$ = 0.74; $[M + H]^+$ = 444.3 |
| 1.83 | [4-(3,4-Dimethyl-phenyl)-pyrimidin-5-yl]-[(S)-2-(7-methylsulfanyl-1H-benzoimidazol-2-yl)-pyrrolidin-1-yl]-methanone. LC-MS: $t_R$ = 0.83; $[M + H]^+$ = 528.0 |
| 1.84 | [4-(4-Bromo-3-chloro-phenyl)-pyrimidin-5-yl]-[(S)-2-(7-methylsulfanyl-1H-benzoimidazol-2-yl)-pyrrolidin-1-yl]-methanone. LC-MS: $t_R$ = 0.77; $[M + H]^+$ = 458.2 |
| 1.85 | [4-(3,4-Dimethyl-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.68; $[M + H]^+$ = 460.2 |
| 1.86 | [4-(3-Methoxy-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.67; $[M + H]^+$ = 430.2 |
| 1.87 | (2-Methyl-4-phenyl-pyrimidin-5-yl)-[(S)-2-(7-methylsulfanyl-1H-benzoimidazol-2-yl)-pyrrolidin-1-yl]-methanone. LC-MS: $t_R$ = 0.70; $[M + H]^+$ = 430.2 |
| 1.88 | [(S)-2-(7-Methylsulfanyl-1H-benzoimidazol-2-yl)-pyrrolidin-1-yl]-(4-m-tolyl-pyrimidin-5-yl)-methanone. LC-MS: $t_R$ = 0.82; $[M + H]^+$ = 484.1 |
| 1.89 | [4-(3,5-Dichloro-phenyl)-pyrimidin-5-yl]-[(S)-2-(7-methylsulfanyl-1H-benzoimidazol-2-yl)-pyrrolidin-1-yl]-methanone. LC-MS: $t_R$ = 0.87; $[M + H]^+$ = 542.1 |
| 1.90 | [4-(4-Bromo-3-chloro-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.86; $[M + H]^+$ = 498.2 |
| 1.91 | [4-(3,5-Dichloro-phenyl)-2-methyl-pyrimidin-5-yl]-[(S)-2-(7-methylsulfanyl-1H-benzoimidazol-2-yl)-pyrrolidin-1-yl]-methanone. LC-MS: $t_R$ = 0.99; $[M + H]^+$ = 491.1 |
| 1.92 | rac-[5-(3-Chloro-phenyl)-2-methyl-thiazol-4-yl]-[2-(5,6-dichloro-1H-benzoimidazol-2-yl)-pyrrolidin-1-yl]-methanone. LC-MS: $t_R$ = 0.86; $[M + H]^+$ = 501.1 |
| 1.93 | rac-[2-(5-Bromo-1H-benzoimidazol-2-yl)-pyrrolidin-1-yl]-[5-(3-chloro-phenyl)-2-methyl-thiazol-4-yl]-methanone. LC-MS: $t_R$ = 0.94; $[M + H]^+$ = 491.1 |
| 1.94 | rac-[5-(3-Chloro-phenyl)-2-methyl-thiazol-4-yl]-[2-(5-trifluoromethyl-1H-benzoimidazol-2-yl)-pyrrolidin-1-yl]-methanone. LC-MS: $t_R$ = 0.82; $[M + H]^+$ = 451.2 |
| 1.95 | rac-[5-(3-Chloro-phenyl)-2-methyl-thiazol-4-yl]-[2-(5,6-dimethyl-1H-benzoimidazol-2-yl)-pyrrolidin-1-yl]-methanone. LC-MS: $t_R$ = 0.78; $[M + H]^+$ = 437.1 |
| 1.96 | rac-[5-(3-Chloro-phenyl)-2-methyl-thiazol-4-yl]-[2-(4-methyl-1H-benzoimidazol-2-yl)-pyrrolidin-1-yl]-methanone. LC-MS: $t_R$ = 0.84; $[M + H]^+$ = 457.1 |
| 1.97 | rac-[2-(5-Chloro-1H-benzoimidazol-2-yl)-pyrrolidin-1-yl]-[5-(3-chloro-phenyl)-2-methyl-thiazol-4-yl]-methanone. LC-MS: $t_R$ = 0.92; $[M + H]^+$ = 475.2 |
| 1.98 | rac-[2-(6-Chloro-5-fluoro-1H-benzoimidazol-2-yl)-pyrrolidin-1-yl]-[5-(3-chloro-phenyl)-2-methyl-thiazol-4-yl]-methanone. LC-MS: $t_R$ = 0.91; $[M + H]^+$ = 479.2 |
| 1.99 | rac-[2-(5-tert-Butyl-1H-benzoimidazol-2-yl)-pyrrolidin-1-yl]-[5-(3-chloro-phenyl)-2-methyl-thiazol-4-yl]-methanone. LC-MS: $t_R$ = 1.12; $[M + H]^+$ = 525.1 |
| 1.100 | rac-[5-(3-Chloro-phenyl)-2-methyl-thiazol-4-yl]-[2-(4-chloro-6-trifluoromethyl-1H-benzoimidazol-2-yl)-pyrrolidin-1-yl]-methanone. LC-MS: $t_R$ = 0.86; $[M + H]^+$ = 471.1 |
| 1.101 | rac-[2-(5-Chloro-6-methyl-1H-benzoimidazol-2-yl)-pyrrolidin-1-yl]-[5-(3-chloro-phenyl)-2-methyl-thiazol-4-yl]-methanone. LC-MS: $t_R$ = 0.83; $[M + H]^+$ = 451.2 |
| 1.102 | rac-[5-(3-Chloro-phenyl)-2-methyl-thiazol-4-yl]-[2-(4,6-dimethyl-1H-benzoimidazol-2-yl)-pyrrolidin-1-yl]-methanone. LC-MS: $t_R$ = 0.71; $[M + H]^+$ = 453.2 |
| 1.103 | rac-[5-(3-Chloro-phenyl)-2-methyl-thiazol-4-yl]-[2-(4-hydroxymethyl-1H-benzoimidazol-2-yl)-pyrrolidin-1-yl]-methanone. LC-MS: $t_R$ = 0.84; $[M + H]^+$ = 441.1 |
| 1.104 | rac-[5-(3-Chloro-phenyl)-2-methyl-thiazol-4-yl]-[2-(4-fluoro-1H-benzoimidazol-2-yl)-pyrrolidin-1-yl]-methanone. LC-MS: $t_R$ = 0.97; $[M + H]^+$ = 491.2 |
| 1.105 | rac-[5-(3-Chloro-phenyl)-2-methyl-thiazol-4-yl]-[2-(4-trifluoromethyl-1H-benzoimidazol-2-yl)-pyrrolidin-1-yl]-methanone. LC-MS: $t_R$ = 0.89; $[M + H]^+$ = 501.1 |
| 1.106 | rac-[2-(4-Bromo-1H-benzoimidazol-2-yl)-pyrrolidin-1-yl]-[5-(3-chloro-phenyl)-2-methyl-thiazol-4-yl]-methanone. LC-MS: $t_R$ = 0.89; $[M + H]^+$ = 515.2 |
| 1.107 | rac-[2-(5-Bromo-7-methyl-1H-benzoimidazol-2-yl)-pyrrolidin-1-yl]-[5-(3-chloro-phenyl)-2-methyl-thiazol-4-yl]-methanone. LC-MS: $t_R$ = 0.92; $[M + H]^+$ = 507.2 |
| 1.108 | rac-[5-(3-Chloro-phenyl)-2-methyl-thiazol-4-yl]-[2-(5-trifluoromethoxy-1H-benzoimidazol-2-yl)-pyrrolidin-1-yl]-methanone. LC-MS: $t_R$ = 0.87; $[M + H]^+$ = 471.2 |
| 1.109 | rac-[2-(5-Chloro-4-methyl-1H-benzoimidazol-2-yl)-pyrrolidin-1-yl]-[5-(3-chloro-phenyl)-2-methyl-thiazol-4-yl]-methanone. LC-MS: $t_R$ = 0.73; $[M + H]^+$ = 483.2 |
| 1.110 | rac-[5-(3-Chloro-phenyl)-2-methyl-thiazol-4-yl]-[2-(5,6-dimethoxy-1H-benzoimidazol-2-yl)-pyrrolidin-1-yl]-methanone. LC-MS: $t_R$ = 1.02; $[M + H]^+$ = 509.1 |
| 1.111 | rac-[5-(3-Chloro-phenyl)-2-methyl-thiazol-4-yl]-[2-(6-fluoro-5-trifluoromethyl-1H-benzoimidazol-2-yl)-pyrrolidin-1-yl]-methanone. LC-MS: $t_R$ = 0.93; $[M + H]^+$ = 519.1 |
| 1.112 | rac-[2-(6-Bromo-5-fluoro-1H-benzoimidazol-2-yl)-pyrrolidin-1-yl]-[5-(3-chloro-phenyl)-2-methyl-thiazol-4-yl]-methanone. LC-MS: $t_R$ = 1.08; $[M + H]^+$ = 525.3 |
| 1.113 | rac-[5-(3-Chloro-phenyl)-2-methyl-thiazol-4-yl]-[2-(6-chloro-5-trifluoromethyl-1H-benzoimidazol-2-yl)-pyrrolidin-1-yl]-methanone. LC-MS: $t_R$ = 0.99; $[M + H]^+$ = 519.1 |
| 1.114 | rac-[2-(4-Bromo-6-fluoro-1H-benzoimidazol-2-yl)-pyrrolidin-1-yl]-[5-(3-chloro-phenyl)-2-methyl-thiazol-4-yl]-methanone. LC-MS: $t_R$ = 0.82; $[M + H]^+$ = 451.2 |
| 1.115 | rac-[5-(3-Chloro-phenyl)-2-methyl-thiazol-4-yl]-[2-(4,5-dimethyl-1H-benzoimidazol-2-yl)-pyrrolidin-1-yl]-methanone. LC-MS: $t_R$ = 0.87; $[M + H]^+$ = 465.2 |
| 1.116 | rac-[5-(3-Chloro-phenyl)-2-methyl-thiazol-4-yl]-[2-(4-isopropyl-1H-benzoimidazol-2-yl)-pyrrolidin-1-yl]-methanone. LC-MS: $t_R$ = 0.75; $[M + H]^+$ = 481.2 |
| 1.117 | rac-[5-(3-Chloro-phenyl)-2-methyl-thiazol-4-yl]-[2-(7,8-dihydro-3H-6,9-dioxa-1,3-diaza-cyclopenta[α]naphthalen-2-yl)-pyrrolidin-1-yl]-methanone. LC-MS: $t_R$ = 1.12; $[M + H]^+$ = 525.1 |
| 1.118 | rac-[2-(4,6-Bis-trifluoromethyl-1H-benzoimidazol-2-yl)-pyrrolidin-1-yl]-(2-methyl-5-phenyl-thiazol-4-yl)-methanone. LC-MS: $t_R$ = 0.92; $[M + H]^+$ = 457.1 |
| 1.119 | rac-[2-(5,6-Dichloro-1H-benzoimidazol-2-yl)-pyrrolidin-1-yl]-(2-methyl-5-phenyl-thiazol-4-yl)-methanone. LC-MS: $t_R$ = 0.79; $[M + H]^+$ = 467.1 |
| 1.120 | rac-[2-(5-Bromo-1H-benzoimidazol-2-yl)-pyrrolidin-1-yl]-(2-methyl-5-phenyl-thiazol-4-yl)-methanone. LC-MS: $t_R$ = 0.87; $[M + H]^+$ = 457.2 |
| 1.121 | rac-(2-Methyl-5-phenyl-thiazol-4-yl)-[2-(5-trifluoromethyl-1H-benzoimidazol-2-yl)-pyrrolidin-1-yl]-methanone. LC-MS: $t_R$ = 0.76; $[M + H]^+$ = 417.2 |
| 1.122 | rac-[2-(5,6-Dimethyl-1H-benzoimidazol-2-yl)-pyrrolidin-1-yl]-(2-methyl-5-phenyl-thiazol-4-yl)-methanone. LC-MS: $t_R$ = 0.71; $[M + H]^+$ = 403.2 |
| 1.123 | rac-[2-(4-Methyl-1H-benzoimidazol-2-yl)-pyrrolidin-1-yl]-(2-methyl-5-phenyl-thiazol-4-yl)-methanone. LC-MS: $t_R$ = 0.85; $[M + H]^+$ = 445.3 |
| 1.124 | rac-[2-(5-tert-Butyl-1H-benzoimidazol-2-yl)-pyrrolidin-1-yl]-(2-methyl-5-phenyl-thiazol-4-yl)-methanone. LC-MS: $t_R$ = 1.06; $[M + H]^+$ = 491.1 |
| 1.125 | rac-[2-(4-Chloro-6-trifluoromethyl-1H-benzoimidazol-2-yl)-pyrrolidin-1-yl]-(2-methyl-5-phenyl-thiazol-4-yl)-methanone. LC-MS: $t_R$ = 0.80; $[M + H]^+$ = 437.2 |
| 1.126 | rac-[2-(5-Chloro-6-methyl-1H-benzoimidazol-2-yl)-pyrrolidin-1-yl]-(2-methyl-5-phenyl-thiazol-4-yl)-methanone. LC-MS: $t_R$ = 0.76; $[M + H]^+$ = 417.2 |

| Example | Compound name. LC-MS data |
|---|---|
| 1.127 | rac-[2-(4,6-Dimethyl-1H-benzoimidazol-2-yl)-pyrrolidin-1-yl]-(2-methyl-5-phenyl-thiazol-4-yl)-methanone. LC-MS: $t_R$ = 0.63; [M + H]$^+$ = 419.1 |
| 1.128 | rac-[2-(4-Hydroxymethyl-1H-benzoimidazol-2-yl)-pyrrolidin-1-yl]-(2-methyl-5-phenyl-thiazol-4-yl)-methanone. LC-MS: $t_R$ = 0.90; [M + H]$^+$ = 457.2 |
| 1.129 | rac-(2-Methyl-5-phenyl-thiazol-4-yl)-[2-(4-trifluoromethyl-1H-benzoimidazol-2-yl)-pyrrolidin-1-yl]-methanone. LC-MS: $t_R$ = 0.81; [M + H]$^+$ = 467.1 |
| 1.130 | rac-[2-(4-Bromo-1H-benzoimidazol-2-yl)-pyrrolidin-1-yl]-(2-methyl-5-phenyl-thiazol-4-yl)-methanone. LC-MS: $t_R$ = 0.82; [M + H]$^+$ = 481.1 |
| 1.131 | rac-[2-(5-Bromo-7-methyl-1H-benzoimidazol-2-yl)-pyrrolidin-1-yl]-(2-methyl-5-phenyl-thiazol-4-yl)-methanone. LC-MS: $t_R$ = 0.86; [M + H]$^+$ = 473.2 |
| 1.132 | rac-(2-Methyl-5-phenyl-thiazol-4-yl)-[2-(5-trifluoromethoxy-1H-benzoimidazol-2-yl)-pyrrolidin-1-yl]-methanone. LC-MS: $t_R$ = 0.81; [M + H]$^+$ = 437.2 |
| 1.133 | rac-[2-(5-Chloro-4-methyl-1H-benzoimidazol-2-yl)-pyrrolidin-1-yl]-(2-methyl-5-phenyl-thiazol-4-yl)-methanone. LC-MS: $t_R$ = 0.67; [M + H]$^+$ = 449.2 |
| 1.134 | rac-[2-(5,6-Dimethoxy-1H-benzoimidazol-2-yl)-pyrrolidin-1-yl]-(2-methyl-5-phenyl-thiazol-4-yl)-methanone. LC-MS: $t_R$ = 0.96; [M + H]$^+$ = 475.2 |
| 1.135 | rac-[2-(6-Fluoro-5-trifluoromethyl-1H-benzoimidazol-2-yl)-pyrrolidin-1-yl]-(2-methyl-5-phenyl-thiazol-4-yl)-methanone. LC-MS: $t_R$ = 0.86; [M + H]$^+$ = 485.1 |
| 1.136 | rac-[2-(6-Bromo-5-fluoro-1H-benzoimidazol-2-yl)-pyrrolidin-1-yl]-(2-methyl-5-phenyl-thiazol-4-yl)-methanone. LC-MS: $t_R$ = 1.01; [M + H]$^+$ = 491.2 |
| 1.137 | rac-[2-(6-Chloro-5-trifluoromethyl-1H-benzoimidazol-2-yl)-pyrrolidin-1-yl]-(2-methyl-5-phenyl-thiazol-4-yl)-methanone. LC-MS: $t_R$ = 0.92; [M + H]$^+$ = 485.1 |
| 1.138 | rac-[2-(4-Bromo-6-fluoro-1H-benzoimidazol-2-yl)-pyrrolidin-1-yl]-(2-methyl-5-phenyl-thiazol-4-yl)-methanone. LC-MS: $t_R$ = 0.75; [M + H]$^+$ = 417.2 |
| 1.139 | rac-[2-(4,5-Dimethyl-1H-benzoimidazol-2-yl)-pyrrolidin-1-yl]-(2-methyl-5-phenyl-thiazol-4-yl)-methanone. LC-MS: $t_R$ = 0.69; [M + H]$^+$ = 447.2 |
| 1.140 | rac-[2-(7,8-Dihydro-3H-6,9-dioxa-1,3-diaza-cyclopenta[α]naphthalen-2-yl)-pyrrolidin-1-yl]-(2-methyl-5-phenyl-thiazol-4-yl)-methanone. LC-MS: $t_R$ = 0.63; [M + H]$^+$ = 403.2 |
| 1.141 | rac-[2-(5-Methoxy-1H-benzoimidazol-2-yl)-pyrrolidin-1-yl]-(5-methyl-2-[1,2,3]triazol-2-yl-phenyl)-methanone. LC-MS: $t_R$ = 0.76; [M + H]$^+$ = 417.2 |
| 1.142 | [(S)-2-(4,6-Dimethyl-1H-benzoimidazol-2-yl)-pyrrolidin-1-yl]-(2-methyl-5-phenyl-thiazol-4-yl)-methanone. LC-MS: $t_R$ = 0.80; [M + H]$^+$ = 437.2 |
| 1.143 | [(S)-2-(5-Chloro-6-methyl-1H-benzoimidazol-2-yl)-pyrrolidin-1-yl]-(2-methyl-5-phenyl-thiazol-4-yl)-methanone. LC-MS: $t_R$ = 0.82; [M + H]$^+$ = 481.1 |
| 1.144 | [(S)-2-(6-Bromo-4-methyl-1H-benzoimidazol-2-yl)-pyrrolidin-1-yl]-(2-methyl-5-phenyl-thiazol-4-yl)-methanone. LC-MS: $t_R$ = 0.81; [M + H]$^+$ = 437.1 |
| 1.145 | [(S)-2-(5-Chloro-4-methyl-1H-benzoimidazol-2-yl)-pyrrolidin-1-yl]-(2-methyl-5-phenyl-thiazol-4-yl)-methanone. LC-MS: $t_R$ = 1.02; [M + H]$^+$ = 491.1 |
| 1.146 | [(S)-2-(5-Chloro-6-trifluoromethyl-1H-benzoimidazol-2-yl)-pyrrolidin-1-yl]-(2-methyl-5-phenyl-thiazol-4-yl)-methanone. LC-MS: $t_R$ = 0.67; [M + H]$^+$ = 423.2 |
| 1.147 | (5-Fluoro-2-[1,2,3]triazol-2-yl-phenyl)-[(S)-2-(6-methylsulfanyl-1H-benzoimidazol-2-yl)-pyrrolidin-1-yl]-methanone. LC-MS: $t_R$ = 0.65; [M + H]$^+$ = 423.2 |
| 1.148 | (2-Fluoro-6-[1,2,3]triazol-2-yl-phenyl)-[(S)-2-(6-methylsulfanyl-1H-benzoimidazol-2-yl)-pyrrolidin-1-yl]-methanone. LC-MS: $t_R$ = 0.72; [M + H]$^+$ = 439.2 |
| 1.149 | (5-Chloro-2-[1,2,3]triazol-2-yl-phenyl)-[(S)-2-(6-methylsulfanyl-1H-benzoimidazol-2-yl)-pyrrolidin-1-yl]-methanone. LC-MS: $t_R$ = 0.66; [M + H]$^+$ = 435.2 |
| 1.150 | (5-Methoxy-2-[1,2,3]triazol-2-yl-phenyl)-[(S)-2-(6-methylsulfanyl-1H-benzoimidazol-2-yl)-pyrrolidin-1-yl]-methanone. LC-MS: $t_R$ = 0.77; [M + H]$^+$ = 473.2 |
| 1.151 | [(S)-2-(6-Methylsulfanyl-1H-benzoimidazol-2-yl)-pyrrolidin-1-yl]-(2-[1,2,3]triazol-2-yl-5-trifluoromethyl-phenyl)-methanone. LC-MS: $t_R$ = 0.65; [M + H]$^+$ = 430.2 |
| 1.152 | 3-[(S)-2-(6-Methylsulfanyl-1H-benzoimidazol-2-yl)-pyrrolidine-1-carbonyl]-4-[1,2,3]triazol-2-yl-benzonitrile. LC-MS: $t_R$ = 0.69; [M + H]$^+$ = 419.2 |
| 1.153 | [(S)-2-(6-Methylsulfanyl-1H-benzoimidazol-2-yl)-pyrrolidin-1-yl]-(4-methyl-2-[1,2,3]triazol-2-yl-phenyl)-methanone. LC-MS: $t_R$ = 0.69; [M + H]$^+$ = 419.2 |
| 1.154 | [(S)-2-(6-Methylsulfanyl-1H-benzoimidazol-2-yl)-pyrrolidin-1-yl]-(2-methyl-6-[1,2,3]triazol-2-yl-phenyl)-methanone. LC-MS: $t_R$ = 0.63; [M + H]$^+$ = 465.2 |
| 1.155 | (4,5-Dimethoxy-2-[1,2,3]triazol-2-yl-phenyl)-[(S)-2-(6-methylsulfanyl-1H-benzoimidazol-2-yl)-pyrrolidin-1-yl]-methanone. LC-MS: $t_R$ = 0.61; [M + H]$^+$ = 407.2 |
| 1.156 | (5-Fluoro-2-[1,2,3]triazol-2-yl-phenyl)-[(S)-2-(6-methoxy-1H-benzoimidazol-2-yl)-pyrrolidin-1-yl]-methanone. LC-MS: $t_R$ = 0.66; [M + H]$^+$ = 423.1 |
| 1.157 | (5-Chloro-2-[1,2,3]triazol-2-yl-phenyl)-[(S)-2-(6-methoxy-1H-benzoimidazol-2-yl)-pyrrolidin-1-yl]-methanone. LC-MS: $t_R$ = 0.61; [M + H]$^+$ = 419.2 |
| 1.158 | [(S)-2-(6-Methoxy-1H-benzoimidazol-2-yl)-pyrrolidin-1-yl]-(5-methoxy-2-[1,2,3]triazol-2-yl-phenyl)-methanone. LC-MS: $t_R$ = 0.59; [M + H]$^+$ = 414.2 |
| 1.159 | 3-[(S)-2-(6-Methoxy-1H-benzoimidazol-2-yl)-pyrrolidine-1-carbonyl]-4-[1,2,3]triazol-2-yl-benzonitrile. LC-MS: $t_R$ = 0.64; [M + H]$^+$ = 403.2 |
| 1.160 | [(S)-2-(6-Methoxy-1H-benzoimidazol-2-yl)-pyrrolidin-1-yl]-(4-methyl-2-[1,2,3]triazol-2-yl-phenyl)-methanone. LC-MS: $t_R$ = 0.63; [M + H]$^+$ = 403.2 |
| 1.161 | [(S)-2-(6-Methoxy-1H-benzoimidazol-2-yl)-pyrrolidin-1-yl]-(2-methyl-6-[1,2,3]triazol-2-yl-phenyl)-methanone. LC-MS: $t_R$ = 0.58; [M + H]$^+$ = 449.2 |
| 1.162 | (4,5-Dimethoxy-2-[1,2,3]triazol-2-yl-phenyl)-[(S)-2-(6-methoxy-1H-benzoimidazol-2-yl)-pyrrolidin-1-yl]-methanone. LC-MS: $t_R$ = 0.67; [M + H]$^+$ = 423.2 |
| 1.163 | (5-Fluoro-2-[1,2,3]triazol-2-yl-phenyl)-[(S)-2-(7-methylsulfanyl-1H-benzoimidazol-2-yl)-pyrrolidin-1-yl]-methanone. LC-MS: $t_R$ = 0.66; [M + H]$^+$ = 423.2 |
| 1.164 | (2-Fluoro-6-[1,2,3]triazol-2-yl-phenyl)-[(S)-2-(7-methylsulfanyl-1H-benzoimidazol-2-yl)-pyrrolidin-1-yl]-methanone. LC-MS: $t_R$ = 0.73; [M + H]$^+$ = 439.1 |
| 1.165 | (5-Chloro-2-[1,2,3]triazol-2-yl-phenyl)-[(S)-2-(7-methylsulfanyl-1H-benzoimidazol-2-yl)-pyrrolidin-1-yl]-methanone. LC-MS: $t_R$ = 0.66; [M + H]$^+$ = 435.2 |
| 1.166 | (5-Methoxy-2-[1,2,3]triazol-2-yl-phenyl)-[(S)-2-(7-methylsulfanyl-1H-benzoimidazol-2-yl)-pyrrolidin-1-yl]-methanone. LC-MS: $t_R$ = 0.66; [M + H]$^+$ = 430.1 |
| 1.167 | 3-[(S)-2-(7-Methylsulfanyl-1H-benzoimidazol-2-yl)-pyrrolidine-1-carbonyl]-4-[1,2,3]triazol-2-yl-benzonitrile. LC-MS: $t_R$ = 0.68; [M + H]$^+$ = 453.2 |
| 1.168 | (2-Fluoro-3-methoxy-6-[1,2,3]triazol-2-yl-phenyl)-[(S)-2-(7-methylsulfanyl-1H-benzoimidazol-2-yl)-pyrrolidin-1-yl]-methanone. LC-MS: $t_R$ = 0.69; [M + H]$^+$ = 419.2 |
| 1.169 | [(S)-2-(7-Methylsulfanyl-1H-benzoimidazol-2-yl)-pyrrolidin-1-yl]-(4-methyl-2-[1,2,3]triazol-2-yl-phenyl)-methanone. LC-MS: $t_R$ = 0.70; [M + H]$^+$ = 419.3 |
| 1.170 | [(S)-2-(7-Methylsulfanyl-1H-benzoimidazol-2-yl)-pyrrolidin-1-yl]-(2-methyl-6-[1,2,3]triazol-2-yl-phenyl)-methanone. LC-MS: $t_R$ = 0.63; [M + H]$^+$ = 402.2 |
| 1.171 | [(S)-2-(5-Methoxy-1H-benzoimidazol-2-yl)-pyrrolidin-1-yl]-(5-methyl-2-pyrazol-1-yl-phenyl)-methanone. LC-MS: $t_R$ = 0.65; [M + H]$^+$ = 421.2 |

| Example | Compound name. LC-MS data |
|---|---|
| 1.172 | (2-Fluoro-3-methyl-6-[1,2,3]triazol-2-yl-phenyl)-[(S)-2-(5-methoxy-1H-benzoimidazol-2-yl)-pyrrolidin-1-yl]-methanone. LC-MS: $t_R$ = 0.59; [M + H]$^+$ = 404.2 |
| 1.173 | [(S)-2-(5-Methoxy-1H-benzoimidazol-2-yl)-pyrrolidin-1-yl]-(6-methyl-3-[1,2,3]triazol-2-yl-pyridin-2-yl)-methanone. LC-MS: $t_R$ = 0.71; [M + H]$^+$ = 437.2 |
| 1.174 | (2-Fluoro-3-methyl-6-[1,2,3]triazol-2-yl-phenyl)-[(S)-2-(4-methylsulfanyl-1H-benzoimidazol-2-yl)-pyrrolidin-1-yl]-methanone. LC-MS: $t_R$ = 0.64; [M + H]$^+$ = 420.2 |
| 1.175 | [(S)-2-(4-Methylsulfanyl-1H-benzoimidazol-2-yl)-pyrrolidin-1-yl]-(6-methyl-3-[1,2,3]triazol-2-yl-pyridin-2-yl)-methanone. LC-MS: $t_R$ = 0.64; [M + H]$^+$ = 404.2 |
| 1.176 | [(S)-2-(5-Methylsulfanyl-1H-benzoimidazol-2-yl)-pyrrolidin-1-yl]-(2-pyrazol-1-yl-phenyl)-methanone. LC-MS: $t_R$ = 0.69; [M + H]$^+$ = 418.2 |
| 1.177 | (5-Methyl-2-pyrazol-1-yl-phenyl)-[(S)-2-(5-methylsulfanyl-1H-benzoimidazol-2-yl)-pyrrolidin-1-yl]-methanone. LC-MS: $t_R$ = 0.64; [M + H]$^+$ = 419.2 |
| 1.178 | (6-Methyl-3-pyrazol-1-yl-pyridin-2-yl)-[(S)-2-(5-methylsulfanyl-1H-benzoimidazol-2-yl)-pyrrolidin-1-yl]-methanone. LC-MS: $t_R$ = 0.71; [M + H]$^+$ = 437.2 |
| 1.179 | (2-Fluoro-3-methyl-6-[1,2,3]triazol-2-yl-phenyl)-[(S)-2-(5-methylsulfanyl-1H-benzoimidazol-2-yl)-pyrrolidin-1-yl]-methanone. LC-MS: $t_R$ = 0.65; [M + H]$^+$ = 420.2 |
| 1.180 | [(S)-2-(5-Methylsulfanyl-1H-benzoimidazol-2-yl)-pyrrolidin-1-yl]-(6-methyl-3-[1,2,3]triazol-2-yl-pyridin-2-yl)-methanone. LC-MS: $t_R$ = 0.72; [M + H]$^+$ = 421.2 |
| 2.1 | [(2S,4S)-2-(5-Chloro-4-methyl-1H-benzoimidazol-2-yl)-4-fluoro-pyrrolidin-1-yl]-(5-methyl-2-[1,2,3]triazol-2-yl-phenyl)-methanone. LC-MS: $t_R$ = 0.75; [M + H]$^+$ = 439.2 |
| 2.2 | [(2S,4S)-4-Fluoro-2-(4-methyl-1H-benzoimidazol-2-yl)-pyrrolidin-1-yl]-(2-methyl-5-phenyl-thiazol-4-yl)-methanone. LC-MS: $t_R$ = 0.72; [M + H]$^+$ = 421.2 |
| 2.3 | [(2S,4R)-4-Fluoro-2-(4-methyl-1H-benzoimidazol-2-yl)-pyrrolidin-1-yl]-(2-methyl-5-phenyl-thiazol-4-yl)-methanone. LC-MS: $t_R$ = 0.73; [M + H]$^+$ = 421.2 |
| 2.4 | [(S)-4,4-Difluoro-2-(4-methyl-1H-benzoimidazol-2-yl)-pyrrolidin-1-yl]-(2-methyl-5-phenyl-thiazol-4-yl)-methanone. LC-MS: $t_R$ = 0.78; [M + H]$^+$ = 439.2 |
| 2.5 | [(2S,4R)-2-(5-Chloro-4-methyl-1H-benzoimidazol-2-yl)-4-fluoro-pyrrolidin-1-yl]-(5-methyl-2-[1,2,3]triazol-2-yl-phenyl)-methanone. LC-MS: $t_R$ = 0.76; [M + H]$^+$ = 439.2 |
| 2.6 | [(S)-2-(5-Chloro-4-methyl-1H-benzoimidazol-2-yl)-4,4-difluoro-pyrrolidin-1-yl]-(5-methyl-2-[1,2,3]triazol-2-yl-phenyl)-methanone. LC-MS: $t_R$ = 0.88; [M + H]$^+$ = 457.2 |
| 2.7 | [(2S,4S)-2-(5-Chloro-4-methyl-1H-benzoimidazol-2-yl)-4-fluoro-pyrrolidin-1-yl]-(2-methyl-5-phenyl-thiazol-4-yl)-methanone. LC-MS: $t_R$ = 0.81; [M + H]$^+$ = 455.2 |
| 2.8 | [(S)-2-(5-Chloro-4-methyl-1H-benzoimidazol-2-yl)-4,4-difluoro-pyrrolidin-1-yl]-(2-methyl-5-phenyl-thiazol-4-yl)-methanone. LC-MS: $t_R$ = 0.94; [M + H]$^+$ = 473.2 |
| 2.9 | [5-(3-Chloro-phenyl)-2-methyl-thiazol-4-yl]-[(2S,4R)-4-fluoro-2-(4-methyl-1H-benzoimidazol-2-yl)-pyrrolidin-1-yl]-methanone. LC-MS: $t_R$ = 0.80; [M + H]$^+$ = 455.2 |
| 2.10 | [(2S,4R)-2-(5-Chloro-4-methyl-1H-benzoimidazol-2-yl)-4-fluoro-pyrrolidin-1-yl]-[5-(3-chloro-phenyl)-2-methyl-thiazol-4-yl]-methanone. LC-MS: $t_R$ = 0.91; [M + H]$^+$ = 489.1 |
| 2.11 | [(2S,4R)-4-Fluoro-2-(4-methyl-1H-benzoimidazol-2-yl)-pyrrolidin-1-yl]-(5-methyl-2-[1,2,3]triazol-2-yl-phenyl)-methanone. LC-MS: $t_R$ = 0.63; [M + H]$^+$ = 405.2 |
| 3.1 | [(2S,4S)-2-(5-Chloro-4-methyl-1H-benzoimidazol-2-yl)-4-methoxy-pyrrolidin-1-yl]-(5-methyl-2-[1,2,3]triazol-2-yl-phenyl)-methanone. LC-MS: $t_R$ = 0.75; [M + H]$^+$ = 451.2 |
| 3.2 | [(2S,4R)-2-(5-Chloro-4-methyl-1H-benzoimidazol-2-yl)-4-methoxy-pyrrolidin-1-yl]-(5-methyl-2-[1,2,3]triazol-2-yl-phenyl)-methanone. LC-MS: $t_R$ = 0.74; [M + H]$^+$ = 451.3 |
| 3.3 | [(2S,4S)-4-Methoxy-2-(4-methyl-1H-benzoimidazol-2-yl)-pyrrolidin-1-yl]-(2-methyl-5-phenyl-thiazol-4-yl)-methanone. LC-MS: $t_R$ = 0.73; [M + H]$^+$ = 433.2 |
| 3.4 | [(2S,4R)-4-Methoxy-2-(4-methyl-1H-benzoimidazol-2-yl)-pyrrolidin-1-yl]-(2-methyl-5-phenyl-thiazol-4-yl)-methanone. LC-MS: $t_R$ = 0.73; [M + H]$^+$ = 433.2 |
| 3.5 | [(2S,4S)-2-(5-Chloro-4-methyl-1H-benzoimidazol-2-yl)-4-methoxy-pyrrolidin-1-yl]-(2-methyl-5-phenyl-thiazol-4-yl)-methanone. LC-MS: $t_R$ = 0.82; [M + H]$^+$ = 467.2 |
| 3.6 | [(2S,4R)-2-(5-Chloro-4-methyl-1H-benzoimidazol-2-yl)-4-methoxy-pyrrolidin-1-yl]-(2-methyl-5-phenyl-thiazol-4-yl)-methanone. LC-MS: $t_R$ = 0.82; [M + H]$^+$ = 467.2 |
| 3.7 | [5-(3-Chloro-phenyl)-2-methyl-thiazol-4-yl]-[(2S,4R)-4-methoxy-2-(4-methyl-1H-benzoimidazol-2-yl)-pyrrolidin-1-yl]-methanone. LC-MS: $t_R$ = 0.80; [M + H]$^+$ = 467.2 |
| 3.8 | [(2S,4S)-2-(5-Chloro-4-methyl-1H-benzoimidazol-2-yl)-4-methoxy-pyrrolidin-1-yl]-[5-(3-chloro-phenyl)-2-methyl-thiazol-4-yl]-methanone. LC-MS: $t_R$ = 0.88; [M + H]$^+$ = 501.2 |
| 3.9 | [(2S,4R)-2-(5-Chloro-4-methyl-1H-benzoimidazol-2-yl)-4-methoxy-pyrrolidin-1-yl]-[5-(3-chloro-phenyl)-2-methyl-thiazol-4-yl]-methanone. LC-MS: $t_R$ = 0.89; [M + H]$^+$ = 501.1 |
| 3.10 | [(2S,4R)-2-(6-Chloro-7-methyl-1H-benzoimidazol-2-yl)-4-methoxy-pyrrolidin-1-yl]-(5-chloro-2-[1,2,3]triazol-2-yl-phenyl)-methanone. LC-MS: $t_R$ = 0.79; [M + H]$^+$ = 471.2 |
| 3.11 | [(2S,4R)-2-(6-Chloro-7-methyl-1H-benzoimidazol-2-yl)-4-methoxy-pyrrolidin-1-yl]-(2-fluoro-3-methoxy-6-[1,2,3]triazol-2-yl-phenyl)-methanone. LC-MS: $t_R$ = 0.74; [M + H]$^+$ = 485.2 |
| 3.12 | [(2S,4R)-2-(6-Chloro-7-methyl-1H-benzoimidazol-2-yl)-4-methoxy-pyrrolidin-1-yl]-(5-methoxy-2-[1,2,3]triazol-2-yl-phenyl)-methanone. LC-MS: $t_R$ = 0.72; [M + H]$^+$ = 467.2 |
| 3.13 | [(2S,4R)-2-(6-Chloro-7-methyl-1H-benzoimidazol-2-yl)-4-methoxy-pyrrolidin-1-yl]-(2-fluoro-3-methyl-6-[1,2,3]triazol-2-yl-phenyl)-methanone. LC-MS: $t_R$ = 0.72; [M + H]$^+$ = 469.3 |
| 3.14 | [(2S,4R)-2-(6-Chloro-7-methyl-1H-benzoimidazol-2-yl)-4-methoxy-pyrrolidin-1-yl]-(2-methyl-6-[1,2,3]triazol-2-yl-phenyl)-methanone. LC-MS: $t_R$ = 0.75; [M + H]$^+$ = 451.2 |
| 3.15 | [(2S,4R)-2-(6-Chloro-7-methyl-1H-benzoimidazol-2-yl)-4-methoxy-pyrrolidin-1-yl]-(4-methyl-2-[1,2,3]triazol-2-yl-phenyl)-methanone. LC-MS: $t_R$ = 07.5; [M + H]$^+$ = 451.2 |
| 3.16 | [(2S,4R)-2-(6-Chloro-7-methyl-1H-benzoimidazol-2-yl)-4-methoxy-pyrrolidin-1-yl]-(4,5-dimethyl-2-[1,2,3]triazol-2-yl-phenyl)-methanone. LC-MS: $t_R$ = 0.77; [M + H]$^+$ = 465.2 |
| 3.17 | [(2S,4R)-2-(6-Chloro-7-methyl-1H-benzoimidazol-2-yl)-4-methoxy-pyrrolidin-1-yl]-(2-[1,2,3]triazol-2-yl-5-trifluoromethyl-phenyl)-methanone. LC-MS: $t_R$ = 0.84; [M + H]$^+$ = 505.2 |
| 3.18 | [(2S,4R)-2-(6-Chloro-7-methyl-1H-benzoimidazol-2-yl)-4-methoxy-pyrrolidin-1-yl]-(5-fluoro-2-[1,2,3]triazol-2-yl-phenyl)-methanone. LC-MS: $t_R$ = 0.74; [M + H]$^+$ = 455.2 |
| 3.19 | (5-Chloro-2-[1,2,3]triazol-2-yl-phenyl)-[(2S,4R)-4-methoxy-2-(6-methoxy-1H-benzoimidazol-2-yl)-pyrrolidin-1-yl]-methanone. LC-MS: $t_R$ = 0.66; [M + H]$^+$ = 453.2 |
| 3.20 | [(2S,4R)-4-Methoxy-2-(6-methoxy-1H-benzoimidazol-2-yl)-pyrrolidin-1-yl]-(5-methoxy-2-[1,2,3]triazol-2-yl-phenyl)-methanone. LC-MS: $t_R$ = 0.60; [M + H]$^+$ = 449.2 |
| 3.21 | [(2S,4R)-4-Methoxy-2-(6-methoxy-1H-benzoimidazol-2-yl)-pyrrolidin-1-yl]-(4-methyl-2-[1,2,3]triazol-2-yl-phenyl)-methanone. LC-MS: $t_R$ = 0.63; [M + H]$^+$ = 433.3 |
| 3.22 | (4,5-Dimethyl-2-[1,2,3]triazol-2-yl-phenyl)-[(2S,4R)-4-methoxy-2-(6-methoxy-1H-benzoimidazol-2-yl)-pyrrolidin-1-yl]-methanone. LC-MS: $t_R$ = 0.67; [M + H]$^+$ = 447.2 |
| 3.23 | (5-Fluoro-2-[1,2,3]triazol-2-yl-phenyl)-[(2S,4R)-4-methoxy-2-(6-methoxy-1H-benzoimidazol-2-yl)-pyrrolidin-1-yl]-methanone. LC-MS: $t_R$ = 0.61; [M + H]$^+$ = 437.2 |
| 3.24 | [(2RS)-(4R)-2-(5-Chloro-4-methyl-1H-benzoimidazol-2-yl)-4-methoxy-2-methyl-pyrrolidin-1-yl]-(2-methyl-5-phenyl-thiazol-4-yl)-methanone. LC-MS: $t_R$ = 0.84; [M + H]$^+$ = 481.2 |
| 3.25 | [(2RS)-(4R)-2-(5-Chloro-4-methyl-1H-benzoimidazol-2-yl)-4-methoxy-2-methyl-pyrrolidin-1-yl]-(5-methyl-2-[1,2,3]triazol-2-yl-phenyl)-methanone. LC-MS: $t_R$ = 0.79; [M + H]$^+$ = 465.2 |
| 3.26 | [(2RS)-(4R)-4-Methoxy-2-methyl-2-(4-methyl-1H-benzoimidazol-2-yl)-pyrrolidin-1-yl]-(5-methyl-2-[1,2,3]triazol-2-yl-phenyl)-methanone. LC-MS: $t_R$ = 0.72; [M + H]$^+$ = 431.2 |
| 3.27 | [(2RS)-(4R)-2-(5-Chloro-4-methyl-1H-benzoimidazol-2-yl)-4-methoxy-2-methyl-pyrrolidin-1-yl]-[5-(3-chloro-phenyl)-2-methyl-thiazol-4-yl]-methanone. LC-MS: $t_R$ = 0.90; [M + H]$^+$ = 515.2 |

| Example | Compound name. LC-MS data |
| --- | --- |
| 3.28 | [5-(3-Chloro-phenyl)-2-methyl-thiazol-4-yl]-[(2RS)-(4R)-4-methoxy-2-methyl-2-(4-methyl-1H-benzoimidazol-2-yl)-pyrrolidin-1-yl]-methanone. LC-MS: $t_R$ = 0.82; [M + H]$^+$ = 481.2 |
| 3.29 | [(2RS)-(4R)-4-Methoxy-2-methyl-2-(4-methyl-1H-benzoimidazol-2-yl)-pyrrolidin-1-yl]-(2-methyl-5-phenyl-thiazol-4-yl)-methanone. LC-MS: $t_R$ = 0.76; [M + H]$^+$ = 447.2 |
| 3.30 | [(2S,4R)-2-(5-Chloro-4-methyl-1H-benzoimidazol-2-yl)-4-methoxy-2-methyl-pyrrolidin-1-yl]-(5-methyl-2-[1,2,3]triazol-2-yl-phenyl)-methanone. LC-MS: $t_R$ = 0.82; [M + H]$^+$ = 465.3 |
| 3.31 | [(2S,4R)-2-(5-Chloro-4-methyl-1H-benzoimidazol-2-yl)-4-methoxy-2-methyl-pyrrolidin-1-yl]-[5-(3-chloro-phenyl)-2-methyl-thiazol-4-yl]-methanone. LC-MS: $t_R$ = 0.95; [M + H]$^+$ = 515.2 |
| 3.32 | [(2S,4R)-2-(6-Chloro-7-methyl-1H-benzoimidazol-2-yl)-4-methoxy-pyrrolidin-1-yl]-(2-methyl-5-m-tolyl-thiazol-4-yl)-methanone. LC-MS: $t_R$ = 0.90; [M + H]$^+$ = 481.2 |
| 3.33 | [(2S,4R)-2-(6-Chloro-7-methyl-1H-benzoimidazol-2-yl)-4-methoxy-pyrrolidin-1-yl]-[2-dimethylamino-5-(3,4-dimethyl-phenyl)-thiazol-4-yl]-methanone. LC-MS: $t_R$ = 0.97; [M + H]$^+$ = 524.3 |
| 3.34 | [(2S,4R)-2-(6-Chloro-7-methyl-1H-benzoimidazol-2-yl)-4-methoxy-pyrrolidin-1-yl]-[5-(3,4-dimethyl-phenyl)-2-methyl-thiazol-4-yl]-methanone. LC-MS: $t_R$ = 0.95; [M + H]$^+$ = 495.3 |
| 3.35 | [(2S,4R)-2-(6-Chloro-7-methyl-1H-benzoimidazol-2-yl)-4-methoxy-pyrrolidin-1-yl]-[5-(4-chloro-phenyl)-2-methyl-thiazol-4-yl]-methanone. LC-MS: $t_R$ = 0.94; [M + H]$^+$ = 501.2 |
| 3.36 | [(2S,4R)-2-(6-Chloro-7-methyl-1H-benzoimidazol-2-yl)-4-methoxy-pyrrolidin-1-yl]-(2-methyl-5-p-tolyl-thiazol-4-yl)-methanone. LC-MS: $t_R$ = 0.91; [M + H]$^+$ = 481.2 |
| 3.37 | [(2S,4R)-2-(6-Chloro-7-methyl-1H-benzoimidazol-2-yl)-4-methoxy-pyrrolidin-1-yl]-[5-(4-methoxy-phenyl)-2-methyl-thiazol-4-yl]-methanone. LC-MS: $t_R$ = 0.86; [M + H]$^+$ = 497.2 |
| 3.38 | [(2S,4R)-2-(6-Chloro-7-methyl-1H-benzoimidazol-2-yl)-4-methoxy-pyrrolidin-1-yl]-(3',4'-dimethyl-biphenyl-2-yl)-methanone. LC-MS: $t_R$ = 0.97; [M + H]$^+$ = 474.3 |
| 3.39 | Biphenyl-2-yl-[(2S,4R)-2-(6-chloro-7-methyl-1H-benzoimidazol-2-yl)-4-methoxy-pyrrolidin-1-yl]-methanone. LC-MS: $t_R$ = 0.87; [M + H]$^+$ = 446.3 |
| 3.40 | [(2S,4R)-2-(6-Chloro-7-methyl-1H-benzoimidazol-2-yl)-4-methoxy-pyrrolidin-1-yl]-(4'-fluoro-3'-methyl-biphenyl-2-yl)-methanone. LC-MS: $t_R$ = 0.94; [M + H]$^+$ = 478.3 |
| 3.41 | [(2S,4R)-2-(6-Chloro-7-methyl-1H-benzoimidazol-2-yl)-4-methoxy-pyrrolidin-1-yl]-[5-(3-chloro-phenyl)-2-dimethylamino-thiazol-4-yl]-methanone. LC-MS: $t_R$ = 0.95; [M + H]$^+$ = 530.3 |
| 3.42 | [(2RS)-(4R)-2-(5-Chloro-4-methyl-1H-benzoimidazol-2-yl)-4-methoxy-2-methyl-pyrrolidin-1-yl]-(2-fluoro-6-[1,2,3]triazol-2-yl-phenyl)-methanone. LC-MS: $t_R$ = 0.80; [M + H]$^+$ = 469.2 |
| 3.43 | [(2RS)-(4R)-2-(5-Chloro-4-methyl-1H-benzoimidazol-2-yl)-4-methoxy-2-methyl-pyrrolidin-1-yl]-(5-fluoro-2-[1,2,3]triazol-2-yl-phenyl)-methanone. LC-MS: $t_R$ = 0.80; [M + H]$^+$ = 469.3 |
| 3.44 | [(2RS)-(4R)-2-(5-Chloro-4-methyl-1H-benzoimidazol-2-yl)-4-methoxy-2-methyl-pyrrolidin-1-yl]-(5-chloro-2-[1,2,3]triazol-2-yl-phenyl)-methanone. LC-MS: $t_R$ = 0.86; [M + H]$^+$ = 485.2 |
| 3.45 | [(2RS)-(4R)-2-(5-Chloro-4-methyl-1H-benzoimidazol-2-yl)-4-methoxy-2-methyl-pyrrolidin-1-yl]-(2-[1,2,3]triazol-2-yl-phenyl)-methanone. LC-MS: $t_R$ = 0.76; [M + H]$^+$ = 451.3 |
| 3.46 | [(2RS)-(4R)-2-(5-Chloro-4-methyl-1H-benzoimidazol-2-yl)-4-methoxy-2-methyl-pyrrolidin-1-yl]-(2-fluoro-3-methoxy-6-[1,2,3]triazol-2-yl-phenyl)-methanone. LC-MS: $t_R$ = 0.81; [M + H]$^+$ = 499.2 |
| 3.47 | [(2RS)-(4R)-2-(5-Chloro-4-methyl-1H-benzoimidazol-2-yl)-4-methoxy-2-methyl-pyrrolidin-1-yl]-(2-fluoro-3-methyl-6-[1,2,3]triazol-2-yl-phenyl)-methanone. LC-MS: $t_R$ = 0.85; [M + H]$^+$ = 483.3 |
| 3.48 | [(2RS)-(4R)-2-(5-Chloro-4-methyl-1H-benzoimidazol-2-yl)-4-methoxy-2-methyl-pyrrolidin-1-yl]-(4,5-dimethyl-2-[1,2,3]triazol-2-yl-phenyl)-methanone. LC-MS: $t_R$ = 0.87; [M + H]$^+$ = 479.3 |
| 3.49 | [(2RS)-(4R)-2-(5-Chloro-4-methyl-1H-benzoimidazol-2-yl)-4-methoxy-2-methyl-pyrrolidin-1-yl]-(4-methyl-2-[1,2,3]triazol-2-yl-phenyl)-methanone. LC-MS: $t_R$ = 0.83; [M + H]$^+$ = 465.3 |
| 3.50 | [(2RS)-(4R)-2-(5-Chloro-4-methyl-1H-benzoimidazol-2-yl)-4-methoxy-2-methyl-pyrrolidin-1-yl]-(2-[1,2,3]triazol-2-yl-5-trifluoromethyl-phenyl)-methanone. LC-MS: $t_R$ = 0.90; [M + H]$^+$ = 519.3 |
| 3.51 | [(2RS)-(4R)-2-(5-Chloro-4-methyl-1H-benzoimidazol-2-yl)-4-methoxy-2-methyl-pyrrolidin-1-yl]-(2-[1,2,3]triazol-2-yl-5-trifluoromethoxy-phenyl)-methanone. LC-MS: $t_R$ = 0.93; [M + H]$^+$ = 535.2 |
| 3.52 | [(2RS)-(4R)-2-(5-Chloro-4-methyl-1H-benzoimidazol-2-yl)-4-methoxy-2-methyl-pyrrolidin-1-yl]-(4,5-dimethoxy-2-[1,2,3]triazol-2-yl-phenyl)-methanone. LC-MS: $t_R$ = 0.77; [M + H]$^+$ = 511.3 |
| 3.53 | [(2RS)-(4R)-2-(5-Chloro-4-methyl-1H-benzoimidazol-2-yl)-4-methoxy-2-methyl-pyrrolidin-1-yl]-(5-methyl-2-pyrazol-1-yl-phenyl)-methanone. LC-MS: $t_R$ = 0.83; [M + H]$^+$ = 464.3 |
| 3.54 | [(2RS)-(4R)-2-(5-Chloro-4-methyl-1H-benzoimidazol-2-yl)-4-methoxy-2-methyl-pyrrolidin-1-yl]-(2-pyrazol-1-yl-phenyl)-methanone. LC-MS: $t_R$ = 0.77; [M + H]$^+$ = 450.3 |
| 3.55 | [(2RS)-(4R)-2-(5-Chloro-4-methyl-1H-benzoimidazol-2-yl)-4-methoxy-2-methyl-pyrrolidin-1-yl]-(6-methyl-3-pyrazol-1-yl-pyridin-2-yl)-methanone. LC-MS: $t_R$ = 0.74; [M + H]$^+$ = 465.3 |
| 3.56 | [(2RS)-(4R)-2-(5-Chloro-4-methyl-1H-benzoimidazol-2-yl)-4-methoxy-2-methyl-pyrrolidin-1-yl]-(6-methyl-3-[1,2,3]triazol-2-yl-pyridin-2-yl)-methanone. LC-MS: $t_R$ = 0.74; [M + H]$^+$ = 466.3 |
| 4.1 | [(2S,3S)-3-Methyl-2-(4-methyl-1H-benzoimidazol-2-yl)-pyrrolidin-1-yl]-(5-methyl-2-[1,2,3]triazol-2-yl-phenyl)-methanone. LC-MS: $t_R$ = 0.66; [M + H]$^+$ = 401.3 |
| 4.2 | [(2S,3S)-3-Methyl-2-(5-methyl-1H-benzoimidazol-2-yl)-pyrrolidin-1-yl]-(5-methyl-2-[1,2,3]triazol-2-yl-phenyl)-methanone. LC-MS: $t_R$ = 0.68; [M + H]$^+$ = 401.2 |
| 4.3 | [5-(3-Chloro-phenyl)-2-methyl-thiazol-4-yl]-[(2S,3S)-3-methyl-2-(5-methyl-1H-benzoimidazol-2-yl)-pyrrolidin-1-yl]-methanone. LC-MS: $t_R$ = 0.81; [M + H]$^+$ = 451.2 |
| 4.4 | [(2S,3S)-3-Methyl-2-(4-methyl-1H-benzoimidazol-2-yl)-pyrrolidin-1-yl]-(2-methyl-5-phenyl-thiazol-4-yl)-methanone. LC-MS: $t_R$ = 0.74; [M + H]$^+$ = 417.2 |
| 4.5 | [(2S,3S)-3-Methyl-2-(5-methyl-1H-benzoimidazol-2-yl)-pyrrolidin-1-yl]-(2-methyl-5-phenyl-thiazol-4-yl)-methanone. LC-MS: $t_R$ = 0.75; [M + H]$^+$ = 417.2 |
| 4.6 | [(2S,3S)-2-(1H-Benzoimidazol-2-yl)-3-methyl-pyrrolidin-1-yl]-[5-(3-chloro-phenyl)-2-methyl-thiazol-4-yl]-methanone. LC-MS: $t_R$ = 0.77; [M + H]$^+$ = 437.2 |
| 4.7 | [5-(3-Chloro-phenyl)-2-methyl-thiazol-4-yl]-[(2S,3S)-3-methyl-2-(4-methyl-1H-benzoimidazol-2-yl)-pyrrolidin-1-yl]-methanone. LC-MS: $t_R$ = 0.81; [M + H]$^+$ = 451.2 |
| 4.8 | 2-{(2S,3S)-1-[5-(3-Chloro-phenyl)-2-methyl-thiazole-4-carbonyl]-3-methyl-pyrrolidin-2-yl}-1H-benzoimidazole-5-carbonitrile. LC-MS: $t_R$ = 0.88; [M + H]$^+$ = 462.2 |
| 4.9 | [5-(3-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 0.97; [M + H]$^+$ = 505.2 |
| 4.10 | [5-(3-Chloro-phenyl)-2-methyl-thiazol-4-yl]-[(2S,3S)-2-(5,6-dimethyl-1H-benzoimidazol-2-yl)-3-methyl-pyrrolidin-1-yl]-methanone. LC-MS: $t_R$ = 0.84; [M + H]$^+$ = 465.2 |
| 4.11 | [(2S,3S)-2-(5-Chloro-1H-benzoimidazol-2-yl)-3-methyl-pyrrolidin-1-yl]-[5-(3-chloro-phenyl)-2-methyl-thiazol-4-yl]-methanone. LC-MS: $t_R$ = 0.87; [M + H]$^+$ = 471.2 |
| 4.12 | [5-(3-Chloro-phenyl)-2-methyl-thiazol-4-yl]-[(2S,3S)-2-(5,6-difluoro-1H-benzoimidazol-2-yl)-3-methyl-pyrrolidin-1-yl]-methanone. LC-MS: $t_R$ = 0.88; [M + H]$^+$ = 473.1 |
| 4.13 | 2-{(2S,3S)-1-[5-(3-Chloro-phenyl)-2-methyl-thiazole-4-carbonyl]-3-methyl-pyrrolidin-2-yl}-1H-benzoimidazole-4-carboxylic acid methyl ester. LC-MS: $t_R$ = 0.88; [M + H]$^+$ = 495.2 |
| 4.14 | [5-(3-Chloro-phenyl)-2-methyl-thiazol-4-yl]-[(2S,3S)-2-(4-methoxy-1H-benzoimidazol-2-yl)-3-methyl-pyrrolidin-1-yl]-methanone. LC-MS: $t_R$ = 0.79; [M + H]$^+$ = 467.2 |
| 4.15 | [(2S,3S)-2-(5-Chloro-6-methyl-1H-benzoimidazol-2-yl)-3-methyl-pyrrolidin-1-yl]-[5-(3-chloro-phenyl)-2-methyl-thiazol-4-yl]-methanone. LC-MS: $t_R$ = 0.89; [M + H]$^+$ = 485.2 |
| 4.16 | [5-(3-Chloro-phenyl)-2-methyl-thiazol-4-yl]-[(2S,3S)-2-(4,6-dimethyl-1H-benzoimidazol-2-yl)-3-methyl-pyrrolidin-1-yl]-methanone. LC-MS: $t_R$ = 0.85; [M + H]$^+$ = 465.2 |
| 4.17 | [5-(3-Chloro-phenyl)-2-methyl-thiazol-4-yl]-[(2S,3S)-2-(4-hydroxymethyl-1H-benzoimidazol-2-yl)-3-methyl-pyrrolidin-1-yl]-methanone. LC-MS: $t_R$ = 0.73; [M + H]$^+$ = 467.2 |

| Example | Compound name. LC-MS data |
|---|---|
| 4.18 | [5-(3-Chloro-phenyl)-2-methyl-thiazol-4-yl]-[(2S,3S)-2-(4-fluoro-1H-benzoimidazol-2-yl)-3-methyl-pyrrolidin-1-yl]-methanone. LC-MS: $t_R = 0.87$; $[M + H]^+ = 455.1$ |
| 4.19 | [5-(3-Chloro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R = 1.01$; $[M + H]^+ = 505.2$ |
| 4.20 | [5-(3-Chloro-phenyl)-2-methyl-thiazol-4-yl]-[(2S,3S)-2-(5-fluoro-1H-benzoimidazol-2-yl)-3-methyl-pyrrolidin-1-yl]-methanone. LC-MS: $t_R = 0.81$; $[M + H]^+ = 455.1$ |
| 4.21 | [(2S,3S)-2-(5-Chloro-4-methyl-1H-benzoimidazol-2-yl)-3-methyl-pyrrolidin-1-yl]-[5-(3-chloro-phenyl)-2-methyl-thiazol-4-yl]-methanone. LC-MS: $t_R = 0.9$; $[M + H]^+ = 485.1$ |
| 4.22 | [(2S,3S)-2-(4-Chloro-1H-benzoimidazol-2-yl)-3-methyl-pyrrolidin-1-yl]-[5-(3-chloro-phenyl)-2-methyl-thiazol-4-yl]-methanone. LC-MS: $t_R = 0.91$; $[M + H]^+ = 471.1$ |
| 4.23 | [5-(3-Chloro-phenyl)-2-methyl-thiazol-4-yl]-[(2S,3S)-2-(4,5-difluoro-1H-benzoimidazol-2-yl)-3-methyl-pyrrolidin-1-yl]-methanone. LC-MS: $t_R = 0.96$; $[M + H]^+ = 473.2$ |
| 4.24 | [5-(3-Chloro-phenyl)-2-methyl-thiazol-4-yl]-[(2S,3S)-2-(4,5-dimethyl-1H-benzoimidazol-2-yl)-3-methyl-pyrrolidin-1-yl]-methanone. LC-MS: $t_R = 0.84$; $[M + H]^+ = 465.2$ |
| 4.25 | [5-(3-Chloro-phenyl)-2-methyl-thiazol-4-yl]-[(2S,3S)-2-(4-isopropyl-1H-benzoimidazol-2-yl)-3-methyl-pyrrolidin-1-yl]-methanone. LC-MS: $t_R = 0.89$; $[M + H]^+ = 479.2$ |
| 4.26 | [5-(3-Chloro-phenyl)-2-methyl-thiazol-4-yl]-[(2S,3S)-2-(5-methoxy-1H-benzoimidazol-2-yl)-3-methyl-pyrrolidin-1-yl]-methanone. LC-MS: $t_R = 0.79$; $[M + H]^+ = 467.2$ |
| 4.27 | [5-(3-Chloro-phenyl)-2-methyl-thiazol-4-yl]-[(2S,3S)-2-(5-hydroxymethyl-1H-benzoimidazol-2-yl)-3-methyl-pyrrolidin-1-yl]-methanone. LC-MS: $t_R = 0.71$; $[M + H]^+ = 467.2$ |
| 4.28 | [(2S,3S)-2-(5-Chloro-7-methyl-1H-benzoimidazol-2-yl)-3-methyl-pyrrolidin-1-yl]-[5-(3-chloro-phenyl)-2-methyl-thiazol-4-yl]-methanone. LC-MS: $t_R = 0.91$; $[M + H]^+ = 485.1$ |
| 4.29 | (5-Methyl-2-[1,2,3]triazol-2-yl-phenyl)-[(2S,3S)-3-methyl-2-(5-trifluoromethyl-1H-benzoimidazol-2-yl)-pyrrolidin-1-yl]-methanone. LC-MS: $t_R = 0.85$; $[M + H]^+ = 455.2$ |
| 4.30 | [(2S,3S)-2-(5,6-Dimethyl-1H-benzoimidazol-2-yl)-3-methyl-pyrrolidin-1-yl]-(5-methyl-2-[1,2,3]triazol-2-yl-phenyl)-methanone. LC-MS: $t_R = 0.72$; $[M + H]^+ = 415.3$ |
| 4.31 | [(2S,3S)-2-(4-Methoxy-1H-benzoimidazol-2-yl)-3-methyl-pyrrolidin-1-yl]-(5-methyl-2-[1,2,3]triazol-2-yl-phenyl)-methanone. LC-MS: $t_R = 0.66$; $[M + H]^+ = 417.2$ |
| 4.32 | [(2S,3S)-2-(5-Chloro-6-methyl-1H-benzoimidazol-2-yl)-3-methyl-pyrrolidin-1-yl]-(5-methyl-2-[1,2,3]triazol-2-yl-phenyl)-methanone. LC-MS: $t_R = 0.77$; $[M + H]^+ = 435.2$ |
| 4.33 | [(2S,3S)-2-(4,6-Dimethyl-1H-benzoimidazol-2-yl)-3-methyl-pyrrolidin-1-yl]-(5-methyl-2-[1,2,3]triazol-2-yl-phenyl)-methanone. LC-MS: $t_R = 0.71$; $[M + H]^+ = 415.3$ |
| 4.34 | (5-Methyl-2-[1,2,3]triazol-2-yl-phenyl)-[(2S,3S)-3-methyl-2-(4-trifluoromethyl-1H-benzoimidazol-2-yl)-pyrrolidin-1-yl]-methanone. LC-MS: $t_R = 0.89$; $[M + H]^+ = 455.2$ |
| 4.35 | [(2S,3S)-2-(5-Chloro-4-methyl-1H-benzoimidazol-2-yl)-3-methyl-pyrrolidin-1-yl]-(5-methyl-2-[1,2,3]triazol-2-yl-phenyl)-methanone. LC-MS: $t_R = 0.76$; $[M + H]^+ = 435.2$ |
| 4.36 | [(2S,3S)-2-(4-Chloro-1H-benzoimidazol-2-yl)-3-methyl-pyrrolidin-1-yl]-(5-methyl-2-[1,2,3]triazol-2-yl-phenyl)-methanone. LC-MS: $t_R = 0.77$; $[M + H]^+ = 421.2$ |
| 4.37 | [(2S,3S)-2-(4,5-Dimethyl-1H-benzoimidazol-2-yl)-3-methyl-pyrrolidin-1-yl]-(5-methyl-2-[1,2,3]triazol-2-yl-phenyl)-methanone. LC-MS: $t_R = 0.7$; $[M + H]^+ = 415.2$ |
| 4.38 | [(2S,3S)-2-(4-Isopropyl-1H-benzoimidazol-2-yl)-3-methyl-pyrrolidin-1-yl]-(5-methyl-2-[1,2,3]triazol-2-yl-phenyl)-methanone. LC-MS: $t_R = 0.75$; $[M + H]^+ = 429.3$ |
| 4.39 | [(2S,3S)-2-(5-Chloro-7-methyl-1H-benzoimidazol-2-yl)-3-methyl-pyrrolidin-1-yl]-(5-methyl-2-[1,2,3]triazol-2-yl-phenyl)-methanone. LC-MS: $t_R = 0.77$; $[M + H]^+ = 435.2$ |
| 4.40 | (5-Chloro-2-[1,2,3]triazol-2-yl-phenyl)-[(2S,3S)-2-(5,6-dimethoxy-1H-benzoimidazol-2-yl)-3-methyl-pyrrolidin-1-yl]-methanone. LC-MS: $t_R = 0.71$; $[M + H]^+ = 467.2$ |
| 4.41 | [(2S,3S)-2-(5,6-Dimethoxy-1H-benzoimidazol-2-yl)-3-methyl-pyrrolidin-1-yl]-(5-fluoro-2-[1,2,3]triazol-2-yl-phenyl)-methanone. LC-MS: $t_R = 0.64$; $[M + H]^+ = 451.3$ |
| 4.42 | [(2S,3S)-2-(5,6-Dimethoxy-1H-benzoimidazol-2-yl)-3-methyl-pyrrolidin-1-yl]-(2-fluoro-6-[1,2,3]triazol-2-yl-phenyl)-methanone. LC-MS: $t_R = 0.63$; $[M + H]^+ = 451.3$ |
| 4.43 | [(2S,3S)-2-(5,6-Dimethoxy-1H-benzoimidazol-2-yl)-3-methyl-pyrrolidin-1-yl]-(5-methoxy-2-[1,2,3]triazol-2-yl-phenyl)-methanone. LC-MS: $t_R = 0.64$; $[M + H]^+ = 463.3$ |
| 4.44 | [(2S,3S)-2-(5,6-Dimethoxy-1H-benzoimidazol-2-yl)-3-methyl-pyrrolidin-1-yl]-(2-fluoro-3-methyl-6-[1,2,3]triazol-2-yl-phenyl)-methanone. LC-MS: $t_R = 0.69$; $[M + H]^+ = 465.3$ |
| 4.45 | [(2S,3S)-2-(5,6-Dimethoxy-1H-benzoimidazol-2-yl)-3-methyl-pyrrolidin-1-yl]-(2-fluoro-3-methoxy-6-[1,2,3]triazol-2-yl-phenyl)-methanone. LC-MS: $t_R = 0.65$; $[M + H]^+ = 481.3$ |
| 4.46 | [(2S,3S)-2-(5,6-Dimethoxy-1H-benzoimidazol-2-yl)-3-methyl-pyrrolidin-1-yl]-(4-methyl-2-[1,2,3]triazol-2-yl-phenyl)-methanone. LC-MS: $t_R = 0.67$; $[M + H]^+ = 447.3$ |
| 4.47 | [(2S,3S)-2-(5,6-Dimethoxy-1H-benzoimidazol-2-yl)-3-methyl-pyrrolidin-1-yl]-(2-[1,2,3]triazol-2-yl-5-trifluoromethyl-phenyl)-methanone. LC-MS: $t_R = 0.76$; $[M + H]^+ = 501.3$ |
| 4.48 | [(2S,3S)-2-(5,6-Dimethoxy-1H-benzoimidazol-2-yl)-3-methyl-pyrrolidin-1-yl]-(2-methyl-6-[1,2,3]triazol-2-yl-phenyl)-methanone. LC-MS: $t_R = 0.66$; $[M + H]^+ = 447.3$ |
| 4.49 | [(2S,3S)-2-(5,6-Dimethoxy-1H-benzoimidazol-2-yl)-3-methyl-pyrrolidin-1-yl]-(2-[1,2,3]triazol-2-yl-phenyl)-methanone. LC-MS: $t_R = 0.62$; $[M + H]^+ = 433.3$ |
| 4.50 | [(2S,3S)-2-(5,6-Dimethoxy-1H-benzoimidazol-2-yl)-3-methyl-pyrrolidin-1-yl]-[2-methyl-5-(4-trifluoromethyl-phenyl)-thiazol-4-yl]-methanone. LC-MS: $t_R = 0.83$; $[M + H]^+ = 531.3$ |
| 4.51 | [(2S,3S)-2-(5,6-Dimethoxy-1H-benzoimidazol-2-yl)-3-methyl-pyrrolidin-1-yl]-(2-methyl-4-p-tolyl-thiazol-5-yl)-methanone. LC-MS: $t_R = 0.7$; $[M + H]^+ = 477.2$ |
| 4.52 | [5-(3,5-Difluoro-phenyl)-2-methyl-thiazol-4-yl]-[(2S,3S)-2-(5,6-dimethoxy-1H-benzoimidazol-2-yl)-3-methyl-pyrrolidin-1-yl]-methanone. LC-MS: $t_R = 0.75$; $[M + H]^+ = 499.3$ |
| 4.53 | [(2S,3S)-2-(5,6-Dimethoxy-1H-benzoimidazol-2-yl)-3-methyl-pyrrolidin-1-yl]-[5-(6-methoxy-pyridin-3-yl)-2-methyl-thiazol-4-yl]-methanone. LC-MS: $t_R = 0.68$; $[M + H]^+ = 494.4$ |
| 4.54 | [(2S,3S)-2-(5,6-Dimethoxy-1H-benzoimidazol-2-yl)-3-methyl-pyrrolidin-1-yl]-[5-(4-fluoro-phenyl)-2-methyl-thiazol-4-yl]-methanone. LC-MS: $t_R = 0.73$; $[M + H]^+ = 481.3$ |
| 4.55 | [5-(3-Chloro-phenyl)-thiazol-4-yl]-[(2S,3S)-2-(5,6-dimethoxy-1H-benzoimidazol-2-yl)-3-methyl-pyrrolidin-1-yl]-methanone. LC-MS: $t_R = 0.72$; $[M + H]^+ = 483.2$ |
| 4.56 | [(2S,3S)-2-(5,6-Dimethoxy-1H-benzoimidazol-2-yl)-3-methyl-pyrrolidin-1-yl]-(2-pyrazol-1-yl-phenyl)-methanone. LC-MS: $t_R = 0.62$; $[M + H]^+ = 432.3$ |
| 4.57 | [(2S,3S)-2-(5,6-Dimethoxy-1H-benzoimidazol-2-yl)-3-methyl-pyrrolidin-1-yl]-(5-methyl-2-pyrazol-1-yl-phenyl)-methanone. LC-MS: $t_R = 0.66$; $[M + H]^+ = 446.3$ |
| 4.58 | [(2S,3S)-2-(5,6-Dimethoxy-1H-benzoimidazol-2-yl)-3-methyl-pyrrolidin-1-yl]-(4'-methyl-biphenyl-2-yl)-methanone. LC-MS: $t_R = 0.80$; $[M + H]^+ = 456.4$ |
| 4.59 | [(2S,3S)-2-(5-Chloro-4-methyl-1H-benzoimidazol-2-yl)-3-methyl-pyrrolidin-1-yl]-(2-[1,2,3]triazol-2-yl-phenyl)-methanone. LC-MS: $t_R = 0.74$; $[M + H]^+ = 421.3$ |
| 4.60 | [(2S,3S)-2-(5-Chloro-4-methyl-1H-benzoimidazol-2-yl)-3-methyl-pyrrolidin-1-yl]-(5-chloro-2-[1,2,3]triazol-2-yl-phenyl)-methanone. LC-MS: $t_R = 0.84$; $[M + H]^+ = 455.2$ |
| 4.61 | [(2S,3S)-2-(5-Chloro-4-methyl-1H-benzoimidazol-2-yl)-3-methyl-pyrrolidin-1-yl]-(4'-methyl-biphenyl-2-yl)-methanone. LC-MS: $t_R = 0.94$; $[M + H]^+ = 444.3$ |
| 4.62 | [(2S,3S)-2-(5-Chloro-4-methyl-1H-benzoimidazol-2-yl)-3-methyl-pyrrolidin-1-yl]-(4-methyl-2-[1,2,3]triazol-2-yl-phenyl)-methanone. LC-MS: $t_R = 0.79$; $[M + H]^+ = 435.3$ |
| 4.63 | [(2S,3S)-2-(5-Chloro-4-methyl-1H-benzoimidazol-2-yl)-3-methyl-pyrrolidin-1-yl]-[5-(4-chloro-phenyl)-2-methyl-thiazol-4-yl]-methanone. LC-MS: $t_R = 0.94$; $[M + H]^+ = 485.2$ |
| 4.64 | [(2S,3S)-2-(5-Chloro-4-methyl-1H-benzoimidazol-2-yl)-3-methyl-pyrrolidin-1-yl]-(5-methyl-2-pyrazol-1-yl-phenyl)-methanone. LC-MS: $t_R = 0.80$; $[M + H]^+ = 434.3$ |
| 4.65 | [(2S,3S)-2-(5-Chloro-4-methyl-1H-benzoimidazol-2-yl)-3-methyl-pyrrolidin-1-yl]-(2-methyl-4-p-tolyl-thiazol-5-yl)-methanone. LC-MS: $t_R = 0.88$; $[M + H]^+ = 465.2$ |
| 4.66 | [(2S,3S)-2-(5-Chloro-4-methyl-1H-benzoimidazol-2-yl)-3-methyl-pyrrolidin-1-yl]-(5-methoxy-2-[1,2,3]triazol-2-yl-phenyl)-methanone. LC-MS: $t_R = 0.77$; $[M + H]^+ = 451.3$ |
| 4.67 | [(2S,3S)-2-(5-Chloro-4-methyl-1H-benzoimidazol-2-yl)-3-methyl-pyrrolidin-1-yl]-[5-(3,5-difluoro-phenyl)-2-methyl-thiazol-4-yl]-methanone. LC-MS: $t_R = 0.92$; $[M + H]^+ = 487.2$ |

| Example | Compound name. LC-MS data |
|---|---|
| 4.68 | [(2S,3S)-2-(5-Chloro-4-methyl-1H-benzoimidazol-2-yl)-3-methyl-pyrrolidin-1-yl]-(2-fluoro-3-methyl-6-[1,2,3]triazol-2-yl-phenyl)-methanone. LC-MS: $t_R$ = 0.83; $[M + H]^+$ = 453.2 |
| 4.69 | [(2S,3S)-2-(5-Chloro-4-methyl-1H-benzoimidazol-2-yl)-3-methyl-pyrrolidin-1-yl]-[5-(6-methoxy-pyridin-3-yl)-2-methyl-thiazol-4-yl]-methanone. LC-MS: $t_R$ = 0.83; $[M + H]^+$ = 482.2 |
| 4.70 | [(2S,3S)-2-(5-Chloro-4-methyl-1H-benzoimidazol-2-yl)-3-methyl-pyrrolidin-1-yl]-[5-(4-fluoro-phenyl)-2-methyl-thiazol-4-yl]-methanone. LC-MS: $t_R$ = 0.89; $[M + H]^+$ = 469.2 |
| 4.71 | [(2S,3S)-2-(5-Chloro-6-methyl-1H-benzoimidazol-2-yl)-3-methyl-pyrrolidin-1-yl]-(5-chloro-2-[1,2,3]triazol-2-yl-phenyl)-methanone. LC-MS: $t_R$ = 0.83; $[M + H]^+$ = 455.2 |
| 4.72 | [(2S,3S)-2-(5-Chloro-6-methyl-1H-benzoimidazol-2-yl)-3-methyl-pyrrolidin-1-yl]-(4-methyl-2-[1,2,3]triazol-2-yl-phenyl)-methanone. LC-MS: $t_R$ = 0.80; $[M + H]^+$ = 435.3 |
| 4.73 | [(2S,3S)-2-(5-Chloro-6-methyl-1H-benzoimidazol-2-yl)-3-methyl-pyrrolidin-1-yl]-(5-methyl-2-pyrazol-1-yl-phenyl)-methanone. LC-MS: $t_R$ = 0.80; $[M + H]^+$ = 434.3 |
| 4.74 | [(2S,3S)-2-(5-Chloro-6-methyl-1H-benzoimidazol-2-yl)-3-methyl-pyrrolidin-1-yl]-(5-methoxy-2-[1,2,3]triazol-2-yl-phenyl)-methanone. LC-MS: $t_R$ = 0.78; $[M + H]^+$ = 451.9 |
| 4.75 | [(2S,3S)-2-(5-Chloro-6-methyl-1H-benzoimidazol-2-yl)-3-methyl-pyrrolidin-1-yl]-(2-fluoro-3-methyl-6-[1,2,3]triazol-2-yl-phenyl)-methanone. LC-MS: $t_R$ = 0.83; $[M + H]^+$ = 453.3 |
| 4.76 | [(2S,3S)-2-(5-Chloro-6-methyl-1H-benzoimidazol-2-yl)-3-methyl-pyrrolidin-1-yl]-(2-[1,2,3]triazol-2-yl-phenyl)-methanone. LC-MS: $t_R$ = 0.74; $[M + H]^+$ = 421.2 |
| 4.77 | [(2S,3S)-2-(5-Chloro-6-methyl-1H-benzoimidazol-2-yl)-3-methyl-pyrrolidin-1-yl]-(4'-methyl-biphenyl-2-yl)-methanone. LC-MS: $t_R$ = 0.93; $[M + H]^+$ = 444.3 |
| 4.78 | [(2S,3S)-2-(5-Chloro-6-methyl-1H-benzoimidazol-2-yl)-3-methyl-pyrrolidin-1-yl]-[5-(4-chloro-phenyl)-2-methyl-thiazol-4-yl]-methanone. LC-MS: $t_R$ = 0.93; $[M + H]^+$ = 485.2 |
| 4.79 | [(2S,3S)-2-(5-Chloro-6-methyl-1H-benzoimidazol-2-yl)-3-methyl-pyrrolidin-1-yl]-(2-methyl-4-p-tolyl-thiazol-5-yl)-methanone. LC-MS: $t_R$ = 0.86; $[M + H]^+$ = 465.3 |
| 4.80 | [(2S,3S)-2-(5-Chloro-6-methyl-1H-benzoimidazol-2-yl)-3-methyl-pyrrolidin-1-yl]-[5-(3,5-difluoro-phenyl)-2-methyl-thiazol-4-yl]-methanone. LC-MS: $t_R$ = 0.91; $[M + H]^+$ = 487.2 |
| 4.81 | (5-Chloro-2-[1,2,3]triazol-2-yl-phenyl)-[(2S,3S)-2-(5,6-dimethyl-1H-benzoimidazol-2-yl)-3-methyl-pyrrolidin-1-yl]-methanone. LC-MS: $t_R$ = 0.78; $[M + H]^+$ = 435.3 |
| 4.82 | [(2S,3S)-2-(5,6-Dimethyl-1H-benzoimidazol-2-yl)-3-methyl-pyrrolidin-1-yl]-(4-methyl-2-[1,2,3]triazol-2-yl-phenyl)-methanone. LC-MS: $t_R$ = 0.75; $[M + H]^+$ = 415.3 |
| 4.83 | [(2S,3S)-2-(5,6-Dimethyl-1H-benzoimidazol-2-yl)-3-methyl-pyrrolidin-1-yl]-(5-methyl-2-pyrazol-1-yl-phenyl)-methanone. LC-MS: $t_R$ = 0.75; $[M + H]^+$ = 414.3 |
| 4.84 | [(2S,3S)-2-(5,6-Dimethyl-1H-benzoimidazol-2-yl)-3-methyl-pyrrolidin-1-yl]-(5-methoxy-2-[1,2,3]triazol-2-yl-phenyl)-methanone. LC-MS: $t_R$ = 0.72; $[M + H]^+$ = 431.3 |
| 4.85 | [(2S,3S)-2-(5,6-Dimethyl-1H-benzoimidazol-2-yl)-3-methyl-pyrrolidin-1-yl]-(2-[1,2,3]triazol-2-yl-phenyl)-methanone. LC-MS: $t_R$ = 0.69; $[M + H]^+$ = 401.3 |
| 4.86 | [(2S,3S)-2-(5,6-Dimethyl-1H-benzoimidazol-2-yl)-3-methyl-pyrrolidin-1-yl]-(4'-methyl-biphenyl-2-yl)-methanone. LC-MS: $t_R$ = 0.87; $[M + H]^+$ = 424.3 |
| 4.87 | [5-(4-Chloro-phenyl)-2-methyl-thiazol-4-yl]-[(2S,3S)-2-(5,6-dimethyl-1H-benzoimidazol-2-yl)-3-methyl-pyrrolidin-1-yl]-methanone. LC-MS: $t_R$ = 0.87; $[M + H]^+$ = 465.2 |
| 4.88 | [(2S,3S)-2-(5,6-Dimethyl-1H-benzoimidazol-2-yl)-3-methyl-pyrrolidin-1-yl]-(2-methyl-4-p-tolyl-thiazol-5-yl)-methanone. LC-MS: $t_R$ = 0.78; $[M + H]^+$ = 445.3 |
| 4.89 | [5-(3,5-Difluoro-phenyl)-2-methyl-thiazol-4-yl]-[(2S,3S)-2-(5,6-dimethyl-1H-benzoimidazol-2-yl)-3-methyl-pyrrolidin-1-yl]-methanone. LC-MS: $t_R$ = 0.85; $[M + H]^+$ = 467.3 |
| 4.90 | [(2S,3S)-2-(5,6-Dimethyl-1H-benzoimidazol-2-yl)-3-methyl-pyrrolidin-1-yl]-[5-(4-fluoro-phenyl)-2-methyl-thiazol-4-yl]-methanone. LC-MS: $t_R$ = 0.82; $[M + H]^+$ = 449.3 |
| 4.91 | [(2S,3S)-2-(6-Chloro-4-methyl-1H-benzoimidazol-2-yl)-3-methyl-pyrrolidin-1-yl]-(5-chloro-2-[1,2,3]triazol-2-yl-phenyl)-methanone. LC-MS: $t_R$ = 0.84; $[M + H]^+$ = 455.2 |
| 4.92 | [(2S,3S)-2-(6-Chloro-4-methyl-1H-benzoimidazol-2-yl)-3-methyl-pyrrolidin-1-yl]-(4'-methyl-biphenyl-2-yl)-methanone. LC-MS: $t_R$ = 0.93; $[M + H]^+$ = 444.3 |
| 4.93 | [(2S,3S)-2-(6-Chloro-4-methyl-1H-benzoimidazol-2-yl)-3-methyl-pyrrolidin-1-yl]-(4-methyl-2-[1,2,3]triazol-2-yl-phenyl)-methanone. LC-MS: $t_R$ = 0.80; $[M + H]^+$ = 435.2 |
| 4.94 | [(2S,3S)-2-(6-Chloro-4-methyl-1H-benzoimidazol-2-yl)-3-methyl-pyrrolidin-1-yl]-[5-(4-chloro-phenyl)-2-methyl-thiazol-4-yl]-methanone. LC-MS: $t_R$ = 0.94; $[M + H]^+$ = 485.2 |
| 4.95 | [(2S,3S)-2-(6-Chloro-4-methyl-1H-benzoimidazol-2-yl)-3-methyl-pyrrolidin-1-yl]-(5-methyl-2-pyrazol-1-yl-phenyl)-methanone. LC-MS: $t_R$ = 0.80; $[M + H]^+$ = 434.3 |
| 4.96 | [(2S,3S)-2-(6-Chloro-4-methyl-1H-benzoimidazol-2-yl)-3-methyl-pyrrolidin-1-yl]-(2-methyl-4-p-tolyl-thiazol-5-yl)-methanone. LC-MS: $t_R$ = 0.88; $[M + H]^+$ = 465.2 |
| 4.97 | [(2S,3S)-2-(6-Chloro-4-methyl-1H-benzoimidazol-2-yl)-3-methyl-pyrrolidin-1-yl]-(5-methoxy-2-[1,2,3]triazol-2-yl-phenyl)-methanone. LC-MS: $t_R$ = 0.77; $[M + H]^+$ = 451.3 |
| 4.98 | [(2S,3S)-2-(6-Chloro-4-methyl-1H-benzoimidazol-2-yl)-3-methyl-pyrrolidin-1-yl]-[5-(3,5-difluoro-phenyl)-2-methyl-thiazol-4-yl]-methanone. LC-MS: $t_R$ = 0.92; $[M + H]^+$ = 487.2 |
| 4.99 | [(2S,3S)-2-(6-Chloro-4-methyl-1H-benzoimidazol-2-yl)-3-methyl-pyrrolidin-1-yl]-(2-fluoro-3-methyl-6-[1,2,3]triazol-2-yl-phenyl)-methanone. LC-MS: $t_R$ = 0.83; $[M + H]^+$ = 453.2 |
| 4.100 | [(2S,3S)-2-(6-Chloro-4-methyl-1H-benzoimidazol-2-yl)-3-methyl-pyrrolidin-1-yl]-[5-(4-fluoro-phenyl)-2-methyl-thiazol-4-yl]-methanone. LC-MS: $t_R$ = 0.89; $[M + H]^+$ = 469.2 |
| 4.101 | [(2S,3S)-2-(6-Chloro-4-methyl-1H-benzoimidazol-2-yl)-3-methyl-pyrrolidin-1-yl]-(2-[1,2,3]triazol-2-yl-phenyl)-methanone. LC-MS: $t_R$ = 0.74; $[M + H]^+$ = 421.3 |
| 4.102 | [(2S,3S)-2-(5-Chloro-6-methyl-1H-benzoimidazol-2-yl)-3-methyl-pyrrolidin-1-yl]-(5-methyl-2-pyridin-2-yl-phenyl)-methanone. LC-MS: $t_R$ = 0.91; $[M + H]^+$ = 445.9 |
| 4.103 | (4-Chloro-biphenyl-2-yl)-[(2S,3S)-2-(5-chloro-6-methyl-1H-benzoimidazol-2-yl)-3-methyl-pyrrolidin-1-yl]-methanone. LC-MS: $t_R$ = 0.99; $[M + H]^+$ = 464.3 |
| 4.104 | [(2S,3S)-2-(5-Chloro-6-methyl-1H-benzoimidazol-2-yl)-3-methyl-pyrrolidin-1-yl]-(5-methyl-2-pyridin-3-yl-phenyl)-methanone. LC-MS: $t_R$ = 0.72; $[M + H]^+$ = 445.3 |
| 4.105 | [(2S,3S)-2-(5-Chloro-6-methyl-1H-benzoimidazol-2-yl)-3-methyl-pyrrolidin-1-yl]-(4-fluoro-biphenyl-2-yl)-methanone. LC-MS: $t_R$ = 0.94; $[M + H]^+$ = 448.3 |
| 4.106 | [(2S,3S)-2-(5-Chloro-6-methyl-1H-benzoimidazol-2-yl)-3-methyl-pyrrolidin-1-yl]-(5-fluoro-2-pyridin-2-yl-phenyl)-methanone. LC-MS: $t_R$ = 0.81; $[M + H]^+$ = 449.3 |
| 4.107 | [(2S,3S)-2-(5-Chloro-6-methyl-1H-benzoimidazol-2-yl)-3-methyl-pyrrolidin-1-yl]-(2-fluoro-6-pyridin-3-yl-phenyl)-methanone. LC-MS: $t_R$ = 0.71; $[M + H]^+$ = 449.3 |
| 4.108 | 2-[(2S,3S)-2-(5-Chloro-6-methyl-1H-benzoimidazol-2-yl)-3-methyl-pyrrolidine-1-carbonyl]-biphenyl-4-carbonitrile. LC-MS: $t_R$ = 0.91; $[M + H]^+$ = 455.3 |
| 4.109 | [(2S,3S)-2-(5-Chloro-6-methyl-1H-benzoimidazol-2-yl)-3-methyl-pyrrolidin-1-yl]-(4-methyl-2-pyridin-2-yl-phenyl)-methanone. LC-MS: $t_R$ = 0.81; $[M + H]^+$ = 445.4 |
| 4.110 | [(2S,3S)-2-(5-Chloro-6-methyl-1H-benzoimidazol-2-yl)-3-methyl-pyrrolidin-1-yl]-(4-methyl-2-pyridin-3-yl-phenyl)-methanone. LC-MS: $t_R$ = 0.72; $[M + H]^+$ = 445.3 |
| 4.111 | [(2S,3S)-2-(5-Chloro-6-methyl-1H-benzoimidazol-2-yl)-3-methyl-pyrrolidin-1-yl]-(5-methyl-biphenyl-2-yl)-methanone. LC-MS: $t_R$ = 0.96; $[M + H]^+$ = 444.3 |
| 4.112 | [(2S,3S)-2-(5-Chloro-6-methyl-1H-benzoimidazol-2-yl)-3-methyl-pyrrolidin-1-yl]-(3-fluoro-biphenyl-2-yl)-methanone. LC-MS: $t_R$ = 0.8; $[M + H]^+$ = 449.3 |
| 4.113 | [(2S,3S)-2-(5-Chloro-6-methyl-1H-benzoimidazol-2-yl)-3-methyl-pyrrolidin-1-yl]-(2-fluoro-3-methyl-6-pyridin-2-yl-phenyl)-methanone. LC-MS: $t_R$ = 0.83; $[M + H]^+$ = 463.3 |
| 4.114 | [(2S,3S)-2-(5-Chloro-6-methyl-1H-benzoimidazol-2-yl)-3-methyl-pyrrolidin-1-yl]-(4-trifluoromethyl-biphenyl-2-yl)-methanone. LC-MS: $t_R$ = 1.02; $[M + H]^+$ = 498.3 |
| 4.115 | [(2S,3S)-2-(5-Chloro-6-methyl-1H-benzoimidazol-2-yl)-3-methyl-pyrrolidin-1-yl]-(3-fluoro-4-methyl-biphenyl-2-yl)-methanone. LC-MS: $t_R$ = 0.99; $[M + H]^+$ = 462.3 |
| 4.116 | [(2S,3S)-2-(5-Chloro-6-methyl-1H-benzoimidazol-2-yl)-3-methyl-pyrrolidin-1-yl]-(4-methyl-biphenyl-2-yl)-methanone. LC-MS: $t_R$ = 0.95; $[M + H]^+$ = 444.3 |
| 4.117 | [(2S,3S)-2-(5-Chloro-6-methyl-1H-benzoimidazol-2-yl)-3-methyl-pyrrolidin-1-yl]-(2-fluoro-3-methyl-6-pyridin-3-yl-phenyl)-methanone. LC-MS: $t_R$ = 0.75; $[M + H]^+$ = 463.3 |

| Example | Compound name. LC-MS data |
|---|---|
| 4.118 | [(2S,3S)-2-(4-Chloro-1H-benzoimidazol-2-yl)-3-methyl-pyrrolidin-1-yl]-[5-(4-fluoro-phenyl)-2-methyl-thiazol-4-yl]-methanone. LC-MS: $t_R$ = 0.92; [M + H]$^+$ = 455.2 |
| 4.119 | [(2S,3S)-2-(4-Chloro-1H-benzoimidazol-2-yl)-3-methyl-pyrrolidin-1-yl]-[5-(3,5-difluoro-phenyl)-2-methyl-thiazol-4-yl]-methanone. LC-MS: $t_R$ = 0.96; [M + H]$^+$ = 473.2 |
| 4.120 | [(2S,3S)-2-(4-Chloro-1H-benzoimidazol-2-yl)-3-methyl-pyrrolidin-1-yl]-[5-(4-chloro-phenyl)-2-methyl-thiazol-4-yl]-methanone. LC-MS: $t_R$ = 0.98; [M + H]$^+$ = 471.2 |
| 4.121 | [(2S,3S)-2-(4-Chloro-1H-benzoimidazol-2-yl)-3-methyl-pyrrolidin-1-yl]-[5-(3-methoxy-phenyl)-2-methyl-thiazol-4-yl]-methanone. LC-MS: $t_R$ = 0.9; [M + H]$^+$ = 467.2 |
| 4.122 | [(2S,3S)-2-(4-Chloro-1H-benzoimidazol-2-yl)-3-methyl-pyrrolidin-1-yl]-(2-methyl-5-m-tolyl-thiazol-4-yl)-methanone. LC-MS: $t_R$ = 0.95; [M + H]$^+$ = 451.3 |
| 4.123 | [5-(4-Bromo-phenyl)-2-methyl-thiazol-4-yl]-[(2S,3S)-2-(4-chloro-1H-benzoimidazol-2-yl)-3-methyl-pyrrolidin-1-yl]-methanone. LC-MS: $t_R$ = 1.0; [M + H]$^+$ = 515.2 |
| 4.124 | [(2S,3S)-2-(4-Chloro-1H-benzoimidazol-2-yl)-3-methyl-pyrrolidin-1-yl]-(2-methyl-5-p-tolyl-thiazol-4-yl)-methanone. LC-MS: $t_R$ = 0.95; [M + H]$^+$ = 451.3 |
| 4.125 | [(2S,3S)-2-(4-Chloro-1H-benzoimidazol-2-yl)-3-methyl-pyrrolidin-1-yl]-[5-(3,4-dimethyl-phenyl)-2-methyl-thiazol-4-yl]-methanone. LC-MS: $t_R$ = 0.99; [M + H]$^+$ = 465.3 |
| 4.126 | [(2S,3S)-2-(4-Chloro-1H-benzoimidazol-2-yl)-3-methyl-pyrrolidin-1-yl]-[5-(3,4-difluoro-phenyl)-2-methyl-thiazol-4-yl]-methanone. LC-MS: $t_R$ = 0.95; [M + H]$^+$ = 473.2 |
| 4.127 | [(2S,3S)-2-(4-Chloro-1H-benzoimidazol-2-yl)-3-methyl-pyrrolidin-1-yl]-[2-(3,4-dimethyl-phenyl)-thiophen-3-yl]-methanone. LC-MS: $t_R$ = 1.02; [M + H]$^+$ = 450.3 |
| 4.128 | [(2S,3S)-2-(4-Chloro-1H-benzoimidazol-2-yl)-3-methyl-pyrrolidin-1-yl]-[2-dimethylamino-5-(3,4-dimethyl-phenyl)-thiazol-4-yl]-methanone. LC-MS: $t_R$ = 1.0; [M + H]$^+$ = 494.3 |
| 4.129 | [(2S,3S)-2-(4-Chloro-1H-benzoimidazol-2-yl)-3-methyl-pyrrolidin-1-yl]-[5-(2-methoxy-phenyl)-2-methyl-thiazol-4-yl]-methanone. LC-MS: $t_R$ = 0.89; [M + H]$^+$ = 467.3 |
| 4.130 | [(2S,3S)-2-(5-Chloro-6-methyl-1H-benzoimidazol-2-yl)-3-methyl-pyrrolidin-1-yl]-(4-methyl-2-pyrimidin-2-yl-phenyl)-methanone. LC-MS: $t_R$ = 0.81; [M + H]$^+$ = 446.3 |
| 4.131 | [(2S,3S)-2-(5-Chloro-6-methyl-1H-benzoimidazol-2-yl)-3-methyl-pyrrolidin-1-yl]-(5-fluoro-2-pyrimidin-2-yl-phenyl)-methanone. LC-MS: $t_R$ = 0.81; [M + H]$^+$ = 450.3 |
| 4.132 | [(2S,3S)-2-(5-Chloro-6-methyl-1H-benzoimidazol-2-yl)-3-methyl-pyrrolidin-1-yl]-(2-fluoro-3-methyl-6-pyrimidin-2-yl-phenyl)-methanone. LC-MS: $t_R$ = 0.83; [M + H]$^+$ = 464.3 |
| 4.133 | [(2S,3S)-2-(5-Chloro-6-methyl-1H-benzoimidazol-2-yl)-3-methyl-pyrrolidin-1-yl]-(2-fluoro-6-pyrimidin-2-yl-phenyl)-methanone. LC-MS: $t_R$ = 0.80; [M + H]$^+$ = 450.3 |
| 4.134 | [(2S,3S)-2-(5-Chloro-4-methyl-1H-benzoimidazol-2-yl)-3-methyl-pyrrolidin-1-yl]-[2-(3-methoxy-phenylethynyl)-phenyl]-methanone. LC-MS: $t_R$=; [M + H]$^+$= |
| 4.135 | [(2S,3S)-2-(5-Chloro-6-methyl-1H-benzoimidazol-2-yl)-3-methyl-pyrrolidin-1-yl]-[2-(3-methoxy-phenylethynyl)-phenyl]-methanone. LC-MS: $t_R$=; [M + H]$^+$= |
| 4.136 | [5-(4-Fluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 0.99; [M + H]$^+$ = 489.3 |
| 4.137 | [5-(3-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 0.98; [M + H]$^+$ = 501.3 |
| 4.138 | (2-Methyl-5-m-tolyl-thiazol-4-yl)-[(2S,3S)-3-methyl-2-(5-trifluoromethyl-1H-benzoimidazol-2-yl)-pyrrolidin-1-yl]-methanone. LC-MS: $t_R$ = 1.02; [M + H]$^+$ = 485.3 |
| 4.139 | [5-(4-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.05; [M + H]$^+$ = 505.3 |
| 4.140 | (2-Methyl-5-p-tolyl-thiazol-4-yl)-[(2S,3S)-3-methyl-2-(5-trifluoromethyl-1H-benzoimidazol-2-yl)-pyrrolidin-1-yl]-methanone. LC-MS: $t_R$ = 1.02; [M + H]$^+$ = 485.3 |
| 4.141 | [5-(4-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 0.97; [M + H]$^+$ = 501.3 |
| 4.142 | [5-(4-Bromo-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.06; [M + H]$^+$ = 549.2 |
| 4.143 | [5-(3,4-Difluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.02; [M + H]$^+$ = 507.3 |
| 4.144 | [2-(3,4-Dimethyl-phenyl)-thiophen-3-yl]-[(2S,3S)-3-methyl-2-(5-trifluoromethyl-1H-benzoimidazol-2-yl)-pyrrolidin-1-yl]-methanone. LC-MS: $t_R$ = 1.09; [M + H]$^+$ = 484.3 |
| 4.145 | [5-(3,4-Dimethyl-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.06; [M + H]$^+$ = 499.3 |
| 4.146 | [5-(2-Chloro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.00; [M + H]$^+$ = 505.2 |
| 4.147 | [5-(2-Methoxy-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 0.97; [M + H]$^+$ = 501.3 |
| 4.148 | [5-(3,5-Difluoro-phenyl)-2-methyl-thiazol-4-yl]-[(2S,3S)-3-methyl-2-(5-trifluoromethyl-1H-benzoimidazol-2-yl)-pyrrolidin-1-yl]-methanone. LC-MS: $t_R$ = 1.02; [M + H]$^+$ = 507.3 |
| 4.149 | [5-(4-Fluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.03; [M + H]$^+$ = 489.3 |
| 4.150 | [5-(4-Chloro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.09; [M + H]$^+$ = 505.2 |
| 4.151 | [5-(4-Bromo-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.11; [M + H]$^+$ = 549.2 |
| 4.152 | [5-(3,4-Dimethyl-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.1; [M + H]$^+$ = 499.3 |
| 4.153 | (2-Methyl-5-p-tolyl-thiazol-4-yl)-[(2S,3S)-3-methyl-2-(4-trifluoromethyl-1H-benzoimidazol-2-yl)-pyrrolidin-1-yl]-methanone. LC-MS: $t_R$ = 1.06; [M + H]$^+$ = 485.3 |
| 4.154 | [5-(3,4-Difluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.06; [M + H]$^+$ = 507.3 |
| 4.155 | [5-(2-Chloro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.04; [M + H]$^+$ = 505.2 |
| 4.156 | [5-(2-Methoxy-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 0.99; [M + H]$^+$ = 501.3 |
| 4.157 | [5-(3,5-Difluoro-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.06; [M + H]$^+$ = 507.3 |
| 4.158 | (2-Methyl-5-m-tolyl-thiazol-4-yl)-[(2S,3S)-3-methyl-2-(4-trifluoromethyl-1H-benzoimidazol-2-yl)-pyrrolidin-1-yl]-methanone. LC-MS: $t_R$ = 1.06; [M + H]$^+$ = 485.3 |
| 4.159 | [5-(4-Methoxy-phenyl)-2-methyl-thiazol-4-yl]-[(2S,3S)-3-methyl-2-(4-trifluoromethyl-1H-benzoimidazol-2-yl)-pyrrolidin-1-yl]-methanone. LC-MS: $t_R$ = 1.00; [M + H]$^+$ = 501.3 |
| 4.160 | [2-(3,4-Dimethyl-phenyl)-thiophen-3-yl]-[(2S,3S)-3-methyl-2-(4-trifluoromethyl-1H-benzoimidazol-2-yl)-pyrrolidin-1-yl]-methanone. LC-MS: $t_R$ = 1.14; [M + H]$^+$ = 484.3 |
| 4.161 | [(2S,3S)-2-(5-Chloro-4-methyl-1H-benzoimidazol-2-yl)-3-methyl-pyrrolidin-1-yl]-(5-methyl-2-pyridin-2-yl-phenyl)-methanone. LC-MS: $t_R$ = 0.81; [M + H]$^+$ = 445.3 |
| 4.162 | (4-Chloro-biphenyl-2-yl)-[(2S,3S)-2-(5-chloro-4-methyl-1H-benzoimidazol-2-yl)-3-methyl-pyrrolidin-1-yl]-methanone. LC-MS: $t_R$ = 0.99; [M + H]$^+$ = 464.3 |
| 4.163 | [(2S,3S)-2-(5-Chloro-4-methyl-1H-benzoimidazol-2-yl)-3-methyl-pyrrolidin-1-yl]-(5-methyl-2-pyridin-3-yl-phenyl)-methanone. LC-MS: $t_R$ = 0.73; [M + H]$^+$ = 445.4 |
| 4.164 | [(2S,3S)-2-(5-Chloro-4-methyl-1H-benzoimidazol-2-yl)-3-methyl-pyrrolidin-1-yl]-(4-fluoro-biphenyl-2-yl)-methanone. LC-MS: $t_R$ = 0.95; [M + H]$^+$ = 448.3 |
| 4.165 | [(2S,3S)-2-(5-Chloro-4-methyl-1H-benzoimidazol-2-yl)-3-methyl-pyrrolidin-1-yl]-(5-fluoro-2-pyridin-2-yl-phenyl)-methanone. LC-MS: $t_R$ = 0.81; [M + H]$^+$ = 445.3 |
| 4.166 | 2-[(2S,3S)-2-(5-Chloro-4-methyl-1H-benzoimidazol-2-yl)-3-methyl-pyrrolidine-1-carbonyl]-biphenyl-4-carbonitrile. LC-MS: $t_R$ = 0.92; [M + H]$^+$ = 455.3 |
| 4.167 | [(2S,3S)-2-(5-Chloro-4-methyl-1H-benzoimidazol-2-yl)-3-methyl-pyrrolidin-1-yl]-(4-methyl-2-pyridin-2-yl-phenyl)-methanone. LC-MS: $t_R$ = 0.81; [M + H]$^+$ = 445.3 |

| Example | Compound name. LC-MS data |
|---|---|
| 4.168 | [(2S,3S)-2-(5-Chloro-4-methyl-1H-benzoimidazol-2-yl)-3-methyl-pyrrolidin-1-yl]-(5-methyl-biphenyl-2-yl)-methanone. LC-MS: $t_R$ = 0.96; [M + H]$^+$ = 444.3 |
| 4.169 | [(2S,3S)-2-(5-Chloro-4-methyl-1H-benzoimidazol-2-yl)-3-methyl-pyrrolidin-1-yl]-(3-fluoro-biphenyl-2-yl)-methanone. LC-MS: $t_R$ = 0.94; [M + H]$^+$ = 448.3 |
| 4.170 | [(2S,3S)-2-(5-Chloro-4-methyl-1H-benzoimidazol-2-yl)-3-methyl-pyrrolidin-1-yl]-(4-trifluoromethyl-biphenyl-2-yl)-methanone. LC-MS: $t_R$ = 1.03; [M + H]$^+$ = 498.3 |
| 4.171 | [(2S,3S)-2-(5-Chloro-4-methyl-1H-benzoimidazol-2-yl)-3-methyl-pyrrolidin-1-yl]-(3-fluoro-4-methyl-biphenyl-2-yl)-methanone. LC-MS: $t_R$ = 1.00; [M + H]$^+$ = 462.3 |
| 4.172 | [(2S,3S)-2-(5-Chloro-4-methyl-1H-benzoimidazol-2-yl)-3-methyl-pyrrolidin-1-yl]-(4-methyl-biphenyl-2-yl)-methanone. LC-MS: $t_R$ = 0.95; [M + H]$^+$ = 444.3 |
| 4.173 | [(2S,3S)-2-(5-Chloro-4-methyl-1H-benzoimidazol-2-yl)-3-methyl-pyrrolidin-1-yl]-(2-fluoro-3-methyl-6-pyridin-3-yl-phenyl)-methanone. LC-MS: $t_R$ = 0.76; [M + H]$^+$ = 463.3 |
| 4.174 | [(2S,3S)-2-(5-Chloro-4-methyl-1H-benzoimidazol-2-yl)-3-methyl-pyrrolidin-1-yl]-(4-methyl-2-pyrimidin-2-yl-phenyl)-methanone. LC-MS: $t_R$ = 0.81; [M + H]$^+$ = 446.3 |
| 4.175 | [(2S,3S)-2-(5-Chloro-4-methyl-1H-benzoimidazol-2-yl)-3-methyl-pyrrolidin-1-yl]-(5-fluoro-2-pyrimidin-2-yl-phenyl)-methanone. LC-MS: $t_R$ = 0.81; [M + H]$^+$ = 450.3 |
| 4.176 | [(2S,3S)-2-(5-Chloro-4-methyl-1H-benzoimidazol-2-yl)-3-methyl-pyrrolidin-1-yl]-(2-fluoro-3-methyl-6-pyrimidin-2-yl-phenyl)-methanone. LC-MS: $t_R$ = 0.80; [M + H]$^+$ = 464.3 |
| 4.177 | [(2S,3S)-2-(5-Chloro-4-methyl-1H-benzoimidazol-2-yl)-3-methyl-pyrrolidin-1-yl]-(2-fluoro-6-pyrimidin-2-yl-phenyl)-methanone. LC-MS: $t_R$ = 0.80; [M + H]$^+$ = 450.3 |
| 4.178 | [(2S,3S)-2-(5-Chloro-4-methyl-1H-benzoimidazol-2-yl)-3-methyl-pyrrolidin-1-yl]-(5-methyl-2-pyrimidin-2-yl-phenyl)-methanone. LC-MS: $t_R$ = 0.80; [M + H]$^+$ = 446.3 |
| 4.179 | [(2S,3S)-2-(5,6-Dimethoxy-1H-benzoimidazol-2-yl)-3-methyl-pyrrolidin-1-yl]-(5-methyl-2-pyrimidin-2-yl-phenyl)-methanone. LC-MS: $t_R$ = 0.68; [M + H]$^+$ = 458.4 |
| 4.180 | [(2S,3S)-2-(5-Chloro-6-methyl-1H-benzoimidazol-2-yl)-3-methyl-pyrrolidin-1-yl]-(5-methyl-2-pyrimidin-2-yl-phenyl)-methanone. LC-MS: $t_R$ = 0.80; [M + H]$^+$ = 446.3 |
| 4.181 | [(2S,3S)-2-(6-Chloro-7-methyl-1H-benzoimidazol-2-yl)-3-methyl-pyrrolidin-1-yl]-(5-methyl-2-pyrimidin-2-yl-phenyl)-methanone. LC-MS: $t_R$ = 0.80; [M + H]$^+$ = 446.3 |
| 4.182 | [(2S,3S)-2-(5-Chloro-7-methyl-1H-benzoimidazol-2-yl)-3-methyl-pyrrolidin-1-yl]-(5-methyl-2-pyrimidin-2-yl-phenyl)-methanone. LC-MS: $t_R$ = 0.80; [M + H]$^+$ = 446.3 |
| 4.183 | [(2S,3S)-2-(5,6-Dimethyl-1H-benzoimidazol-2-yl)-3-methyl-pyrrolidin-1-yl]-(5-methyl-2-pyrimidin-2-yl-phenyl)-methanone. LC-MS: $t_R$ = 0.76; [M + H]$^+$ = 426.4 |
| 5.1 | [(S)-2-Methyl-2-(4-methyl-1H-benzoimidazol-2-yl)-pyrrolidin-1-yl]-(2-methyl-5-phenyl-thiazol-4-yl)-methanone. LC-MS: $t_R$ = 0.79; [M + H]$^+$ = 417.3 |
| 5.2 | [(S)-2-(5-Chloro-4-methyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.81; [M + H]$^+$ = 435.3 |
| 5.3 | [(S)-2-(5-Chloro-4-methyl-1H-benzoimidazol-2-yl)-2-methyl-pyrrolidin-1-yl]-(2-methyl-5-phenyl-thiazol-4-yl)-methanone. LC-MS: $t_R$ = 0.83; [M + H]$^+$ = 451.2 |
| 5.4 | [5-(3-Chloro-phenyl)-2-methyl-thiazol-4-yl]-[(S)-2-methyl-2-(4-methyl-1H-benzoimidazol-2-yl)-pyrrolidin-1-yl]-methanone. LC-MS: $t_R$ = 0.82; [M + H]$^+$ = 451.2 |
| 5.5 | [(S)-2-(5-Chloro-4-methyl-1H-benzoimidazol-2-yl)-2-methyl-pyrrolidin-1-yl]-[5-(3-chloro-phenyl)-2-methyl-thiazol-4-yl]-methanone. LC-MS: $t_R$ = 0.9; [M + H]$^+$ = 485.2 |
| 5.6 | [(S)-2-Methyl-2-(4-methyl-1H-benzoimidazol-2-yl)-pyrrolidin-1-yl]-(5-methyl-2-[1,2,3]triazol-2-yl-phenyl)-methanone. LC-MS: $t_R$ = 0.68; [M + H]$^+$ = 401.2 |
| 5.7 | [(S)-2-(5,6-Dichloro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.92; [M + H]$^+$ = 455.2 |
| 5.8 | [(S)-2-(5-Bromo-1H-benzoimidazol-2-yl)-2-methyl-pyrrolidin-1-yl]-(5-methyl-2-[1,2,3]triazol-2-yl-phenyl)-methanone. LC-MS: $t_R$ = 0.74; [M + H]$^+$ = 465.2 |
| 5.9 | (5-Methyl-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.83; [M + H]$^+$ = 455.3 |
| 5.10 | [(S)-2-(5,6-Dimethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.75; [M + H]$^+$ = 415.4 |
| 5.11 | [(S)-2-(5-Chloro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.73; [M + H]$^+$ = 421.2 |
| 5.12 | [(S)-2-(6-Chloro-5-fluoro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.81; [M + H]$^+$ = 439.2 |
| 5.13 | [(S)-2-(5-tert-Butyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.81; [M + H]$^+$ = 443.3 |
| 5.14 | [(S)-2-(4-Chloro-6-trifluoromethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 1.11; [M + H]$^+$ = 489.2 |
| 5.15 | [(S)-2-(5-Chloro-6-methyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.76; [M + H]$^+$ = 435.2 |
| 5.16 | [(S)-2-(4,6-Dimethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.76; [M + H]$^+$ = 415.4 |
| 5.17 | (5-Methyl-2-[1,2,3]triazol-2-yl-phenyl)-[(S)-2-methyl-2-(4-trifluoromethyl-1H-benzoimidazol-2-yl)-pyrrolidin-1-yl]-methanone. LC-MS: $t_R$ = 0.96; [M + H]$^+$ = 455.2 |
| 5.18 | [(S)-2-(4-Bromo-1H-benzoimidazol-2-yl)-2-methyl-pyrrolidin-1-yl]-(5-methyl-2-[1,2,3]triazol-2-yl-phenyl)-methanone. LC-MS: $t_R$ = 0.82; [M + H]$^+$ = 465.2 |
| 5.19 | [(S)-2-(5-Bromo-7-methyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.82; [M + H]$^+$ = 479.2 |
| 5.20 | (5-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone. LC-MS: $t_R$ = 0.82; [M + H]$^+$ = 471.2 |
| 5.21 | [(S)-2-(5,6-Dimethoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.68; [M + H]$^+$ = 447.4 |
| 5.22 | [(S)-2-(6-Fluoro-5-trifluoromethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.95; [M + H]$^+$ = 473.3 |
| 5.23 | [(S)-2-(6-Bromo-5-fluoro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.82; [M + H]$^+$ = 483.2 |
| 5.24 | [(S)-2-(6-Chloro-5-trifluoromethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 1.01; [M + H]$^+$ = 489.2 |
| 5.25 | [(S)-2-(4-Bromo-6-fluoro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.99; [M + H]$^+$ = 483.2 |
| 5.26 | [(S)-2-(4-Chloro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.79; [M + H]$^+$ = 421.2 |
| 5.27 | [(S)-2-(4,5-Difluoro-1H-benzoimidazol-2-yl)-2-methyl-pyrrolidin-1-yl]-(5-methyl-2-[1,2,3]triazol-2-yl-phenyl)-methanone. LC-MS: $t_R$ = 0.88; [M + H]$^+$ = 423.3 |
| 5.28 | [(S)-2-(4,5-Dimethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.73; [M + H]$^+$ = 415.3 |
| 5.29 | [(S)-2-(4-Isopropyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.81; [M + H]$^+$ = 429.4 |
| 5.30 | (5-Methyl-2-[1,2,3]triazol-2-yl-phenyl)-[(S)-2-methyl-2-(5-trifluoromethylsulfanyl-1H-benzoimidazol-2-yl)-pyrrolidin-1-yl]-methanone. LC-MS: $t_R$ = 0.89; [M + H]$^+$ = 487.2 |
| 5.31 | [(S)-2-(4,7-Dimethoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.72; [M + H]$^+$ = 447.3 |
| 5.32 | [(S)-2-(5-Methoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.66; [M + H]$^+$ = 417.2 |
| 5.33 | [(S)-2-(7,8-Dihydro-3H-6,9-dioxa-1,3-diaza-cyclopenta[a]naphthalen-2-yl)-2-methyl-pyrrolidin-1-yl]-(5-methyl-2-[1,2,3]triazol-2-yl-phenyl)-methanone. LC-MS: $t_R$ = 0.67; [M + H]$^+$ = 445.2 |

| Example | Compound name. LC-MS data |
|---|---|
| 5.34 | [(S)-2-(5-Chloro-4-methyl-1H-benzoimidazol-2-yl)-2-methyl-pyrrolidin-1-yl]-(5-chloro-2-[1,2,3]triazol-2-yl-phenyl)-methanone. LC-MS: $t_R$ = 0.84; [M + H]$^+$ = 455.2 |
| 5.35 | [(S)-2-(5-Chloro-4-methyl-1H-benzoimidazol-2-yl)-2-methyl-pyrrolidin-1-yl]-(2-[1,2,3]triazol-2-yl-5-trifluoromethoxy-phenyl)-methanone. LC-MS: $t_R$ = 0.88; [M + H]$^+$ = 505.2 |
| 5.36 | [(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone. LC-MS: $t_R$ = 0.78; [M + H]$^+$ = 451.3 |
| 5.37 | [(S)-2-(5-Chloro-4-methyl-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 0.79; [M + H]$^+$ = 469.3 |
| 5.38 | [(S)-2-(5-Chloro-4-methyl-1H-benzoimidazol-2-yl)-2-methyl-pyrrolidin-1-yl]-(4-methyl-2-[1,2,3]triazol-2-yl-phenyl)-methanone. LC-MS: $t_R$ = 0.77; [M + H]$^+$ = 435.2 |
| 5.39 | [(S)-2-(5-Chloro-4-methyl-1H-benzoimidazol-2-yl)-2-methyl-pyrrolidin-1-yl]-(4,5-dimethoxy-2-[1,2,3]triazol-2-yl-phenyl)-methanone. LC-MS: $t_R$ = 0.72; [M + H]$^+$ = 481.2 |
| 5.40 | [(S)-2-(5-Chloro-4-methyl-1H-benzoimidazol-2-yl)-2-methyl-pyrrolidin-1-yl]-(2-[1,2,3]triazol-2-yl-5-trifluoromethyl-phenyl)-methanone. LC-MS: $t_R$ = 0.86; [M + H]$^+$ = 489.2 |
| 5.41 | [(S)-2-(5-Chloro-4-methyl-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.82; [M + H]$^+$ = 449.2 |
| 5.42 | [(S)-2-(5-Chloro-4-methyl-1H-benzoimidazol-2-yl)-2-methyl-pyrrolidin-1-yl]-(2-pyrazol-1-yl-phenyl)-methanone. LC-MS: $t_R$ = 0.73; [M + H]$^+$ = 420.2 |
| 5.43 | [(S)-2-(5-Chloro-4-methyl-1H-benzoimidazol-2-yl)-2-methyl-pyrrolidin-1-yl]-(5-methyl-2-pyrazol-1-yl-phenyl)-methanone. LC-MS: $t_R$ = 0.78; [M + H]$^+$ = 434.2 |
| 5.44 | [(S)-2-(5-Chloro-4-methyl-1H-benzoimidazol-2-yl)-2-methyl-pyrrolidin-1-yl]-(6-methyl-3-pyrazol-1-yl-pyridin-2-yl)-methanone. LC-MS: $t_R$ = 0.71; [M + H]$^+$ = 435.2 |
| 5.45 | [(S)-2-(5-Chloro-4-methyl-1H-benzoimidazol-2-yl)-2-methyl-pyrrolidin-1-yl]-(5-fluoro-2-[1,2,3]triazol-2-yl-phenyl)-methanone. LC-MS: $t_R$ = 0.75; [M + H]$^+$ = 439.1 |
| 5.46 | [(S)-2-(5-Chloro-4-methyl-1H-benzoimidazol-2-yl)-2-methyl-pyrrolidin-1-yl]-(2-[1,2,3]triazol-2-yl-phenyl)-methanone. LC-MS: $t_R$ = 0.72; [M + H]$^+$ = 421.2 |
| 5.47 | [(S)-2-(5-Chloro-4-methyl-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.71; [M + H]$^+$ = 436.2 |
| 5.48 | [(S)-2-(5-Chloro-4-methyl-1H-benzoimidazol-2-yl)-2-methyl-pyrrolidin-1-yl]-(2-fluoro-6-[1,2,3]triazol-2-yl-phenyl)-methanone. LC-MS: $t_R$ = 0.77; [M + H]$^+$ = 439.2 |
| 5.49 | (5-Chloro-2-[1,2,3]triazol-2-yl-phenyl)-[(S)-2-methyl-2-(4-methyl-1H-benzoimidazol-2-yl)-pyrrolidin-1-yl]-methanone. LC-MS: $t_R$ = 0.71; [M + H]$^+$ = 421.2 |
| 5.50 | (5-Methoxy-2-[1,2,3]triazol-2-yl-phenyl)-[(S)-2-methyl-2-(4-methyl-1H-benzoimidazol-2-yl)-pyrrolidin-1-yl]-methanone. LC-MS: $t_R$ = 0.65; [M + H]$^+$ = 417.2 |
| 5.51 | (4,5-Dimethyl-2-[1,2,3]triazol-2-yl-phenyl)-[(S)-2-methyl-2-(4-methyl-1H-benzoimidazol-2-yl)-pyrrolidin-1-yl]-methanone. LC-MS: $t_R$ = 0.76; [M + H]$^+$ = 415.4 |
| 5.52 | [(S)-2-Methyl-2-(4-methyl-1H-benzoimidazol-2-yl)-pyrrolidin-1-yl]-(2-[1,2,3]triazol-2-yl-phenyl)-methanone. LC-MS: $t_R$ = 0.65; [M + H]$^+$ = 387.3 |
| 5.53 | (5-Chloro-2-[1,2,3]triazol-2-yl-phenyl)-[(S)-2-(5,6-dimethyl-1H-benzoimidazol-2-yl)-2-methyl-pyrrolidin-1-yl]-methanone. LC-MS: $t_R$ = 0.75; [M + H]$^+$ = 435.2 |
| 5.54 | [(S)-2-(5,6-Dimethyl-1H-benzoimidazol-2-yl)-2-methyl-pyrrolidin-1-yl]-(5-methoxy-2-[1,2,3]triazol-2-yl-phenyl)-methanone. LC-MS: $t_R$ = 0.73; [M + H]$^+$ = 431.4 |
| 5.55 | [(S)-2-(5,6-Dimethyl-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 0.7; [M + H]$^+$ = 449.3 |
| 5.56 | [(S)-2-(5,6-Dimethyl-1H-benzoimidazol-2-yl)-2-methyl-pyrrolidin-1-yl]-(4-methyl-2-[1,2,3]triazol-2-yl-phenyl)-methanone. LC-MS: $t_R$ = 0.76; [M + H]$^+$ = 415.4 |
| 5.57 | (4,5-Dimethoxy-2-[1,2,3]triazol-2-yl-phenyl)-[(S)-2-(5,6-dimethyl-1H-benzoimidazol-2-yl)-2-methyl-pyrrolidin-1-yl]-methanone. LC-MS: $t_R$ = 0.67; [M + H]$^+$ = 461.3 |
| 5.58 | [(S)-2-(5,6-Dimethyl-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.77; [M + H]$^+$ = 429.3 |
| 5.59 | [(S)-2-(5,6-Dimethyl-1H-benzoimidazol-2-yl)-2-methyl-pyrrolidin-1-yl]-(5-methyl-2-pyrazol-1-yl-phenyl)-methanone. LC-MS: $t_R$ = 0.77; [M + H]$^+$ = 414.4 |
| 5.60 | [(S)-2-(5,6-Dimethyl-1H-benzoimidazol-2-yl)-2-methyl-pyrrolidin-1-yl]-(5-fluoro-2-[1,2,3]triazol-2-yl-phenyl)-methanone. LC-MS: $t_R$ = 0.7; [M + H]$^+$ = 419.2 |
| 5.61 | [(S)-2-(5,6-Dimethyl-1H-benzoimidazol-2-yl)-2-methyl-pyrrolidin-1-yl]-(2-[1,2,3]triazol-2-yl-phenyl)-methanone. LC-MS: $t_R$ = 0.67; [M + H]$^+$ = 401.2 |
| 5.62 | [(S)-2-(5,6-Dimethyl-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.68; [M + H]$^+$ = 416.2 |
| 5.64 | (5-Chloro-2-[1,2,3]triazol-2-yl-phenyl)-[(S)-2-(5,6-dimethoxy-1H-benzoimidazol-2-yl)-2-methyl-pyrrolidin-1-yl]-methanone. LC-MS: $t_R$ = 0.69; [M + H]$^+$ = 467.2 |
| 5.65 | [(S)-2-(5,6-Dimethoxy-1H-benzoimidazol-2-yl)-2-methyl-pyrrolidin-1-yl]-(5-fluoro-2-[1,2,3]triazol-2-yl-phenyl)-methanone. LC-MS: $t_R$ = 0.63; [M + H]$^+$ = 451.3 |
| 5.66 | [(S)-2-(5,6-Dimethoxy-1H-benzoimidazol-2-yl)-2-methyl-pyrrolidin-1-yl]-(2-fluoro-6-[1,2,3]triazol-2-yl-phenyl)-methanone. LC-MS: $t_R$ = 0.61; [M + H]$^+$ = 451.3 |
| 5.67 | [(S)-2-(5,6-Dimethoxy-1H-benzoimidazol-2-yl)-2-methyl-pyrrolidin-1-yl]-(5-methoxy-2-[1,2,3]triazol-2-yl-phenyl)-methanone. LC-MS: $t_R$ = 0.64; [M + H]$^+$ = 463.3 |
| 5.68 | [(S)-2-(5,6-Dimethoxy-1H-benzoimidazol-2-yl)-2-methyl-pyrrolidin-1-yl]-(2-fluoro-3-methyl-6-[1,2,3]triazol-2-yl-phenyl)-methanone. LC-MS: $t_R$ = 0.67; [M + H]$^+$ = 465.3 |
| 5.69 | [(S)-2-(5,6-Dimethoxy-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 0.63; [M + H]$^+$ = 481.3 |
| 5.70 | [(S)-2-(5,6-Dimethoxy-1H-benzoimidazol-2-yl)-2-methyl-pyrrolidin-1-yl]-(4-methyl-2-[1,2,3]triazol-2-yl-phenyl)-methanone. LC-MS: $t_R$ = 0.67; [M + H]$^+$ = 447.3 |
| 5.71 | [(S)-2-(5,6-Dimethoxy-1H-benzoimidazol-2-yl)-2-methyl-pyrrolidin-1-yl]-(2-[1,2,3]triazol-2-yl-5-trifluoromethyl-phenyl)-methanone. LC-MS: $t_R$ = 0.75; [M + H]$^+$ = 501.3 |
| 5.72 | [(S)-2-(5,6-Dimethoxy-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.72; [M + H]$^+$ = 461.3 |
| 5.73 | [(S)-2-(5,6-Dimethoxy-1H-benzoimidazol-2-yl)-2-methyl-pyrrolidin-1-yl]-(2-[1,2,3]triazol-2-yl-phenyl)-methanone. LC-MS: $t_R$ = 0.61; [M + H]$^+$ = 433.3 |
| 5.74 | [(S)-2-(5,6-Dimethoxy-1H-benzoimidazol-2-yl)-2-methyl-pyrrolidin-1-yl]-[2-methyl-5-(4-trifluoromethyl-phenyl)-thiazol-4-yl]-methanone. LC-MS: $t_R$ = 0.85; [M + H]$^+$ = 531.3 |
| 5.75 | [(S)-2-(5,6-Dimethoxy-1H-benzoimidazol-2-yl)-2-methyl-pyrrolidin-1-yl]-(2-methyl-4-p-tolyl-thiazol-5-yl)-methanone. LC-MS: $t_R$ = 0.71; [M + H]$^+$ = 477.2 |
| 5.76 | [5-(3,5-Difluoro-phenyl)-2-methyl-thiazol-4-yl]-[(S)-2-(5,6-dimethoxy-1H-benzoimidazol-2-yl)-2-methyl-pyrrolidin-1-yl]-methanone. LC-MS: $t_R$ = 0.77; [M + H]$^+$ = 499.3 |
| 5.77 | [(S)-2-(5,6-Dimethoxy-1H-benzoimidazol-2-yl)-2-methyl-pyrrolidin-1-yl]-[5-(6-methoxy-pyridin-3-yl)-2-methyl-thiazol-4-yl]-methanone. LC-MS: $t_R$ = 0.69; [M + H]$^+$ = 494.3 |
| 5.78 | [(S)-2-(5,6-Dimethoxy-1H-benzoimidazol-2-yl)-2-methyl-pyrrolidin-1-yl]-[5-(4-fluoro-phenyl)-2-methyl-thiazol-4-yl]-methanone. LC-MS: $t_R$ = 0.75; [M + H]$^+$ = 481.2 |
| 5.79 | [5-(4-Chloro-phenyl)-2-methyl-thiazol-4-yl]-[(S)-2-(5,6-dimethoxy-1H-benzoimidazol-2-yl)-2-methyl-pyrrolidin-1-yl]-methanone. LC-MS: $t_R$ = 0.81; [M + H]$^+$ = 497.3 |
| 5.80 | [5-(3-Chloro-phenyl)-thiazol-4-yl]-[(S)-2-(5,6-dimethoxy-1H-benzoimidazol-2-yl)-2-methyl-pyrrolidin-1-yl]-methanone. LC-MS: $t_R$ = 0.74; [M + H]$^+$ = 483.2 |
| 5.81 | [(S)-2-(5,6-Dimethoxy-1H-benzoimidazol-2-yl)-2-methyl-pyrrolidin-1-yl]-(2-pyrazol-1-yl-phenyl)-methanone. LC-MS: $t_R$ = 0.61; [M + H]$^+$ = 432.3 |
| 5.82 | [(S)-2-(5,6-Dimethoxy-1H-benzoimidazol-2-yl)-2-methyl-pyrrolidin-1-yl]-(5-methyl-2-pyrazol-1-yl-phenyl)-methanone. LC-MS: $t_R$ = 0.67; [M + H]$^+$ = 446.3 |
| 5.83 | [(S)-2-(5,6-Dimethoxy-1H-benzoimidazol-2-yl)-2-methyl-pyrrolidin-1-yl]-(6-methyl-3-pyrazol-1-yl-pyridin-2-yl)-methanone. LC-MS: $t_R$ = 0.61; [M + H]$^+$ = 447.3 |
| 5.84 | [(S)-2-(5,6-Dimethoxy-1H-benzoimidazol-2-yl)-2-methyl-pyrrolidin-1-yl]-(2-[1,2,3]triazol-2-yl-5-trifluoromethoxy-phenyl)-methanone. LC-MS: $t_R$ = 0.77; [M + H]$^+$ = 517.3 |

| Example | Compound name. LC-MS data |
|---|---|
| 5.85 | [(S)-2-(5,6-Dimethoxy-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.62; [M + H]$^+$ = 448.3 |
| 5.86 | [(S)-2-(5,6-Dimethoxy-1H-benzoimidazol-2-yl)-2-methyl-pyrrolidin-1-yl]-(4,5-dimethoxy-2-[1,2,3]triazol-2-yl-phenyl)-methanone. LC-MS: $t_R$ = 0.62; [M + H]$^+$ = 493.3 |
| 5.87 | [(S)-2-(5,6-Dimethoxy-1H-benzoimidazol-2-yl)-2-methyl-pyrrolidin-1-yl]-(3'-methyl-biphenyl-2-yl)-methanone. LC-MS: $t_R$ = 0.8; [M + H]$^+$ = 456.3 |
| 5.88 | [(S)-2-(5,6-Dimethoxy-1H-benzoimidazol-2-yl)-2-methyl-pyrrolidin-1-yl]-(4'-methyl-biphenyl-2-yl)-methanone. LC-MS: $t_R$ = 0.8; [M + H]$^+$ = 456.3 |
| 5.89 | [(S)-2-(5,6-Dimethoxy-1H-benzoimidazol-2-yl)-2-methyl-pyrrolidin-1-yl]-(2-methyl-4-m-tolyl-pyrimidin-5-yl)-methanone. LC-MS: $t_R$ = 0.68; [M + H]$^+$ = 472.3 |
| 5.90 | [(S)-2-(5,6-Dimethoxy-1H-benzoimidazol-2-yl)-2-methyl-pyrrolidin-1-yl]-(4-phenyl-pyrimidin-5-yl)-methanone. LC-MS: $t_R$ = 0.59; [M + H]$^+$ = 444.3 |
| 5.91 | [(S)-2-(5,6-Dimethyl-1H-benzoimidazol-2-yl)-2-methyl-pyrrolidin-1-yl]-(4'-fluoro-4,2'-dimethyl-biphenyl-2-yl)-methanone. LC-MS: $t_R$ = 0.95; [M + H]$^+$ = 456.4 |
| 5.92 | [(S)-2-(5,6-Dimethyl-1H-benzoimidazol-2-yl)-2-methyl-pyrrolidin-1-yl]-(2'-methoxy-4-methyl-biphenyl-2-yl)-methanone. LC-MS: $t_R$ = 0.89; [M + H]$^+$ = 454.4 |
| 5.93 | [(S)-2-(5,6-Dimethyl-1H-benzoimidazol-2-yl)-2-methyl-pyrrolidin-1-yl]-(3'-methoxy-4-methyl-biphenyl-2-yl)-methanone. LC-MS: $t_R$ = 0.89; [M + H]$^+$ = 454.3 |
| 5.94 | [(S)-2-(5,6-Dimethyl-1H-benzoimidazol-2-yl)-2-methyl-pyrrolidin-1-yl]-(4'-methoxy-4-methyl-biphenyl-2-yl)-methanone. LC-MS: $t_R$ = 0.89; [M + H]$^+$ = 454.4 |
| 5.95 | [(S)-2-(5,6-Dimethyl-1H-benzoimidazol-2-yl)-2-methyl-pyrrolidin-1-yl]-(2'-fluoro-4-methyl-biphenyl-2-yl)-methanone. LC-MS: $t_R$ = 0.88; [M + H]$^+$ = 442.3 |
| 5.96 | [(S)-2-(5,6-Dimethyl-1H-benzoimidazol-2-yl)-2-methyl-pyrrolidin-1-yl]-(4'-fluoro-4-methyl-biphenyl-2-yl)-methanone. LC-MS: $t_R$ = 0.89; [M + H]$^+$ = 442.3 |
| 5.97 | [(S)-2-(5,6-Dimethyl-1H-benzoimidazol-2-yl)-2-methyl-pyrrolidin-1-yl]-(3'-fluoro-4-methyl-biphenyl-2-yl)-methanone. LC-MS: $t_R$ = 0.9; [M + H]$^+$ = 442.3 |
| 5.98 | [(S)-2-(5,6-Dimethyl-1H-benzoimidazol-2-yl)-2-methyl-pyrrolidin-1-yl]-(4,2'-dimethyl-biphenyl-2-yl)-methanone. LC-MS: $t_R$ = 0.93; [M + H]$^+$ = 438.4 |
| 5.99 | [(S)-2-(5,6-Dimethyl-1H-benzoimidazol-2-yl)-2-methyl-pyrrolidin-1-yl]-(4,3'-dimethyl-biphenyl-2-yl)-methanone. LC-MS: $t_R$ = 0.93; [M + H]$^+$ = 438.4 |
| 5.100 | [(S)-2-(5,6-Dimethyl-1H-benzoimidazol-2-yl)-2-methyl-pyrrolidin-1-yl]-(4,4'-dimethyl-biphenyl-2-yl)-methanone. LC-MS: $t_R$ = 0.93; [M + H]$^+$ = 438.4 |
| 5.101 | [(S)-2-(5,6-Dimethyl-1H-benzoimidazol-2-yl)-2-methyl-pyrrolidin-1-yl]-(3'-methoxy-biphenyl-2-yl)-methanone. LC-MS: $t_R$ = 0.83; [M + H]$^+$ = 440.3 |
| 5.102 | [(S)-2-(5,6-Dimethyl-1H-benzoimidazol-2-yl)-2-methyl-pyrrolidin-1-yl]-(4'-methoxy-biphenyl-2-yl)-methanone. LC-MS: $t_R$ = 0.82; [M + H]$^+$ = 440.3 |
| 5.103 | [(S)-2-(5,6-Dimethyl-1H-benzoimidazol-2-yl)-2-methyl-pyrrolidin-1-yl]-(2'-fluoro-biphenyl-2-yl)-methanone. LC-MS: $t_R$ = 0.82; [M + H]$^+$ = 428.3 |
| 5.104 | [(S)-2-(5,6-Dimethyl-1H-benzoimidazol-2-yl)-2-methyl-pyrrolidin-1-yl]-(4'-fluoro-biphenyl-2-yl)-methanone. LC-MS: $t_R$ = 0.83; [M + H]$^+$ = 428.3 |
| 5.105 | [(S)-2-(5,6-Dimethyl-1H-benzoimidazol-2-yl)-2-methyl-pyrrolidin-1-yl]-(3'-fluoro-biphenyl-2-yl)-methanone. LC-MS: $t_R$ = 0.83; [M + H]$^+$ = 428.3 |
| 5.106 | [(S)-2-(5,6-Dimethyl-1H-benzoimidazol-2-yl)-2-methyl-pyrrolidin-1-yl]-(3'-methyl-biphenyl-2-yl)-methanone. LC-MS: $t_R$ = 0.87; [M + H]$^+$ = 424.4 |
| 5.107 | [(S)-2-(5,6-Dimethyl-1H-benzoimidazol-2-yl)-2-methyl-pyrrolidin-1-yl]-(4'-methyl-biphenyl-2-yl)-methanone. LC-MS: $t_R$ = 0.87; [M + H]$^+$ = 424.3 |
| 5.108 | [(S)-2-(4,5-Dimethyl-1H-benzoimidazol-2-yl)-2-methyl-pyrrolidin-1-yl]-(4'-fluoro-4,2'-dimethyl-biphenyl-2-yl)-methanone. LC-MS: $t_R$ = 0.95; [M + H]$^+$ = 456.4 |
| 5.109 | [(S)-2-(4,5-Dimethyl-1H-benzoimidazol-2-yl)-2-methyl-pyrrolidin-1-yl]-(3'-fluoro-4-methyl-biphenyl-2-yl)-methanone. LC-MS: $t_R$ = 0.9; [M + H]$^+$ = 442.3 |
| 5.110 | [(S)-2-(4,5-Dimethyl-1H-benzoimidazol-2-yl)-2-methyl-pyrrolidin-1-yl]-(3'-methoxy-4-methyl-biphenyl-2-yl)-methanone. LC-MS: $t_R$ = 0.89; [M + H]$^+$ = 454.4 |
| 5.111 | [(S)-2-(4,5-Dimethyl-1H-benzoimidazol-2-yl)-2-methyl-pyrrolidin-1-yl]-(4,3'-dimethyl-biphenyl-2-yl)-methanone. LC-MS: $t_R$ = 0.93; [M + H]$^+$ = 438.4 |
| 5.112 | [(S)-2-(4,5-Dimethyl-1H-benzoimidazol-2-yl)-2-methyl-pyrrolidin-1-yl]-(4'-methoxy-4-methyl-biphenyl-2-yl)-methanone. LC-MS: $t_R$ = 0.89; [M + H]$^+$ = 454.3 |
| 5.113 | [(S)-2-(4,5-Dimethyl-1H-benzoimidazol-2-yl)-2-methyl-pyrrolidin-1-yl]-(4,4'-dimethyl-biphenyl-2-yl)-methanone. LC-MS: $t_R$ = 0.94; [M + H]$^+$ = 438.4 |
| 5.114 | [(S)-2-(4,5-Dimethyl-1H-benzoimidazol-2-yl)-2-methyl-pyrrolidin-1-yl]-(2'-fluoro-4-methyl-biphenyl-2-yl)-methanone. LC-MS: $t_R$ = 0.89; [M + H]$^+$ = 442.3 |
| 5.115 | [(S)-2-(4,5-Dimethyl-1H-benzoimidazol-2-yl)-2-methyl-pyrrolidin-1-yl]-(4'-fluoro-4-methyl-biphenyl-2-yl)-methanone. LC-MS: $t_R$ = 0.90; [M + H]$^+$ = 442.3 |
| 5.116 | [(S)-2-(4,5-Dimethyl-1H-benzoimidazol-2-yl)-2-methyl-pyrrolidin-1-yl]-(3'-fluoro-biphenyl-2-yl)-methanone. LC-MS: $t_R$ = 0.84; [M + H]$^+$ = 428.3 |
| 5.117 | [(S)-2-(4,5-Dimethyl-1H-benzoimidazol-2-yl)-2-methyl-pyrrolidin-1-yl]-(3'-methoxy-biphenyl-2-yl)-methanone. LC-MS: $t_R$ = 0.83; [M + H]$^+$ = 440.3 |
| 5.118 | [(S)-2-(4,5-Dimethyl-1H-benzoimidazol-2-yl)-2-methyl-pyrrolidin-1-yl]-(3'-methyl-biphenyl-2-yl)-methanone. LC-MS: $t_R$ = 0.88; [M + H]$^+$ = 424.3 |
| 5.119 | [(S)-2-(4,5-Dimethyl-1H-benzoimidazol-2-yl)-2-methyl-pyrrolidin-1-yl]-(4'-methoxy-biphenyl-2-yl)-methanone. LC-MS: $t_R$ = 0.83; [M + H]$^+$ = 440.3 |
| 5.120 | [(S)-2-(4,5-Dimethyl-1H-benzoimidazol-2-yl)-2-methyl-pyrrolidin-1-yl]-(4'-methyl-biphenyl-2-yl)-methanone. LC-MS: $t_R$ = 0.88; [M + H]$^+$ = 424.4 |
| 5.121 | [(S)-2-(4,5-Dimethyl-1H-benzoimidazol-2-yl)-2-methyl-pyrrolidin-1-yl]-(2'-fluoro-biphenyl-2-yl)-methanone. LC-MS: $t_R$ = 0.83; [M + H]$^+$ = 428.3 |
| 5.122 | [(S)-2-(4,5-Dimethyl-1H-benzoimidazol-2-yl)-2-methyl-pyrrolidin-1-yl]-(4'-fluoro-biphenyl-2-yl)-methanone. LC-MS: $t_R$ = 0.84; [M + H]$^+$ = 428.3 |
| 5.123 | [(S)-2-(6-Bromo-5-fluoro-1H-benzoimidazol-2-yl)-2-methyl-pyrrolidin-1-yl]-(2-fluoro-6-[1,2,3]triazol-2-yl-phenyl)-methanone. LC-MS: $t_R$ = 0.83; [M + H]$^+$ = 487.1 |
| 5.124 | [(S)-2-(6-Bromo-5-fluoro-1H-benzoimidazol-2-yl)-2-methyl-pyrrolidin-1-yl]-(2-fluoro-3-methyl-6-[1,2,3]triazol-2-yl-phenyl)-methanone. LC-MS: $t_R$ = 0.90; [M + H]$^+$ = 501.1 |
| 5.125 | [(S)-2-(6-Bromo-5-fluoro-1H-benzoimidazol-2-yl)-2-methyl-pyrrolidin-1-yl]-(4,5-dimethoxy-2-[1,2,3]triazol-2-yl-phenyl)-methanone. LC-MS: $t_R$ = 0.79; [M + H]$^+$ = 529.2 |
| 5.126 | [(S)-2-(6-Bromo-5-fluoro-1H-benzoimidazol-2-yl)-2-methyl-pyrrolidin-1-yl]-(5-fluoro-2-[1,2,3]triazol-2-yl-phenyl)-methanone. LC-MS: $t_R$ = 0.83; [M + H]$^+$ = 487.2 |
| 5.127 | [(S)-2-(6-Bromo-5-fluoro-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.90; [M + H]$^+$ = 497.2 |
| 5.128 | [(S)-2-(6-Bromo-5-fluoro-1H-benzoimidazol-2-yl)-2-methyl-pyrrolidin-1-yl]-(5-methyl-2-pyrazol-1-yl-phenyl)-methanone. LC-MS: $t_R$ = 0.86; [M + H]$^+$ = 482.2 |
| 5.129 | [(S)-2-(6-Bromo-5-fluoro-1H-benzoimidazol-2-yl)-2-methyl-pyrrolidin-1-yl]-(5-chloro-2-[1,2,3]triazol-2-yl-phenyl)-methanone. LC-MS: $t_R$ = 0.90; [M + H]$^+$ = 503.1 |
| 5.130 | [(S)-2-(6-Bromo-5-fluoro-1H-benzoimidazol-2-yl)-2-methyl-pyrrolidin-1-yl]-(4-methyl-2-[1,2,3]triazol-2-yl-phenyl)-methanone. LC-MS: $t_R$ = 0.85; [M + H]$^+$ = 483.2 |
| 5.131 | [(S)-2-(6-Bromo-5-fluoro-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.75; [M + H]$^+$ = 484.2 |
| 5.132 | [(S)-2-(6-Bromo-5-fluoro-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 0.85; [M + H]$^+$ = 517.2 |
| 5.133 | [(S)-2-(6-Chloro-5-trifluoromethyl-1H-benzoimidazol-2-yl)-2-methyl-pyrrolidin-1-yl]-(2-fluoro-6-[1,2,3]triazol-2-yl-phenyl)-methanone. LC-MS: $t_R$ = 1.04; [M + H]$^+$ = 493.2 |
| 5.134 | [(S)-2-(6-Chloro-5-trifluoromethyl-1H-benzoimidazol-2-yl)-2-methyl-pyrrolidin-1-yl]-(2-fluoro-3-methyl-6-[1,2,3]triazol-2-yl-phenyl)-methanone. LC-MS: $t_R$ = 1.14; [M + H]$^+$ = 507.2 |

| Example | Compound name. LC-MS data |
|---|---|
| 5.135 | [(S)-2-(6-Chloro-5-trifluoromethyl-1H-benzoimidazol-2-yl)-2-methyl-pyrrolidin-1-yl]-(4,5-dimethoxy-2-[1,2,3]triazol-2-yl-phenyl)-methanone. LC-MS: $t_R$ = 0.98; [M + H]$^+$ = 535.2 |
| 5.136 | [(S)-2-(6-Chloro-5-trifluoromethyl-1H-benzoimidazol-2-yl)-2-methyl-pyrrolidin-1-yl]-(5-fluoro-2-[1,2,3]triazol-2-yl-phenyl)-methanone. LC-MS: $t_R$ = 1.03; [M + H]$^+$ = 493.2 |
| 5.137 | [(S)-2-(6-Chloro-5-trifluoromethyl-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 1.09.; [M + H]$^+$ = 503.3 |
| 5.138 | [(S)-2-(6-Chloro-5-trifluoromethyl-1H-benzoimidazol-2-yl)-2-methyl-pyrrolidin-1-yl]-(5-methyl-2-pyrazol-1-yl-phenyl)-methanone. LC-MS: $t_R$ = 1.05.; [M + H]$^+$ = 488.2 |
| 5.139 | (5-Chloro-2-[1,2,3]triazol-2-yl-phenyl)-[(S)-2-(6-chloro-5-trifluoromethyl-1H-benzoimidazol-2-yl)-2-methyl-pyrrolidin-1-yl]-methanone. LC-MS: $t_R$ = 1.09; [M + H]$^+$ = 509.2 |
| 5.140 | [(S)-2-(6-Chloro-5-trifluoromethyl-1H-benzoimidazol-2-yl)-2-methyl-pyrrolidin-1-yl]-(4-methyl-2-[1,2,3]triazol-2-yl-phenyl)-methanone. LC-MS: $t_R$ = 1.05; [M + H]$^+$ = 489.2 |
| 5.141 | [(S)-2-(6-Chloro-5-trifluoromethyl-1H-benzoimidazol-2-yl)-2-methyl-pyrrolidin-1-yl]-(2-pyrazol-1-yl-phenyl)-methanone. LC-MS: $t_R$ = 1.00; [M + H]$^+$ = 474.2 |
| 5.142 | [(S)-2-(6-Chloro-5-trifluoromethyl-1H-benzoimidazol-2-yl)-2-methyl-pyrrolidin-1-yl]-(2-[1,2,3]triazol-2-yl-phenyl)-methanone. LC-MS: $t_R$ = 0.99; [M + H]$^+$ = 475.2 |
| 5.143 | [(S)-2-(6-Chloro-5-trifluoromethyl-1H-benzoimidazol-2-yl)-2-methyl-pyrrolidin-1-yl]-(6-methyl-3-pyrazol-1-yl-pyridin-2-yl)-methanone. LC-MS: $t_R$ = 0.94; [M + H]$^+$ = 489.2 |
| 5.144 | [(S)-2-(6-Chloro-5-trifluoromethyl-1H-benzoimidazol-2-yl)-2-methyl-pyrrolidin-1-yl]-(2-[1,2,3]triazol-2-yl-5-trifluoromethyl-phenyl)-methanone. LC-MS: $t_R$ = 1.12; [M + H]$^+$ = 543.2 |
| 5.145 | [(S)-2-(6-Chloro-5-trifluoromethyl-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.94; [M + H]$^+$ = 490.2 |
| 5.146 | [(S)-2-(6-Chloro-5-trifluoromethyl-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 1.05; [M + H]$^+$ = 523.2 |
| 5.147 | [(S)-2-(6-Chloro-5-trifluoromethyl-1H-benzoimidazol-2-yl)-2-methyl-pyrrolidin-1-yl]-(2-[1,2,3]triazol-2-yl-5-trifluoromethoxy-phenyl)-methanone. LC-MS: $t_R$ = 1.14; [M + H]$^+$ = 559.2 |
| 5.148 | [(S)-2-(6-Chloro-5-trifluoromethyl-1H-benzoimidazol-2-yl)-2-methyl-pyrrolidin-1-yl]-(2'-methoxy-4-methyl-biphenyl-2-yl)-methanone. LC-MS: $t_R$ = 1.18; [M + H]$^+$ = 528.2 |
| 5.149 | [(S)-2-(6-Chloro-5-trifluoromethyl-1H-benzoimidazol-2-yl)-2-methyl-pyrrolidin-1-yl]-(3'-methoxy-4-methyl-biphenyl-2-yl)-methanone. LC-MS: $t_R$ = 1.18; [M + H]$^+$ = 528.3 |
| 5.150 | [(S)-2-(6-Chloro-5-trifluoromethyl-1H-benzoimidazol-2-yl)-2-methyl-pyrrolidin-1-yl]-(4'-methoxy-4-methyl-biphenyl-2-yl)-methanone. LC-MS: $t_R$ = 1.19; [M + H]$^+$ = 528.2 |
| 5.151 | [(S)-2-(6-Chloro-5-trifluoromethyl-1H-benzoimidazol-2-yl)-2-methyl-pyrrolidin-1-yl]-(2'-fluoro-4-methyl-biphenyl-2-yl)-methanone. LC-MS: $t_R$ = 1.18; [M + H]$^+$ = 516.2 |
| 5.152 | [(S)-2-(6-Chloro-5-trifluoromethyl-1H-benzoimidazol-2-yl)-2-methyl-pyrrolidin-1-yl]-(4'-fluoro-4-methyl-biphenyl-2-yl)-methanone. LC-MS: $t_R$ = 1.19; [M + H]$^+$ = 516.2 |
| 5.153 | [(S)-2-(6-Chloro-5-trifluoromethyl-1H-benzoimidazol-2-yl)-2-methyl-pyrrolidin-1-yl]-(3'-fluoro-4-methyl-biphenyl-2-yl)-methanone. LC-MS: $t_R$ = 1.19; [M + H]$^+$ = 516.2 |
| 5.154 | [(S)-2-(6-Chloro-5-trifluoromethyl-1H-benzoimidazol-2-yl)-2-methyl-pyrrolidin-1-yl]-(4,4'-dimethyl-biphenyl-2-yl)-methanone. LC-MS: $t_R$ = 1.24; [M + H]$^+$ = 512.3 |
| 5.155 | [(S)-2-(6-Chloro-5-trifluoromethyl-1H-benzoimidazol-2-yl)-2-methyl-pyrrolidin-1-yl]-(4-methyl-3'-trifluoromethyl-biphenyl-2-yl)-methanone. LC-MS: $t_R$ = 1.25; [M + H]$^+$ = 566.2 |
| 5.156 | (2-Benzo[1,3]dioxol-5-yl-5-methyl-phenyl)-[(S)-2-(6-chloro-5-trifluoromethyl-1H-benzoimidazol-2-yl)-2-methyl-pyrrolidin-1-yl]-methanone. LC-MS: $t_R$ = 1.16; [M + H]$^+$ = 542.2 |
| 5.157 | [(S)-2-(6-Chloro-5-trifluoromethyl-1H-benzoimidazol-2-yl)-2-methyl-pyrrolidin-1-yl]-(4-methyl-4'-trifluoromethyl-biphenyl-2-yl)-methanone. LC-MS: $t_R$ = 1.26; [M + H]$^+$ = 566.2 |
| 5.158 | [(S)-2-(6-Chloro-5-trifluoromethyl-1H-benzoimidazol-2-yl)-2-methyl-pyrrolidin-1-yl]-(4-methyl-4'-trifluoromethoxy-biphenyl-2-yl)-methanone. LC-MS: $t_R$ = 1.28; [M + H]$^+$ = 582.3 |
| 5.159 | 2'-[(S)-2-(6-Chloro-5-trifluoromethyl-1H-benzoimidazol-2-yl)-2-methyl-pyrrolidine-1-carbonyl]-4'-methyl-biphenyl-3-carbonitrile. LC-MS: $t_R$ = 1.13; [M + H]$^+$ = 523.2 |
| 5.160 | 2'-[(S)-2-(6-Chloro-5-trifluoromethyl-1H-benzoimidazol-2-yl)-2-methyl-pyrrolidine-1-carbonyl]-4'-methyl-biphenyl-4-carbonitrile. LC-MS: $t_R$ = 1.13; [M + H]$^+$ = 523.3 |
| 5.161 | [(S)-2-(6-Chloro-5-trifluoromethyl-1H-benzoimidazol-2-yl)-2-methyl-pyrrolidin-1-yl]-(4,2',3'-trimethyl-biphenyl-2-yl)-methanone. LC-MS: $t_R$ = 1.27; [M + H]$^+$ = 526.3 |
| 5.162 | [(S)-2-(6-Chloro-5-trifluoromethyl-1H-benzoimidazol-2-yl)-2-methyl-pyrrolidin-1-yl]-(4'-ethoxy-4-methyl-biphenyl-2-yl)-methanone. LC-MS: $t_R$ = 1.24; [M + H]$^+$ = 542.3 |
| 5.163 | [(S)-2-(6-Chloro-5-trifluoromethyl-1H-benzoimidazol-2-yl)-2-methyl-pyrrolidin-1-yl]-(4-methyl-3'-trifluoromethoxy-biphenyl-2-yl)-methanone. LC-MS: $t_R$ = 1.27; [M + H]$^+$ = 582.2 |
| 5.164 | (2-Fluoro-6-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.82; [M + H]$^+$ = 459.2 |
| 5.165 | (5-Fluoro-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.82; [M + H]$^+$ = 459.2 |
| 5.166 | (5-Chloro-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.89; [M + H]$^+$ = 475.2 |
| 5.167 | [(S)-2-Methyl-2-(5-trifluoromethyl-1H-benzoimidazol-2-yl)-pyrrolidin-1-yl]-(2-[1,2,3]triazol-2-yl-phenyl)-methanone. LC-MS: $t_R$ = 078.; [M + H]$^+$ = 441.3 |
| 5.168 | (2-Fluoro-3-methoxy-6-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.84; [M + H]$^+$ = 489.3 |
| 5.169 | (2-Fluoro-3-methyl-6-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.89; [M + H]$^+$ = 473.3 |
| 5.170 | (4,5-Dimethyl-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.89; [M + H]$^+$ = 469.3 |
| 5.171 | (4-Methyl-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.84; [M + H]$^+$ = 455.3 |
| 5.172 | [(S)-2-Methyl-2-(5-trifluoromethyl-1H-benzoimidazol-2-yl)-pyrrolidin-1-yl]-(2-[1,2,3]triazol-2-yl-5-trifluoromethyl-phenyl)-methanone. LC-MS: $t_R$ = 0.93; [M + H]$^+$ = 509.2 |
| 5.173 | [(S)-2-Methyl-2-(5-trifluoromethyl-1H-benzoimidazol-2-yl)-pyrrolidin-1-yl]-(2-[1,2,3]triazol-2-yl-5-trifluoromethoxy-phenyl)-methanone. LC-MS: $t_R$ = 0.95; [M + H]$^+$ = 525.3 |
| 5.174 | (4,5-Dimethoxy-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.78; [M + H]$^+$ = 501.3 |
| 5.175 | (5-Methyl-2-pyrazol-1-yl-phenyl)-[(S)-2-methyl-2-(5-trifluoromethyl-1H-benzoimidazol-2-yl)-pyrrolidin-1-yl]-methanone. LC-MS: $t_R$ = 0.85; [M + H]$^+$ = 454.3 |
| 5.176 | [(S)-2-Methyl-2-(5-trifluoromethyl-1H-benzoimidazol-2-yl)-pyrrolidin-1-yl]-(2-pyrazol-1-yl-phenyl)-methanone. LC-MS: $t_R$ = 0.79; [M + H]$^+$ = 440.3 |
| 5.177 | (6-Methyl-3-pyrazol-1-yl-pyridin-2-yl)-[(S)-2-methyl-2-(5-trifluoromethyl-1H-benzoimidazol-2-yl)-pyrrolidin-1-yl]-methanone. LC-MS: $t_R$ = 0.75; [M + H]$^+$ = 455.3 |
| 5.178 | (6-Methyl-3-[1,2,3]triazol-2-yl-pyridin-2-yl)-[(S)-2-methyl-2-(5-trifluoromethyl-1H-benzoimidazol-2-yl)-pyrrolidin-1-yl]-methanone. LC-MS: $t_R$ = 0.75; [M + H]$^+$ = 456.3 |
| 5.179 | (3-Methyl-2-[1,2,3]triazol-2-yl-phenyl)-[(S)-2-methyl-2-(5-trifluoromethyl-1H-benzoimidazol-2-yl)-pyrrolidin-1-yl]-methanone. LC-MS: $t_R$ = 0.80; [M + H]$^+$ = 455.3 |
| 5.180 | 3-[(S)-2-Methyl-2-(5-trifluoromethyl-1H-benzoimidazol-2-yl)-pyrrolidine-1-carbonyl]4-[1,2,3]triazol-2-yl-benzonitrile. LC-MS: $t_R$ = 0.80; [M + H]$^+$ = 466.2 |
| 5.181 | (4'-Fluoro-4,2'-dimethyl-biphenyl-2-yl)-[(S)-2-methyl-2-(5-trifluoromethyl-1H-benzoimidazol-2-yl)-pyrrolidin-1-yl]-methanone. LC-MS: $t_R$ = 1.03; [M + H]$^+$ = 496.3 |
| 5.182 | (3'-Fluoro-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.99; [M + H]$^+$ = 482.3 |
| 5.183 | [(S)-2-Methyl-2-(5-trifluoromethyl-1H-benzoimidazol-2-yl)-pyrrolidin-1-yl]-(4-methyl-4'-trifluoromethyl-biphenyl-2-yl)-methanone. LC-MS: $t_R$ = 1.08; [M + H]$^+$ = 532.3 |
| 5.184 | (4-Methyl-3'-trifluoromethoxy-biphenyl-2-yl)-[(S)-2-methyl-2-(5-trifluoromethyl-1H-benzoimidazol-2-yl)-pyrrolidin-1-yl]-methanone. LC-MS: $t_R$ = 1.09; [M + H]$^+$ = 548.3 |

-continued

| Example | Compound name. LC-MS data |
|---|---|
| 5.185 | (2'-Methoxy-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.98; [M + H]$^+$ = 494.3 |
| 5.186 | (4,2'-Dimethyl-biphenyl-2-yl)-[(S)-2-methyl-2-(5-trifluoromethyl-1H-benzoimidazol-2-yl)-pyrrolidin-1-yl]-methanone. LC-MS: $t_R$ = 1.02; [M + H]$^+$ = 478.3 |
| 5.187 | (4-Methyl-4'-trifluoromethoxy-biphenyl-2-yl)-[(S)-2-methyl-2-(5-trifluoromethyl-1H-benzoimidazol-2-yl)-pyrrolidin-1-yl]-methanone. LC-MS: $t_R$ = 1.09; [M + H]$^+$ = 548.3 |
| 5.188 | (3'-Methoxy-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.98; [M + H]$^+$ = 494.3 |
| 5.189 | (4,3'-Dimethyl-biphenyl-2-yl)-[(S)-2-methyl-2-(5-trifluoromethyl-1H-benzoimidazol-2-yl)-pyrrolidin-1-yl]-methanone. LC-MS: $t_R$ = 1.03; [M + H]$^+$ = 478.3 |
| 5.190 | 4'-Methyl-2'-[(S)-2-methyl-2-(5-trifluoromethyl-1H-benzoimidazol-2-yl)-pyrrolidine-1-carbonyl]-biphenyl-3-carbonitrile. LC-MS: $t_R$ = 0.94; [M + H]$^+$ = 489.3 |
| 5.191 | (4'-Methoxy-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.98; [M + H]$^+$ = 494.3 |
| 5.192 | (4,4'-Dimethyl-biphenyl-2-yl)-[(S)-2-methyl-2-(5-trifluoromethyl-1H-benzoimidazol-2-yl)-pyrrolidin-1-yl]-methanone. LC-MS: $t_R$ = 1.04; [M + H]$^+$ = 478.3 |
| 5.193 | 4'-Methyl-2'-[(S)-2-methyl-2-(5-trifluoromethyl-1H-benzoimidazol-2-yl)-pyrrolidine-1-carbonyl]-biphenyl-4-carbonitrile. LC-MS: $t_R$ = 0.95; [M + H]$^+$ = 489.3 |
| 5.194 | (2'-Fluoro-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.98; [M + H]$^+$ = 482.3 |
| 5.195 | [(S)-2-Methyl-2-(5-trifluoromethyl-1H-benzoimidazol-2-yl)-pyrrolidin-1-yl]-(4-methyl-3'-trifluoromethyl-biphenyl-2-yl)-methanone. LC-MS: $t_R$ = 1.07; [M + H]$^+$ = 532.3 |
| 5.196 | [(S)-2-Methyl-2-(5-trifluoromethyl-1H-benzoimidazol-2-yl)-pyrrolidin-1-yl]-(4,2',3'-trimethyl-biphenyl-2-yl)-methanone. LC-MS: $t_R$ = 1.06; [M + H]$^+$ = 492.3 |
| 5.197 | (4'-Fluoro-4-methyl-biphenyl-2-yl)-[(S)-2-methyl-2-(5-trifluoromethyl-1H-benzoimidazol-2-yl)-pyrrolidin-1-yl]-methanone. LC-MS: $t_R$ = 0.99; [M + H]$^+$ = 482.2 |
| 5.198 | (2-Benzo[1,3]dioxol-5-yl-5-methyl-phenyl)-[(S)-2-methyl-2-(5-trifluoromethyl-1H-benzoimidazol-2-yl)-pyrrolidin-1-yl]-methanone. LC-MS: $t_R$ = 0.96; [M + H]$^+$ = 508.3 |
| 5.199 | [(S)-2-(4,5-Difluoro-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.92; [M + H]$^+$ = 437.3 |
| 5.200 | (5-Chloro-2-[1,2,3]triazol-2-yl-phenyl)-[(S)-2-(4,5-difluoro-1H-benzoimidazol-2-yl)-2-methyl-pyrrolidin-1-yl]-methanone. LC-MS: $t_R$ = 0.90; [M + H]$^+$ = 443.2 |
| 5.201 | [(S)-2-(4,5-Difluoro-1H-benzoimidazol-2-yl)-2-methyl-pyrrolidin-1-yl]-(5-methyl-2-pyrazol-1-yl-phenyl)-methanone. LC-MS: $t_R$ = 0.86; [M + H]$^+$ = 422.3 |
| 5.202 | [(S)-2-(4,5-Difluoro-1H-benzoimidazol-2-yl)-2-methyl-pyrrolidin-1-yl]-(4-methyl-2-[1,2,3]triazol-2-yl-phenyl)-methanone. LC-MS: $t_R$ = 0.86; [M + H]$^+$ = 423.3 |
| 5.203 | [(S)-2-(4,5-Difluoro-1H-benzoimidazol-2-yl)-2-methyl-pyrrolidin-1-yl]-(2-fluoro-3-methoxy-6-[1,2,3]triazol-2-yl-phenyl)-methanone. LC-MS: $t_R$ = 0.85; [M + H]$^+$ = 457.3 |
| 5.204 | [(S)-2-(4,5-Difluoro-1H-benzoimidazol-2-yl)-2-methyl-pyrrolidin-1-yl]-(5-fluoro-2-[1,2,3]triazol-2-yl-phenyl)-methanone. LC-MS: $t_R$ = 0.83; [M + H]$^+$ = 427.3 |
| 5.205 | [(S)-2-(4,5-Difluoro-1H-benzoimidazol-2-yl)-2-methyl-pyrrolidin-1-yl]-(6-methyl-3-[1,2,3]triazol-2-yl-pyridin-2-yl)-methanone. LC-MS: $t_R$ = 0.73; [M + H]$^+$ = 424.2 |
| 5.206 | [(S)-2-(4,5-Difluoro-1H-benzoimidazol-2-yl)-2-methyl-pyrrolidin-1-yl]-(2-methyl-5-phenyl-thiazol-4-yl)-methanone. LC-MS: $t_R$ = 0.90; [M + H]$^+$ = 439.2 |
| 5.207 | [5-(3-Chloro-phenyl)-2-methyl-thiazol-4-yl]-[(S)-2-(4,5-difluoro-1H-benzoimidazol-2-yl)-2-methyl-pyrrolidin-1-yl]-methanone. LC-MS: $t_R$ = 0.98; [M + H]$^+$ = 473.2 |
| 5.208 | [(S)-2-(4,5-Difluoro-1H-benzoimidazol-2-yl)-2-methyl-pyrrolidin-1-yl]-[5-(4-fluoro-phenyl)-2-methyl-thiazol-4-yl]-methanone. LC-MS: $t_R$ = 0.92; [M + H]$^+$ = 457.3 |
| 5.209 | [(S)-2-(4,5-Difluoro-1H-benzoimidazol-2-yl)-2-methyl-pyrrolidin-1-yl]-(2-methyl-5-p-tolyl-thiazol-4-yl)-methanone. LC-MS: $t_R$ = 0.97; [M + H]$^+$ = 453.3 |
| 5.210 | [(S)-2-(4,5-Difluoro-1H-benzoimidazol-2-yl)-2-methyl-pyrrolidin-1-yl]-(2-methyl-5-m-tolyl-thiazol-4-yl)-methanone. LC-MS: $t_R$ = 0.96; [M + H]$^+$ = 453.3 |
| 5.211 | [5-(4-Chloro-phenyl)-2-methyl-thiazol-4-yl]-[(S)-2-(4,5-difluoro-1H-benzoimidazol-2-yl)-2-methyl-pyrrolidin-1-yl]-methanone. LC-MS: $t_R$ = 0.99; [M + H]$^+$ = 473.2 |
| 5.212 | [(S)-2-(4,5-Difluoro-1H-benzoimidazol-2-yl)-2-methyl-pyrrolidin-1-yl]-[5-(3-fluoro-phenyl)-2-methyl-thiazol-4-yl]-methanone. LC-MS: $t_R$ = 0.92; [M + H]$^+$ = 457.2 |
| 5.213 | [(S)-2-(4,5-Difluoro-1H-benzoimidazol-2-yl)-2-methyl-pyrrolidin-1-yl]-[5-(3-methoxy-phenyl)-2-methyl-thiazol-4-yl]-methanone. LC-MS: $t_R$ = 0.91; [M + H]$^+$ = 469.3 |
| 5.214 | [(S)-2-(5-Chloro-4-methyl-1H-benzoimidazol-2-yl)-2-methyl-pyrrolidin-1-yl]-(5-methyl-2-pyrimidin-2-yl-phenyl)-methanone. LC-MS: $t_R$ = 77; [M + H]$^+$ = 446.2 |
| 5.215 | [(S)-2-(5-Chloro-4-methyl-1H-benzoimidazol-2-yl)-2-methyl-pyrrolidin-1-yl]-(5-methyl-2-pyridin-2-yl-phenyl)-methanone. LC-MS: $t_R$ = 0.75; [M + H]$^+$ = 445.2 |
| 5.216 | [(S)-2-(5-Chloro-4-methyl-1H-benzoimidazol-2-yl)-2-methyl-pyrrolidin-1-yl]-(5-methyl-2-pyridin-3-yl-phenyl)-methanone. LC-MS: $t_R$ = 0.66; [M + H]$^+$ = 445.2 |
| 5.217 | [(S)-2-(5-Chloro-4-methyl-1H-benzoimidazol-2-yl)-2-methyl-pyrrolidin-1-yl]-(5-methyl-2-pyridin-3-yl-phenyl)-methanone. LC-MS: $t_R$ = 0.7; [M + H]$^+$ = 445.3 |
| 5.218 | [(S)-2-(5-Chloro-4-methyl-1H-benzoimidazol-2-yl)-2-methyl-pyrrolidin-1-yl]-(4-fluoro-biphenyl-2-yl)-methanone. LC-MS: $t_R$ = 0.95; [M + H]$^+$ = 448.3 |
| 5.219 | [(S)-2-(5-Chloro-4-methyl-1H-benzoimidazol-2-yl)-2-methyl-pyrrolidin-1-yl]-(5-fluoro-2-pyridin-2-yl-phenyl)-methanone. LC-MS: $t_R$ = 0.8; [M + H]$^+$ = 449.3 |
| 5.220 | [(S)-2-(5-Chloro-4-methyl-1H-benzoimidazol-2-yl)-2-methyl-pyrrolidin-1-yl]-(5-fluoro-2-pyridin-3-yl-phenyl)-methanone. LC-MS: $t_R$ = 0.7; [M + H]$^+$ = 449.3 |
| 5.221 | [(S)-2-(5-Chloro-4-methyl-1H-benzoimidazol-2-yl)-2-methyl-pyrrolidin-1-yl]-(2-fluoro-6-pyridin-2-yl-phenyl)-methanone. LC-MS: $t_R$ = 0.82; [M + H]$^+$ = 449.3 |
| 5.222 | [(S)-2-(5-Chloro-4-methyl-1H-benzoimidazol-2-yl)-2-methyl-pyrrolidin-1-yl]-(2-fluoro-6-pyrimidin-2-yl-phenyl)-methanone. LC-MS: $t_R$ = 0.8; [M + H]$^+$ = 450.3 |
| 5.223 | [(S)-2-(5-Chloro-4-methyl-1H-benzoimidazol-2-yl)-2-methyl-pyrrolidin-1-yl]-(4-methyl-biphenyl-2-yl)-methanone. LC-MS: $t_R$ = 0.82; [M + H]$^+$ = 446.3 |
| 5.224 | [(S)-2-(5-Chloro-4-methyl-1H-benzoimidazol-2-yl)-2-methyl-pyrrolidin-1-yl]-(5-methyl-2-pyrimidin-2-yl-phenyl)-methanone. LC-MS: $t_R$ = 0.81; [M + H]$^+$ = 450.3 |
| 5.225 | [(S)-2-(5-Chloro-4-methyl-1H-benzoimidazol-2-yl)-2-methyl-pyrrolidin-1-yl]-(3-fluoro-biphenyl-2-yl)-methanone. LC-MS: $t_R$ = 0.94; [M + H]$^+$ = 448.3 |
| 5.226 | [(S)-2-(5-Chloro-4-methyl-1H-benzoimidazol-2-yl)-2-methyl-pyrrolidin-1-yl]-[5-(4-fluoro-phenyl)-2-phenyl-thiazol-4-yl]-methanone. LC-MS: $t_R$ = 1.09; [M + H]$^+$ = 531.3 |
| 5.227 | [2,5-Bis-(4-fluoro-phenyl)-thiazol-4-yl]-[(S)-2-(5-chloro-4-methyl-1H-benzoimidazol-2-yl)-2-methyl-pyrrolidin-1-yl]-methanone. LC-MS: $t_R$ = 1.09; [M + H]$^+$ = 549.4 |
| 5.228 | [(S)-2-(5-Chloro-4-methyl-1H-benzoimidazol-2-yl)-2-methyl-pyrrolidin-1-yl]-[5-(4-fluoro-phenyl)-2-#o!-tolyl-thiazol-4-yl]-methanone. LC-MS: $t_R$ = 1.12.; [M + H]$^+$ = 545.3 |
| 5.229 | [(S)-2-(5-Chloro-4-methyl-1H-benzoimidazol-2-yl)-2-methyl-pyrrolidin-1-yl]-[5-(4-fluoro-phenyl)-2-(2-methoxy-phenyl)-thiazol-4-yl]-methanone. LC-MS: $t_R$ = 1.09; [M + H]$^+$ = 561.3 |
| 5.230 | [(S)-2-(5-Chloro-4-methyl-1H-benzoimidazol-2-yl)-2-methyl-pyrrolidin-1-yl]-[5-(4-fluoro-phenyl)-2-m-tolyl-thiazol-4-yl]-methanone. LC-MS: $t_R$ = 1.14; [M + H]$^+$ = 545.3 |
| 5.231 | [(S)-2-(5-Chloro-4-methyl-1H-benzoimidazol-2-yl)-2-methyl-pyrrolidin-1-yl]-[5-(4-fluoro-phenyl)-2-(3-methoxy-phenyl)-thiazol-4-yl]-methanone. LC-MS: $t_R$ = 1.1; [M + H]$^+$ = 561.3 |
| 5.232 | [(S)-2-(5-Chloro-4-methyl-1H-benzoimidazol-2-yl)-2-methyl-pyrrolidin-1-yl]-[5-(4-fluoro-phenyl)-2-p-tolyl-thiazol-4-yl]-methanone. LC-MS: $t_R$ = 1.14; [M + H]$^+$ = 545.3 |
| 5.233 | [(S)-2-(5-Chloro-4-methyl-1H-benzoimidazol-2-yl)-2-methyl-pyrrolidin-1-yl]-[5-(4-fluoro-phenyl)-2-(2-fluoro-phenyl)-thiazol-4-yl]-methanone. LC-MS: $t_R$ = 1.1; [M + H]$^+$ = 549.3 |
| 5.234 | [(S)-2-(5-Chloro-4-methyl-1H-benzoimidazol-2-yl)-2-methyl-pyrrolidin-1-yl]-[5-(4-fluoro-phenyl)-2-(3-fluoro-phenyl)-thiazol-4-yl]-methanone. LC-MS: $t_R$ = 1.1; [M + H]$^+$ = 549.3 |

| Example | Compound name. LC-MS data |
|---|---|
| 5.235 | (4,5-Dimethyl-2-[1,2,3]triazol-2-yl-phenyl)-[(S)-2-methyl-2-(5-trifluoromethoxy-1H-benzoimidazol-2-yl)-pyrrolidin-1-yl]-methanone. LC-MS: $t_R$ = 0.93; [M + H]$^+$ = 485.3 |
| 5.236 | (4-Methyl-biphenyl-2-yl)-[(S)-2-methyl-2-(5-trifluoromethoxy-1H-benzoimidazol-2-yl)-pyrrolidin-1-yl]-methanone. LC-MS: $t_R$ = 1.01; [M + H]$^+$ = 480.3 |
| 5.237 | (5-Methoxy-2-[1,2,3]triazol-2-yl-phenyl)-[(S)-2-methyl-2-(5-trifluoromethoxy-1H-benzoimidazol-2-yl)-pyrrolidin-1-yl]-methanone. LC-MS: $t_R$ = 0.85; [M + H]$^+$ = 487.3 |
| 5.238 | (4-Methyl-2-[1,2,3]triazol-2-yl-phenyl)-[(S)-2-methyl-2-(5-trifluoromethoxy-1H-benzoimidazol-2-yl)-pyrrolidin-1-yl]-methanone. LC-MS: $t_R$ = 0.88; [M + H]$^+$ = 471.3 |
| 5.239 | (5-Methyl-2-pyridin-2-yl-phenyl)-[(S)-2-methyl-2-(5-trifluoromethoxy-1H-benzoimidazol-2-yl)-pyrrolidin-1-yl]-methanone. LC-MS: $t_R$ = 0.83; [M + H]$^+$ = 481.3 |
| 5.240 | (4-Methyl-2-pyridin-2-yl-phenyl)-[(S)-2-methyl-2-(5-trifluoromethoxy-1H-benzoimidazol-2-yl)-pyrrolidin-1-yl]-methanone. LC-MS: $t_R$ = 0.83; [M + H]$^+$ = 481.3 |
| 5.241 | (4-Methyl-2-pyridin-3-yl-phenyl)-[(S)-2-methyl-2-(5-trifluoromethoxy-1H-benzoimidazol-2-yl)-pyrrolidin-1-yl]-methanone. LC-MS: $t_R$ = 0.74; [M + H]$^+$ = 481.3 |
| 5.242 | (5-Methyl-biphenyl-2-yl)-[(S)-2-methyl-2-(5-trifluoromethoxy-1H-benzoimidazol-2-yl)-pyrrolidin-1-yl]-methanone. LC-MS: $t_R$ = 1.01; [M + H]$^+$ = 480.3 |
| 5.243 | (2-Methyl-5-o-tolyl-thiazol-4-yl)-[(S)-2-methyl-2-(5-trifluoromethoxy-1H-benzoimidazol-2-yl)-pyrrolidin-1-yl]-methanone. LC-MS: $t_R$ = 0.98; [M + H]$^+$ = 501.3 |
| 5.244 | [5-(2,3-Dichloro-phenyl)-2-methyl-thiazol-4-yl]-[(S)-2-methyl-2-(5-trifluoromethoxy-1H-benzoimidazol-2-yl)-pyrrolidin-1-yl]-methanone. LC-MS: $t_R$ = 1.03; [M + H]$^+$ = 555.2 |
| 5.245 | [5-(3,4-Dimethyl-phenyl)-2-methyl-thiazol-4-yl]-[(S)-2-methyl-2-(5-trifluoromethoxy-1H-benzoimidazol-2-yl)-pyrrolidin-1-yl]-methanone. LC-MS: $t_R$ = 1.03; [M + H]$^+$ = 515.3 |
| 5.246 | [5-(3,5-Difluoro-phenyl)-2-methyl-thiazol-4-yl]-[(S)-2-methyl-2-(5-trifluoromethoxy-1H-benzoimidazol-2-yl)-pyrrolidin-1-yl]-methanone. LC-MS: $t_R$ = 0.99; [M + H]$^+$ = 523.3 |
| 5.247 | [5-(3-Methoxy-phenyl)-2-methyl-thiazol-4-yl]-[(S)-2-methyl-2-(5-trifluoromethoxy-1H-benzoimidazol-2-yl)-pyrrolidin-1-yl]-methanone. LC-MS: $t_R$ = 0.95; [M + H]$^+$ = 517.3 |
| 5.248 | [5-(4-Fluoro-phenyl)-2-methyl-thiazol-4-yl]-[(S)-2-methyl-2-(5-trifluoromethoxy-1H-benzoimidazol-2-yl)-pyrrolidin-1-yl]-methanone. LC-MS: $t_R$ = 0.96; [M + H]$^+$ = 505.3 |
| 5.249 | [(S)-2-(6-Bromo-4-methyl-1H-benzoimidazol-2-yl)-2-methyl-pyrrolidin-1-yl]-[2-(3-methoxy-phenylethynyl)-phenyl]-methanone. LC-MS: $t_R$ = 1.0; [M + H]$^+$ = 528.3 |
| 5.250 | [2-(3-Methoxy-phenylethynyl)-phenyl]-[(S)-2-methyl-2-(5-trifluoromethyl-1H-benzoimidazol-2-yl)-pyrrolidin-1-yl]-methanone. LC-MS: $t_R$ = 1.05; [M + H]$^+$ = 504.4 |
| 5.251 | [(S)-2-(5-Chloro-4-methyl-1H-benzoimidazol-2-yl)-2-methyl-pyrrolidin-1-yl]-[2-(2,3-difluoro-phenyl)-5-(4-fluoro-phenyl)-thiazol-4-yl]-methanone. LC-MS: $t_R$ = 1.12; [M + H]$^+$ = 567.3 |
| 5.252 | [(S)-2-(5-Chloro-4-methyl-1H-benzoimidazol-2-yl)-2-methyl-pyrrolidin-1-yl]-[2-(4-fluoro-3-methyl-phenyl)-5-(4-fluoro-phenyl)-thiazol-4-yl]-methanone. LC-MS: $t_R$ = 1.15; [M + H]$^+$ = 563.3 |
| 5.253 | [(S)-2-(5-Chloro-4-methyl-1H-benzoimidazol-2-yl)-2-methyl-pyrrolidin-1-yl]-[2-(2-fluoro-4-methyl-phenyl)-5-(4-fluoro-phenyl)-thiazol-4-yl]-methanone. LC-MS: $t_R$ = 1.15; [M + H]$^+$ = 563.3 |
| 5.254 | [(S)-2-(5-Chloro-4-methyl-1H-benzoimidazol-2-yl)-2-methyl-pyrrolidin-1-yl]-[2-(3,4-dimethyl-phenyl)-5-(4-fluoro-phenyl)-thiazol-4-yl]-methanone. LC-MS: $t_R$ = 1.18; [M + H]$^+$ = 559.4 |
| 5.255 | 3-[4-[(S)-2-(5-Chloro-4-methyl-1H-benzoimidazol-2-yl)-2-methyl-pyrrolidine-1-carbonyl]-5-(4-fluoro-phenyl)-thiazol-2-yl]-benzonitrile. LC-MS: $t_R$ = 1.03; [M + H]$^+$ = 556.3 |
| 5.256 | [(S)-2-(5-Chloro-4-methyl-1H-benzoimidazol-2-yl)-2-methyl-pyrrolidin-1-yl]-[2-(2-chloro-phenyl)-5-(4-fluoro-phenyl)-thiazol-4-yl]-methanone. LC-MS: $t_R$ = 1.13; [M + H]$^+$ = 565.3 |
| 5.257 | [(S)-2-(5-Chloro-4-methyl-1H-benzoimidazol-2-yl)-2-methyl-pyrrolidin-1-yl]-[2-(3-chloro-phenyl)-5-(4-fluoro-phenyl)-thiazol-4-yl]-methanone. LC-MS: $t_R$ = 1.15; [M + H]$^+$ = 565.3 |
| 5.258 | [(S)-2-(5-Chloro-4-methyl-1H-benzoimidazol-2-yl)-2-methyl-pyrrolidin-1-yl]-[2-(3-chloro-4-methyl-phenyl)-5-(4-fluoro-phenyl)-thiazol-4-yl]-methanone. LC-MS: $t_R$ = 1.2; [M + H]$^+$ = 579.3 |
| 5.259 | [(S)-2-(5-Chloro-4-methyl-1H-benzoimidazol-2-yl)-2-methyl-pyrrolidin-1-yl]-[2-(4-fluoro-2-methyl-phenyl)-5-(4-fluoro-phenyl)-thiazol-4-yl]-methanone. LC-MS: $t_R$ = 1.13; [M + H]$^+$ = 563.3 |
| 5.260 | [(S)-2-(5-Chloro-4-methyl-1H-benzoimidazol-2-yl)-2-methyl-pyrrolidin-1-yl]-[2-(4-fluoro-2-methoxy-phenyl)-5-(4-fluoro-phenyl)-thiazol-4-yl]-methanone. LC-MS: $t_R$ = 1.1; [M + H]$^+$ = 579.4 |
| 5.261 | [(S)-2-(5-Chloro-4-methyl-1H-benzoimidazol-2-yl)-2-methyl-pyrrolidin-1-yl]-[2-(2,5-difluoro-phenyl)-5-(4-fluoro-phenyl)-thiazol-4-yl]-methanone. LC-MS: $t_R$ = 1.11; [M + H]$^+$ = 567.3 |
| 5.262 | (4-Bromo-biphenyl-2-yl)-[(S)-2-methyl-2-(5-trifluoromethyl-1H-benzoimidazol-2-yl)-pyrrolidin-1-yl]-methanone. LC-MS: $t_R$ = 1.08; [M + H]$^+$ = 528.2 |
| 5.263 | [(S)-2-(5-Chloro-4-methyl-1H-benzoimidazol-2-yl)-2-methyl-pyrrolidin-1-yl]-(2-methyl-5-[1,2,3]triazol-2-yl-pyridin-4-yl)-methanone. LC-MS: $t_R$ = 0.73; [M + H]$^+$ = 436.3 |
| 5.264 | [(S)-2-(5-Chloro-4-methyl-1H-benzoimidazol-2-yl)-2-methyl-pyrrolidin-1-yl]-(2-methyl-5-phenyl-pyridin-4-yl)-methanone. LC-MS: $t_R$ = 0.73; [M + H]$^+$ = 445.3 |
| 5.265 | [(S)-2-Methyl-2-(5-trifluoromethyl-1H-benzoimidazol-2-yl)-pyrrolidin-1-yl]-(4-pyridin-3-yl-biphenyl-2-yl)-methanone. LC-MS: $t_R$ = 0.82; [M + H]$^+$ = 527.3 |
| 5.266 | [(S)-2-(6-Bromo-4,5-dimethyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.89; [M + H]$^+$ = 493.3 |
| 5.267 | [(S)-2-(6-Bromo-4,5-dimethyl-1H-benzoimidazol-2-yl)-2-methyl-pyrrolidin-1-yl]-(3,4-dimethyl-2-[1,2,3]triazol-2-yl-phenyl)-methanone. LC-MS: $t_R$ = 0.88; [M + H]$^+$ = 507.3 |
| 5.268 | [(S)-2-(6-Bromo-4,5-dimethyl-1H-benzoimidazol-2-yl)-2-methyl-pyrrolidin-1-yl]-(2-fluoro-6-[1,2,3]triazol-2-yl-phenyl)-methanone. LC-MS: $t_R$ = 0.86; [M + H]$^+$ = 497.3 |
| 5.269 | Biphenyl-2-yl-[(S)-2-(6-bromo-4,5-dimethyl-1H-benzoimidazol-2-yl)-2-methyl-pyrrolidin-1-yl]-methanone. LC-MS: $t_R$ = 0.96; [M + H]$^+$ = 488.3 |
| 5.270 | [(S)-2-(6-Bromo-4,5-dimethyl-1H-benzoimidazol-2-yl)-2-methyl-pyrrolidin-1-yl]-(4-methyl-biphenyl-2-yl)-methanone. LC-MS: $t_R$ = 1.01; [M + H]$^+$ = 502.3 |
| 5.271 | [(S)-2-(6-Bromo-4,5-dimethyl-1H-benzoimidazol-2-yl)-2-methyl-pyrrolidin-1-yl]-(2-methyl-5-o-tolyl-thiazol-4-yl)-methanone. LC-MS: $t_R$ = 1.0; [M + H]$^+$ = 523.3 |
| 5.272 | [(S)-2-(6-Bromo-4,5-dimethyl-1H-benzoimidazol-2-yl)-2-methyl-pyrrolidin-1-yl]-[5-(2,3-dichloro-phenyl)-2-methyl-thiazol-4-yl]-methanone. LC-MS: $t_R$ = 1.04; [M + H]$^+$ = 577.2 |
| 5.273 | [(S)-2-(6-Bromo-4,5-dimethyl-1H-benzoimidazol-2-yl)-2-methyl-pyrrolidin-1-yl]-[5-(3,4-dimethyl-phenyl)-2-methyl-thiazol-4-yl]-methanone. LC-MS: $t_R$ = 1.04; [M + H]$^+$ = 537.3 |
| 5.274 | [(S)-2-(6-Bromo-4,5-dimethyl-1H-benzoimidazol-2-yl)-2-methyl-pyrrolidin-1-yl]-[5-(3,5-difluoro-phenyl)-2-methyl-thiazol-4-yl]-methanone. LC-MS: $t_R$ = 0.99; [M + H]$^+$ = 545.3 |
| 5.275 | [(S)-2-(6-Bromo-4,5-dimethyl-1H-benzoimidazol-2-yl)-2-methyl-pyrrolidin-1-yl]-[5-(3-methoxy-phenyl)-2-methyl-thiazol-4-yl]-methanone. LC-MS: $t_R$ = 0.96; [M + H]$^+$ = 539.3 |
| 5.276 | [(S)-2-(6-Bromo-4,5-dimethyl-1H-benzoimidazol-2-yl)-2-methyl-pyrrolidin-1-yl]-[5-(4-fluoro-phenyl)-2-methyl-thiazol-4-yl]-methanone. LC-MS: $t_R$ = 0.97; [M + H]$^+$ = 527.3 |
| 5.277 | [(S)-2-(5-Bromo-7-methyl-1H-benzoimidazol-2-yl)-2-methyl-pyrrolidin-1-yl]-(5-methyl-2-pyrimidin-2-yl-phenyl)-methanone. LC-MS: $t_R$ = 0.84; [M + H]$^+$ = 490.3 |
| 5.278 | [(S)-2-Methyl-2-(7-methyl-1H-benzoimidazol-2-yl)-pyrrolidin-1-yl]-(5-methyl-2-pyrimidin-2-yl-phenyl)-methanone. LC-MS: $t_R$ = 0.73; [M + H]$^+$ = 412.3 |
| 5.279 | [(S)-2-(6-Chloro-5-trifluoromethyl-1H-benzoimidazol-2-yl)-2-methyl-pyrrolidin-1-yl]-(5-methyl-2-pyrimidin-2-yl-phenyl)-methanone. LC-MS: $t_R$ = 1.07; [M + H]$^+$ = 500.3 |
| 5.280 | [(S)-2-(5,6-Dimethoxy-1H-benzoimidazol-2-yl)-2-methyl-pyrrolidin-1-yl]-(5-methyl-2-pyrimidin-2-yl-phenyl)-methanone. LC-MS: $t_R$ = 0.7; [M + H]$^+$ = 458.4 |
| 5.281 | (5-Methyl-2-pyrimidin-2-yl-phenyl)-[(S)-2-methyl-2-(5-trifluoromethoxy-1H-benzoimidazol-2-yl)-pyrrolidin-1-yl]-methanone. LC-MS: $t_R$ = 0.86; [M + H]$^+$ = 482.3 |
| 5.282 | [(S)-2-(6-Bromo-5-fluoro-1H-benzoimidazol-2-yl)-2-methyl-pyrrolidin-1-yl]-(5-methyl-2-pyrimidin-2-yl-phenyl)-methanone. LC-MS: $t_R$ = 0.86; [M + H]$^+$ = 494.2 |

| Example | Compound name. LC-MS data |
|---|---|
| 5.283 | [(S)-2-(6,7-Difluoro-1H-benzoimidazol-2-yl)-2-methyl-pyrrolidin-1-yl]-(5-methyl-2-pyrimidin-2-yl-phenyl)-methanone. LC-MS: $t_R$ = 0.89; [M + H]$^+$ = 434.3 |
| 5.284 | [(S)-2-(5,6-Dimethyl-1H-benzoimidazol-2-yl)-2-methyl-pyrrolidin-1-yl]-(5-methyl-2-pyrimidin-2-yl-phenyl)-methanone. LC-MS: $t_R$ = 0.77; [M + H]$^+$ = 426.4 |
| 5.285 | [(S)-2-(5-Chloro-6-trifluoromethyl-1H-benzoimidazol-2-yl)-2-methyl-pyrrolidin-1-yl]-[5-(4-fluoro-phenyl)-2-phenyl-thiazol-4-yl]-methanone. LC-MS: $t_R$ = 1.29; [M + H]$^+$ = 585.3 |
| 5.286 | [(S)-2-(5-Chloro-6-trifluoromethyl-1H-benzoimidazol-2-yl)-2-methyl-pyrrolidin-1-yl]-[5-(4-fluoro-phenyl)-2-o-tolyl-thiazol-4-yl]-methanone. LC-MS: $t_R$ = 1.32; [M + H]$^+$ = 599.3 |
| 5.287 | [(S)-2-(5-Chloro-6-trifluoromethyl-1H-benzoimidazol-2-yl)-2-methyl-pyrrolidin-1-yl]-[5-(4-fluoro-phenyl)-2-m-tolyl-thiazol-4-yl]-methanone. LC-MS: $t_R$ = 1.34; [M + H]$^+$ = 599.3 |
| 5.288 | [(S)-2-(5-Chloro-6-trifluoromethyl-1H-benzoimidazol-2-yl)-2-methyl-pyrrolidin-1-yl]-[5-(4-fluoro-phenyl)-2-p-tolyl-thiazol-4-yl]-methanone. LC-MS: $t_R$ = 1.34; [M + H]$^+$ = 599.3 |
| 5.289 | [(S)-2-(5-Chloro-6-trifluoromethyl-1H-benzoimidazol-2-yl)-2-methyl-pyrrolidin-1-yl]-[5-(4-fluoro-phenyl)-2-(2-fluoro-phenyl)-thiazol-4-yl]-methanone. LC-MS: $t_R$ = 1.31; [M + H]$^+$ = 603.3 |
| 5.290 | [(S)-2-(5-Chloro-6-trifluoromethyl-1H-benzoimidazol-2-yl)-2-methyl-pyrrolidin-1-yl]-[5-(4-fluoro-phenyl)-2-(3-fluoro-phenyl)-thiazol-4-yl]-methanone. LC-MS: $t_R$ = 1.30; [M + H]$^+$ = 603.3 |
| 5.291 | [2,5-Bis-(4-fluoro-phenyl)-thiazol-4-yl]-[(S)-2-(5-chloro-6-trifluoromethyl-1H-benzoimidazol-2-yl)-2-methyl-pyrrolidin-1-yl]-methanone. LC-MS: $t_R$ = 1.30; [M + H]$^+$ = 603.3 |
| 5.292 | [(S)-2-(5-Chloro-6-trifluoromethyl-1H-benzoimidazol-2-yl)-2-methyl-pyrrolidin-1-yl]-[5-(4-fluoro-phenyl)-2-(3-methoxy-phenyl)-thiazol-4-yl]-methanone. LC-MS: $t_R$ = 1.30; [M + H]$^+$ = 615.3 |
| 5.293 | [(S)-2-(5-Chloro-6-trifluoromethyl-1H-benzoimidazol-2-yl)-2-methyl-pyrrolidin-1-yl]-[5-(4-fluoro-phenyl)-2-(4-methoxy-phenyl)-thiazol-4-yl]-methanone. LC-MS: $t_R$ = 1.28; [M + H]$^+$ = 615.3 |
| 5.294 | [5-(4-Fluoro-phenyl)-2-(2-fluoro-phenyl)-thiazol-4-yl]-[(S)-2-methyl-2-(6-trifluoromethyl-1H-benzoimidazol-2-yl)-pyrrolidin-1-yl]-methanone. LC-MS: $t_R$ = 1.15; [M + H]$^+$ = 569.3 |
| 5.295 | 3'-[(S)-2-Methyl-2-(5-trifluoromethyl-1H-benzoimidazol-2-yl)-pyrrolidine-1-carbonyl]-4'-[1,2,3]triazol-2-yl-biphenyl-3-carbonitrile. LC-MS: $t_R$ = 0.99; [M + H]$^+$ = 542.3 |
| 5.296 | [(S)-2-(5-Chloro-4-methyl-1H-benzoimidazol-2-yl)-2-methyl-pyrrolidin-1-yl]-(3-fluoro-4,3'-dimethoxy-biphenyl-2-yl)-methanone. LC-MS: $t_R$ = 0.95; [M + H]$^+$ = 508.3 |
| 5.297 | [(S)-2-(5-Chloro-4-methyl-1H-benzoimidazol-2-yl)-2-methyl-pyrrolidin-1-yl]-(3-fluoro-4,4'-dimethoxy-biphenyl-2-yl)-methanone. LC-MS: $t_R$ = 0.93; [M + H]$^+$ = 508.3 |
| 5.298 | [(S)-2-(5-Chloro-4-methyl-1H-benzoimidazol-2-yl)-2-methyl-pyrrolidin-1-yl]-(3,2'-difluoro-4-methoxy-biphenyl-2-yl)-methanone. LC-MS: $t_R$ = 0.95; [M + H]$^+$ = 496.3 |
| 5.299 | [(S)-2-(5-Chloro-4-methyl-1H-benzoimidazol-2-yl)-2-methyl-pyrrolidin-1-yl]-(3,4'-difluoro-4-methoxy-biphenyl-2-yl)-methanone. LC-MS: $t_R$ = 0.96; [M + H]$^+$ = 496.3 |
| 5.300 | [(S)-2-(5-Chloro-4-methyl-1H-benzoimidazol-2-yl)-2-methyl-pyrrolidin-1-yl]-(3,3'-difluoro-4-methoxy-biphenyl-2-yl)-methanone. LC-MS: $t_R$ = 0.96; [M + H]$^+$ = 496.3 |
| 5.301 | [(S)-2-(5-Chloro-4-methyl-1H-benzoimidazol-2-yl)-2-methyl-pyrrolidin-1-yl]-(3-fluoro-4-methoxy-3'-methyl-biphenyl-2-yl)-methanone. LC-MS: $t_R$ = 1.00; [M + H]$^+$ = 492.3 |
| 5.302 | [(S)-2-(5-Chloro-4-methyl-1H-benzoimidazol-2-yl)-2-methyl-pyrrolidin-1-yl]-(3-fluoro-4-methoxy-4'-methyl-biphenyl-2-yl)-methanone. LC-MS: $t_R$ = 1.01; [M + H]$^+$ = 492.3 |
| 5.303 | [(S)-2-(5-Chloro-4-methyl-1H-benzoimidazol-2-yl)-2-methyl-pyrrolidin-1-yl]-(3-fluoro-4-methoxy-3'-trifluoromethyl-biphenyl-2-yl)-methanone. LC-MS: $t_R$ = 1.05; [M + H]$^+$ = 546.3 |
| 5.304 | (6-Benzo[1,3]dioxol-5-yl-2-fluoro-3-methoxy-phenyl)-[(S)-2-(5-chloro-4-methyl-1H-benzoimidazol-2-yl)-2-methyl-pyrrolidin-1-yl]-methanone. LC-MS: $t_R$ = 0.93; [M + H]$^+$ = 522.3 |
| 5.305 | [(S)-2-(5-Chloro-4-methyl-1H-benzoimidazol-2-yl)-2-methyl-pyrrolidin-1-yl]-(3-fluoro-4-methoxy-4'-trifluoromethyl-biphenyl-2-yl)-methanone. LC-MS: $t_R$ = 1.06; [M + H]$^+$ = 546.3 |
| 5.306 | [(S)-2-(5-Chloro-4-methyl-1H-benzoimidazol-2-yl)-2-methyl-pyrrolidin-1-yl]-(3-fluoro-4-methoxy-4'-trifluoromethoxy-biphenyl-2-yl)-methanone. LC-MS: $t_R$ = 1.07; [M + H]$^+$ = 562.4 |
| 5.307 | 2'-[(S)-2-(5-Chloro-4-methyl-1H-benzoimidazol-2-yl)-2-methyl-pyrrolidine-1-carbonyl]-3'-fluoro-4'-methoxy-biphenyl-3-carbonitrile. LC-MS: $t_R$ = 0.92; [M + H]$^+$ = 503.3 |
| 5.308 | 2'-[(S)-2-(5-Chloro-4-methyl-1H-benzoimidazol-2-yl)-2-methyl-pyrrolidine-1-carbonyl]-3'-fluoro-4'-methoxy-biphenyl-4-carbonitrile. LC-MS: $t_R$ = 0.93; [M + H]$^+$ = 503.3 |
| 5.309 | [(S)-2-(5-Chloro-4-methyl-1H-benzoimidazol-2-yl)-2-methyl-pyrrolidin-1-yl]-(3-fluoro-4-methoxy-3'-trifluoromethoxy-biphenyl-2-yl)-methanone. LC-MS: $t_R$ = 1.07; [M + H]$^+$ = 562.3 |
| 5.310 | [(S)-2-(6-Bromo-4-methyl-1H-benzoimidazol-2-yl)-2-methyl-pyrrolidin-1-yl]-(2-methyl-5-phenyl-pyridin-4-yl)-methanone. LC-MS: $t_R$ = 0.75; [M + H]$^+$ = 489.3 |
| 6.1 | [5-(4-Fluoro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.74; [M + H]$^+$ = 449.2 |
| 6.2 | [(S)-2-(5-Methoxy-1H-benzoimidazol-2-yl)4-methylene-pyrrolidin-1-yl]-[5-(4-methoxy-phenyl)-2-methyl-thiazol-4-yl]-methanone. LC-MS: $t_R$ = 0.73; [M + H]$^+$ = 461.2 |
| 6.3 | [(S)-2-(5-Methoxy-1H-benzoimidazol-2-yl)4-methylene-pyrrolidin-1-yl]-(2-methyl-5-phenyl-thiazol-4-yl)-methanone. LC-MS: $t_R$ = 0.72; [M + H]$^+$ = 431.2 |
| 6.4 | [(S)-2-(5-Methoxy-1H-benzoimidazol-2-yl)4-methylene-pyrrolidin-1-yl]-(3-p-tolyl-pyrazin-2-yl)-methanone. LC-MS: $t_R$ = 0.67; [M + H]$^+$ = 426.2 |
| 6.5 | [5-(4-Chloro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.79; [M + H]$^+$ = 465.2 |
| 6.6 | [(S)-2-(5-Methoxy-1H-benzoimidazol-2-yl)4-methylene-pyrrolidin-1-yl]-(3-m-tolyl-pyrazin-2-yl)-methanone. LC-MS: $t_R$ = 0.67; [M + H]$^+$ = 426.2 |
| 6.7 | [(S)-2-(5-Methoxy-1H-benzoimidazol-2-yl)4-methylene-pyrrolidin-1-yl]-(2-methyl-5-m-tolyl-thiazol-4-yl)-methanone. LC-MS: $t_R$ = 0.77; [M + H]$^+$ = 445.2 |
| 6.8 | [5-(3-Chloro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.79; [M + H]$^+$ = 465.1 |
| 6.9 | [5-(3,4-Dimethyl-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.81; [M + H]$^+$ = 459.3 |
| 6.10 | (2-Cyclopropyl-5-phenyl-thiazol-4-yl)-[(S)-2-(5-methoxy-1H-benzoimidazol-2-yl)-4-methylene-pyrrolidin-1-yl]-methanone. LC-MS: $t_R$ = 0.80; [M + H]$^+$ = 457.2 |
| 6.11 | [(S)-2-(5-Methoxy-1H-benzoimidazol-2-yl)4-methylene-pyrrolidin-1-yl]-(2-methyl-4-m-tolyl-pyrimidin-5-yl)-methanone. LC-MS: $t_R$ = 0.68; [M + H]$^+$ = 440.2 |
| 6.12 | [(S)-2-(5-Methoxy-1H-benzoimidazol-2-yl)4-methylene-pyrrolidin-1-yl]-(5-methyl-2-[1,2,3]triazol-2-yl-phenyl)-methanone. LC-MS: $t_R$ = 0.67; [M + H]$^+$ = 415.2 |
| 6.13 | [(S)-2-(5-Methoxy-1H-benzoimidazol-2-yl)4-methylene-pyrrolidin-1-yl]-(2-[1,2,3]triazol-2-yl-phenyl)-methanone. LC-MS: $t_R$ = 0.61; [M + H]$^+$ = 401.2 |
| 6.14 | [(S)-2-(5-Methoxy-1H-benzoimidazol-2-yl)4-methylene-pyrrolidin-1-yl]-(3'-methyl-biphenyl-2-yl)-methanone. LC-MS: $t_R$ = 0.79; [M + H]$^+$ = 424.2 |
| 6.15 | [(S)-2-(5-Methoxy-1H-benzoimidazol-2-yl)4-methylene-pyrrolidin-1-yl]-(4'-methyl-biphenyl-2-yl)-methanone. LC-MS: $t_R$ = 0.79; [M + H]$^+$ = 424.2 |
| 6.16 | [(S)-2-(5-Methoxy-1H-benzoimidazol-2-yl)4-methylene-pyrrolidin-1-yl]-(2-methyl-4-phenyl-pyrimidin-5-yl)-methanone. LC-MS: $t_R$ = 0.62; [M + H]$^+$ = 426.2 |
| 6.17 | [(S)-2-(5-Methoxy-1H-benzoimidazol-2-yl)4-methylene-pyrrolidin-1-yl]-(4-m-tolyl-pyrimidin-5-yl)-methanone. LC-MS: $t_R$ = 0.64; [M + H]$^+$ = 426.3 |
| 6.18 | (5-Fluoro-2-[1,2,3]triazol-2-yl-phenyl)-[(S)-2-(5-methoxy-1H-benzoimidazol-2-yl)-4-methylene-pyrrolidin-1-yl]-methanone. LC-MS: $t_R$ = 0.64; [M + H]$^+$ = 419.2 |
| 6.19 | (2-Fluoro-6-[1,2,3]triazol-2-yl-phenyl)-[(S)-2-(5-methoxy-1H-benzoimidazol-2-yl)-4-methylene-pyrrolidin-1-yl]-methanone. LC-MS: $t_R$ = 0.63; [M + H]$^+$ = 419.2 |

| Example | Compound name. LC-MS data |
|---|---|
| 6.20 | [(S)-2-(5-Methoxy-1H-benzoimidazol-2-yl)4-methylene-pyrrolidin-1-yl]-[2-(3-methyl-[1,2,4]oxadiazol-5-yl)-phenyl]-methanone. LC-MS: $t_R$ = 0.62; [M + H]$^+$ = 416.2 |
| 6.21 | [(S)-2-(5-Methoxy-1H-benzoimidazol-2-yl)4-methylene-pyrrolidin-1-yl]-[2-(2-methyl-thiazol-4-yl)-phenyl]-methanone. LC-MS: $t_R$ = 0.67; [M + H]$^+$ = 431.2 |
| 6.22 | [5-(4-Bromo-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.80; [M + H]$^+$ = 509.1 |
| 6.23 | [5-(2,3-Dichloro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.84; [M + H]$^+$ = 499.2 |
| 6.24 | [5-(3-Bromo-4-fluoro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.81; [M + H]$^+$ = 527.1 |
| 6.25 | [2-Cyclopropyl-5-(3-fluoro-4-methyl-phenyl)-thiazol-4-yl]-[(S)-2-(5-methoxy-1H-benzoimidazol-2-yl)4-methylene-pyrrolidin-1-yl]-methanone. LC-MS: $t_R$ = 0.87; [M + H]$^+$ = 489.2 |
| 6.26 | (2-Cyclopropyl-5-m-tolyl-thiazol-4-yl)-[(S)-2-(5-methoxy-1H-benzoimidazol-2-yl)-4-methylene-pyrrolidin-1-yl]-methanone. LC-MS: $t_R$ = 0.85; [M + H]$^+$ = 471.3 |
| 6.27 | [2-Dimethylamino-5-(3,4-dimethyl-phenyl)-thiazol-4-yl]-[(S)-2-(5-methoxy-1H-benzoimidazol-2-yl)-4-methylene-pyrrolidin-1-yl]-methanone. LC-MS: $t_R$ = 0.85; [M + H]$^+$ = 488.3 |
| 6.28 | [5-(3-Bromo-phenyl)-2-cyclopropyl-thiazol-4-yl]-[(S)-2-(5-methoxy-1H-benzoimidazol-2-yl)-4-methylene-pyrrolidin-1-yl]-methanone. LC-MS: $t_R$ = 0.88; [M + H]$^+$ = 535.1 |
| 6.29 | [5-(3-Fluoro-phenyl)-2-pyrrolidin-1-yl-thiazol-4-yl]-[(S)-2-(5-methoxy-1H-benzoimidazol-2-yl)-4-methylene-pyrrolidin-1-yl]-methanone. LC-MS: $t_R$ = 0.86; [M + H]$^+$ = 504.3 |
| 6.30 | [(S)-2-(5-Methoxy-1H-benzoimidazol-2-yl)4-methylene-pyrrolidin-1-yl]-[2-methyl-5-(3-trifluoromethyl-phenyl)-thiazol-4-yl]-methanone. LC-MS: $t_R$ = 0.83; [M + H]$^+$ = 499.2 |
| 6.31 | [2-Cyclopropyl-5-(3-methoxy-phenyl)-thiazol-4-yl]-[(S)-2-(5-methoxy-1H-benzoimidazol-2-yl)-4-methylene-pyrrolidin-1-yl]-methanone. LC-MS: $t_R$ = 0.81; [M + H]$^+$ = 487.2 |
| 6.32 | [5-(3-Chloro-phenyl)-thiazol-4-yl]-[(S)-2-(5-methoxy-1H-benzoimidazol-2-yl)-4-methylene-pyrrolidin-1-yl]-methanone. LC-MS: $t_R$ = 0.74; [M + H]$^+$ = 451.1 |
| 6.33 | [5-(3-Fluoro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.74; [M + H]$^+$ = 449.2 |
| 6.34 | [5-(2-Chloro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.79; [M + H]$^+$ = 465.2 |
| 6.35 | (2-Cyclopropyl-5-p-tolyl-thiazol-4-yl)-[(S)-2-(5-methoxy-1H-benzoimidazol-2-yl)-4-methylene-pyrrolidin-1-yl]-methanone. LC-MS: $t_R$ = 0.85; [M + H]$^+$ = 471.3 |
| 6.36 | [2-(3,4-Dimethyl-phenyl)-5-methyl-thiophen-3-yl]-[(S)-2-(5-methoxy-1H-benzoimidazol-2-yl)-4-methylene-pyrrolidin-1-yl]-methanone. LC-MS: $t_R$ = 0.86; [M + H]$^+$ = 458.2 |
| 6.37 | [5-(3,5-Difluoro-phenyl)-2-methyl-thiazol-4-yl]-[(S)-2-(5-methoxy-1H-benzoimidazol-2-yl)-4-methylene-pyrrolidin-1-yl]-methanone. LC-MS: $t_R$ = 0.76; [M + H]$^+$ = 467.2 |
| 6.38 | [(S)-2-(5-Methoxy-1H-benzoimidazol-2-yl)4-methylene-pyrrolidin-1-yl]-(2-m-tolyl-thiophen-3-yl)-methanone. LC-MS: $t_R$ = 0.77; [M + H]$^+$ = 430.1 |
| 6.39 | [2-(3,4-Dimethyl-phenyl)-thiophen-3-yl]-[(S)-2-(5-methoxy-1H-benzoimidazol-2-yl)-4-methylene-pyrrolidin-1-yl]-methanone. LC-MS: $t_R$ = 0.81; [M + H]$^+$ = 444.2 |
| 6.40 | [(S)-2-(4-Methyl-1H-benzoimidazol-2-yl)-4-methylene-pyrrolidin-1-yl]-(2-methyl-5-phenyl-thiazol-4-yl)-methanone. LC-MS: $t_R$ = 0.74; [M + H]$^+$ = 415.2 |
| 6.41 | [(S)-2-(5-Chloro-4-methyl-1H-benzoimidazol-2-yl)-4-methylene-pyrrolidin-1-yl]-(2-methyl-5-phenyl-thiazol-4-yl)-methanone. LC-MS: $t_R$ = 0.86; [M + H]$^+$ = 449.2 |
| 6.42 | [(S)-2-(5-Chloro-4-methyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.80; [M + H]$^+$ = 433.2 |
| 6.43 | [(S)-2-(1H-Benzoimidazol-2-yl)-4-methylene-pyrrolidin-1-yl]-[5-(3-chloro-phenyl)-2-methyl-thiazol-4-yl]-methanone. LC-MS: $t_R$ = 0.78; [M + H]$^+$ = 435.1 |
| 6.44 | [5-(3-Chloro-phenyl)-2-methyl-thiazol-4-yl]-[(S)-2-(4-methyl-1H-benzoimidazol-2-yl)-4-methylene-pyrrolidin-1-yl]-methanone. LC-MS: $t_R$ = 0.81; [M + H]$^+$ = 449.2 |
| 6.45 | [(S)-2-(5-Chloro-4-methyl-1H-benzoimidazol-2-yl)-4-methylene-pyrrolidin-1-yl]-[5-(3-chloro-phenyl)-2-methyl-thiazol-4-yl]-methanone. LC-MS: $t_R$ = 0.93; [M + H]$^+$ = 483.1 |
| 6.46 | [5-(3,4-Dimethyl-phenyl)-2-methyl-thiazol-4-yl]-[(S)-2-(6-methoxy-1H-benzoimidazol-2-yl)-4-methylene-pyrrolidin-1-yl]-methanone. LC-MS: $t_R$ = 0.81; [M + H]$^+$ = 459.2 |
| 6.47 | [(S)-2-(4,5-Dimethyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.86; [M + H]$^+$ = 457.2 |
| 6.48 | [(S)-2-(4,7-Dimethoxy-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.85; [M + H]$^+$ = 489.3 |
| 6.49 | [5-(3,4-Dimethyl-phenyl)-2-methyl-thiazol-4-yl]-[(S)-4-methylene-2-(4-methylsulfanyl-1H-benzoimidazol-2-yl)-pyrrolidin-1-yl]-methanone. LC-MS: $t_R$ = 0.88; [M + H]$^+$ = 475.3 |
| 6.50 | [(S)-2-(4-Bromo-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.97; [M + H]$^+$ = 507.2 |
| 6.51 | [(S)-2-(4-Chloro-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.96; [M + H]$^+$ = 463.2 |
| 6.52 | [5-(3,4-Dimethyl-phenyl)-2-methyl-thiazol-4-yl]-[(S)-4-methylene-2-(5-methylsulfanyl-1H-benzoimidazol-2-yl)-pyrrolidin-1-yl]-methanone. LC-MS: $t_R$ = 0.86; [M + H]$^+$ = 475.3 |
| 6.53 | [5-(3,4-Dimethyl-phenyl)-2-methyl-thiazol-4-yl]-[(S)-2-(4-methyl-1H-benzoimidazol-2-yl)-4-methylene-pyrrolidin-1-yl]-methanone. LC-MS: $t_R$ = 0.83; [M + H]$^+$ = 443.2 |
| 6.54 | [(S)-2-(5-Chloro-4-methyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.94; [M + H]$^+$ = 477.2 |
| 6.55 | [(S)-2-(5-Chloro-6-methyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.92; [M + H]$^+$ = 477.2 |
| 6.56 | [(S)-2-(5,6-Dimethyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.86; [M + H]$^+$ = 457.3 |
| 6.57 | [(S)-2-(5-tert-Butyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.95; [M + H]$^+$ = 485.3 |
| 6.58 | [(S)-2-(4,6-Dimethyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 0.87; [M + H]$^+$ = 457.2 |
| 6.59 | [(S)-4-Methylene-2-(7-methylsulfanyl-1H-benzoimidazol-2-yl)-pyrrolidin-1-yl]-(5-methyl-2-[1,2,3]triazol-2-yl-phenyl)-methanone. LC-MS: $t_R$ = 0.74; [M + H]$^+$ = 431.2 |
| 6.60 | [(S)-4-Methylene-2-(5-methylsulfanyl-1H-benzoimidazol-2-yl)-pyrrolidin-1-yl]-(5-methyl-2-[1,2,3]triazol-2-yl-phenyl)-methanone. LC-MS: $t_R$ = 0.73; [M + H]$^+$ = 431.2 |
| 6.61 | [(S)-2-(5,6-Dimethyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.73; [M + H]$^+$ = 413.2 |
| 6.62 | [(S)-2-(4,6-Dimethyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.72; [M + H]$^+$ = 413.2 |
| 6.63 | [(S)-2-(4,5-Dimethyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.72; [M + H]$^+$ = 413.2 |
| 6.64 | [(S)-2-(4-Bromo-1H-benzoimidazol-2-yl)-4-methylene-pyrrolidin-1-yl]-(5-methyl-2-[1,2,3]triazol-2-yl-phenyl)-methanone. LC-MS: $t_R$ = 0.84; [M + H]$^+$ = 463.1 |
| 6.65 | [(S)-2-(5-Chloro-6-methyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.80; [M + H]$^+$ = 433.2 |
| 6.66 | [(S)-2-(5-tert-Butyl-1H-benzoimidazol-2-yl)-4-methylene-pyrrolidin-1-yl]-(5-methyl-2-[1,2,3]triazol-2-yl-phenyl)-methanone. LC-MS: $t_R$ = 0.82; [M + H]$^+$ = 441.3 |
| 6.67 | [(S)-2-(5-Chloro-6-trifluoromethyl-1H-benzoimidazol-2-yl)-4-methylene-pyrrolidin-1-yl]-(5-methyl-2-[1,2,3]triazol-2-yl-phenyl)-methanone. LC-MS: $t_R$ = 1.05; [M + H]$^+$ = 487.2 |
| 6.68 | [(S)-2-(4,7-Dimethoxy-1H-benzoimidazol-2-yl)-4-methylene-pyrrolidin-1-yl]-(5-methyl-2-[1,2,3]triazol-2-yl-phenyl)-methanone. LC-MS: $t_R$ = 0.73; [M + H]$^+$ = 445.2 |
| 6.69 | [(S)-2-(7-Chloro-1H-benzoimidazol-2-yl)-4-methylene-pyrrolidin-1-yl]-(5-methyl-2-[1,2,3]triazol-2-yl-phenyl)-methanone. LC-MS: $t_R$ = 0.82; [M + H]$^+$ = 419.1 |

| Example | Compound name. LC-MS data |
|---|---|
| 6.71 | rac-[2-(3,4-Dimethyl-phenyl)-5-methyl-thiophen-3-yl]-[2-(5-methoxy-1H-benzoimidazol-2-yl)-4-methylene-pyrrolidin-1-yl]-methanone. LC-MS: $t_R$ = 0.86; [M + H]$^+$ = 458.2 |
| 6.72 | rac-[2-(3,4-Dimethyl-phenyl)-5-methyl-thiophen-3-yl]-[4-methylene-2-(7-methylsulfanyl-1H-benzoimidazol-2-yl)-pyrrolidin-1-yl]-methanone. LC-MS: $t_R$ = 0.94; [M + H]$^+$ = 474.2 |
| 6.73 | rac-[2-(3,4-Dimethyl-phenyl)-5-methyl-thiophen-3-yl]-[4-methylene-2-(5-methylsulfanyl-1H-benzoimidazol-2-yl)-pyrrolidin-1-yl]-methanone. LC-MS: $t_R$ = 0.92; [M + H]$^+$ = 474.2 |
| 6.74 | rac-[2-(5-Chloro-4-methyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.99; [M + H]$^+$ = 476.2 |
| 6.75 | rac-[2-(5,6-Dimethyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.76; [M + H]$^+$ = 456.1 |
| 6.76 | rac-[2-(4,6-Dimethyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.91; [M + H]$^+$ = 456.3 |
| 6.77 | rac-[2-(4,5-Dimethyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.90; [M + H]$^+$ = 456.2 |
| 6.78 | rac-[2-(4-Bromo-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 1.06; [M + H]$^+$ = 506.2 |
| 6.79 | rac-[2-(3,4-Dimethyl-phenyl)-5-methyl-thiophen-3-yl]-[2-(4-methyl-1H-benzoimidazol-2-yl)-4-methylene-pyrrolidin-1-yl]-methanone. LC-MS: $t_R$ = 0.88; [M + H]$^+$ = 442.2 |
| 6.80 | rac-[2-(5-Chloro-6-methyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 1.00; [M + H]$^+$ = 476.2 |
| 6.81 | rac-[2-(5-tert-Butyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.99; [M + H]$^+$ = 484.3 |
| 6.82 | rac-[2-(5-Chloro-6-trifluoromethyl-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 1.24; [M + H]$^+$ = 530.2 |
| 6.83 | rac-[2-(4,7-Dimethoxy-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 0.90; [M + H]$^+$ = 488.3 |
| 6.84 | rac-[2-(7-Chloro-1H-benzoimidazol-2-yl)-4-methylene-pyrrolidin-1-yl]-[2-(3,4-dimethyl-phenyl)-5-methyl-thiophen-3-yl]-methanone. LC-MS: $t_R$ = 1.04; [M + H]$^+$ = 462.2 |
| 6.85 | rac-[2-(3,4-Dimethyl-phenyl)-5-methyl-thiophen-3-yl]-[4-methylene-2-(1H-naphtho[2,3-d]imidazol-2-yl)-pyrrolidin-1-yl]-methanone. LC-MS: $t_R$ = 0.94; [M + H]$^+$ = 478.3 |
| 6.86 | rac-(2-Cyclopropyl-5-m-tolyl-thiazol-4-yl)-[2-(5-methoxy-1H-benzoimidazol-2-yl)-4-methylene-pyrrolidin-1-yl]-methanone. LC-MS: $t_R$ = 0.85; [M + H]$^+$ = 471.3 |
| 6.87 | rac-(2-Cyclopropyl-5-m-tolyl-thiazol-4-yl)-[4-methylene-2-(7-methylsulfanyl-1H-benzoimidazol-2-yl)-pyrrolidin-1-yl]-methanone. LC-MS: $t_R$ = 0.92; [M + H]$^+$ = 487.2 |
| 6.88 | rac-(2-Cyclopropyl-5-m-tolyl-thiazol-4-yl)-[4-methylene-2-(5-methylsulfanyl-1H-benzoimidazol-2-yl)-pyrrolidin-1-yl]-methanone. LC-MS: $t_R$ = 0.90; [M + H]$^+$ = 487.2 |
| 6.89 | rac-[2-(5-Chloro-4-methyl-1H-benzoimidazol-2-yl)-4-methylene-pyrrolidin-1-yl]-(2-cyclopropyl-5-m-tolyl-thiazol-4-yl)-methanone. LC-MS: $t_R$ = 0.97; [M + H]$^+$ = 489.2 |
| 6.90 | rac-(2-Cyclopropyl-5-m-tolyl-thiazol-4-yl)-[2-(5,6-dimethyl-1H-benzoimidazol-2-yl)-4-methylene-pyrrolidin-1-yl]-methanone. LC-MS: $t_R$ = 0.90; [M + H]$^+$ = 469.3 |
| 6.91 | rac-(2-Cyclopropyl-5-m-tolyl-thiazol-4-yl)-[2-(4,6-dimethyl-1H-benzoimidazol-2-yl)-4-methylene-pyrrolidin-1-yl]-methanone. LC-MS: $t_R$ = 0.91; [M + H]$^+$ = 469.3 |
| 6.92 | rac-(2-Cyclopropyl-5-m-tolyl-thiazol-4-yl)-[2-(4,5-dimethyl-1H-benzoimidazol-2-yl)-4-methylene-pyrrolidin-1-yl]-methanone. LC-MS: $t_R$ = 0.90; [M + H]$^+$ = 469.3 |
| 6.93 | rac-[2-(4-Bromo-1H-benzoimidazol-2-yl)-4-methylene-pyrrolidin-1-yl]-(2-cyclopropyl-5-m-tolyl-thiazol-4-yl)-methanone. LC-MS: $t_R$ = 1.01; [M + H]$^+$ = 519.1 |
| 6.94 | rac-(2-Cyclopropyl-5-m-tolyl-thiazol-4-yl)-[2-(4-methyl-1H-benzoimidazol-2-yl)-4-methylene-pyrrolidin-1-yl]-methanone. LC-MS: $t_R$ = 0.87; [M + H]$^+$ = 455.3 |
| 6.95 | rac-[2-(5-Chloro-6-methyl-1H-benzoimidazol-2-yl)-4-methylene-pyrrolidin-1-yl]-(2-cyclopropyl-5-m-tolyl-thiazol-4-yl)-methanone. LC-MS: $t_R$ = 0.96; [M + H]$^+$ = 489.2 |
| 6.96 | rac-[2-(5-tert-Butyl-1H-benzoimidazol-2-yl)-4-methylene-pyrrolidin-1-yl]-(2-cyclopropyl-5-m-tolyl-thiazol-4-yl)-methanone. LC-MS: $t_R$ = 0.98; [M + H]$^+$ = 497.3 |
| 6.97 | rac-[2-(5-Chloro-6-trifluoromethyl-1H-benzoimidazol-2-yl)4-methylene-pyrrolidin-1-yl]-(2-cyclopropyl-5-m-tolyl-thiazol-4-yl)-methanone. LC-MS: $t_R$ = 1.19; [M + H]$^+$ = 543.1 |
| 6.98 | rac-(2-Cyclopropyl-5-m-tolyl-thiazol-4-yl)-[2-(4,7-dimethoxy-1H-benzoimidazol-2-yl)-4-methylene-pyrrolidin-1-yl]-methanone. LC-MS: $t_R$ = 0.89; [M + H]$^+$ = 501.3 |
| 6.99 | rac-[2-(7-Chloro-1H-benzoimidazol-2-yl)-4-methylene-pyrrolidin-1-yl]-(2-cyclopropyl-5-m-tolyl-thiazol-4-yl)-methanone. LC-MS: $t_R$ = 1.00; [M + H]$^+$ = 475.2 |
| 6.100 | [5-(4-Bromo-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.83; [M + H]$^+$ = 493.2 |
| 6.101 | [(S)-2-(7-Methyl-1H-benzoimidazol-2-yl)-4-methylene-pyrrolidin-1-yl]-(2-methyl-5-m-tolyl-thiazol-4-yl)-methanone. LC-MS: $t_R$ = 0.80; [M + H]$^+$ = 429.2 |
| 6.102 | (5-Chloro-2-[1,2,3]triazol-2-yl-phenyl)-[(S)-2-(7-methyl-1H-benzoimidazol-2-yl)-4-methylene-pyrrolidin-1-yl]-methanone. LC-MS: $t_R$ = 0.71; [M + H]$^+$ = 419.2 |
| 6.103 | [5-(6-Methoxy-pyridin-3-yl)-2-methyl-thiazol-4-yl]-[(S)-2-(7-methyl-1H-benzoimidazol-2-yl)4-methylene-pyrrolidin-1-yl]-methanone. LC-MS: $t_R$ = 0.71; [M + H]$^+$ = 446.2 |
| 6.104 | [5-(3-Bromo-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.83; [M + H]$^+$ = 493.1 |
| 6.105 | [(S)-2-(7-Methyl-1H-benzoimidazol-2-yl)-4-methylene-pyrrolidin-1-yl]-(6-methyl-3-pyrazol-1-yl-pyridin-2-yl)-methanone. LC-MS: $t_R$ = 0.65; [M + H]$^+$ = 399.2 |
| 6.106 | [5-(4-Fluoro-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.76; [M + H]$^+$ = 433.2 |
| 6.107 | [5-(3,5-Dimethyl-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.85; [M + H]$^+$ = 443.2 |
| 6.108 | (4,5-Dimethyl-2-[1,2,3]triazol-2-yl-phenyl)-[(S)-2-(7-methyl-1H-benzoimidazol-2-yl)-4-methylene-pyrrolidin-1-yl]-methanone. LC-MS: $t_R$ = 0.72; [M + H]$^+$ = 413.2 |
| 6.109 | [5-(4-Chloro-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.81; [M + H]$^+$ = 449.1 |
| 6.110 | [5-(3-Bromo-4-fluoro-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.84; [M + H]$^+$ = 511.1 |
| 6.111 | (5-Methoxy-2-[1,2,3]triazol-2-yl-phenyl)-[(S)-2-(7-methyl-1H-benzoimidazol-2-yl)-4-methylene-pyrrolidin-1-yl]-methanone. LC-MS: $t_R$ = 0.65; [M + H]$^+$ = 415.2 |
| 6.112 | [(S)-2-(7-Methyl-1H-benzoimidazol-2-yl)-4-methylene-pyrrolidin-1-yl]-[2-methyl-5-(3-trifluoromethyl-phenyl)-thiazol-4-yl]-methanone. LC-MS: $t_R$ = 0.85; [M + H]$^+$ = 483.2 |
| 6.113 | [5-(3,4-Dichloro-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.87; [M + H]$^+$ = 483.1 |
| 6.114 | [5-(3-Methoxy-phenyl)-2-methyl-thiazol-4-yl]-[(S)-2-(7-methyl-1H-benzoimidazol-2-yl)-4-methylene-pyrrolidin-1-yl]-methanone. LC-MS: $t_R$ = 0.75; [M + H]$^+$ = 445.2 |
| 6.115 | [(S)-2-(7-Methyl-1H-benzoimidazol-2-yl)-4-methylene-pyrrolidin-1-yl]-(6-methyl-3-[1,2,3]triazol-2-yl-pyridin-2-yl)-methanone. LC-MS: $t_R$ = 0.65; [M + H]$^+$ = 400.2 |
| 6.116 | [5-(4-Bromo-phenyl)-2-methyl-thiazol-4-yl]-[(S)-2-(6-chloro-7-methyl-1H-benzoimidazol-2-yl)-4-methylene-pyrrolidin-1-yl]-methanone. LC-MS: $t_R$ = 0.95; [M + H]$^+$ = 527.2 |
| 6.117 | [(S)-2-(6-Chloro-7-methyl-1H-benzoimidazol-2-yl)-4-methylene-pyrrolidin-1-yl]-[5-(6-methoxy-pyridin-3-yl)-2-methyl-thiazol-4-yl]-methanone. LC-MS: $t_R$ = 0.82; [M + H]$^+$ = 480.2 |
| 6.118 | [(S)-2-(6-Chloro-7-methyl-1H-benzoimidazol-2-yl)-4-methylene-pyrrolidin-1-yl]-[5-(4-fluoro-phenyl)-2-methyl-thiazol-4-yl]-methanone. LC-MS: $t_R$ = 0.88; [M + H]$^+$ = 467.2 |

-continued

| Example | Compound name. LC-MS data |
|---|---|
| 6.119 | [(S)-2-(6-Chloro-7-methyl-1H-benzoimidazol-2-yl)-4-methylene-pyrrolidin-1-yl]-[5-(4-chloro-phenyl)-2-methyl-thiazol-4-yl]-methanone. LC-MS: $t_R$ = 0.93; [M + H]$^+$ = 483.1 |
| 6.120 | [(S)-2-(6-Chloro-7-methyl-1H-benzoimidazol-2-yl)-4-methylene-pyrrolidin-1-yl]-[2-methyl-5-(3-trifluoromethyl-phenyl)-thiazol-4-yl]-methanone. LC-MS: $t_R$ = 0.96; [M + H]$^+$ = 517.2 |
| 6.121 | [(S)-2-(6-Chloro-7-methyl-1H-benzoimidazol-2-yl)-4-methylene-pyrrolidin-1-yl]-[5-(3-methoxy-phenyl)-2-methyl-thiazol-4-yl]-methanone. LC-MS: $t_R$ = 0.86; [M + H]$^+$ = 479.2 |
| 6.122 | [(S)-2-(6-Chloro-7-methyl-1H-benzoimidazol-2-yl)-4-methylene-pyrrolidin-1-yl]-(2-methyl-5-m-tolyl-thiazol-4-yl)-methanone. LC-MS: $t_R$ = 0.90; [M + H]$^+$ = 463.2 |
| 6.123 | [5-(3-Bromo-phenyl)-2-methyl-thiazol-4-yl]-[(S)-2-(6-chloro-7-methyl-1H-benzoimidazol-2-yl)-4-methylene-pyrrolidin-1-yl]-methanone. LC-MS: $t_R$ = 0.94; [M + H]$^+$ = 527.1 |
| 6.124 | [(S)-2-(6-Chloro-7-methyl-1H-benzoimidazol-2-yl)-4-methylene-pyrrolidin-1-yl]-[5-(3,5-dimethyl-phenyl)-2-methyl-thiazol-4-yl]-methanone. LC-MS: $t_R$ = 0.95; [M + H]$^+$ = 477.2 |
| 6.125 | [5-(3-Bromo-4-fluoro-phenyl)-2-methyl-thiazol-4-yl]-[(S)-2-(6-chloro-7-methyl-1H-benzoimidazol-2-yl)-4-methylene-pyrrolidin-1-yl]-methanone. LC-MS: $t_R$ = 0.95; [M + H]$^+$ = 545.1 |
| 6.126 | [(S)-2-(6-Chloro-7-methyl-1H-benzoimidazol-2-yl)-4-methylene-pyrrolidin-1-yl]-[5-(3,4-dichloro-phenyl)-2-methyl-thiazol-4-yl]-methanone. LC-MS: $t_R$ = 0.99; [M + H]$^+$ = 517 |
| 6.127 | [(S)-2-(6-Chloro-7-methyl-1H-benzoimidazol-2-yl)-4-methylene-pyrrolidin-1-yl]-(6-methyl-3-[1,2,3]triazol-2-yl-pyridin-2-yl)-methanone. LC-MS: $t_R$ = 0.74; [M + H]$^+$ = 434.2 |
| 6.128 | [(S)-2-(6-Chloro-7-methyl-1H-benzoimidazol-2-yl)-4-methylene-pyrrolidin-1-yl]-(5-chloro-2-[1,2,3]triazol-2-yl-phenyl)-methanone. LC-MS: $t_R$ = 0.84; [M + H]$^+$ = 453.1 |
| 6.129 | [(S)-2-(6-Chloro-7-methyl-1H-benzoimidazol-2-yl)-4-methylene-pyrrolidin-1-yl]-(2-[1,2,3]triazol-2-yl-5-trifluoromethyl-phenyl)-methanone. LC-MS: $t_R$ = 0.89; [M + H]$^+$ = 487.2 |
| 6.130 | [(S)-2-(6-Chloro-7-methyl-1H-benzoimidazol-2-yl)-4-methylene-pyrrolidin-1-yl]-(4,5-dimethyl-2-[1,2,3]triazol-2-yl-phenyl)-methanone. LC-MS: $t_R$ = 0.84; [M + H]$^+$ = 447.2 |
| 6.131 | [(S)-2-(6-Chloro-7-methyl-1H-benzoimidazol-2-yl)-4-methylene-pyrrolidin-1-yl]-(5-methoxy-2-[1,2,3]triazol-2-yl-phenyl)-methanone. LC-MS: $t_R$ = 0.78; [M + H]$^+$ = 449.2 |
| 6.132 | [(S)-2-(6-Chloro-7-methyl-1H-benzoimidazol-2-yl)-4-methylene-pyrrolidin-1-yl]-(2-fluoro-3-methyl-6-[1,2,3]triazol-2-yl-phenyl)-methanone. LC-MS: $t_R$ = 0.83; [M + H]$^+$ = 451.2 |
| 6.133 | [(S)-2-(6-Chloro-7-methyl-1H-benzoimidazol-2-yl)-4-methylene-pyrrolidin-1-yl]-(2-fluoro-3-methoxy-6-[1,2,3]triazol-2-yl-phenyl)-methanone. LC-MS: $t_R$ = 0.80; [M + H]$^+$ = 467.2 |
| 6.134 | [(S)-2-(6-Chloro-7-methyl-1H-benzoimidazol-2-yl)-4-methylene-pyrrolidin-1-yl]-(5-methyl-2-pyrazol-1-yl-phenyl)-methanone. LC-MS: $t_R$ = 0.81; [M + H]$^+$ = 432.2 |
| 6.135 | [(S)-2-(6-Chloro-7-methyl-1H-benzoimidazol-2-yl)-4-methylene-pyrrolidin-1-yl]-(6-methyl-3-pyrazol-1-yl-pyridin-2-yl)-methanone. LC-MS: $t_R$ = 0.75; [M + H]$^+$ = 433.2 |
| 6.136 | (5-Chloro-2-[1,2,3]triazol-2-yl-phenyl)-[(S)-2-(6-methoxy-1H-benzoimidazol-2-yl)-4-methylene-pyrrolidin-1-yl]-methanone. LC-MS: $t_R$ = 0.70; [M + H]$^+$ = 435.1 |
| 6.137 | [(S)-2-(6-Methoxy-1H-benzoimidazol-2-yl)4-methylene-pyrrolidin-1-yl]-(5-methyl-2-pyrazol-1-yl-phenyl)-methanone. LC-MS: $t_R$ = 0.67; [M + H]$^+$ = 414.2 |
| 6.138 | [(S)-2-(6-Methoxy-1H-benzoimidazol-2-yl)4-methylene-pyrrolidin-1-yl]-(6-methyl-3-pyrazol-1-yl-pyridin-2-yl)-methanone. LC-MS: $t_R$ = 0.63; [M + H]$^+$ = 415.2 |
| 6.139 | (4,5-Dimethyl-2-[1,2,3]triazol-2-yl-phenyl)-[(S)-2-(6-methoxy-1H-benzoimidazol-2-yl)-4-methylene-pyrrolidin-1-yl]-methanone. LC-MS: $t_R$ = 0.72; [M + H]$^+$ = 429.2 |
| 6.140 | [(S)-2-(6-Methoxy-1H-benzoimidazol-2-yl)4-methylene-pyrrolidin-1-yl]-(5-methoxy-2-[1,2,3]triazol-2-yl-phenyl)-methanone. LC-MS: $t_R$ = 0.65; [M + H]$^+$ = 431.2 |
| 6.141 | (2-Fluoro-3-methyl-6-[1,2,3]triazol-2-yl-phenyl)-[(S)-2-(6-methoxy-1H-benzoimidazol-2-yl)-4-methylene-pyrrolidin-1-yl]-methanone. LC-MS: $t_R$ = 0.69; [M + H]$^+$ = 433.2 |
| 6.142 | [(S)-2-(6-Chloro-5-trifluoromethyl-1H-benzoimidazol-2-yl)-4-methylene-pyrrolidin-1-yl]-[5-(3,4-dimethyl-phenyl)-2-methyl-thiazol-4-yl]-methanone. LC-MS: $t_R$ = 1.15; [M + H]$^+$ = 531.2 |
| 6.143 | rac-[2-(5-Methoxy-1H-benzoimidazol-2-yl)-2-methyl-4-methylene-pyrrolidin-1-yl]-(2-methyl-5-m-tolyl-thiazol-4-yl)-methanone. LC-MS: $t_R$ = 0.85; [M + H]$^+$ = 459.3 |
| 6.144 | rac-[2-Dimethylamino-5-(3,4-dimethyl-phenyl)-thiazol-4-yl]-[2-(5-methoxy-1H-benzoimidazol-2-yl)-2-methyl-4-methylene-pyrrolidin-1-yl]-methanone. LC-MS: $t_R$ = 0.96; [M + H]$^+$ = 502.3 |
| 6.145 | rac-[5-(3,4-Dimethyl-phenyl)-2-methyl-thiazol-4-yl]-[2-(5-methoxy-1H-benzoimidazol-2-yl)-2-methyl-4-methylene-pyrrolidin-1-yl]-methanone. LC-MS: $t_R$ = 0.90; [M + H]$^+$ = 473.3 |
| 6.146 | rac-[5-(4-Chloro-phenyl)-2-methyl-thiazol-4-yl]-[2-(5-methoxy-1H-benzoimidazol-2-yl)-2-methyl-4-methylene-pyrrolidin-1-yl]-methanone. LC-MS: $t_R$ = 0.86; [M + H]$^+$ = 479.2 |
| 6.147 | rac-[2-(5-Methoxy-1H-benzoimidazol-2-yl)-2-methyl-4-methylene-pyrrolidin-1-yl]-[5-(4-methoxy-phenyl)-2-methyl-thiazol-4-yl]-methanone. LC-MS: $t_R$ = 0.80; [M + H]$^+$ = 475.3 |
| 6.148 | rac-[2-(5-Methoxy-1H-benzoimidazol-2-yl)-2-methyl-4-methylene-pyrrolidin-1-yl]-(2-methyl-5-p-tolyl-thiazol-4-yl)-methanone. LC-MS: $t_R$ = 0.85; [M + H]$^+$ = 459.3 |
| 6.149 | rac-(3',4'-Dimethyl-biphenyl-2-yl)-[2-(5-methoxy-1H-benzoimidazol-2-yl)-2-methyl-4-methylene-pyrrolidin-1-yl]-methanone. LC-MS: $t_R$ = 0.90; [M + H]$^+$ = 452.3 |
| 6.150 | rac-Biphenyl-2-yl-[2-(5-methoxy-1H-benzoimidazol-2-yl)-2-methyl-4-methylene-pyrrolidin-1-yl]-methanone. LC-MS: $t_R$ = 0.80; [M + H]$^+$ = 424.3 |
| 6.151 | rac-(4'-Fluoro-3'-methyl-biphenyl-2-yl)-[2-(5-methoxy-1H-benzoimidazol-2-yl)-2-methyl-4-methylene-pyrrolidin-1-yl]-methanone. LC-MS: $t_R$ = 0.87; [M + H]$^+$ = 456.3 |
| 6.152 | rac-[5-(3-Chloro-phenyl)-2-dimethylamino-thiazol-4-yl]-[2-(5-methoxy-1H-benzoimidazol-2-yl)-2-methyl-4-methylene-pyrrolidin-1-yl]-methanone. LC-MS: $t_R$ = 0.92; [M + H]$^+$ = 508.2 |
| 6.153 | rac-[5-(3-Chloro-phenyl)-2-methyl-thiazol-4-yl]-[2-(5-methoxy-1H-benzoimidazol-2-yl)-2-methyl-4-methylene-pyrrolidin-1-yl]-methanone. LC-MS: $t_R$ = 0.86; [M + H]$^+$ = 479.2 |
| 6.154 | rac-[2-(5-Methoxy-1H-benzoimidazol-2-yl)-2-methyl-4-methylene-pyrrolidin-1-yl]-(2-methyl-5-phenyl-thiazol-4-yl)-methanone. LC-MS: $t_R$ = 0.79; [M + H]$^+$ = 445.3 |
| 6.155 | rac-[2-(5-Methoxy-1H-benzoimidazol-2-yl)-2-methyl-4-methylene-pyrrolidin-1-yl]-(2-[1,2,3]triazol-2-yl-phenyl)-methanone. LC-MS: $t_R$ = 0.66; [M + H]$^+$ = 415.3 |
| 6.156 | rac-[2-(5-Methoxy-1H-benzoimidazol-2-yl)-2-methyl-4-methylene-pyrrolidin-1-yl]-(5-methyl-2-[1,2,3]triazol-2-yl-phenyl)-methanone. LC-MS: $t_R$ = 0.72; [M + H]$^+$ = 429.3 |
| 6.157 | rac-(5-Chloro-2-[1,2,3]triazol-2-yl-phenyl)-[2-(5-methoxy-1H-benzoimidazol-2-yl)-2-methyl-4-methylene-pyrrolidin-1-yl]-methanone. LC-MS: $t_R$ = 0.75; [M + H]$^+$ = 449.2 |
| 6.158 | rac-[2-(5-Methoxy-1H-benzoimidazol-2-yl)-2-methyl-4-methylene-pyrrolidin-1-yl]-(5-methoxy-2-[1,2,3]triazol-2-yl-phenyl)-methanone. LC-MS: $t_R$ = 0.70; [M + H]$^+$ = 445.3 |
| 6.159 | rac-(4,5-Dimethyl-2-[1,2,3]triazol-2-yl-phenyl)-[2-(5-methoxy-1H-benzoimidazol-2-yl)-2-methyl-4-methylene-pyrrolidin-1-yl]-methanone. LC-MS: $t_R$ = 0.78; [M + H]$^+$ = 443.3 |
| 6.160 | [(S)-2-(5-tert-Butyl-1H-benzoimidazol-2-yl)-4-methylene-pyrrolidin-1-yl]-(5-fluoro-2-[1,2,3]triazol-2-yl-phenyl)-methanone. LC-MS: $t_R$ = 0.81; [M + H]$^+$ = 445.3 |
| 6.161 | [(S)-2-(5-tert-Butyl-1H-benzoimidazol-2-yl)-4-methylene-pyrrolidin-1-yl]-(5-chloro-2-[1,2,3]triazol-2-yl-phenyl)-methanone. LC-MS: $t_R$ = 0.86; [M + H]$^+$ = 461.3 |
| 6.162 | [(S)-2-(5-tert-Butyl-1H-benzoimidazol-2-yl)-4-methylene-pyrrolidin-1-yl]-(2-[1,2,3]triazol-2-yl-phenyl)-methanone. LC-MS: $t_R$ = 0.79; [M + H]$^+$ = 427.3 |
| 6.163 | [(S)-2-(5-tert-Butyl-1H-benzoimidazol-2-yl)-4-methylene-pyrrolidin-1-yl]-(2-fluoro-3-methoxy-6-[1,2,3]triazol-2-yl-phenyl)-methanone. LC-MS: $t_R$ = 0.81; [M + H]$^+$ = 475.3 |
| 6.164 | [(S)-2-(5-tert-Butyl-1H-benzoimidazol-2-yl)-4-methylene-pyrrolidin-1-yl]-(2-fluoro-3-methyl-6-[1,2,3]triazol-2-yl-phenyl)-methanone. LC-MS: $t_R$ = 0.84; [M + H]$^+$ = 459.3 |
| 6.165 | [(S)-2-(5-tert-Butyl-1H-benzoimidazol-2-yl)-4-methylene-pyrrolidin-1-yl]-(4,5-dimethyl-2-[1,2,3]triazol-2-yl-phenyl)-methanone. LC-MS: $t_R$ = 0.87; [M + H]$^+$ = 455.3 |
| 6.166 | [(S)-2-(5-tert-Butyl-1H-benzoimidazol-2-yl)-4-methylene-pyrrolidin-1-yl]-(4-methyl-2-[1,2,3]triazol-2-yl-phenyl)-methanone. LC-MS: $t_R$ = 0.84; [M + H]$^+$ = 441.4 |
| 6.167 | [(S)-2-(5-tert-Butyl-1H-benzoimidazol-2-yl)-4-methylene-pyrrolidin-1-yl]-(2-methyl-6-[1,2,3]triazol-2-yl-phenyl)-methanone. LC-MS: $t_R$ = 0.83; [M + H]$^+$ = 441.3 |
| 6.168 | [(S)-2-(5-tert-Butyl-1H-benzoimidazol-2-yl)-4-methylene-pyrrolidin-1-yl]-(2-[1,2,3]triazol-2-yl-5-trifluoromethyl-phenyl)-methanone. LC-MS: $t_R$ = 0.91; [M + H]$^+$ = 495.3 |

| Example | Compound name. LC-MS data |
|---|---|
| 6.169 | [(S)-2-(5-tert-Butyl-1H-benzoimidazol-2-yl)-4-methylene-pyrrolidin-1-yl]-(2-[1,2,3]triazol-2-yl-5-trifluoromethoxy-phenyl)-methanone. LC-MS: $t_R$ = 0.93; [M + H]$^+$ = 511.3 |
| 6.170 | [(S)-2-(5-tert-Butyl-1H-benzoimidazol-2-yl)-4-methylene-pyrrolidin-1-yl]-(4,5-dimethoxy-2-[1,2,3]triazol-2-yl-phenyl)-methanone. LC-MS: $t_R$ = 0.78; [M + H]$^+$ = 487.3 |
| 6.171 | [(S)-2-(5-tert-Butyl-1H-benzoimidazol-2-yl)-4-methylene-pyrrolidin-1-yl]-(5-methyl-2-pyrazol-1-yl-phenyl)-methanone. LC-MS: $t_R$ = 0.84; [M + H]$^+$ = 440.3 |
| 6.172 | [(S)-2-(5-tert-Butyl-1H-benzoimidazol-2-yl)-4-methylene-pyrrolidin-1-yl]-(2-pyrazol-1-yl-phenyl)-methanone. LC-MS: $t_R$ = 0.8; [M + H]$^+$ = 426.3 |
| 6.173 | [(S)-2-(5-tert-Butyl-1H-benzoimidazol-2-yl)-4-methylene-pyrrolidin-1-yl]-(6-methyl-3-pyrazol-1-yl-pyridin-2-yl)-methanone. LC-MS: $t_R$ = 0.80; [M + H]$^+$ = 441.3 |
| 6.174 | [(S)-2-(5-tert-Butyl-1H-benzoimidazol-2-yl)-4-methylene-pyrrolidin-1-yl]-(6-methyl-3-[1,2,3]triazol-2-yl-pyridin-2-yl)-methanone. LC-MS: $t_R$ = 0.80; [M + H]$^+$ = 442.3 |
| 6.175 | [(S)-2-(5-Chloro-6-trifluoromethyl-1H-benzoimidazol-2-yl)-4-methylene-pyrrolidin-1-yl]-(2-fluoro-6-[1,2,3]triazol-2-yl-phenyl)-methanone. LC-MS: $t_R$ = 1.05; [M + H]$^+$ = 491.2 |
| 6.176 | [(S)-2-(5-Chloro-6-trifluoromethyl-1H-benzoimidazol-2-yl)-4-methylene-pyrrolidin-1-yl]-(5-fluoro-2-[1,2,3]triazol-2-yl-phenyl)-methanone. LC-MS: $t_R$ = 1.04; [M + H]$^+$ = 491.2 |
| 6.177 | (5-Chloro-2-[1,2,3]triazol-2-yl-phenyl)-[(S)-2-(5-chloro-6-trifluoromethyl-1H-benzoimidazol-2-yl)-4-methylene-pyrrolidin-1-yl]-methanone. LC-MS: $t_R$ = 1.09.; [M + H]$^+$ = 507.2 |
| 6.178 | [(S)-2-(5-Chloro-6-trifluoromethyl-1H-benzoimidazol-2-yl)-4-methylene-pyrrolidin-1-yl]-(2-[1,2,3]triazol-2-yl-phenyl)-methanone. LC-MS: $t_R$ = 1.01; [M + H]$^+$ = 473.2 |
| 6.179 | [(S)-2-(5-Chloro-6-trifluoromethyl-1H-benzoimidazol-2-yl)-4-methylene-pyrrolidin-1-yl]-(2-fluoro-3-methoxy-6-[1,2,3]triazol-2-yl-phenyl)-methanone. LC-MS: $t_R$ = 1.06; [M + H]$^+$ = 521.2 |
| 6.180 | [(S)-2-(5-Chloro-6-trifluoromethyl-1H-benzoimidazol-2-yl)-4-methylene-pyrrolidin-1-yl]-(2-fluoro-3-methyl-6-[1,2,3]triazol-2-yl-phenyl)-methanone. LC-MS: $t_R$ = 1.11; [M + H]$^+$ = 505.2 |
| 6.181 | [(S)-2-(5-Chloro-6-trifluoromethyl-1H-benzoimidazol-2-yl)-4-methylene-pyrrolidin-1-yl]-(4,5-dimethyl-2-[1,2,3]triazol-2-yl-phenyl)-methanone. LC-MS: $t_R$ = 1.1; [M + H]$^+$ = 501.2 |
| 6.182 | [(S)-2-(5-Chloro-6-trifluoromethyl-1H-benzoimidazol-2-yl)-4-methylene-pyrrolidin-1-yl]-(4-methyl-2-[1,2,3]triazol-2-yl-phenyl)-methanone. LC-MS: $t_R$ = 1.07; [M + H]$^+$ = 487.2 |
| 6.183 | [(S)-2-(5-Chloro-6-trifluoromethyl-1H-benzoimidazol-2-yl)-4-methylene-pyrrolidin-1-yl]-(2-methyl-6-[1,2,3]triazol-2-yl-phenyl)-methanone. LC-MS: $t_R$ = 1.09; [M + H]$^+$ = 487.3 |
| 6.184 | [(S)-2-(5-Chloro-6-trifluoromethyl-1H-benzoimidazol-2-yl)-4-methylene-pyrrolidin-1-yl]-(2-[1,2,3]triazol-2-yl-5-trifluoromethyl-phenyl)-methanone. LC-MS: $t_R$ = 1.12; [M + H]$^+$ = 541.1 |
| 6.185 | [(S)-2-(5-Chloro-6-trifluoromethyl-1H-benzoimidazol-2-yl)-4-methylene-pyrrolidin-1-yl]-(2-[1,2,3]triazol-2-yl-5-trifluoromethoxy-phenyl)-methanone. LC-MS: $t_R$ = 1.14; [M + H]$^+$ = 557.2 |
| 6.186 | [(S)-2-(5-Chloro-6-trifluoromethyl-1H-benzoimidazol-2-yl)-4-methylene-pyrrolidin-1-yl]-(4,5-dimethoxy-2-[1,2,3]triazol-2-yl-phenyl)-methanone. LC-MS: $t_R$ = 0.99; [M + H]$^+$ = 533.2 |
| 6.187 | [(S)-2-(5-Chloro-6-trifluoromethyl-1H-benzoimidazol-2-yl)-4-methylene-pyrrolidin-1-yl]-(5-methyl-2-pyrazol-1-yl-phenyl)-methanone. LC-MS: $t_R$ = 1.06; [M + H]$^+$ = 486.2 |
| 6.188 | [(S)-2-(5-Chloro-6-trifluoromethyl-1H-benzoimidazol-2-yl)-4-methylene-pyrrolidin-1-yl]-(2-pyrazol-1-yl-phenyl)-methanone. LC-MS: $t_R$ = 1.02; [M + H]$^+$ = 472.2 |
| 6.189 | [(S)-2-(5-Chloro-6-trifluoromethyl-1H-benzoimidazol-2-yl)-4-methylene-pyrrolidin-1-yl]-(6-methyl-3-pyrazol-1-yl-pyridin-2-yl)-methanone. LC-MS: $t_R$ = 0.98; [M + H]$^+$ = 487.3 |
| 6.190 | [(S)-2-(5-Chloro-6-trifluoromethyl-1H-benzoimidazol-2-yl)-4-methylene-pyrrolidin-1-yl]-(6-methyl-3-[1,2,3]triazol-2-yl-pyridin-2-yl)-methanone. LC-MS: $t_R$ = 0.98; [M + H]$^+$ = 488.2 |
| 6.191 | [(S)-2-(5,6-Dimethyl-1H-benzoimidazol-2-yl)-4-methylene-pyrrolidin-1-yl]-(2-fluoro-6-[1,2,3]triazol-2-yl-phenyl)-methanone. LC-MS: $t_R$ = 0.69; [M + H]$^+$ = 417.3 |
| 6.192 | [(S)-2-(5,6-Dimethyl-1H-benzoimidazol-2-yl)-4-methylene-pyrrolidin-1-yl]-(5-fluoro-2-[1,2,3]triazol-2-yl-phenyl)-methanone. LC-MS: $t_R$ = 0.70; [M + H]$^+$ = 417.3 |
| 6.193 | (5-Chloro-2-[1,2,3]triazol-2-yl-phenyl)-[(S)-2-(5,6-dimethyl-1H-benzoimidazol-2-yl)-4-methylene-pyrrolidin-1-yl]-methanone. LC-MS: $t_R$ = 0.76; [M + H]$^+$ = 433.2 |
| 6.194 | [(S)-2-(5,6-Dimethyl-1H-benzoimidazol-2-yl)-4-methylene-pyrrolidin-1-yl]-(2-[1,2,3]triazol-2-yl-phenyl)-methanone. LC-MS: $t_R$ = 0.68; [M + H]$^+$ = 399.3 |
| 6.195 | [(S)-2-(5,6-Dimethyl-1H-benzoimidazol-2-yl)-4-methylene-pyrrolidin-1-yl]-(2-fluoro-3-methoxy-6-[1,2,3]triazol-2-yl-phenyl)-methanone. LC-MS: $t_R$ = 0.70; [M + H]$^+$ = 447.3 |
| 6.196 | [(S)-2-(5,6-Dimethyl-1H-benzoimidazol-2-yl)-4-methylene-pyrrolidin-1-yl]-(2-fluoro-3-methyl-6-[1,2,3]triazol-2-yl-phenyl)-methanone. LC-MS: $t_R$ = 0.74; [M + H]$^+$ = 431.3 |
| 6.197 | [(S)-2-(5,6-Dimethyl-1H-benzoimidazol-2-yl)-4-methylene-pyrrolidin-1-yl]-(4,5-dimethyl-2-[1,2,3]triazol-2-yl-phenyl)-methanone. LC-MS: $t_R$ = 0.78; [M + H]$^+$ = 427.3 |
| 6.198 | [(S)-2-(5,6-Dimethyl-1H-benzoimidazol-2-yl)-4-methylene-pyrrolidin-1-yl]-(4-methyl-2-[1,2,3]triazol-2-yl-phenyl)-methanone. LC-MS: $t_R$ = 0.8; [M + H]$^+$ = 413.4 |
| 6.199 | [(S)-2-(5,6-Dimethyl-1H-benzoimidazol-2-yl)-4-methylene-pyrrolidin-1-yl]-(2-methyl-6-[1,2,3]triazol-2-yl-phenyl)-methanone. LC-MS: $t_R$ = 0.79; [M + H]$^+$ = 413.4 |
| 6.200 | (4,5-Dimethoxy-2-[1,2,3]triazol-2-yl-phenyl)-[(S)-2-(5,6-dimethyl-1H-benzoimidazol-2-yl)-4-methylene-pyrrolidin-1-yl]-methanone. LC-MS: $t_R$ = 0.74; [M + H]$^+$ = 459.4 |
| 6.201 | [(S)-2-(5,6-Dimethyl-1H-benzoimidazol-2-yl)-4-methylene-pyrrolidin-1-yl]-(5-methyl-2-pyrazol-1-yl-phenyl)-methanone. LC-MS: $t_R$ = 0.8; [M + H]$^+$ = 412.4 |
| 6.202 | [(S)-2-(5,6-Dimethyl-1H-benzoimidazol-2-yl)-4-methylene-pyrrolidin-1-yl]-(6-methyl-3-[1,2,3]triazol-2-yl-pyridin-2-yl)-methanone. LC-MS: $t_R$ = 0.75; [M + H]$^+$ = 414.4 |
| 7.1 | [(2S,4R)-2-(6-Chloro-1,7-dimethyl-1H-benzoimidazol-2-yl)-4-methoxy-pyrrolidin-1-yl]-(5-methoxy-2-[1,2,3]triazol-2-yl-phenyl)-methanone and/or [(2S,4R)-2-(5-Chloro-1,4-dimethyl-1H-benzoimidazol-2-yl)-4-methoxy-pyrrolidin-1-yl]-(5-methoxy-2-[1,2,3]triazol-2-yl-phenyl)-methanone (mixture of isomers). LC-MS: $t_R$ = 0.78; [M + H]$^+$ = 481.3 |
| 7.2 | [(S)-4-Methylene-2-(1,5,6-trimethyl-1H-benzoimidazol-2-yl)-pyrrolidin-1-yl]-(5-methyl-2-[1,2,3]triazol-2-yl-phenyl)-methanone. LC-MS: $t_R$ = 0.77; [M + H]$^+$ = 427.4 |
| 7.3 | [(S)-2-(5-Chloro-1,4-dimethyl-1H-benzoimidazol-2-yl)-2-methyl-pyrrolidin-1-yl]-(5-methyl-2-[1,2,3]triazol-2-yl-phenyl)-methanone and/or [(S)-2-(6-Chloro-1,7-dimethyl-1H-benzoimidazol-2-yl)-2-methyl-pyrrolidin-1-yl]-(5-methyl-2-[1,2,3]triazol-2-yl-phenyl)-methanone (mixture of isomers). LC-MS: $t_R$ = 0.84; [M + H]$^+$ = 449.3 |
| 7.4 | [(S)-2-(5-Bromo-1,7-dimethyl-1H-benzoimidazol-2-yl)-2-methyl-pyrrolidin-1-yl]-(5-methyl-2-[1,2,3]triazol-2-yl-phenyl)-methanone and/or [(S)-2-(6-Bromo-1,4-dimethyl-1H-benzoimidazol-2-yl)-2-methyl-pyrrolidin-1-yl]-(5-methyl-2-[1,2,3]triazol-2-yl-phenyl)-methanone (mixture of isomers). LC-MS: $t_R$ = 0.86; [M + H]$^+$ = 493.2 |
| 7.5 | (S)-(5-(3-chlorophenyl)-2-methylthiazol-4-yl)(2-(1,4-dimethyl-1H-benzo[d]imidazol-2-yl)-2-methylpyrrolidin-1-yl)methanone and/or (S)-(5-(3-chlorophenyl)-2-methylthiazol-4-yl)(2-(1,7-dimethyl-1H-benzo[d]imidazol-2-yl)-2-methylpyrrolidin-1-yl)methanone (mixture of isomers). LC-MS: $t_R$ = 0.88; [M + H]$^+$ = 465.1 |
| 7.6 | (S)-(5-(3-chlorophenyl)-2-methylthiazol-4-yl)(2-(1-ethyl-4-methyl-1H-benzo[d]imidazol-2-yl)-2-methylpyrrolidin-1-yl)methanone and/or (S)-(5-(3-chlorophenyl)-2-methylthiazol-4-yl)(2-(1-ethyl-7-methyl-1H-benzo[d]imidazol-2-yl)-2-methylpyrrolidin-1-yl)methanone (mixture of isomers). LC-MS: $t_R$ = 0.93; [M + H]$^+$ = 479.1 |
| 7.7 | (S)-(2-(5-chloro-1,4-dimethyl-1H-benzo[d]imidazol-2-yl)-2-methylpyrrolidin-1-yl)(2-methyl-5-phenylthiazol-4-yl)methanone and/or (S)-(2-(6-chloro-1,7-dimethyl-1H-benzo[d]imidazol-2-yl)-2-methylpyrrolidin-1-yl)(2-methyl-5-phenylthiazol-4-yl)methanone (mixture of isomers). LC-MS: $t_R$ = 0.93; [M + H]$^+$ = 465.1 |

| Example | Compound name. LC-MS data |
|---|---|
| 7.8 | (S)-(2-(5-chloro-1-ethyl-4-methyl-1H-benzo[d]imidazol-2-yl)-2-methylpyrrolidin-1-yl)(2-methyl-5-phenylthiazol-4-yl)methanone and/or (S)-(2-(6-chloro-1-ethyl-7-methyl-1H-benzo[d]imidazol-2-yl)-2-methylpyrrolidin-1-yl)(2-methyl-5-phenylthiazol-4-yl)methanone (mixture of isomers). LC-MS: $t_R$ = 0.97; [M + H]$^+$ = 479.2 |
| 7.9 | [(S)-2-(5,6-Dimethoxy-1-methyl-1H-benzoimidazol-2-yl)-2-methyl-pyrrolidin-1-yl]-(5-methyl-2-[1,2,3]triazol-2-yl-phenyl)-methanone. LC-MS: $t_R$ = 0.74; [M + H]$^+$ = 461.4 |
| 7.10 | [(S)-2-(1-Ethyl-5,6-dimethoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.78; [M + H]$^+$ = 475.4 |
| 7.11 | (4-Methyl-2-[1,2,3]triazol-2-yl-phenyl)-[(S)-2-methyl-2-(1,5,6-trimethyl-1H-benzoimidazol-2-yl)-pyrrolidin-1-yl]-methanone. LC-MS: $t_R$ = 0.82; [M + H]$^+$ = 429.4 |
| 7.12 | [(S)-2-(1-Ethyl-5,6-dimethyl-1H-benzoimidazol-2-yl)-2-methyl-pyrrolidin-1-yl]-(4-methyl-2-[1,2,3]triazol-2-yl-phenyl)-methanone. LC-MS: $t_R$ = 0.87; [M + H]$^+$ = 443.4 |
| 7.13 | [(S)-2-(5,6-Dimethoxy-1-methyl-1H-benzoimidazol-2-yl)-2-methyl-pyrrolidin-1-yl]-(4,5-dimethyl-2-[1,2,3]triazol-2-yl-phenyl)-methanone. LC-MS: $t_R$ = 0.80; [M + H]$^+$ = 475.4 |
| 7.14 | (4,5-Dimethyl-2-[1,2,3]triazol-2-yl-phenyl)-[(S)-2-(1-ethyl-5,6-dimethoxy-1H-benzoimidazol-2-yl)-2-methyl-pyrrolidin-1-yl]-methanone. LC-MS: $t_R$ = 0.83; [M + H]$^+$ = 489.4 |
| 7.15 | (4'-Fluoro-4-methyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 0.97; [M + H]$^+$ = 456.4 |
| 7.16 | [(S)-2-(1-Ethyl-5,6-dimethyl-1H-benzoimidazol-2-yl)-2-methyl-pyrrolidin-1-yl]-(4'-fluoro-4-methyl-biphenyl-2-yl)-methanone. LC-MS: $t_R$ = 1.0; [M + H]$^+$ = 470.4 |
| 7.17 | (4,5-Dimethyl-2-[1,2,3]triazol-2-yl-phenyl)-[(S)-2-methyl-2-(1,5,6-trimethyl-1H-benzoimidazol-2-yl)-pyrrolidin-1-yl]-methanone. LC-MS: $t_R$ = 0.87; [M + H]$^+$ = 443.4 |
| 7.18 | [(S)-2-(5-Chloro-1,4-dimethyl-1H-benzoimidazol-2-yl)-2-methyl-pyrrolidin-1-yl]-(6-methyl-3-[1,2,3]triazol-2-yl-pyridin-2-yl)-methanone and/or [(S)-2-(3-Chloro-1,2-dimethyl-1H-benzoimidazol-2-yl)-2-methyl-pyrrolidin-1-yl]-(6-methyl-3-[1,2,3]triazol-2-yl-pyridin-2-yl)-methanone (mixture of isomers). LC-MS: $t_R$ = 0.83; [M + H]$^+$ = 450.3 |
| 7.19 | [(S)-2-(5-Chloro-1,4-dimethyl-1H-benzoimidazol-2-yl)-2-methyl-pyrrolidin-1-yl]-(2-[1,2,3]triazol-2-yl-phenyl)-methanone and/or [(S)-2-(3-Chloro-1,2-dimethyl-1H-benzoimidazol-2-yl)-2-methyl-pyrrolidin-1-yl]-(2-[1,2,3]triazol-2-yl-phenyl)-methanone (mixtures of isomers). LC-MS: $t_R$ = 0.81; [M + H]$^+$ = 435.3 |
| 7.20 | [(S)-2-(6-Chloro-1-methyl-5-trifluoromethyl-1H-benzoimidazol-2-yl)-2-methyl-pyrrolidin-1-yl]-(5-methyl-2-[1,2,3]triazol-2-yl-phenyl)-methanone and or [(S)-2-(5-Chloro-1-methyl-6-trifluoromethyl-1H-benzoimidazol-2-yl)-2-methyl-pyrrolidin-1-yl]-(5-methyl-2-[1,2,3]triazol-2-yl-phenyl)-methanone (mixtures of isomers). LC-MS: $t_R$ = 1.09; [M + H]$^+$ = 531.3 |
| 7.21 | [(S)-2-(5-Chloro-1-ethyl-4-methyl-1H-benzoimidazol-2-yl)-2-methyl-pyrrolidin-1-yl]-(5-methyl-2-[1,2,3]triazol-2-yl-phenyl)-methanone and/or [(S)-2-(3-Chloro-1-ethyl-2-methyl-1H-benzoimidazol-2-yl)-2-methyl-pyrrolidin-1-yl]-(5-methyl-2-[1,2,3]triazol-2-yl-phenyl)-methanone (mixtures of isomers). LC-MS: $t_R$ = 0.93; [M + H]$^+$ = 463.3 |
| 7.22 | [(S)-2-(5-Chloro-1,4-dimethyl-1H-benzoimidazol-2-yl)-2-methyl-pyrrolidin-1-yl]-(5-chloro-2-[1,2,3]triazol-2-yl-phenyl)-methanone and/or [(S)-2-(3-Chloro-1,2-dimethyl-1H-benzoimidazol-2-yl)-2-methyl-pyrrolidin-1-yl]-(5-chloro-2-[1,2,3]triazol-2-yl-phenyl)-methanone (mixtures of isomers). LC-MS: $t_R$ = 0.93; [M + H]$^+$ = 469.3 |
| 7.23 | [(S)-2-(5-Chloro-1,4-dimethyl-1H-benzoimidazol-2-yl)-2-methyl-pyrrolidin-1-yl]-(5-methoxy-2-[1,2,3]triazol-2-yl-phenyl)-methanone and/or [(S)-2-(3-Chloro-1,2-dimethyl-1H-benzoimidazol-2-yl)-2-methyl-pyrrolidin-1-yl]-(5-methoxy-2-[1,2,3]triazol-2-yl-phenyl)-methanone (mixtures of isomers). LC-MS: $t_R$ = 0.86; [M + H]$^+$ = 465.4 |
| 7.24 | (5-Chloro-2-[1,2,3]triazol-2-yl-phenyl)-[(S)-2-(5,6-dimethoxy-1-methyl-1H-benzoimidazol-2-yl)-2-methyl-pyrrolidin-1-yl]-methanone. LC-MS: $t_R$ = 0.77; [M + H]$^+$ = 481.3 |
| 7.25 | (4,3'-Dimethyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 1.01; [M + H]$^+$ = 452.4 |
| 7.26 | [(S)-2-(1-Cyclopropylmethyl-5,6-dimethyl-1H-benzoimidazol-2-yl)-2-methyl-pyrrolidin-1-yl]-(4,3'-dimethyl-biphenyl-2-yl)-methanone. LC-MS: $t_R$ = 1.1; [M + H]$^+$ = 492.4 |
| 7.27 | (4,3'-Dimethyl-biphenyl-2-yl)-[(S)-2-(1-ethyl-5,6-dimethyl-1H-benzoimidazol-2-yl)-2-methyl-pyrrolidin-1-yl]-methanone. LC-MS: $t_R$ = 1.04; [M + H]$^+$ = 466.4 |
| 7.28 | (4,3'-Dimethyl-biphenyl-2-yl)-{(S)-2-[1-(2-fluoro-ethyl)-5,6-dimethyl-1H-benzoimidazol-2-yl]-2-methyl-pyrrolidin-1-yl}-methanone. LC-MS: $t_R$ = 1.03; [M + H]$^+$ = 484.4 |
| 7.29 | (4,3'-Dimethyl-biphenyl-2-yl)-{(S)-2-[1-(2-methoxy-ethyl)-5,6-dimethyl-1H-benzoimidazol-2-yl]-2-methyl-pyrrolidin-1-yl}-methanone. LC-MS: $t_R$ = 1.06; [M + H]$^+$ = 496.4 |
| 7.30 | (3'-Fluoro-4-methyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 0.97; [M + H]$^+$ = 456.4 |
| 7.31 | [(S)-2-(1-Ethyl-5,6-dimethyl-1H-benzoimidazol-2-yl)-2-methyl-pyrrolidin-1-yl]-(3'-fluoro-4-methyl-biphenyl-2-yl)-methanone. LC-MS: $t_R$ = 1.0; [M + H]$^+$ = 470.4 |
| 7.32 | [(S)-2-(6-Bromo-5-fluoro-1-methyl-1H-benzoimidazol-2-yl)-2-methyl-pyrrolidin-1-yl]-(5-methyl-2-[1,2,3]triazol-2-yl-phenyl)-methanone and/or [(S)-2-(4-Bromo-3-fluoro-1-methyl-1H-benzoimidazol-2-yl)-2-methyl-pyrrolidin-1-yl]-(5-methyl-2-[1,2,3]triazol-2-yl-phenyl)-methanone (mixtures of isomers). LC-MS: $t_R$ = 0.89; [M + H]$^+$ = 497.3 |
| 7.33 | [(S)-2-(5-Chloro-1,4-dimethyl-1H-benzoimidazol-2-yl)-2-methyl-pyrrolidin-1-yl]-[5-(3-chloro-phenyl)-2-methyl-thiazol-4-yl]-methanone and/or [(S)-2-(3-Chloro-1,2-dimethyl-1H-benzoimidazol-2-yl)-2-methyl-pyrrolidin-1-yl]-[5-(3-chloro-phenyl)-2-methyl-thiazol-4-yl]-methanone (mixtures of isomers). LC-MS: $t_R$ = 1.05; [M + H]$^+$ = 499.2 |
| 7.34 | [(S)-2-(1-Cyclopropylmethyl-5,6-dimethyl-1H-benzoimidazol-2-yl)-2-methyl-pyrrolidin-1-yl]-(3'-fluoro-4-methyl-biphenyl-2-yl)-methanone. LC-MS: $t_R$ = 1.06; [M + H]$^+$ = 496.4 |
| 7.35 | {(S)-2-[1-(2-Fluoro-ethyl)-5,6-dimethyl-1H-benzoimidazol-2-yl]-2-methyl-pyrrolidin-1-yl}-(3'-fluoro-4-methyl-biphenyl-2-yl)-methanone. LC-MS: $t_R$ = 0.99; [M + H]$^+$ = 488.4 |
| 7.36 | (3'-Fluoro-4-methyl-biphenyl-2-yl)-{(S)-2-[1-(2-methoxy-ethyl)-5,6-dimethyl-1H-benzoimidazol-2-yl]-2-methyl-pyrrolidin-1-yl}-methanone. LC-MS: $t_R$ = 1.02; [M + H]$^+$ = 500.4 |
| 7.37 | (4,4'-Dimethyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 1.02; [M + H]$^+$ = 452.5 |
| 7.38 | (4,4'-Dimethyl-biphenyl-2-yl)-[(S)-2-(1-ethyl-5,6-dimethyl-1H-benzoimidazol-2-yl)-2-methyl-pyrrolidin-1-yl]-methanone. LC-MS: $t_R$ = 1.04; [M + H]+ = 466.4 |
| 7.39 | [(S)-2-(1-Cyclopropylmethyl-5,6-dimethyl-1H-benzoimidazol-2-yl)-2-methyl-pyrrolidin-1-yl]-(4,4'-dimethyl-biphenyl-2-yl)-methanone. LC-MS: $t_R$ = 1.1; [M + H]$^+$ = 492.4 |
| 7.40 | (4,4'-Dimethyl-biphenyl-2-yl)-{(S)-2-[1-(2-fluoro-ethyl)-5,6-dimethyl-1H-benzoimidazol-2-yl]-2-methyl-pyrrolidin-1-yl}-methanone. LC-MS: $t_R$ = 1.03; [M + H]$^+$ = 484.4 |
| 7.41 | (4,4'-Dimethyl-biphenyl-2-yl)-{(S)-2-[1-(2-methoxy-ethyl)-5,6-dimethyl-1H-benzoimidazol-2-yl]-2-methyl-pyrrolidin-1-yl}-methanone. LC-MS: $t_R$ = 1.06; [M + H]$^+$ = 496.4 |
| 7.42 | (3'-Methoxy-4-methyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 0.98; [M + H]$^+$ = 468.4 |
| 7.43 | (2'-Fluoro-4-methyl-biphenyl-2-yl)-[(S)-2-methyl-2-(1,5,6-trimethyl-1H-benzoimidazol-2-yl)-pyrrolidin-1-yl]-methanone. LC-MS: $t_R$ = 0.97; [M + H]$^+$ = 456.4 |
| 7.44 | [(S)-2-(1-Ethyl-5,6-dimethyl-1H-benzoimidazol-2-yl)-2-methyl-pyrrolidin-1-yl]-(3'-methoxy-4-methyl-biphenyl-2-yl)-methanone. LC-MS: $t_R$ = 1.01; [M + H]$^+$ = 482.4 |
| 7.45 | [(S)-2-(1-Ethyl-5,6-dimethyl-1H-benzoimidazol-2-yl)-2-methyl-pyrrolidin-1-yl]-(2'-fluoro-4-methyl-biphenyl-2-yl)-methanone. LC-MS: $t_R$ = 1.00; [M + H]$^+$ = 470.4 |
| 7.46 | {(S)-2-[5,6-Dimethoxy-1-(2-methoxy-ethyl)-1H-benzoimidazol-2-yl]-2-methyl-pyrrolidin-1-yl}-(5-methyl-2-[1,2,3]triazol-2-yl-phenyl)-methanone. LC-MS: $t_R$ = 0.81; [M + H]$^+$ = 505.4 |

-continued

| Example | Compound name. LC-MS data |
|---|---|
| 7.47 | [(S)-2-(1-Cyclopropylmethyl-5,6-dimethoxy-1H-benzoimidazol-2-yl)-2-methyl-pyrrolidin-1-yl]-(5-methyl-2-[1,2,3]triazol-2-yl-phenyl)-methanone. LC-MS: $t_R$ = 0.86; $[M + H]^+$ = 501.4 |
| 7.48 | {(S)-2-[1-(2-Fluoro-ethyl)-5,6-dimethoxy-1H-benzoimidazol-2-yl]-2-methyl-pyrrolidin-1-yl}-(5-methyl-2-[1,2,3]triazol-2-yl-phenyl)-methanone. LC-MS: $t_R$ = 0.78; $[M + H]^+$ = 493.4 |
| 7.49 | [(S)-2-(1-Cyclopropylmethyl-5,6-dimethyl-1H-benzoimidazol-2-yl)-2-methyl-pyrrolidin-1-yl]-(3'-methoxy-4-methyl-biphenyl-2-yl)-methanone. LC-MS: $t_R$ = 1.07; $[M + H]^+$ = 508.4 |
| 7.50 | [(S)-2-(1-Cyclopropylmethyl-5,6-dimethyl-1H-benzoimidazol-2-yl)-2-methyl-pyrrolidin-1-yl]-(2'-fluoro-4-methyl-biphenyl-2-yl)-methanone. LC-MS: $t_R$ = 1.06; $[M + H]^+$ = 496.4 |
| 7.51 | {(S)-2-[1-(2-Fluoro-ethyl)-5,6-dimethyl-1H-benzoimidazol-2-yl]-2-methyl-pyrrolidin-1-yl}-(3'-methoxy-4-methyl-biphenyl-2-yl)-methanone. LC-MS: $t_R$ = 0.99; $[M + H]^+$ = 500.4 |
| 7.52 | {(S)-2-[1-(2-Fluoro-ethyl)-5,6-dimethyl-1H-benzoimidazol-2-yl]-2-methyl-pyrrolidin-1-yl}-(2'-fluoro-4-methyl-biphenyl-2-yl)-methanone. LC-MS: $t_R$ = 0.99; $[M + H]^+$ = 488.4 |
| 7.53 | {(S)-2-[1-(2-Methoxy-ethyl)-5,6-dimethyl-1H-benzoimidazol-2-yl]-2-methyl-pyrrolidin-1-yl}-(3'-methoxy-4-methyl-biphenyl-2-yl)-methanone. LC-MS: $t_R$ = 1.02; $[M + H]^+$ = 512.4 |
| 7.54 | (2'-Fluoro-4-methyl-biphenyl-2-yl)-{(S)-2-[1-(2-methoxy-ethyl)-5,6-dimethyl-1H-benzoimidazol-2-yl]-2-methyl-pyrrolidin-1-yl}-methanone. LC-MS: $t_R$ = 1.02; $[M + H]^+$ = 500.4 |

II—Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$.

Human orexin-A as an agonist is prepared as 1 mM stock solution in MeOH: water (1:1), diluted in HBSS containing 0.1% bovine serum albumin (BSA), $NaHCO_3$: 0.375 g/l and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/l and 20 mM HEPES. On the day of the assay, 50 µl of staining buffer (HBSS containing 1% FCS, 20 mM HEPES, $NaHCO_3$: 0.375 g/l, 5 mM probenecid (Sigma) and 3 M of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at RT for 30 min before measurement.

Within the Fluorescent Imaging Plate Reader (FLIPR Tetra, Molecular Devices), antagonists are added to the plate in a volume of 10 µl/well, incubated for 120 min and finally 10 µl/well of agonist is added. Fluorescence is measured for each well at 1 second intervals, and the height of each fluorescence peak is compared to the height of the fluorescence peak induced by an approximate $EC_{70}$ (for example 5 nM) of orexin-A with vehicle in place of antagonist. The $IC_{50}$ value (the concentration of compound needed to inhibit 50% of the agonistic response) is determined and may be normalized using the obtained $IC_{50}$ value of a on-plate reference compound. Optimized conditions are achieved by adjustment of pipetting speed and cell splitting regime. The calculated $IC_{50}$ values may fluctuate depending on the daily cellular assay performance. Fluctuations of this kind are known to those skilled in the art. Average $IC_{50}$ values from several measurements are given as geometric mean values. Antagonistic activities of example compounds with respect to the $Ox_1$ and the $Ox_2$ receptor are displayed in Table 1.

TABLE 1

| Example Number | $IC_{50}$ Ox1 [nM] | $IC_{50}$ Ox2 [nM] | Example Number | $IC_{50}$ Ox1 [nM] | $IC_{50}$ Ox2 [nM] | Example Number | $IC_{50}$ Ox1 [nM] | $IC_{50}$ Ox2 [nM] |
|---|---|---|---|---|---|---|---|---|
| Ex. 1.1 | 1500 | 108 | Ex. 1.10 | 98 | 248 | Ex. 1.100 | 27 | 104 |
| Ex. 1.101 | 21 | 50 | Ex. 1.102 | 17 | 17 | Ex. 1.103 | 364 | 112 |
| Ex. 1.104 | 657 | 769 | Ex. 1.105 | 45 | 89 | Ex. 1.106 | 17 | 31 |
| Ex. 1.107 | 28 | 58 | Ex. 1.108 | 171 | 835 | Ex. 1.109 | 5 | 10 |
| Ex. 1.11 | 110 | 54 | Ex. 1.110 | 164 | 46 | Ex. 1.111 | 32 | 243 |
| Ex. 1.112 | 69 | 289 | Ex. 1.113 | 5 | 58 | Ex. 1.114 | 30 | 74 |
| Ex. 1.115 | 37 | 19 | Ex. 1.116 | 86 | 248 | Ex. 1.117 | 136 | 56 |
| Ex. 1.118 | 191 | 364 | Ex. 1.119 | 27 | 77 | Ex. 1.12 | 273 | 344 |
| Ex. 1.120 | 147 | 557 | Ex. 1.121 | 76 | 287 | Ex. 1.122 | 55 | 45 |
| Ex. 1.123 | 147 | 70 | Ex. 1.124 | 119 | 42 | Ex. 1.125 | 39 | 73 |
| Ex. 1.126 | 18 | 24 | Ex. 1.127 | 33 | 22 | Ex. 1.128 | 1480 | 331 |
| Ex. 1.129 | 93 | 124 | Ex. 1.13 | 15 | 24 | Ex. 1.130 | 113 | 75 |
| Ex. 1.131 | 37 | 48 | Ex. 1.132 | 90 | 614 | Ex. 1.133 | 4 | 11 |
| Ex. 1.134 | 116 | 26 | Ex. 1.135 | 32 | 194 | Ex. 1.136 | 81 | 278 |
| Ex. 1.137 | 4 | 33 | Ex. 1.138 | 35 | 109 | Ex. 1.139 | 103 | 26 |
| Ex. 1.14 | 34 | 32 | Ex. 1.140 | 192 | 46 | Ex. 1.141 | 507 | 13 |
| Ex. 1.142 | 24 | 13 | Ex. 1.143 | 14 | 16 | Ex. 1.144 | 33 | 27 |
| Ex. 1.145 | 3 | 7 | Ex. 1.146 | 7 | 23 | Ex. 1.147 | 685 | 24 |
| Ex. 1.148 | 1170 | 44 | Ex. 1.149 | 143 | 9 | Ex. 1.15 | 67 | 45 |
| Ex. 1.150 | 301 | 11 | Ex. 1.151 | 763 | 110 | Ex. 1.152 | 282 | 23 |
| Ex. 1.153 | 40 | 3 | Ex. 1.154 | 483 | 21 | Ex. 1.155 | 36 | 16 |
| Ex. 1.156 | 1810 | 29 | Ex. 1.157 | 419 | 10 | Ex. 1.158 | 538 | 20 |
| Ex. 1.159 | 903 | 23 | Ex. 1.16 | 245 | 5 | Ex. 1.160 | 245 | 5 |
| Ex. 1.161 | 1450 | 22 | Ex. 1.162 | 458 | 27 | Ex. 1.163 | 167 | 17 |
| Ex. 1.164 | 217 | 24 | Ex. 1.165 | 76 | 9 | Ex. 1.166 | 45 | 4 |
| Ex. 1.167 | 97 | 15 | Ex. 1.168 | 20 | 57 | Ex. 1.169 | 37 | 3 |
| Ex. 1.17 | 97 | 8 | Ex. 1.170 | 258 | 20 | Ex. 1.171 | 2210 | 36 |
| Ex. 1.172 | 1160 | 19 | Ex. 1.173 | 3930 | 54 | Ex. 1.174 | 68 | 87 |
| Ex. 1.175 | 528 | 76 | Ex. 1.176 | 2190 | 99 | Ex. 1.177 | 842 | 30 |

TABLE 1-continued

| Example Number | IC$_{50}$ Ox1 [nM] | IC$_{50}$ Ox2 [nM] | Example Number | IC$_{50}$ Ox1 [nM] | IC$_{50}$ Ox2 [nM] | Example Number | IC$_{50}$ Ox1 [nM] | IC$_{50}$ Ox2 [nM] |
|---|---|---|---|---|---|---|---|---|
| Ex. 1.178 | 2680 | 96 | Ex. 1.179 | 486 | 28 | Ex. 1.18 | 935 | 153 |
| Ex. 1.180 | 1490 | 50 | | | | Ex. 1.19 | 660 | 76 |
| Ex. 1.2 | 349 | 7 | Ex. 1.20 | 692 | 121 | Ex. 1.21 | 1180 | 149 |
| Ex. 1.22 | 415 | 52 | Ex. 1.23 | 523 | 212 | Ex. 1.24 | 850 | 81 |
| Ex. 1.25 | 364 | 90 | Ex. 1.26 | 125 | 22 | Ex. 1.27 | 1040 | 35 |
| Ex. 1.28 | 114 | 110 | Ex. 1.29 | 369 | 182 | Ex. 1.3 | 265 | 51 |
| Ex. 1.30 | 624 | 147 | Ex. 1.31 | 195 | 78 | Ex. 1.32 | 347 | 139 |
| Ex. 1.33 | 76 | 48 | Ex. 1.34 | 124 | 56 | Ex. 1.35 | 117 | 99 |
| Ex. 1.36 | 109 | 27 | Ex. 1.37 | 154 | 62 | Ex. 1.38 | 360 | 110 |
| Ex. 1.39 | 157 | 73 | Ex. 1.4 | 241 | 30 | Ex. 1.40 | 74 | 23 |
| Ex. 1.41 | 115 | 64 | Ex. 1.42 | 263 | 65 | Ex. 1.43 | 97 | 58 |
| Ex. 1.44 | 404 | 120 | Ex. 1.45 | 501 | 109 | Ex. 1.46 | 128 | 13 |
| Ex. 1.47 | 446 | 13 | Ex. 1.49 | 32 | 42 | Ex. 1.5 | 56 | 23 |
| Ex. 1.50 | 394 | 107 | Ex. 1.51 | 66 | 21 | Ex. 1.52 | 737 | 121 |
| Ex. 1.53 | 616 | 90 | Ex. 1.54 | 726 | 80 | Ex. 1.55 | 35 | 10 |
| Ex. 1.56 | 252 | 88 | Ex. 1.57 | 76 | 22 | Ex. 1.58 | 32 | 24 |
| Ex. 1.59 | 77 | 252 | Ex. 1.6 | 202 | 46 | Ex. 1.60 | 61 | 48 |
| Ex. 1.61 | 21 | 21 | Ex. 1.62 | 128 | 197 | Ex. 1.63 | 12 | 9 |
| Ex. 1.64 | 12 | 18 | Ex. 1.65 | 63 | 147 | Ex. 1.66 | 20 | 47 |
| Ex. 1.67 | 127 | 84 | Ex. 1.68 | 7 | 8 | Ex. 1.69 | 37 | 31 |
| Ex. 1.7 | 93 | 5 | Ex. 1.70 | 26 | 26 | Ex. 1.71 | 95 | 162 |
| Ex. 1.72 | 112 | 180 | Ex. 1.73 | 136 | 282 | Ex. 1.74 | 52 | 100 |
| Ex. 1.75 | 5 | 9 | Ex. 1.76 | 279 | 17 | Ex. 1.78 | 102 | 408 |
| Ex. 1.79 | 5 | 46 | | | | Ex. 1.80 | 41 | 564 |
| Ex. 1.81 | 20 | 116 | Ex. 1.82 | 13 | 17 | Ex. 1.83 | 17 | 36 |
| Ex. 1.84 | 14 | 20 | Ex. 1.85 | 5 | 23 | Ex. 1.86 | 56 | 118 |
| Ex. 1.87 | 30 | 77 | Ex. 1.88 | 102 | 109 | Ex. 1.89 | 39 | 180 |
| Ex. 1.9 | 337 | 69 | Ex. 1.90 | 2 | 14 | Ex. 1.91 | 13 | 25 |
| Ex. 1.92 | 23 | 69 | Ex. 1.93 | 102 | 458 | Ex. 1.94 | 42 | 414 |
| Ex. 1.95 | 18 | 15 | Ex. 1.96 | 54 | 43 | Ex. 1.97 | 95 | 314 |
| Ex. 1.98 | 105 | 387 | Ex. 1.99 | 58 | 50 | Ex. 2.1 | 56 | 53 |
| Ex. 2.10 | 5 | 8 | Ex. 2.11 | 69 | 124 | Ex. 2.2 | 1300 | 317 |
| Ex. 2.3 | 67 | 61 | Ex. 2.4 | 425 | 131 | Ex. 2.5 | 6 | 12 |
| Ex. 2.6 | 52 | 59 | Ex. 2.7 | 66 | 42 | Ex. 2.8 | 70 | 51 |
| Ex. 2.9 | 17 | 18 | Ex. 3.1 | 102 | 69 | Ex. 3.10 | 45 | 5 |
| Ex. 3.11 | 6 | 9 | Ex. 3.12 | 13 | 1 | Ex. 3.13 | 16 | 7 |
| Ex. 3.14 | 674 | 23 | Ex. 3.15 | 96 | 4 | Ex. 3.16 | 24 | 2 |
| Ex. 3.17 | 368 | 51 | Ex. 3.18 | 97 | 4 | Ex. 3.19 | 1930 | 21 |
| Ex. 3.2 | 13 | 6 | Ex. 3.20 | 1860 | 40 | Ex. 3.21 | 2510 | 33 |
| Ex. 3.22 | 576 | 9 | Ex. 3.23 | 3890 | 67 | Ex. 3.24 | 5 | 12 |
| Ex. 3.25 | 5 | 7 | Ex. 3.26 | 50 | 66 | Ex. 3.27 | 5 | 16 |
| Ex. 3.28 | 10 | 19 | Ex. 3.29 | 28 | 20 | Ex. 3.3 | 1290 | 255 |
| Ex. 3.30 | 2 | 2 | Ex. 3.31 | 5 | 4 | Ex. 3.32 | 0.9 | 5 |
| Ex. 3.33 | 0.8 | 10 | Ex. 3.34 | 0.9 | 8 | Ex. 3.35 | 3 | 4 |
| Ex. 3.36 | 5 | 9 | Ex. 3.37 | 8 | 8 | Ex. 3.38 | 6 | 13 |
| Ex. 3.39 | 74 | 57 | Ex. 3.4 | 44 | 14 | Ex. 3.40 | 8 | 7 |
| Ex. 3.41 | 0.7 | 7 | Ex. 3.42 | 193 | 395 | Ex. 3.43 | 10 | 13 |
| Ex. 3.44 | 3 | 6 | Ex. 3.45 | 16 | 19 | Ex. 3.46 | 223 | 288 |
| Ex. 3.47 | 225 | 471 | Ex. 3.48 | 3 | 4 | Ex. 3.49 | 13 | 18 |
| Ex. 3.5 | 109 | 74 | Ex. 3.50 | 232 | 252 | Ex. 3.51 | 94 | 44 |
| Ex. 3.52 | 28 | 27 | Ex. 3.53 | 10 | 20 | Ex. 3.54 | 52 | 44 |
| Ex. 3.55 | 18 | 45 | Ex. 3.56 | 18 | 37 | Ex. 3.6 | 5 | 4 |
| Ex. 3.7 | 9 | 5 | Ex. 3.8 | 22 | 12 | Ex. 3.9 | 1 | 2 |
| Ex. 4.1 | 29 | 778 | Ex. 4.10 | 2 | 833 | Ex. 4.100 | 6 | 1280 |
| Ex. 4.101 | 18 | 183 | Ex. 4.11 | 10 | 4060 | Ex. 4.12 | 23 | 4870 |
| Ex. 4.13 | 26 | 4910 | Ex. 4.14 | 15 | 4030 | Ex. 4.15 | 2 | 670 |
| Ex. 4.16 | 1 | 250 | Ex. 4.17 | 14 | 1670 | Ex. 4.18 | 43 | 2930 |
| Ex. 4.19 | 2 | 422 | Ex. 4.2 | 132 | 669 | Ex. 4.20 | 28 | 2450 |
| Ex. 4.21 | 1 | 133 | Ex. 4.22 | 6 | 1075 | Ex. 4.23 | 9 | 1940 |
| Ex. 4.24 | 2 | 367 | Ex. 4.25 | 4 | 441 | Ex. 4.26 | 17 | 2280 |
| Ex. 4.27 | 59 | 5590 | Ex. 4.28 | 2 | 486 | Ex. 4.29 | 30 | 353 |
| Ex. 4.3 | 8 | 1350 | Ex. 4.30 | 12 | 155 | Ex. 4.31 | 77 | 774 |
| Ex. 4.32 | 7 | 156 | Ex. 4.33 | 9 | 294 | Ex. 4.34 | 37 | 1880 |
| Ex. 4.35 | 3 | 193 | Ex. 4.36 | 70 | 2740 | Ex. 4.37 | 24 | 988 |
| Ex. 4.38 | 55 | 756 | Ex. 4.39 | 14 | 315 | Ex. 4.4 | 11 | 1170 |
| Ex. 4.40 | 21 | 28 | Ex. 4.41 | 182 | 248 | Ex. 4.42 | 365 | 1130 |
| Ex. 4.43 | 39 | 97 | Ex. 4.44 | 38 | 246 | Ex. 4.45 | 124 | 5780 |
| Ex. 4.46 | 14 | 51 | Ex. 4.47 | 176 | 281 | Ex. 4.48 | 391 | 1320 |
| Ex. 4.49 | 221 | 533 | Ex. 4.5 | 29 | 3190 | Ex. 4.50 | 373 | 4220 |
| Ex. 4.51 | 99 | 677 | Ex. 4.52 | 19 | 1067 | Ex. 4.53 | 111 | 4440 |
| Ex. 4.54 | 21 | 2322 | Ex. 4.55 | 167 | 7970 | Ex. 4.56 | 283 | 2620 |
| Ex. 4.57 | 59 | 250 | Ex. 4.58 | 66 | 2170 | Ex. 4.59 | 6 | 67 |
| Ex. 4.6 | 29 | 3890 | Ex. 4.60 | 2 | 65 | Ex. 4.61 | 0.9 | 72 |
| Ex. 4.62 | 3 | 19 | Ex. 4.63 | 0.8 | 122 | Ex. 4.64 | 5 | 800 |
| Ex. 4.65 | 8 | 207 | Ex. 4.66 | 1 | 23 | Ex. 4.67 | 0.9 | 251 |
| Ex. 4.68 | 2 | 400 | Ex. 4.69 | 2 | 191 | Ex. 4.7 | 2 | 603 |
| Ex. 4.70 | 0.6 | 404 | Ex. 4.71 | 7 | 133 | Ex. 4.72 | 4 | 51 |

TABLE 1-continued

| Example Number | IC$_{50}$ Ox1 [nM] | IC$_{50}$ Ox2 [nM] | Example Number | IC$_{50}$ Ox1 [nM] | IC$_{50}$ Ox2 [nM] | Example Number | IC$_{50}$ Ox1 [nM] | IC$_{50}$ Ox2 [nM] |
|---|---|---|---|---|---|---|---|---|
| Ex. 4.73 | 17 | 1290 | Ex. 4.74 | 4 | 78 | Ex. 4.75 | 8 | 636 |
| Ex. 4.76 | 8 | 113 | Ex. 4.77 | 5 | 790 | Ex. 4.78 | 3 | 1630 |
| Ex. 4.79 | 18 | 541 | Ex. 4.8 | 68 | 9930 | Ex. 4.80 | 3 | 2020 |
| Ex. 4.81 | 4 | 79 | Ex. 4.82 | 4 | 32 | Ex. 4.83 | 159 | 2322 |
| Ex. 4.84 | 8 | 58 | Ex. 4.85 | 7 | 43 | Ex. 4.86 | 7 | 352 |
| Ex. 4.87 | 4 | 2076 | Ex. 4.88 | 11 | 182 | Ex. 4.89 | 3 | 2170 |
| Ex. 4.9 | 2 | 2780 | Ex. 4.90 | 6 | 2350 | Ex. 4.91 | 17 | 183 |
| Ex. 4.92 | 5 | 212 | Ex. 4.93 | 4 | 74 | Ex. 4.94 | 3 | 543 |
| Ex. 4.95 | 28 | 1170 | Ex. 4.96 | 31 | 996 | Ex. 4.97 | 4 | 129 |
| Ex. 4.98 | 4 | 1300 | Ex. 4.99 | 13 | 981 | Ex. 4.102 | 10 | 103 |
| Ex. 4.103 | 4 | 178 | Ex. 4.104 | 14 | 1660 | Ex. 4.105 | 5 | 177 |
| Ex. 4.106 | 23 | 529 | Ex. 4.107 | 47 | 1760 | Ex. 4.108 | 7 | 419 |
| Ex. 4.109 | 3 | 108 | Ex. 4.110 | 13 | 1520 | Ex. 4.111 | 2 | 110 |
| Ex. 4.112 | 3 | 1060 | Ex. 4.113 | 9 | 2040 | Ex. 4.114 | 33 | 1360 |
| Ex. 4.115 | 7 | 754 | Ex. 4.116 | 6 | 198 | Ex. 4.117 | 16 | 2570 |
| Ex. 4.118 | 50 | 4350 | Ex. 4.119 | 21 | 2050 | Ex. 4.120 | 14 | 725 |
| Ex. 4.121 | 6 | 475 | Ex. 4.122 | 3 | 610 | Ex. 4.123 | 21 | 871 |
| Ex. 4.124 | 8 | 591 | Ex. 4.125 | 1 | 81 | Ex. 4.126 | 43 | 2380 |
| Ex. 4.127 | 1 | 19 | Ex. 4.128 | 1 | 387 | Ex. 4.129 | 35 | 2750 |
| Ex. 4.130 | 11 | 128 | Ex. 4.131 | 23 | 501 | Ex. 4.132 | 87 | 1320 |
| Ex. 4.133 | 25 | 359 | Ex. 4.134 | 1 | 86 | Ex. 4.135 | 4 | 203 |
| Ex. 4.136 | 14 | 4360 | Ex. 4.137 | 5 | 3090 | Ex. 4.138 | 2 | 1340 |
| Ex. 4.139 | 5 | 2260 | Ex. 4.140 | 7 | 2170 | Ex. 4.141 | 5 | 2760 |
| Ex. 4.142 | 6 | 2160 | Ex. 4.143 | 24 | 3680 | Ex. 4.144 | 9 | 463 |
| Ex. 4.145 | 3 | 635 | Ex. 4.146 | 6 | 2110 | Ex. 4.147 | 13 | 9650 |
| Ex. 4.148 | 7 | 3180 | Ex. 4.149 | 14 | 752 | Ex. 4.150 | 6 | 180 |
| Ex. 4.151 | 5 | 185 | Ex. 4.152 | 2 | 40 | Ex. 4.153 | 3 | 80 |
| Ex. 4.154 | 26 | 4800 | Ex. 4.155 | 42 | 891 | Ex. 4.156 | 14 | 489 |
| Ex. 4.157 | 13 | 1710 | Ex. 4.158 | 2 | 308 | Ex. 4.159 | 4 | 215 |
| Ex. 4.160 | 2 | 27 | Ex. 4.161 | 2 | 191 | Ex. 4.162 | 2 | 299 |
| Ex. 4.163 | 20 | 4400 | Ex. 4.164 | 7 | 725 | Ex. 4.165 | 20 | 968 |
| Ex. 4.166 | 2 | 568 | Ex. 4.167 | 13 | 144 | Ex. 4.168 | 10 | 486 |
| Ex. 4.169 | 4 | 892 | Ex. 4.170 | 11 | 1430 | Ex. 4.171 | 1.5 | 571 |
| Ex. 4.172 | 2 | 457 | Ex. 4.173 | 13 | 6330 | Ex. 4.174 | 12 | 132 |
| Ex. 4.175 | 14 | 249 | Ex. 4.176 | 15 | 1067 | Ex. 4.177 | 9 | 219 |
| Ex. 4.178 | 7 | 350 | Ex. 4.179 | 27 | 69 | Ex. 4.180 | 8 | 304 |
| Ex. 4.181 | 3 | 230 | Ex. 4.182 | 7 | 694 | Ex. 4.183 | 93 | 2256 |
|  |  |  |  |  |  | Ex. 5.1 | 26 | 13 |
| Ex. 5.10 | 6 | 16 | Ex. 5.100 | 17 | 27 | Ex. 5.101 | 59 | 54 |
| Ex. 5.102 | 34 | 82 | Ex. 5.103 | 46 | 70 | Ex. 5.104 | 92 | 97 |
| Ex. 5.105 | 24 | 28 | Ex. 5.106 | 25 | 37 | Ex. 5.107 | 58 | 53 |
| Ex. 5.108 | 265 | 161 | Ex. 5.109 | 3 | 4 | Ex. 5.11 | 29 | 413 |
| Ex. 5.110 | 13 | 14 | Ex. 5.111 | 5 | 7 | Ex. 5.112 | 12 | 16 |
| Ex. 5.113 | 12 | 15 | Ex. 5.114 | 10 | 21 | Ex. 5.115 | 22 | 18 |
| Ex. 5.116 | 39 | 19 | Ex. 5.117 | 57 | 38 | Ex. 5.118 | 25 | 35 |
| Ex. 5.119 | 30 | 29 | Ex. 5.12 | 15 | 134 | Ex. 5.120 | 48 | 26 |
| Ex. 5.121 | 56 | 43 | Ex. 5.122 | 99 | 74 | Ex. 5.123 | 146 | 304 |
| Ex. 5.124 | 113 | 411 | Ex. 5.125 | 84 | 126 | Ex. 5.126 | 117 | 396 |
| Ex. 5.127 | 1 | 6 | Ex. 5.128 | 20 | 219 | Ex. 5.129 | 20 | 62 |
| Ex. 5.13 | 6 | 31 | Ex. 5.130 | 24 | 58 | Ex. 5.131 | 15 | 178 |
| Ex. 5.132 | 54 | 615 | Ex. 5.133 | 11 | 45 | Ex. 5.134 | 8 | 20 |
| Ex. 5.135 | 10 | 49 | Ex. 5.136 | 6 | 35 | Ex. 5.137 | 3 | 6 |
| Ex. 5.138 | 2 | 10 | Ex. 5.139 | 2 | 21 | Ex. 5.14 | 6 | 31 |
| Ex. 5.140 | 5 | 28 | Ex. 5.141 | 27 | 244 | Ex. 5.142 | 8 | 24 |
| Ex. 5.143 | 7 | 82 | Ex. 5.144 | 20 | 210 | Ex. 5.145 | 6 | 30 |
| Ex. 5.146 | 15 | 43 | Ex. 5.147 | 27 | 112 | Ex. 5.148 | 35 | 159 |
| Ex. 5.149 | 21 | 26 | Ex. 5.15 | 5 | 22 | Ex. 5.150 | 37 | 49 |
| Ex. 5.151 | 20 | 40 | Ex. 5.152 | 24 | 51 | Ex. 5.153 | 22 | 35 |
| Ex. 5.154 | 59 | 61 | Ex. 5.155 | 134 | 249 | Ex. 5.156 | 38 | 54 |
| Ex. 5.157 | 367 | 538 | Ex. 5.158 | 525 | 879 | Ex. 5.159 | 23 | 37 |
| Ex. 5.16 | 16 | 18 | Ex. 5.160 | 38 | 113 | Ex. 5.161 | 405 | 388 |
| Ex. 5.162 | 252 | 250 | Ex. 5.163 | 142 | 401 | Ex. 5.164 | 104 | 419 |
| Ex. 5.165 | 65 | 355 | Ex. 5.166 | 13 | 59 | Ex. 5.167 | 91 | 351 |
| Ex. 5.168 | 64 | 570 | Ex. 5.169 | 63 | 197 | Ex. 5.17 | 11 | 76 |
| Ex. 5.170 | 2 | 13 | Ex. 5.171 | 12 | 58 | Ex. 5.172 | 92 | 704 |
| Ex. 5.173 | 290 | 1138 | Ex. 5.174 | 59 | 133 | Ex. 5.175 | 24 | 355 |
| Ex. 5.176 | 389 | 1067 | Ex. 5.177 | 76 | 860 | Ex. 5.178 | 20 | 280 |
| Ex. 5.179 | 368 | 1125 | Ex. 5.18 | 23 | 84 | Ex. 5.180 | 42 | 261 |
| Ex. 5.181 | 385 | 556 | Ex. 5.182 | 10 | 55 | Ex. 5.183 | 339 | 1165 |
| Ex. 5.184 | 300 | 413 | Ex. 5.185 | 91 | 283 | Ex. 5.186 | 120 | 294 |
| Ex. 5.187 | 310 | >2589 | Ex. 5.188 | 23 | 119 | Ex. 5.189 | 16 | 62 |
| Ex. 5.19 | 9 | 20 | Ex. 5.190 | 58 | 119 | Ex. 5.191 | 18 | 69 |
| Ex. 5.192 | 23 | 88 | Ex. 5.193 | 24 | 203 | Ex. 5.194 | 13 | 98 |
| Ex. 5.195 | 73 | 102 | Ex. 5.196 | 91 | 199 | Ex. 5.197 | 18 | 166 |
| Ex. 5.198 | 18 | 34 | Ex. 5.199 | 12 | 83 | Ex. 5.2 | 2 | 5 |
| Ex. 5.20 | 19 | 161 | Ex. 5.200 | 115 | 517 | Ex. 5.201 | 265 | 861 |
| Ex. 5.202 | 227 | 924 | Ex. 5.203 | 195 | 1380 | Ex. 5.204 | 360 | 900 |

TABLE 1-continued

| Example Number | IC$_{50}$ Ox1 [nM] | IC$_{50}$ Ox2 [nM] | Example Number | IC$_{50}$ Ox1 [nM] | IC$_{50}$ Ox2 [nM] | Example Number | IC$_{50}$ Ox1 [nM] | IC$_{50}$ Ox2 [nM] |
|---|---|---|---|---|---|---|---|---|
| Ex. 5.205 | 149 | 852 | Ex. 5.206 | 19 | 117 | Ex. 5.207 | 15 | 78 |
| Ex. 5.208 | 53 | 284 | Ex. 5.209 | 17 | 101 | Ex. 5.21 | 22 | 18 |
| Ex. 5.210 | 3 | 27 | Ex. 5.211 | 27 | 159 | Ex. 5.212 | 26 | 239 |
| Ex. 5.213 | 16 | 51 | Ex. 5.214 | 2 | 4 | Ex. 5.215 | 4 | 11 |
| Ex. 5.216 | 15 | 45 | Ex. 5.22 | 7 | 86 | Ex. 5.23 | 15 | 80 |
| Ex. 5.24 | 2 | 9 | Ex. 5.25 | 27 | 81 | Ex. 5.26 | 39 | 197 |
| Ex. 5.27 | 46 | 507 | Ex. 5.28 | 4 | 19 | Ex. 5.29 | 13 | 59 |
| Ex. 5.3 | 2 | 4 | Ex. 5.30 | 57 | 164 | Ex. 5.31 | 44 | 740 |
| Ex. 5.32 | 90 | 46 | Ex. 5.33 | 25 | 29 | Ex. 5.34 | 2 | 9 |
| Ex. 5.35 | 102 | 99 | Ex. 5.36 | 2 | 3 | Ex. 5.37 | 10 | 16 |
| Ex. 5.38 | 4 | 12 | Ex. 5.39 | 36 | 20 | Ex. 5.4 | 10 | 6 |
| Ex. 5.40 | 44 | 91 | Ex. 5.41 | 2 | 2 | Ex. 5.42 | 49 | 75 |
| Ex. 5.43 | 3 | 14 | Ex. 5.44 | 8 | 29 | Ex. 5.45 | 5 | 12 |
| Ex. 5.46 | 6 | 14 | Ex. 5.47 | 5 | 15 | Ex. 5.48 | 12 | 25 |
| Ex. 5.49 | 85 | 114 | Ex. 5.5 | 3 | 5 | Ex. 5.50 | 49 | 33 |
| Ex. 5.51 | 10 | 18 | Ex. 5.52 | 107 | 43 | Ex. 5.53 | 24 | 23 |
| Ex. 5.54 | 33 | 20 | Ex. 5.55 | 113 | 202 | Ex. 5.56 | 12 | 15 |
| Ex. 5.57 | 57 | 55 | Ex. 5.58 | 3 | 6 | Ex. 5.59 | 42 | 84 |
| Ex. 5.6 | 32 | 59 | Ex. 5.60 | 156 | 54 | Ex. 5.61 | 112 | 26 |
| Ex. 5.62 | 35 | 130 | | | | Ex. 5.64 | 17 | 19 |
| Ex. 5.65 | 200 | 154 | Ex. 5.66 | 872 | 458 | Ex. 5.67 | 27 | 23 |
| Ex. 5.68 | 141 | 150 | Ex. 5.69 | 414 | 1200 | Ex. 5.7 | 5 | 29 |
| Ex. 5.70 | 31 | 83 | Ex. 5.71 | 56 | 22 | Ex. 5.72 | 19 | 16 |
| Ex. 5.73 | 98 | 57 | Ex. 5.74 | 592 | 414 | Ex. 5.75 | 300 | 126 |
| Ex. 5.76 | 33 | 47 | Ex. 5.77 | 64 | 153 | Ex. 5.78 | 31 | 72 |
| Ex. 5.79 | 43 | 97 | Ex. 5.8 | 13 | 129 | Ex. 5.80 | 548 | 360 |
| Ex. 5.81 | 258 | 130 | Ex. 5.82 | 27 | 15 | Ex. 5.83 | 426 | 104 |
| Ex. 5.84 | 138 | 76 | Ex. 5.85 | 316 | 114 | Ex. 5.86 | 94 | 85 |
| Ex. 5.87 | 203 | 157 | Ex. 5.88 | 192 | 166 | Ex. 5.89 | 148 | 119 |
| Ex. 5.9 | 8 | 81 | Ex. 5.90 | 232 | 473 | Ex. 5.91 | 217 | 1290 |
| Ex. 5.92 | 62 | 177 | Ex. 5.93 | 15 | 19 | Ex. 5.94 | 14 | 37 |
| Ex. 5.95 | 11 | 29 | Ex. 5.96 | 13 | 32 | Ex. 5.97 | 6 | 11 |
| Ex. 5.98 | 120 | 264 | Ex. 5.99 | 6 | 11 | Ex. 5.217 | 98 | 274 |
| Ex. 5.218 | 13 | 36 | Ex. 5.219 | 19 | 72 | Ex. 5.220 | 98 | 249 |
| Ex. 5.221 | 19 | 83 | Ex. 5.222 | 26 | 68 | Ex. 5.223 | 3 | 12 |
| Ex. 5.224 | 7 | 21 | Ex. 5.225 | 16 | 44 | Ex. 5.226 | 7 | 155 |
| Ex. 5.227 | 20 | 521 | Ex. 5.228 | 56 | 2030 | Ex. 5.229 | 54 | 858 |
| Ex. 5.230 | 21 | 530 | Ex. 5.231 | 15 | 135 | Ex. 5.232 | 20 | 2055 |
| Ex. 5.233 | 5 | 263 | Ex. 5.234 | 8 | 131 | Ex. 5.235 | 5 | 16.5 |
| Ex. 5.236 | 26 | 173 | Ex. 5.237 | 58 | 223 | Ex. 5.238 | 23 | 91 |
| Ex. 5.239 | 35 | 594 | Ex. 5.240 | 38 | 232 | Ex. 5.241 | 54 | 1000 |
| Ex. 5.242 | 56 | 401 | Ex. 5.243 | 88 | 1120 | Ex. 5.244 | 62 | 641 |
| Ex. 5.245 | 14 | 80 | Ex. 5.246 | 28 | 533 | Ex. 5.247 | 10 | 136 |
| Ex. 5.248 | 22 | 494 | Ex. 5.249 | 38 | 53 | Ex. 5.250 | 184 | 992 |
| Ex. 5.251 | 13 | 774 | Ex. 5.252 | 20 | 1640 | Ex. 5.253 | 12 | 1187 |
| Ex. 5.254 | 39 | 9270 | Ex. 5.255 | 1 | 145 | Ex. 5.256 | 13 | 402 |
| Ex. 5.257 | 13 | 329 | Ex. 5.258 | 36 | 6520 | Ex. 5.259 | 29 | 4660 |
| Ex. 5.260 | 20 | 2870 | Ex. 5.261 | 4 | 466 | Ex. 5.262 | 113 | 1 |
| Ex. 5.263 | 56 | 304 | Ex. 5.264 | 25 | 65 | Ex. 5.265 | 9 | 32 |
| Ex. 5.266 | 1 | 1 | Ex. 5.267 | 12 | 105 | Ex. 5.268 | 6 | 9 |
| Ex. 5.269 | 15 | 22 | Ex. 5.270 | 7 | 9 | Ex. 5.271 | 5 | 6 |
| Ex. 5.272 | 8 | 12 | Ex. 5.273 | 7 | 12 | Ex. 5.274 | 3 | 8 |
| Ex. 5.275 | 5 | 6 | Ex. 5.276 | 3 | 8 | Ex. 5.277 | 6 | 21 |
| Ex. 5.278 | 22 | 31 | Ex. 5.279 | 3 | 8 | Ex. 5.280 | 36 | 16 |
| Ex. 5.281 | 34 | 380 | Ex. 5.282 | 47 | 97 | Ex. 5.283 | 87 | 397 |
| Ex. 5.284 | 10 | 18 | Ex. 5.285 | 32 | 452 | Ex. 5.286 | 40 | 4592 |
| Ex. 5.287 | 53 | 1165 | Ex. 5.288 | 38 | 1340 | Ex. 5.289 | 38 | 532 |
| Ex. 5.290 | 33 | 2140 | Ex. 5.291 | 48 | 347 | Ex. 5.292 | 34 | 671 |
| Ex. 5.293 | 77 | 4040 | Ex. 5.294 | 39 | 714 | Ex. 5.295 | 8 | 254 |
| Ex. 5.296 | 25 | 31 | Ex. 5.297 | 41 | 57 | Ex. 5.298 | 15 | 21 |
| Ex. 5.299 | 17 | 21 | Ex. 5.300 | 10 | 18 | Ex. 5.301 | 24 | 16 |
| Ex. 5.302 | 28 | 42 | Ex. 5.303 | 29 | 21 | Ex. 5.304 | 19 | 86 |
| Ex. 5.305 | 35 | 41 | Ex. 5.306 | 33 | 69 | Ex. 5.307 | 20 | 49 |
| Ex. 5.308 | 21 | 122 | Ex. 5.309 | 23 | 21 | Ex. 5.310 | 32 | 70 |
| | | | | | | Ex. 6.1 | 367 | 33 |
| Ex. 6.10 | 206 | 81 | Ex. 6.100 | 55 | 4 | Ex. 6.101 | 10 | 0.9 |
| Ex. 6.102 | 364 | 32 | Ex. 6.103 | 184 | 6 | Ex. 6.104 | 13 | 0.8 |
| Ex. 6.105 | 1060 | 77 | Ex. 6.106 | 99 | 5 | Ex. 6.107 | 74 | 16 |
| Ex. 6.108 | 414 | 7 | Ex. 6.109 | 112 | 7 | Ex. 6.11 | 135 | 56 |
| Ex. 6.110 | 15 | 1 | Ex. 6.111 | 272 | 14 | Ex. 6.112 | 15 | 0.7 |
| Ex. 6.113 | 5 | 1 | Ex. 6.114 | 16 | 0.7 | Ex. 6.115 | 333 | 9 |
| Ex. 6.116 | 14 | 3 | Ex. 6.117 | 19 | 3 | Ex. 6.118 | 21 | 4 |
| Ex. 6.119 | 14 | 3 | Ex. 6.12 | 317 | 6 | Ex. 6.120 | 8 | 0.6 |
| Ex. 6.121 | 1 | 0.5 | Ex. 6.122 | 0.9 | 0.6 | Ex. 6.123 | 2 | 0.7 |
| Ex. 6.124 | 15 | 4 | Ex. 6.125 | 2 | 0.8 | Ex. 6.126 | 3 | 0.8 |
| Ex. 6.127 | 17 | 4 | Ex. 6.128 | 20 | 1 | Ex. 6.129 | 215 | 39 |
| Ex. 6.13 | 155 | 17 | Ex. 6.130 | 11 | 0.6 | Ex. 6.131 | 9 | 0.5 |

TABLE 1-continued

| Example Number | IC$_{50}$ Ox1 [nM] | IC$_{50}$ Ox2 [nM] | Example Number | IC$_{50}$ Ox1 [nM] | IC$_{50}$ Ox2 [nM] | Example Number | IC$_{50}$ Ox1 [nM] | IC$_{50}$ Ox2 [nM] |
|---|---|---|---|---|---|---|---|---|
| Ex. 6.132 | 13 | 4 | Ex. 6.133 | 3 | 2 | Ex. 6.134 | 75 | 10 |
| Ex. 6.135 | 83 | 5 | Ex. 6.136 | 765 | 4 | Ex. 6.137 | 4950 | 23 |
| Ex. 6.138 | >6970 | 34 | Ex. 6.139 | 137 | 0.6 | Ex. 6.14 | 87 | 12 |
| Ex. 6.140 | 667 | 10 | Ex. 6.141 | 883 | 9 | Ex. 6.142 | 17 | 22 |
| Ex. 6.143 | 13 | 32 | Ex. 6.144 | 15 | 56 | Ex. 6.145 | 21 | 75 |
| Ex. 6.146 | 16 | 33 | Ex. 6.147 | 13 | 34 | Ex. 6.148 | 19 | 40 |
| Ex. 6.149 | 59 | 90 | Ex. 6.15 | 298 | 37 | Ex. 6.150 | 218 | 91 |
| Ex. 6.151 | 46 | 44 | Ex. 6.152 | 5 | 20 | Ex. 6.153 | 8 | 16 |
| Ex. 6.154 | 32 | 38 | Ex. 6.155 | 649 | 105 | Ex. 6.156 | 34 | 12 |
| Ex. 6.157 | 70 | 21 | Ex. 6.158 | 57 | 35 | Ex. 6.159 | 11 | 10 |
| Ex. 6.16 | 307 | 151 | Ex. 6.160 | 326 | 8 | Ex. 6.161 | 51 | 3 |
| Ex. 6.162 | 330 | 7 | Ex. 6.163 | 259 | 72 | Ex. 6.164 | 100 | 9 |
| Ex. 6.165 | 9 | 3 | Ex. 6.166 | 33 | 4 | Ex. 6.167 | 573 | 25 |
| Ex. 6.168 | 261 | 54 | Ex. 6.169 | 344 | 479 | Ex. 6.17 | 308 | 47 |
| Ex. 6.170 | 18 | 15 | Ex. 6.171 | 162 | 19 | Ex. 6.172 | 1260 | 67 |
| Ex. 6.173 | 842 | 64 | Ex. 6.174 | 233 | 15 | Ex. 6.175 | 77 | 19 |
| Ex. 6.176 | 58 | 18 | Ex. 6.177 | 13 | 6 | Ex. 6.178 | 44 | 10 |
| Ex. 6.179 | 6 | 7 | Ex. 6.18 | 1530 | 29 | Ex. 6.180 | 5 | 4 |
| Ex. 6.181 | 2 | 2 | Ex. 6.182 | 12 | 6 | Ex. 6.183 | 127 | 21 |
| Ex. 6.184 | 67 | 73 | Ex. 6.185 | 239 | 103 | Ex. 6.186 | 27 | 6 |
| Ex. 6.187 | 24 | 15 | Ex. 6.188 | 115 | 66 | Ex. 6.189 | 47 | 25 |
| Ex. 6.19 | 1530 | 61 | Ex. 6.190 | 10 | 9 | Ex. 6.191 | 134 | 7 |
| Ex. 6.192 | 48 | 7 | Ex. 6.193 | 41 | 4 | Ex. 6.194 | 51 | 5 |
| Ex. 6.195 | 43 | 11 | Ex. 6.196 | 59 | 12 | Ex. 6.197 | 6 | 2 |
| Ex. 6.2 | 223 | 17 | Ex. 6.20 | 1750 | 49 | Ex. 6.21 | 1970 | 76 |
| Ex. 6.22 | 410 | 19 | Ex. 6.23 | 452 | 67 | Ex. 6.24 | 53 | 17 |
| Ex. 6.25 | 154 | 52 | Ex. 6.26 | 26 | 24 | Ex. 6.27 | 5 | 9 |
| Ex. 6.28 | 20 | 15 | Ex. 6.29 | 69 | 92 | Ex. 6.3 | 243 | 18 |
| Ex. 6.30 | 203 | 31 | Ex. 6.31 | 41 | 22 | Ex. 6.32 | 814 | 103 |
| Ex. 6.33 | 213 | 23 | Ex. 6.34 | 398 | 66 | Ex. 6.35 | 146 | 80 |
| Ex. 6.36 | 15 | 2 | Ex. 6.37 | 422 | 45 | Ex. 6.38 | 269 | 19 |
| Ex. 6.39 | 106 | 9 | Ex. 6.4 | 2510 | 118 | Ex. 6.40 | 70 | 9 |
| Ex. 6.41 | 4 | 2 | Ex. 6.42 | 12 | 2 | Ex. 6.43 | 368 | 62 |
| Ex. 6.44 | 10 | 2 | Ex. 6.45 | 1 | 1 | Ex. 6.46 | 30 | 4 |
| Ex. 6.47 | 6 | 1 | Ex. 6.48 | 14 | 7 | Ex. 6.49 | 3 | 1 |
| Ex. 6.5 | 216 | 19 | Ex. 6.50 | 5 | 1 | Ex. 6.51 | 8 | 3 |
| Ex. 6.52 | 8 | 2 | Ex. 6.53 | 4 | 1 | Ex. 6.54 | 3 | 1 |
| Ex. 6.55 | 5 | 1 | Ex. 6.56 | 6 | 1 | Ex. 6.57 | 11 | 11 |
| Ex. 6.58 | 4 | 1 | Ex. 6.59 | 76 | 10 | Ex. 6.6 | 477 | 52 |
| Ex. 6.60 | 83 | 3 | Ex. 6.61 | 41 | 4 | Ex. 6.62 | 44 | 4 |
| Ex. 6.63 | 88 | 3 | Ex. 6.64 | 142 | 33 | Ex. 6.65 | 34 | 3 |
| Ex. 6.66 | 57 | 2 | Ex. 6.67 | 9 | 5 | Ex. 6.68 | 767 | 62 |
| Ex. 6.69 | 389 | 51 | Ex. 6.7 | 15 | 3 | | | |
| Ex. 6.71 | 24 | 2 | Ex. 6.72 | 4 | 6 | Ex. 6.73 | 10 | 4 |
| Ex. 6.74 | 4 | 11 | Ex. 6.75 | 8 | 4 | Ex. 6.76 | 4 | 4 |
| Ex. 6.77 | 3 | 9 | Ex. 6.78 | 5 | 12 | Ex. 6.79 | 2 | 4 |
| Ex. 6.8 | 21 | 7 | Ex. 6.80 | 13 | 19 | Ex. 6.81 | 19 | 23 |
| Ex. 6.82 | 36 | 208 | Ex. 6.83 | 8 | 23 | Ex. 6.84 | 8 | 14 |
| Ex. 6.85 | 108 | 42 | Ex. 6.86 | 22 | 20 | Ex. 6.87 | 1 | 2 |
| Ex. 6.88 | 20 | 15 | Ex. 6.89 | 2 | 2 | Ex. 6.9 | 7 | 4 |
| Ex. 6.90 | 6 | 1 | Ex. 6.91 | 2 | 1 | Ex. 6.92 | 4 | 2 |
| Ex. 6.93 | 0.9 | 3 | Ex. 6.94 | 2 | 1 | Ex. 6.95 | 9 | 2 |
| Ex. 6.96 | 234 | 68 | Ex. 6.97 | 14 | 10 | Ex. 6.98 | 4 | 3 |
| Ex. 6.99 | 5 | 1 | Ex. 6.198 | 12 | 3 | Ex. 6.199 | 143 | 6 |
| Ex. 6.200 | 58 | 10 | Ex. 6.201 | 148 | 25 | Ex. 6.202 | 89 | 13 |
| | | | Ex. 7.1 | 16 | 162 | Ex. 7.2 | 420 | 69 |
| Ex. 7.3 | 1 | 3 | Ex. 7.4 | 7 | 6 | Ex. 7.5 | 9 | 2 |
| Ex. 7.6 | 5 | 6 | Ex. 7.7 | 2 | 3 | Ex. 7.8 | 2 | 4 |
| Ex. 7.9 | 28 | 28 | Ex. 7.10 | 33 | 42 | Ex. 7.11 | 17 | 720 |
| Ex. 7.12 | 15 | 52 | Ex. 7.13 | 21 | 49 | Ex. 7.14 | 23 | 50 |
| Ex. 7.15 | 11 | 65 | Ex. 7.16 | 8 | 21 | Ex. 7.17 | 4 | 19 |
| Ex. 7.18 | 1 | 4 | Ex. 7.19 | 5 | 8 | Ex. 7.20 | 2 | 14 |
| Ex. 7.21 | 1 | 2 | Ex. 7.22 | 1 | 4 | Ex. 7.23 | 1 | 3 |
| Ex. 7.24 | 33 | 33 | Ex. 7.25 | 15 | 18 | Ex. 7.26 | 42 | 54 |
| Ex. 7.27 | 23 | 17 | Ex. 7.28 | 14 | 19 | Ex. 7.29 | 23 | 70 |
| Ex. 7.30 | 9 | 12 | Ex. 7.31 | 8 | 19 | Ex. 7.32 | 7 | 124 |
| Ex. 7.33 | 1 | 3 | Ex. 7.34 | 16 | 84 | Ex. 7.35 | 6 | 20 |
| Ex. 7.36 | 16 | 115 | Ex. 7.37 | 11 | 20 | Ex. 7.38 | 8 | 30 |
| Ex. 7.39 | 43 | 61 | Ex. 7.40 | 23 | 39 | Ex. 7.41 | 44 | 106 |
| Ex. 7.42 | 38 | 28 | Ex. 7.43 | 24 | 42 | Ex. 7.44 | 21 | 35 |
| Ex. 7.45 | 31 | 60 | Ex. 7.46 | 78 | 77 | Ex. 7.47 | 39 | 60 |
| Ex. 7.48 | 33 | 40 | Ex. 7.49 | 96 | 173 | Ex. 7.50 | 66 | 171 |
| Ex. 7.51 | 19 | 27 | Ex. 7.52 | 27 | 60 | Ex. 7.53 | 46 | 190 |
| Ex. 7.54 | 87 | 270 | | | | | | |

Compounds of the present invention may be further characterized with regard to their general pharmacokinetic and pharmacological properties using conventional assays well known in the art; for example relating to their bioavailability in different species (such as rat or dog); or relating to their ability to cross the blood-brain barrier, using for example a human P-glycoprotein 1 (MDR 1) substrate assay, or an in vivo assay to determine drug concentrations in the brain, e.g. in rats after oral dosing; or relating to their functional behavior in different disease related animal models {for example: the sedative effect of the compound using Electroencephalography (EEG) and Electromyography (EMG) signal measurements [F. Jenck et al., Nature Medicine 2007, 13, 150-155]; the effect of the compound in the fear-potentiated startle paradigm [Fendt M et al., Neuroscience Biobehav Rev. 1999, 23, 743-760; WO2009/0047723]; the effect of the compound on stress-induced hyperthermia [Vinkers C H et al., European J Pharmacol. 2008, 585, 407-425]; the effect of the compound on morphine-induced locomotor sensitization [Vanderschuren L J M J et al., in Self D W, Staley J K (eds.) "Behavioral Neuroscience of Drug Addiction", Current Topics in Behavioral Neurosciences 3 (2009), 179-195]}; or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

Measurement of Brain and Systemic Concentration after Oral Administration:

In order to assess brain penetration, the concentration of the compound is measured in plasma ([P]), and brain ([B]), sampled 3 h (or at different time points) following oral administration (e.g. 100 mg/kg) to male wistar rats. The compounds are formulated e.g. in 100% PEG 400. Samples are collected in the same animal at the same time point (+/−5 min).

Blood is sampled from the vena cava caudalis into containers with EDTA as anticoagulant and centrifuged to yield plasma. Brain is sampled after cardiac perfusion of 10 mL NaCl 0.9% and homogenized into one volume of cold phosphate buffer (pH 7.4). All samples are extracted with MeOH and analyzed by LC-MS/MS. Concentrations are determined with the help of calibration curves.

Results obtained for the compound of Example 5.19:
(3 h after oral administration (100 mg/kg), n=3): [P]=2095 ng/ml; [B]=3880 ng/g.

Results obtained for the compound of Example 5.36:
(3 h after oral administration (100 mg/kg), n=3): [P]=1280 ng/ml; [B]=1808 ng/g.

Results obtained for the compound of Example 5.277:
(3 h after oral administration (100 mg/kg), n=3): [P]=3560 ng/ml; [B]=5880 ng/g.

Sedative Effects: EEG, EMG and Behavioural Indices of Alertness Recorded by Radiotelemetry In Vivo in Wistar Rats.

Electroencephalography (EEG) and Electromyography (EMG) signals were measured by telemetry using TL11M2-F20-EET miniature radiotelemetric implants (Data Science Int.) with two pairs of differential leads.

Surgical implantation was performed under general anesthesia with Ketamin/Xylazin, for cranial placement of one differential pair of EEG electrodes and one pair of EMG leads inserted in either side of the muscles of the neck. After surgery, rats recovered in a thermoregulated chamber and received analgesic treatment with subcutaneous buprenorphine twice a day for 2 d. They were then housed individually and allowed to recover for a minimum of 2 weeks. Thereafter, rats—in their home cage—were placed in a ventilated sound-attenuating box, on a 12-h light/12-h dark cycle, for acclimatization before continuous EEG/EMG recordings started. The telemetric technology that we used in this study allows accurate and stress-free acquisition of biosignals in rats placed in their familiar home cage environment, with no recording leads restricting their movements. Variables analyzed included four different stages of vigilance and sleep, spontaneous activity in the home cage and body temperature. Sleep and wake stages were evaluated using a rodent scoring software (Somnologica Science) directly processing electrical biosignals on 10 s contiguous epochs. The scoring is based on frequency estimation for EEG and amplitude discrimination for EMG and locomotor activity. Using these measurements, the software determines the probability that all components within each epoch best represent active waking (AW), quiet waking (QW), non-REM-sleep (NREM) or REM-sleep (REM). The percentage of total time spent in AW, QW, NREM- and REM-sleep was calculated per 12 h light or dark period. The latency to the onset of the first significant NREM- and REM-sleep episodes and the frequency and duration of those episodes were also calculated. AW, QW, NREM- and REM-sleep, home cage activity and body temperature were measured at baseline for at least one total circadian cycle (12 h-night, 12 h-day) before a test compound was administered. If baseline measurements indicated that animals were stable, test compound or vehicle was given in the evening by oral gavage at the end of the baseline 12-h day period, immediately before the nocturnal rise in orexin and activity in rats. All variables were subsequently recorded for 12 h following administration of the orexin receptor antagonist.

The compound of Example 5.19 has been tested in this assay (oral dosage: 30 mg/kg po; effects analyzed over 6 hours): Results are: −28% on active wake, −46% on home cage activity, +31% on NREM sleep, +69% on REM sleep; when compared to vehicle controls. The compound of Example 5.36 has been tested in this assay (oral dosage: 30 mg/kg po; effects analyzed over 6 hours): Results are: −24% on active wake, −31% on home cage activity, +27% on NREM sleep, +53% on REM sleep; when compared to vehicle controls. The compound of Example 5.277 has been tested in this assay (oral dosage: 30 mg/kg po; effects analyzed over 6 hours): Results are: −22% on active wake, −42% on home cage activity, +21% on NREM sleep, +52% on REM sleep; when compared to vehicle controls.

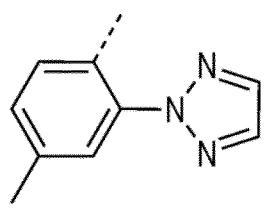 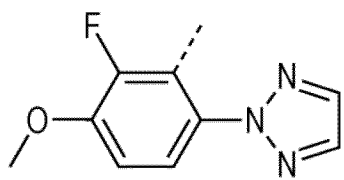

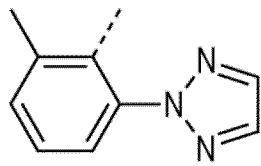 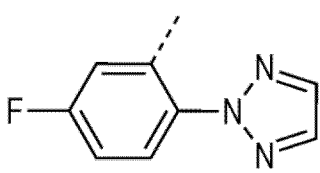

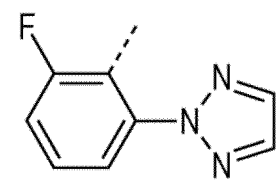 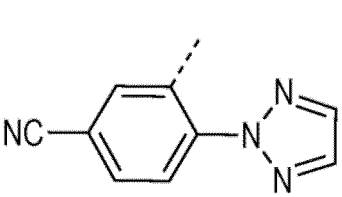

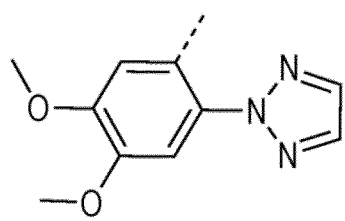 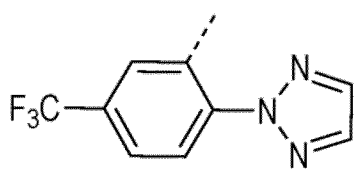

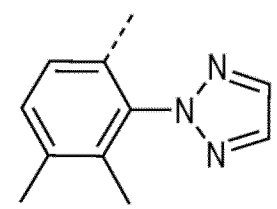 and 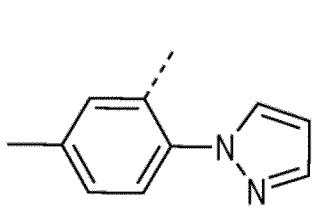

The invention claimed is:

1. A compound of the formula (V); wherein the absolute configuration is as depicted in formula (V):

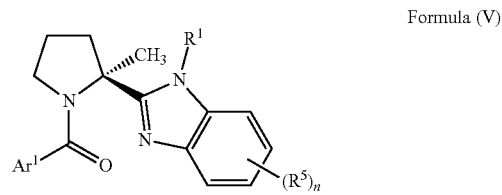

Formula (V)

wherein $Ar^1$ represents a group independently selected from a member of the following groups A and L:

A.

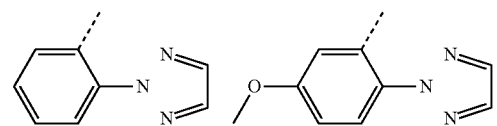

-continued

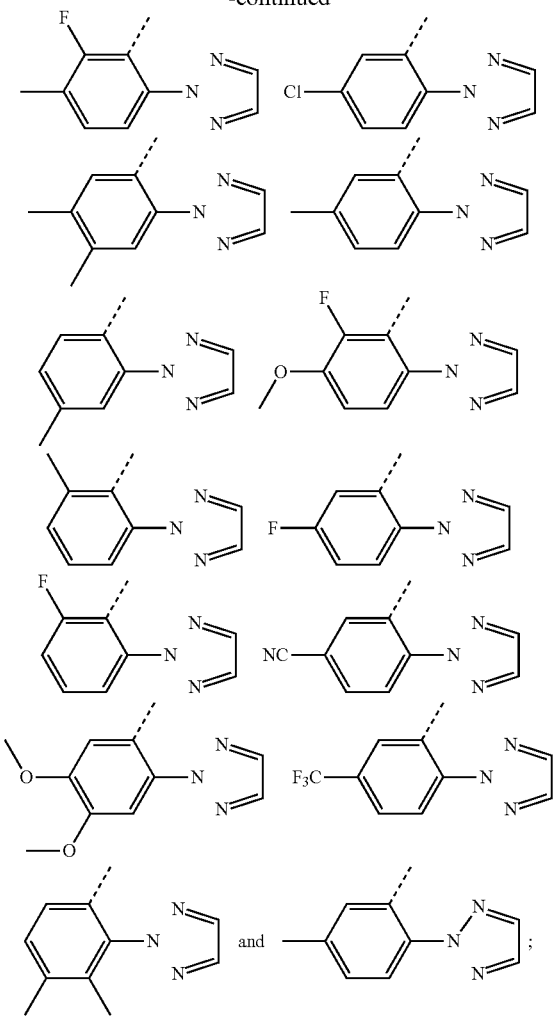

and
L.

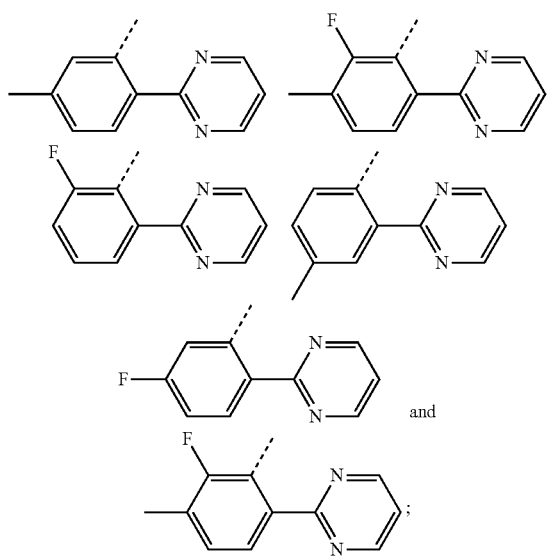

and the fragment:

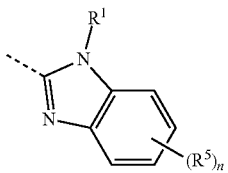

represents a group independently selected from one of the following groups:

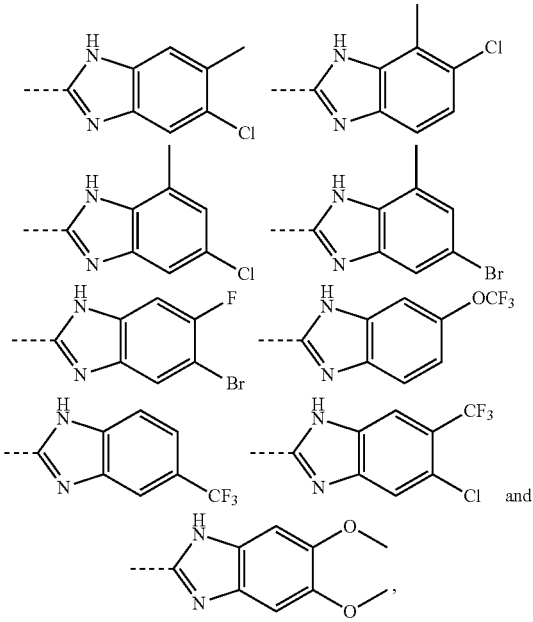

or a pharmaceutically acceptable salt thereof.

2. A pharmaceutical composition comprising, as active principle, one or more compounds according to claim 1, or a pharmaceutically acceptable salt thereof, and at least one therapeutically inert excipient.

3. A method to treat a disease or disorder selected from
a) a sleep disorder selected from an insomnia; a primary insomnia; an idiopathic insomnia; an insomnia associated with depression, emotional/mood disorders, aging, Alzheimer's disease or cognitive impairment; REM sleep interruptions; a breathing-related sleep disorder; a sleep apnea; a periodic limb movement disorder, a restless leg syndrome; a circadian rhythm sleep disorder; a shift work sleep disorder; and a jet-lag syndrome; and
b) an anxiety disorder;
comprising administering to a patient in need thereof, the compound of claim 1 in free or pharmaceutically acceptable salt form.

4. The compound [(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone; or a pharmaceutically acceptable salt thereof.

5. The compound [(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone in pharmaceutically acceptable salt form.

6. The compound [(S)-2-(5-Chloro-4-methyl-1H-benzoimidazol-2-yl)-2-methyl-pyrrolidin-1-yl]-(5-methoxy-2-[1,2,3]triazol-2-yl-phenyl)-methanone in free form.

7. A pharmaceutical composition comprising, as active principle, the compound according to claim 4, or a pharmaceutically acceptable salt thereof, and at least one therapeutically inert excipient.

8. A pharmaceutical composition comprising, as active principle, the compound according to claim 5, and at least one therapeutically inert excipient.

9. A pharmaceutical composition comprising, as active principle, the compound according to claim 6, and at least one therapeutically inert excipient.

10. A method to treat a disease or disorder selected from
a) a sleep disorder selected from an insomnia; a primary insomnia; an idiopathic insomnia; an insomnia associated with depression, emotional/mood disorders, aging, Alzheimer's disease or cognitive impairment; REM sleep interruptions; a breathing-related sleep disorder; a sleep apnea; a periodic limb movement disorder, a restless leg syndrome; a circadian rhythm sleep disorder; a shift work sleep disorder; and a jet-lag syndrome; and
b) an anxiety disorder selected from a post-traumatic stress disorder, an obsessive compulsive disorder, a panic attack, a phobic anxiety, and an avoidance;
comprising administering to a patient in need thereof, the compound of claim 4 in free or pharmaceutically acceptable salt form.

11. A method to treat a disease or disorder selected from
a) a sleep disorder selected from an insomnia; a primary insomnia; an idiopathic insomnia; an insomnia associated with depression, emotional/mood disorders, aging, Alzheimer's disease or cognitive impairment; REM sleep interruptions; a breathing-related sleep disorder; a sleep apnea; a periodic limb movement disorder, a restless leg syndrome; a circadian rhythm sleep disorder; a shift work sleep disorder; and a jet-lag syndrome; and
b) an anxiety disorder selected from a post-traumatic stress disorder, an obsessive compulsive disorder, a panic attack, a phobic anxiety, and an avoidance;
comprising administering to a patient in need thereof, the compound of claim 5.

12. A method to treat a disease or disorder selected from
a) a sleep disorder selected from an insomnia; a primary insomnia; an idiopathic insomnia; an insomnia associated with depression, emotional/mood disorders, aging, Alzheimer's disease or cognitive impairment; REM sleep interruptions; a breathing-Related sleep disorder; a sleep apnea; a periodic limb movement disorder, a restless leg syndrome; a circadian rhythm sleep disorder; a shift work sleep disorder; and a jet-lag syndrome; and
b) an anxiety disorder selected from a post-traumatic stress disorder, an obsessive compulsive disorder, a panic attack, a phobic anxiety, and an avoidance;
comprising administering to a patient in need thereof, the compound of claim 6.

* * * * *

UNITED STATES PATENT AND TRADEMARK OFFICE
CERTIFICATE OF CORRECTION

PATENT NO. : 9,732,075 B2
APPLICATION NO. : 14/405649
DATED : August 15, 2017
INVENTOR(S) : Christoph Boss et al.

Page 1 of 2

It is certified that error appears in the above-identified patent and that said Letters Patent is hereby corrected as shown below:

In the Claims

Claim 1, Column 168, Line 60, to Column 169, Line 40, the structures should be replaced with the following structures:

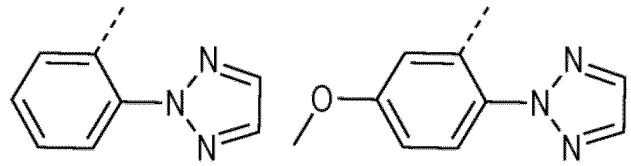

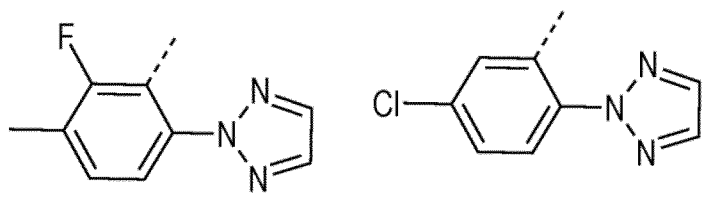

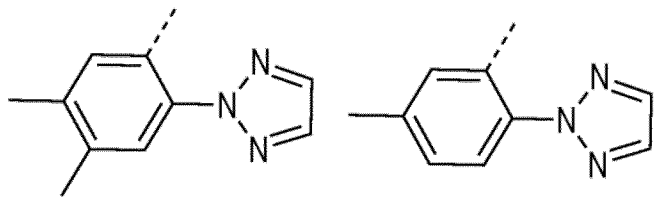

Signed and Sealed this
Fourteenth Day of June, 2022

Katherine Kelly Vidal
Director of the United States Patent and Trademark Office

CERTIFICATE OF CORRECTION (continued) Page 2 of 2
U.S. Pat. No. 9,732,075 B2